United States Patent
Zhou et al.

(10) Patent No.: US 7,635,572 B2
(45) Date of Patent: Dec. 22, 2009

(54) METHODS FOR CONDUCTING ASSAYS FOR ENZYME ACTIVITY ON PROTEIN MICROARRAYS

(75) Inventors: Fang X. Zhou, New Haven, CT (US); Barry Schweitzer, Cheshire, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 10/865,431

(22) Filed: Jun. 9, 2004

(65) Prior Publication Data

US 2005/0118665 A1    Jun. 2, 2005

(51) Int. Cl.
*C12Q 1/50* (2006.01)
(52) U.S. Cl. ......................................... 435/17
(58) Field of Classification Search .................. None
See application file for complete search history.

(56) References Cited

U.S. PATENT DOCUMENTS

| | | |
|---|---|---|
| 4,071,409 A | 1/1978 | Messing et al. |
| 4,281,061 A | 7/1981 | Zuk et al. |
| 4,444,879 A | 4/1984 | Forster et al. |
| 4,483,929 A | 11/1984 | Szoka |
| 4,514,508 A | 4/1985 | Hirschfield |
| 4,562,147 A | 12/1985 | Joo |
| 4,562,157 A | 12/1985 | Lowe et al. |
| 4,591,570 A | 5/1986 | Chang |
| 4,722,896 A | 2/1988 | Kadish et al. |
| 4,728,591 A | 3/1988 | Clark et al. |
| 4,802,951 A | 2/1989 | Clark et al. |
| 4,816,567 A | 3/1989 | Cabilly et al. |
| 4,894,146 A | 1/1990 | Giddings |
| 4,987,032 A | 1/1991 | Miyasaka et al. |
| 5,096,807 A | 3/1992 | Leaback et al. |
| 5,143,854 A | 9/1992 | Pirrung et al. |
| 5,154,808 A | 10/1992 | Miyasaka et al. |
| 5,242,828 A | 9/1993 | Bergstrom et al. |
| 5,252,743 A | 10/1993 | Barrett et al. |
| 5,262,322 A | 11/1993 | Liu et al. |
| 5,270,167 A | 12/1993 | Francoeur et al. |
| 5,283,173 A | 2/1994 | Fields et al. |
| 5,304,487 A | 4/1994 | Wilding et al. |
| 5,348,886 A | 9/1994 | Lee et al. |
| 5,376,252 A | 12/1994 | Ekstrom et al. |
| 5,384,261 A | 1/1995 | Winkler et al. |
| 5,405,766 A | 4/1995 | Kallury et al. |
| 5,405,783 A | 4/1995 | Pirrung et al. |
| 5,412,087 A | 5/1995 | McGall et al. |
| 5,424,186 A | 6/1995 | Fodor et al. |
| 5,429,807 A | 7/1995 | Matson et al. |
| 5,432,099 A | 7/1995 | Ekins |
| 5,441,876 A | 8/1995 | Singh et al. |
| 5,445,934 A | 8/1995 | Fodor et al. |
| 5,466,589 A | 11/1995 | Olinger et al. |
| 5,489,678 A | 2/1996 | Fodor et al. |
| 5,498,545 A | 3/1996 | Vestal et al. |
| 5,506,121 A | 4/1996 | Skerra et al. |
| 5,510,270 A | 4/1996 | Fodor et al. |
| 5,512,492 A | 4/1996 | Herron et al. |
| 5,516,635 A | 5/1996 | Ekins et al. |
| 5,532,128 A | 7/1996 | Eggers |
| 5,538,897 A | 7/1996 | Yates, III et al. |
| 5,541,070 A | 7/1996 | Kauvar |
| 5,545,531 A | 8/1996 | Rava et al. |
| 5,580,733 A | 12/1996 | Levis et al. |
| 5,585,069 A | 12/1996 | Zanzucchi et al. |
| 5,585,639 A | 12/1996 | Dorsel et al. |
| 5,593,838 A | 1/1997 | Zanzucchi et al. |
| 5,605,662 A | 2/1997 | Heller et al. |
| 5,620,850 A | 4/1997 | Bamdad et al. |
| 5,624,711 A | 4/1997 | Sundberg et al. |
| 5,627,369 A | 5/1997 | Vestal et al. |
| 5,629,213 A | 5/1997 | Kornguth et al. |

(Continued)

FOREIGN PATENT DOCUMENTS

| | | |
|---|---|---|
| EP | 596421 | 10/1993 |
| EP | 0619321 | 12/1994 |
| EP | 0664452 | 7/1995 |
| EP | 0818467 | 1/1998 |
| EP | 0895082 | 2/1998 |
| EP | 0972564 | 1/2000 |
| EP | 1086742 | 3/2001 |
| JP | 02272081 | 11/1990 |
| WO | WO 89/04675 | 6/1989 |
| WO | WO 89/10977 | 11/1989 |

(Continued)

OTHER PUBLICATIONS

Zhu et al. Nature Genetics 2000;26:283-289.*
Zhu et al. Science 2001;293:2101-2105.*
Final Office Action issued by U.S. Patent Office, mailed Mar. 1, 2007, for U.S. Appl. No. 10/458,720.
Non-Final Office Action issued by U.S. Patent Office, mailed May 26, 2006, for U.S. Appl. No. 10/458,720.

(Continued)

*Primary Examiner*—Jon P Weber
*Assistant Examiner*—Bin Shen

(57) ABSTRACT

The present invention relates to methods of conducting assays for enzymatic activity on microarrays useful for the large-scale study of protein function, screening assays, and high-throughput analysis of enzymatic reactions. The invention relates to methods of using protein chips to assay the presence, amount, activity and/or function of enzymes present in a protein sample on a protein chip. In particular, the methods of the invention relate to conducting enzymatic assays using a microarray wherein a protein and a substance are immobilized on the surface of a solid support and wherein the protein and the substance are in proximity to each other sufficient for the occurrence of an enzymatic reaction between the substance and the protein. The invention also relates to microarrays that have an enzyme and a substrate immobilized on their surface wherein the enzyme and the substrate are in proximity to each other sufficient for the occurrence of an enzymatic reaction between the enzyme and the substrate.

29 Claims, 7 Drawing Sheets

U.S. PATENT DOCUMENTS

Figure 1:
Figure 1:
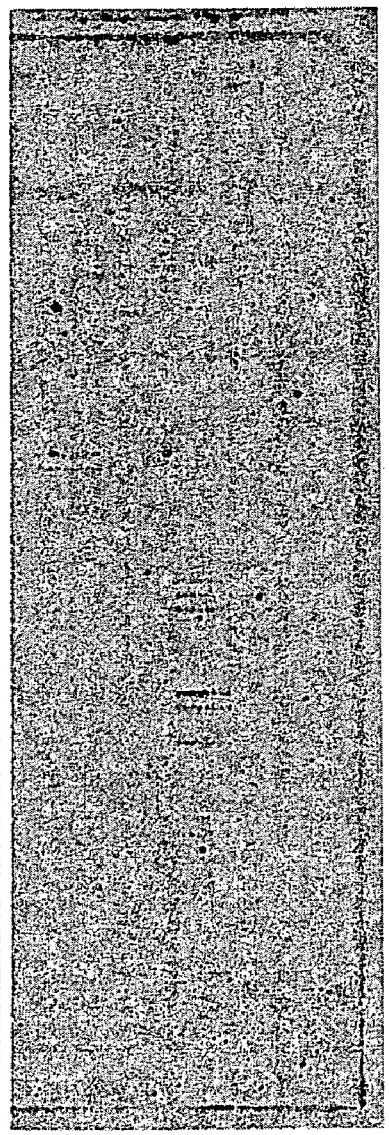

| | | | |
|---|---|---|---|
| 5,637,469 | A | 6/1997 | Wilding et al. |
| 5,643,948 | A | 7/1997 | Driedger et al. |
| 5,653,939 | A | 8/1997 | Hollis et al. |
| 5,677,195 | A | 10/1997 | Winkler et al. |
| 5,677,196 | A | 10/1997 | Herron et al. |
| 5,681,484 | A | 10/1997 | Zanzucchi et al. |
| 5,688,642 | A | 11/1997 | Chrisey et al. |
| 5,720,928 | A | 2/1998 | Schwartz |
| 5,726,026 | A | 3/1998 | Wilding et al. |
| 5,741,700 | A | 4/1998 | Ershov et al. |
| 5,744,305 | A | 4/1998 | Fodor et al. |
| 5,763,263 | A | 6/1998 | Dehlinger et al. |
| 5,766,908 | A | 6/1998 | Klein et al. |
| 5,776,674 | A | 7/1998 | Ulmer |
| 5,776,706 | A | 7/1998 | Siiman et al. |
| 5,776,748 | A | 7/1998 | Singhvi et al. |
| 5,807,522 | A | 9/1998 | Brown et al. |
| 5,807,755 | A | 9/1998 | Ekins |
| 5,821,063 | A | 10/1998 | Patterson et al. |
| 5,827,658 | A | 10/1998 | Liang |
| 5,834,319 | A | 11/1998 | Ekins |
| 5,837,551 | A | 11/1998 | Ekins |
| 5,837,832 | A | 11/1998 | Chee et al. |
| 5,843,767 | A | 12/1998 | Beattie |
| 5,846,819 | A | 12/1998 | Pausch et al. |
| 5,854,018 | A | 12/1998 | Hitzeman et al. |
| 5,858,188 | A | 1/1999 | Soane et al. |
| 5,858,804 | A | 1/1999 | Zanzucchi et al. |
| 5,861,242 | A | 1/1999 | Chee et al. |
| 5,861,254 | A | 1/1999 | Schneider et al. |
| 5,866,345 | A | 2/1999 | Wilding et al. |
| 5,866,362 | A | 2/1999 | Cousens et al. |
| 5,866,363 | A | 2/1999 | Pieczenik |
| 5,874,219 | A | 2/1999 | Rava et al. |
| 5,885,793 | A | 3/1999 | Griffiths et al. |
| 5,905,024 | A | 5/1999 | Mirzabekov et al. |
| 5,919,523 | A | 7/1999 | Sundberg et al. |
| 5,922,591 | A | 7/1999 | Anderson et al. |
| 5,922,617 | A | 7/1999 | Wang et al. |
| 5,925,552 | A | 7/1999 | Keogh et al. |
| 5,942,443 | A | 8/1999 | Parce et al. |
| 5,945,334 | A | 8/1999 | Besemer et al. |
| 5,948,621 | A | 9/1999 | Turner et al. |
| 5,965,124 | A | 10/1999 | Feinberg et al. |
| 5,965,389 | A | 10/1999 | Raymond et al. |
| 5,981,734 | A | 11/1999 | Mirzabekov et al. |
| 6,001,607 | A | 12/1999 | Tang et al. |
| 6,040,193 | A | 3/2000 | Winkler et al. |
| 6,051,380 | A | 4/2000 | Sosnowski et al. |
| 6,061,476 | A | 5/2000 | Nichani |
| 6,064,754 | A | 5/2000 | Parekh et al. |
| 6,075,875 | A | 6/2000 | Gu |
| 6,083,763 | A | 7/2000 | Balch |
| 6,087,102 | A | 7/2000 | Chenchik et al. |
| 6,087,103 | A | 7/2000 | Burmer |
| 6,100,099 | A | 8/2000 | Gordon et al. |
| 6,103,479 | A | 8/2000 | Taylor et al. |
| 6,107,059 | A | 8/2000 | Hart |
| 6,110,426 | A | 8/2000 | Shalon et al. |
| 6,121,048 | A | 9/2000 | Zaffaroni et al. |
| 6,122,408 | A | 9/2000 | Fang et al. |
| 6,124,102 | A | 9/2000 | Fodor et al. |
| 6,146,830 | A | 11/2000 | Friend et al. |
| 6,190,619 | B1 | 2/2001 | Kilcoin et al. |
| 6,190,908 | B1 | 2/2001 | Kang |
| 6,194,612 | B1 | 2/2001 | Boger et al. |
| 6,197,506 | B1 | 3/2001 | Fodor et al. |
| 6,197,599 | B1 | 3/2001 | Chin et al. |
| 6,225,047 | B1 | 5/2001 | Hutchens et al. |
| 6,303,344 | B1 | 10/2001 | Patten et al. |
| 6,316,186 | B1 | 11/2001 | Ekins |
| 6,329,209 | B1 | 12/2001 | Wagner et al. |
| 6,346,413 | B1 | 2/2002 | Fodor et al. |
| 6,365,418 | B1 | 4/2002 | Wagner et al. |
| 6,391,625 | B1 | 5/2002 | Park et al. |
| 6,399,365 | B2 | 6/2002 | Besemer et al. |
| 6,403,320 | B1 | 6/2002 | Read et al. |
| 6,406,921 | B1 | 6/2002 | Wagner et al. |
| 6,416,952 | B1 | 7/2002 | Pirrung et al. |
| 6,454,924 | B2 | 9/2002 | Jedrzejewski et al. |
| 6,475,808 | B1 | 11/2002 | Wagner et al. |
| 6,475,809 | B1 | 11/2002 | Wagner et al. |
| 6,476,215 | B1 | 11/2002 | Okamoto et al. |
| 6,531,283 | B1 | 3/2003 | Kingsmore et al. |
| 6,544,739 | B1 | 4/2003 | Fodor et al. |
| 6,576,478 | B1 | 6/2003 | Wagner et al. |
| 6,582,969 | B1 | 6/2003 | Wagner et al. |
| 6,596,545 | B1 | 7/2003 | Wagner et al. |
| 6,600,031 | B1 | 7/2003 | Fodor et al. |
| 6,610,482 | B1 | 8/2003 | Fodor et al. |
| 6,630,358 | B1 | 10/2003 | Wagner et al. |
| 6,682,942 | B1 | 1/2004 | Wagner et al. |
| 6,692,751 | B1 | 2/2004 | Zebedee et al. |
| 6,699,665 | B1 | 3/2004 | Kim et al. |
| 6,720,149 | B1 | 4/2004 | Rava et al. |
| 6,720,157 | B2 | 4/2004 | Indermuhle et al. |
| 6,780,582 | B1 | 8/2004 | Wagner et al. |
| 6,790,940 | B1 | 9/2004 | Zentgraf et al. |
| 6,818,411 | B2 | 11/2004 | Hutchens et al. |
| 6,844,165 | B2 | 1/2005 | Hutchens et al. |
| 6,881,586 | B2 | 4/2005 | Hutchens et al. |
| 6,897,073 | B2 | 5/2005 | Wagner et al. |
| 6,919,211 | B1 | 7/2005 | Fodor et al. |
| 6,943,034 | B1 | 9/2005 | Winkler et al. |
| 6,960,457 | B1 | 11/2005 | Spudich et al. |
| 2002/0106702 | A1 | 8/2002 | Wagner |
| 2002/0110932 | A1 | 8/2002 | Wagner et al. |
| 2002/0110933 | A1 | 8/2002 | Wagner et al. |
| 2002/0115225 | A1 | 8/2002 | Wagner et al. |
| 2002/0119579 | A1 | 8/2002 | Wagner et al. |
| 2002/0132272 | A1 | 9/2002 | Wagner et al. |
| 2002/0164656 | A1 | 11/2002 | Hoeffler et al. |
| 2003/0003599 | A1 | 1/2003 | Wagner et al. |
| 2003/0017149 | A1 | 1/2003 | Hoeffler et al. |
| 2003/0073811 | A1 | 4/2003 | Kozlowski et al. |
| 2003/0138973 | A1 | 7/2003 | Wagner et al. |
| 2003/0207467 | A1 | 11/2003 | Snyder et al. |
| 2004/0197931 | A1 | 10/2004 | Pierre et al. |
| 2004/0241751 | A1 | 12/2004 | Wagner et al. |
| 2004/0248323 | A1 | 12/2004 | Zhou et al. |
| 2005/0008674 | A1 | 1/2005 | Wagner et al. |
| 2005/0014292 | A1 | 1/2005 | Wagner et al. |
| 2005/0026215 | A1 | 2/2005 | Predki et al. |
| 2005/0095646 | A1 | 5/2005 | Sherman |
| 2005/0100947 | A1 | 5/2005 | Wagner et al. |
| 2005/0118665 | A1 | 6/2005 | Zhou et al. |
| 2005/0182242 | A1 | 8/2005 | Snyder et al. |
| 2005/0233473 | A1 | 10/2005 | Cicero et al. |
| 2005/0244854 | A1 | 11/2005 | Cahill et al. |
| 2006/0035387 | A1 | 2/2006 | Wagner et al. |
| 2006/0099704 | A1 | 5/2006 | Predki et al. |

FOREIGN PATENT DOCUMENTS

| | | |
|---|---|---|
| WO | WO 90/05144 | 5/1990 |
| WO | WO 92/01047 | 1/1992 |
| WO | WO 92/10588 | 6/1992 |
| WO | WO 92/20791 | 11/1992 |
| WO | WO 93/12248 | 6/1993 |
| WO | WO 93/19172 | 9/1993 |
| WO | WO 95/35505 | 12/1995 |
| WO | WO 96/36436 | 11/1996 |
| WO | WO 97/32017 | 9/1997 |
| WO | WO 97/42507 | 11/1997 |

| | | |
|---|---|---|
| WO | WO 98/23948 | 6/1998 |
| WO | WO 98/27229 | 6/1998 |
| WO | WO 98/39481 | 9/1998 |
| WO | WO 98/43086 | 10/1998 |
| WO | WO 98/50773 | 11/1998 |
| WO | WO 98/59360 | 12/1998 |
| WO | WO 98/59361 | 12/1998 |
| WO | WO 98/59362 | 12/1998 |
| WO | WO 99/20749 | 4/1999 |
| WO | WO 99/28502 | 6/1999 |
| WO | WO 99/39210 | 8/1999 |
| WO | WO 99/40434 | 8/1999 |
| WO | WO 99/45130 | 9/1999 |
| WO | WO 99/45149 | 9/1999 |
| WO | WO 99/57311 | 11/1999 |
| WO | WO 99/57312 | 11/1999 |
| WO | WO 00/06770 | 2/2000 |
| WO | WO 00/07024 | 2/2000 |
| WO | WO 00/20475 | 4/2000 |
| WO | WO 00/54046 | 7/2000 |
| WO | WO 00/63701 | 10/2000 |
| WO | WO 01/04265 | 1/2001 |
| WO | WO 01/14425 | 3/2001 |
| WO | WO 01/18545 | 3/2001 |
| WO | WO 01/29220 | 4/2001 |
| WO | WO 01/36681 | 5/2001 |
| WO | WO 01/81924 | 11/2001 |
| WO | WO 01/83827 | 11/2001 |
| WO | WO 02/36342 | 5/2002 |
| WO | WO 02/48676 | 6/2002 |
| WO | WO 02/053775 | 7/2002 |
| WO | WO 02/086491 | 10/2002 |
| WO | WO 02/092118 | 11/2002 |
| WO | WO 02/099099 | 12/2002 |
| WO | WO 03/018854 | 3/2003 |
| WO | WO 03/043487 | 5/2003 |

OTHER PUBLICATIONS

Restriction Requirement issued by U.S. Patent Office, mailed Nov. 186, 2005, for U.S. Appl. No. 10/458,720.

Abstract XP002291800, Derwent Publication Ltd., London, GB; AN 1997-011913.

Ahluwalia, et al, "A comparative study of protein immobilization techniques for optical immunosensors", Biosens. Bioelectron. 7(3):207-214, 1992.

Ames et al., "Conversion of murine Fabs isolated from a combinatorial phage display library to full length immunoglobulins", 1995, J. Immunol. Methods 184:177-86.

Anderson et al., "Analytical techniques in combinatorial chemistry: MAS CH correlation in solvent swollen resin", 1995, J. Org. Chem., 60:2650-2651.

Arenkov et al., "Protein microchips: use for immunoassay and enzymatic reactions", 2000, Anal. Biochem., 278(2):123-131.

Baecher-Allan et al., "Differential epitope expression of Ly-48 (mouse leukosialin)." Immunogenetics. 1993;37(3):183-92.

Bailis, J. M., & Roeder, G. S. Synaptonemal complex morphogenesis and sisterchromatid cohesion require Mek1-dependent phosphorylation of a meiotic chromosomal protein. Genes & Dev. 12, 3551-3563 (1998).

Barral et al. "Niml-related kinases coordinate cell cycle progression with the organization of the peripheral cytoskeleton in yeast." Genes & Dev. 13, 176-187 (1999).

Bhatia, et al, Anal. Biochem. 178(2):408-413, 1989.

Bielke et al., "Characterization of a novel murine testis-specific serine/threonine kinase." Gene. Feb. 25, 1994;139(2):235-9.

Biere et al., Micropatterned immobilization of a G protein-coupled receptor and direst detection of G protein activtion, Nat. Biotechnol., 1999, 17 (11):1105-1108.

Blachere et al., "Heat shock protein vaccines against cancer" 1993, J. Immunotherapy 14:352-6.

Brummel et al., "A mass spectrometric solution to the address problem of combinatorial libraries", 1994, Science, 264:399-402.

Bussow et al., "A human cDNA library for high-throughput protein expression screening." 2000, Genomics 65:1.

Caveman, "I'll have a genome with chips, please", J. Cell Sci., 2000, 113:3543-3544.

Cha et al. Expression of fused protein, human interleukin-2 simplified as a fusion with green fluorescent protein, in suspended Sf-9 insect cells J. Biotechnology 69, 9-17 (1999).

Chapman-Smith, A., and J. E. Cronan, J. (1999). Molecular Biology of Biotin Attachment to Proteins, J. Nutr. 129, 477S-484S.

Cheung et al. A dynamic approach to mapping coordinates between microplates and microarrays. J Biomed Inform. Oct.-Dec. 2002;35(5-6):306-12.

Cheung et al. "YMD: a microarray database for large-scale gene expression analysis." Proc AMIA Symp. 2002;:140-4.

Christendat et al. "Structural proteomics: prospects for high throughput sample preparation." Prog Biophys Mol Biol. 2000;73(5):339-45. Review. No. abstract available.

Christendat et al., "Structural proteomics of an archaeon." Nat Struct Biol. Oct. 2000;7(10):903-9.

Chu et al., "Free solution identification of candidate peptides from combinatorial libraries by affinity capillary electrophoresis/mass spectrometry", J. Am. Chem. Soc., 1995, 117:5419-5420.

Cohen P. "Classification of protein-serine/threonine phosphatases: identification and quantitation in cell extracts." Methods Enzymol. 1991;201:389-98. Review. No abstract available.

Cohen P. "A microchip-based enzyme assay for protein kinase A", Anal. Biochem., 1999; 273(1):89-97.

Cohen, et al., "An artificial cell-cycle inhibitor isolated from a combinatorial library.", Proc. Natl. Acad. Sci. USA, 95:14272-7, 1998.

Collioud et al. (1993). Oriented and covalent immobilization of target molecules to solid supports: Synthesis and application of a light-activatable and thiol-reactive cross-linking reagent. Bioconjugate Chem. 4:528-536.

Costanzo et al., "YPD, PombePD and WormPD: model organism volumes of the BioKnowledge library, an integrated resource for protein information.", Nucleic Acids Res. 29, 75 (2001).

Couchman et al., "p53lyn and p56lyn: a new signaling pathway in human endometrium and endometrial adenocarcinomas.", J Soc Gynecol Investig. Mar.-Apr. 1997;4(2):103-9.

Cupo JF. "Electrophoretic analysis of nuclear matrix proteins and the potential clinical applications.", J Chromatogr. Sep. 13, 1991;569(1-2):389-406.

Davies and Benzer: Generation of cDNA expression libraries enriched for in-frame sequences PNAS v. 94, 2128-2132, 1997.

Davies et al. "Profiling of amyloid beta peptide variants using SELDI Protein Chip arrays." Biotechniques. Dec. 1999;27(6):1258-61.

Dawson et al., "Peptide-derived self-assembled monolayers: adsorption of N-stearoyl 1-Cysteine methyl ester on gold," Journal of Molecular Recognition, 10:18-25 (1997).

Derisi et al., Exploring the metabolic and genetic control of gene expression on a genomic scale. Science 278, 680-686 (1997).

Duschl et al., "Surface engineering: optimization of antigen presentation in self-assembled monolayers," Biophysical Journal, 70:1985-1995 (1996).

Dzgoev et al "Microformat imaging ELISA for pesticide determination" Anal. Chem. 68(19):3364 (1996).

Egner et al., "Solid phase chemistry: direct monitoring by matris-assisted laser desorption/ionization time of flight mass spectrometry: A tool for combinatorial chemistry", J. Org. Chem., 1995, 60:2652-2653.

Ekins "Ligand assays" from electrophoresis to miniaturized microarrays Clin. Chem. 44(9):2015-2030 (1998).

Ekins et al., "Multianalyte microspot immunoassay—microanalytical "compact disk" of the future", Clin Chem. Nov. 1991;37(11):1955-67.

Ekins et al., Multianalyte microspot immunoassay. The microanalytical 'compact disk' of the future. Ann Biol Clin (Paris). 1992;50(5):337-53.

Ekins, et al., << Fluorescence spectroscopy and its application to new generation of high sensitivity, multi-microspot, multianalyte, immunoassay, Clinica Chimica Acta., 1990, 194:91-114.

Emili et al., "Large scale functional analysis using peptides or protein arrays", Nat. Biotech., 2000, 18(4):393-397.

Engvali, et al., "Enzyme-linked immunosorbent assay, ELISA. 3. Quantitation of specific antibodies by enzyme-labeled anti-immunoglobulin in antigen-coated tubes", J. Immunol., 1972, 109(1):129-135.

Evans, et al., "Semisynthesis of cytotoxic proteins using a modified protein splicing element.", Protein Science 7:2256-2264, 1998.

Ferrigno et al. "Regulated nucleo/cytoplasmic exchange of HOGI MAPK requires the importin beta homologs NMD5 and XPO1." EMBO J. 17, 5606-5614 (1998).

Fields et al., "Functional Genomics", Proc. Natl. Acad. Sci., 1999, 96(16):8825-8826.

Fini et al., 1999, "Development of a chemiluminescence competitive PCR for the detection and quantification of parvovirus B19 DNA using a microplate luminometer", Clin Chem. 45(9):1391-6.

Fitch, W. M. & Margoliash, E. Construction of phylogenetic trees. Science. 155, 279-284 (1967).

Fitch et al., "High-resolution H NMR in solid-phase organic synthesis", J. Org. Chem., 1994, 59:7955-7956.

Freij-Larsson, et al, Biomaterials 17(22): 2199-2207, 1996.

Fruman et al., "Phosphoinositide kinases", Annu. Rev. Biochem. 67, 481 (1998).

Fukuda, et al., "Specific RNA aptamers to NS3 protease domain and hepatitis C virus", Nucleic Acids Symp. Ser., (37):237-8, 1997.

Ganz et al., "Characterization of plasminogen binding to human capillary and arterial endothelial cells.", Biochem Cell Biol. Jul. 1991;69(7):442-8.

Geohegan et al. "Fluorescence-based continuous assay for the aspartyl protease of human immunodeficiency virus-1" FEBS 262:119-122 (1990).

George et al., "Protein domain identification and improved sequence similarity searching using PSI-BLAST.", 2002, Proteins 48, 672-81.

Georgiou et al., "Display of heterologous proteins on the surface of microorganisms: from the screening of combinatorial libraries to live recombinant vaccines", Nat. Biotechnol., 15:29-34, 1997.

Gerstein, "Patterns of protein-fold usage in eight microbial genomes: a comprehensive structural census.", Proteins 33, 518 (1998).

Goffeau, A., et al. Life with 6000 genes. Science 274, 563-567 (1996).

Gonnet, G. H., Cohen, M. A., and Benner, S. A. Exhaustive matching of the entire protein sequence database. Science. 256, 1443-1445 (1992).

Guenthner and Hart, 1998, "Quantitative, competitive PCR assay for HIV-1 using a microplate-based detection system", Biotechniques, 24(5):810-6.

Guerra et al., 2000, Biosci. Rep. 20: 41.

Haab et al., Protein microarrays for highly paralle detection and quantitation of specific proteins and antibodies in complex solutions., Genome Biol. 2001;2(2) Epub Jan. 22, 2001.

Hanks, S. K. & Hunter, T. Protein Kinases 6. The eukaryotic Protein kinase superfamily: kinase (catalytic) domain structure and classification. FASEB J. 9, 576-596 (1995).

Hardie et al., "The Protein Kinase Facts Book I and II", Academic press, San Diego, CA 1995.

Harrison et al., 2002, "A question of size: the eukaryotic proteome and the problems in defining it.", Nucleic Acid Res 30, 1083-1090.

Hatch et al., "Rolling circle amplification of DNA immobilized on solid surfaces and its application to multiple mutation detection", Genet. Anal., 1999, 1592):35-40.

Hegner et al., "Ultralarge atomically flat template-stripped Au surfaces for scanning probe microscopy," Surface Science, 291:39-46 (1993).

Heyman, J. A., et al. Genome-scale cloning and expression of individual open reading frames using topoisomerase I-mediated ligation. Genome Res. 9, 383-392 (1999).

Higgins, D. G., Thompson, J. D., and Gibson, T. J. Usage CLUSTAL for muliple sequence alignments. Methods Enzymol. 266, 383-402 (1996).

Ho, U., Mason, S., Kobayashi, R., Heokstra, M., and Andrew, B. Role of the casein kinase I isoform, Hrr25, and the cell cycle-regulatory transcription factor, SBF, in the transcriptional response to DNA damage in *Saccharomyces cerevisiae*. Proc. Natl. Acad. Sci. 94, 581-586 (1997).

Holly et al. PAK-family kinases regulate cell and actin polarization throughout the cell cycle of *Saccharomyces cerevisiae*. J. Cell Biol. 147, 845-856 (1999).

Hook, "Ca(2+)/CaM-dependent kinases: from activation to function.", Annu. Rev. Pharmacol. Toxicol.41, 471 (2001).

Horak et al. "ChIP-chip: a genomic approach for identifying transcription factor binding sites." Methods Enzymol. 2002;350:469-83. No abstract available.

Huang RP. "Detection of multiple proteins in an antibody-based protein microarray system." J Immunol Methods. Sep. 1, 2001;255(1-2):1-13.

Hudson, J. R., et al. The complete set of predicted genes from *Saccharomyces cerevisiae* in a readily usable form. Genome Res. 7, 1169-1173 (1997).

Hunter, T., & Plowman, G. D. The protein kinases of budding yeast: six score and more. TIBS 22, 18-22 (1997).

Ito et al., "A comprehensive two-hybrid analysis to explore the yeast protein interactome." Proc Natl Acad Sci USA 98, 4569-74 (2001).

Ito et al., "Toward a protein-protein interaction map of the budding yeast: A comprehensive system to examine two-hybrid interactions in all possible combinations between the yeast proteins." Proc. Natl. Acad. Sci. USA. 97, 1143 (2000).

Jackman et al., "Using elastomeric membranes as dry resists for lift-off", Langmuir, 1999, 15:2973-2984.

Jaquenoud, M., Gulli, M. P., Peter, K., and Peter, M. The Cdc42p effector Gic2p is targeted for ubiquitin-dependent degradation by the SCFGrr1 complex. EMBO J. 17, 5360-5373 (1998).

Jona G, Snyder M., Recent developments in analytical and functional protein microARRAYs. Curr Opin Mol Ther. Jun. 2003;5(3):271-7. Review.

Jones et al. "Microminiaturized immunoassays using atomic force microscopy and compositionally patterned antigen arrays" Anal. Chem. 70(7):1223-1241 (1998).

Jonsson et al. "Immobilization of immunoglobulins on silica surfaces. Kinetics of immobilization and influence of ionic strength." Biochem J. Apr. 15, 1985;227(2):373-8.

Kane et al., "Patterning proteins and cells using soft lithography", Biomaterials, 1999, 20:2363-2376.

Kaouass, M., et al. The STK2 gene, which encodes a putative Ser/Thr protein kinase, is required for high-affinity spermidine transport in *Saccharomyces cerevisiae*. Mol. Cell Biol. 17, 2994-3004 (1997).

Kaplan et al. "Selection of multiple human immunodeficiency virus type 1 variants that encode viral proteases with decreased sensitivity to an inhibitor of the viral inhibitor" Proc. Natl. Acad. Sci. USA 91:5597-5601 (1994).

Kemeny "Enyme-linked immunoassays" In Immuno Chemistry 1 (eds Johnstone and Turner) p. 147-175 (Nov. 1997).

Kettleborough et al., "Isolation of tumor cell-specific single-chain Fv from immunized mice using phage-antibody libraries and the reconstruction of whole antibodies from these antibody fragments." Eur. J. Immunol. 24:952-8 (1994).

Knezevic et al., "Proteomic profiling of the cancer microenvironment by antibody arrays", 2001, Proteomics 1, 1271-8.

Kodadek T. "Protein microarrays: prospects and problems." Chem Biol. Feb. 2001;8(2):105-15.

Kovacs, Micromachined Transducers Sourcebook, The McGraw-Hill Companies Inc., 1998.

Kricka "Miniaturization of analytical systems" Clin. Chem. 44(9):2008-2014 (1998).

Kruse et al., "Detection and quantitative measurement of transforming growth factor-$\beta1$ (TGF-$\beta1$) gene expression using a semi-nested competitive PCR assay", Cytokine, 1999, 11(2):179-185.

Kumar et al. "An integrated approach for finding overlooked genes in yeast." Nat Biotechnol. Jan. 2002;20(1):58-63.

Lakey et al., "Measuring protein-protein interactions", Curr Opin Struct Biol. 8:119-23 (1998).

Lam et al., "The "one-bead-one compound" combinatorial library method", Chem. Rev., 1997, 97(2):4110448.

Lijnen et al., "Screening panels of monoclonal antibodies using phage-displayed antigen", Anal Biochem. Jun. 1, 1997;248(2):211-5.

Lipman, D. J. & Pearson, W. R. Rapid and sensitive protein similarity searches. Science. 277, 1435-1441 (1985).

Loeb et al. "Complete mutegenesis of the HIV-1 protease" Nature 340:397-400 (1989).

Look et al., J. Org. Chem., 1994, 49:7588-7590.

Louis et al. "Autoprocessing of the HIV-1 protease using purified wild-type and mutated fusion proteins expressed at high levels in *Escherichia coli*" Eur. J. Biochem. 199:361-369 (1991).

Lueking et al. "Protein microarrays for gene expression and antibodyscreening", Anal., Biochem., 1999, 270:103-111.

Luscombe et al. "ExpressYourself: A modular platform for processing and visualizing microarray data." Nucleic Acids Res. Jul. 1, 2003;31(13):3477-82.

MacBeath et al., "Printing proteins as microarrays for high-throughput function determination", Science, 2000, 289:1760-1762.

Madden, K., Sheu, Y.-J., Baetz, K., Andrews, B., and Snyder, M., "SBF cell cycle regulator as a target of the yeast PKC-MAP kinase pathway", Science 275, 1781-1784 (1997).

Madou, Fundamentals of Microfabrication, CRC Press, 1997.

Madoz-Gurpide et al. "Protein based microarrays: a tool for probing the proteome of cancer cells and tissues." Proteomics. Oct. 2001;1(10):1279-87.

Maier et al.., "Automated array technologies for gene expression profiling", Drug Discovery Today, 2(8), 315-324, (1997).

Malathi, K., Xiao, Y., and Mitchell, A. P. Catalytic roles of yeast GSK3beta/shaggy homolog Rim11p in meiotic activation. Genetics 153, 1145-1152 (1999).

Manning et al., "The protein kinase complement of the human genome.", 2002, Science 298:1912-1934.

Marks et al. "By-passing immunication-Human antibodies from V-gene libraries displayed on phage" J. Mol. Biol. 222:581-597 (1991).

Marshall et al., "DNA chips: an array of possibilities." Nat Biotechnol. Jan. 1998;16(1):27-31.

Martin, "Phosphoinisitide lipids as signaling molecules: Transduction, cytoskeletal Regulation, and membrane trafficking" Annu. Rev. Cell Dev. Biol. 14, 231 (2000).

Martzen et al., "A biochemical genomics approach for identifying genes by the activity of their products", Science, 1999, 286:1153-1155.

Maskos et al., "Oligonucleotide hybridizations on glass supports: a novel linker for oligonucleotide synthesis and hybridization properties of oligonucleotides synthesised in situ", Nucleic Acids Res. Apr. 11, 1992;20(7):1679-84.

Mateos et al., Systematic learning of gene functional classes from DNA array expression data by using multilayer perceptrons. Genome Res. Nov. 2002;12(11):1703-15.

Mathys, et al., "Characterization of a self-splicing mini-intein and its conversion into autocatalytic N- and C-terminal cleavage elements: facile production of protein building blocks for protein ligation.", Gene 231:1-13, 1999.

Memeny. Enzyme-linked immunoassays. In Immuno-Chemistry 1 (eds Johnstone and Turner). p. 147-175, Nov. 1997.

Menees, T. M., Ross-MacDonald, P. B., and Roeder, G. S. MEI4, a meiosis-specific yeast gene required for chromosome synapsis. Mol. Cell Biol. 12, 1340-1351 (1992).

Menendez, "Isolation of the *Pichia pastoris* PYC1 gene encoding pyruvate carboxylase and identification of a suppressor of the pyc phenotype.", Yeast 14, 647 (1998).

Metzger et al.,"Ion-spray mass spectrometry and high-performance liquid chromatography-mass spectrometry of synthesized peptide libraries", Agnew. Chem. Int. Ed. Engl., 1993, 32(6):894-896.

Michaud et al. "Proteomic approaches for the global analysis of proteins. Biotechniques." Dec. 2002;33(6):1308-16. Review.

Mitchell, D. A., Marshall, T. K., and Deschenes, R. J., "Vector for the inducible overexpression of glutathione S-transferase fusion protein in yeast", Yeast 9, 715-23 (1993).

Moody et al. "Array-based ELISAs for high-throughput analysis of human cytokines. Biotechniques." Jul. 2001;31(1):186-90, 192-4.

Moreau, Semiconductor Lithography: Principles, Practices and Materials, Plenum Press, 1998.

Moore et al. "Peptide substrates and indibitors of HIV-1 protease" Biochem. Biophys. Res. Com. 159:420-425 (1989).

Mylin et al. Regulated GAL4 expression cassette providing controllable and high-level output from high-copy galactose promoters in yeast. Methods Enzymol. 185, 297-308 (1990).

Nefzi et al., "The current status of heterocyclic combinatorial libraries", Chem. Rev., 1997, 97: 449-472.

Nock, "Reversible, site-specific immobilization of polyarginine-tagged fusio proteins on mice surfaces," FEBS, 414-233-238 (1997).

Odorizzi, et al. "Phosphoinositide signaling and the regulation of membrane trafficking in yeast.", TIBS 25, 229 (2000).

Ohlmeyer et al., "Complex synthetic chemical libraries indexed with molecular tags", Proc. Natl. Acad. Sci. USA, 1993; 90:10922-10926.

Owen, D. J., Noble, M. E., Garman, E. F., Papageorgiou, A. C., and Johnson, L. N. Two structures of the catalytic domain of phosphorylase kinase: an active protein kinase complexed with substrate analogue and product. Structure, 3, 467-474 (1995).

Pale-Grosdemange et al. "Formation of self-assembled monolayers by chemisorption of derivatives of oligo(ethylene glycol) of structure HS(CH2)11(OCH2CH2)mOH on gold" J. Am. Chem. Soc. 113(1)12-20 (1991).

Palladino et al., "Expression of a shared tumor-specific antigen by two chemically induced BALB/c sarcomas.", 1987, Cancer Res. 47:5074-9.

Pandey et al., "Proteomics to study genes and genomes", Nature, 2000, 405:837-846.

Pearson, W. R. & Lipman, D. J. Improved tools for biological sequence comparison. Proc. Natl. Acad. Sci. 85, 2444-2448 (1988).

Pease et al., "Light-generated oligonucleotide arrays for rapid DNA sequence analysis" Proc. Natl. Acad. Sci. USA, 1994, 91:5022-5026.

Peraldi et al., protein-tyrosine-phosphatase 2C is phosphorylated and inhibited by 44-kDa Mitogen-activated protein kinase, PNAS USA, 1994, 91(11):5002-5006.

Persic et al., "An integrated vector system for the eukaryotic expression of antibodies or their fragments after selection from phage display libraries", 1997, Gene 187:9-18.

Pham, et al. "Human Interleukin-2 Production in Insect (*Trichoplusia ni*) Larvae: Effects and Partial Control of Proteolysis", Biotechnology and Bioengineering vol. 62(2) pp. 175-182; Jan. 20, 1999.

Plowman et al. "The protein kinases of *Caenorhabditis elegans*: A model for signal transduction in multicellular organisms." Proc. Natl. Acad. Sci. 96, 13603-12610 (1999).

Prime et al., "Self-assembled organic monolayers: model systems for studying absorption of proteins at surfaces," Science, 252:1164-1167 (1991).

Ragg et al., FASEB, (9)73-80, Jan. 1995.

Ramsay G., "DNA chips: state-of-the-art.", Nat Biotechnol. Jan. 1998;16(1):40-4.

Richman, T. J., Sawyer, M. M., and Johnson, D. I. The Cdc42p GTPase is involved in a G2/M morphogenetic checkpoint regulating the apical-isotropic switch and nuclear division in yeast. J. Biol. Chem. 274, 16861-16870 (1999).

Roberts et al. "RNA-peptide fusions for the in vitro selection of peptides and proteins." Proc. Natl. Acad. Sci. USA, 94:12297-302, 1997.

Roberts et al. "Rationale design of peptide-based HIV proteinase inhibitors" Science 248:358-361 (1990).

Rogers et al. "Immobilzation og oligonucleotides onto a glass support via disulfide bonds: A method for preparation of DNA microarrays", Anal. Biochem., 1999, 266(1):23-30.

Roemer, T. K., et al. "Selection of axial growth sites in yeast requires Ax12p, a novel plasma membrane glycoprotein", Genes & Dev. 10, 777-793 (1996).

Ross-MacDonald et al. "Large-scale analysis of the yeast genome by transposon tagging and gene disruption", Nature, 1999, 402:413-418.

Rowe et al. "Array biosensor for simultaneous identification of bacterial, viral and protein analytes" Anal. Chem. 71(17):3846-3852 (1999).

Santos, T. & Hollingsworth, N. M. Red1p, a MEK1-dependent phosphoprotein that physically interacts with Hop1p during meiosis in yeast. J. Biol. Chem. 274, 17831O 1790 (1999).

Schuh et al., "Determination of monoclonal antibody specificity by immunoadsorption and western blotting.", J Immunol Methods, Jul. 31, 1992;152(1):59-67.

Schweitzer et al., "Multiplexed protein profiling on microarrays by rolling-circle amplification." 2002, Nat Biotechnol 20, 359-65.

Schweitzer, B. and S. F. Kingsmore, Measuring proteins on microarrays. Curr Opin Biotechnol, 2002. 13(1): p. 14-9.

Schweitzer et al., "Immunoassays with rolling circle DNA amplification: A versatile platform for ultra sensitive antigen detection" PNAS USA, 2000, 97:10113-10119.

Sigal et al. (1996). A self-assembled monolayer for the binding and study of histidine-tagged proteins by surface plasmon resonance. Anal. Chem. 68:490-497.

Silzel et al. "Mass-sensing, multianalyte microarray immunoassay with imaging detection" Clin. Chem. 44(9):2036-2043 (1998).

Sobel et al., "A highly divergent gamma-tubulin gene is essential for cell growth and proper microtubule organization in *Saccharomyces cerevisiae*." J. Cell Biol. 131, 1775-1788 (1995).

Stern et al., "Spk1, a new kinase from *Saccharomyces cervevisiae*, phodphorylates proteins on serine, threonine and tyrosine" Molecular and cellular Biology, 1991, 11(2):987-1001.

Stevenson et al., Biomarkers, (2)63-65, 1997.

Stevanovic et al., "Natural and synthetic peptide pools: Characterization by sequencing and electrospray mass spectrometry", Bioorg. Med. Chem. Lett., 1991, 3:431-436.

Stimpson et al., "Real-time detection of DNA hybridization and melting on oligonucleotide arrays using optical wave guides", PNAS USA, 1995, 92(14):6379-6383.

Sundberg et al., "Spatially-addressable immobilization of macromolecules on solid supports," J. Am. Chem. Soc., 117:12050-12057 (1995).

Uetz et al., "A comprehensive analysis of protein-protein interactions in *Saccharaomyces cerevisiae*" Nature, 2000, 403:623-627.

Wagner et al., "Covalent immobilization of native biomolecules onto Au(111) via N-hydroxysuccinimide ester functionalized self-assembled monolayers for scanning probe microscopy," Biophysical Journal, 70:2052-2066 (1996).

Wagner et al., "Formation and in Situ modification of monolayers chemisorbed on ultraflat template-stripped gold surfaces," Langmuir, 11(10):3867-3875 (1995).

Wagner et al., Journal of Structural Biology, 1997, 119:189-201.

Weiner et al. "Site-directed mutagenesis of double-stranded DNA by the polymerase chain reaction" Gene 151:119-123 (1994).

Weinert, T. A. & Hartwell, L. H. Cell Cycle arrest of cdc mutants and specificity of the RAD9 checkpoint. Genetics 134, 63-80 (1993).

Wera, J. C. T. Bergsma, "Phosphoinositides in yeast: genetically tractable signalling." FEMS Yeast Res. Apr. 2001;1(1):9-13.

Winzler et al.,"Functional characterization of the *S. cerevisiae* genome by gene dletion and parallel analysis", Science, 1999, 285:901-906.

Woo et al., Methods in Enzy,mology, vol. 68, 389-395, 1979.

Wu et al. "Structural basis for a specificity of retroviral proteases" Biochemistry 37:4518-4526 (1998).

Wurgler-Murphy et al., "Regulation of the *Saccharomyces cerevisiae* HOG1 mitogen-activated protein kinase by the PTP2 and PTP3 protein tyrosine phosphatases." Mol. Cell Biol. 17, 1289-1297 (1997).

Xia et al., "Complex optical surfaces formed by replica molding against elastomeric masters", Science, 1996, 273:347-349.

Xia, Y. & Whitesides, G. M. Angew. Chem. Int. Ed. 37, 550-(1997).

Youngquist et al., "Matrix-assited laser desorption ionization for rapid determination of the sequences of biological active peptides isolated from support-bound combinatorial peptide libraries", Rapid Commun. Mass Spect., 1994, 8:77-81.

Zhang et al., "Protein tyrosine phosphatases: mechanism of catalysis and substrate specificity" Adv Enzymol Relat Areas Mol Biol. 1994;68:1-36. Review.

Zhu et al. "Global analysis of protein activities using proteome chips." Science. Sep. 14, 2001;293(5537):2101-5. Epub Jul. 26, 2001.

Zhu et al. ,"Protein arrays and microarrays", Curr Opin Chem Biol. 2001, 5(1):40-45 Review.

Zhu et al. ,"Analysis of yeast protein kinases using protein chips", Nat. Genet., 2000, 26(3):283-289.

Zhu et al. "Protein chip technology." Curr Opin Chem Biol. Feb. 2003;7(1):55-63. Review.

Zhu et al. "Proteomics." Annu Rev Biochem. 2003;72:783-812. Review.

Ziauddin, J. and D. M. Sabatini, Microarrays of cells expressing defined cDNAs. Nature, 2001. 411(6833): p. 107-10.

Ziegler et al., Cucumber mosaic cucumovirus antibodies from a synthetic phage display library. Virology. Dec. 1, 1995;214(1):235-8.

\* cited by examiner with Substrate Coating | without Substrate Coating

METHODS FOR CONDUCTING ASSAYS FOR ENZYME ACTIVITY ON PROTEIN MICROARRAYS

STATEMENT OF GOVERNMENT INTEREST

The present invention was developed with U.S. government funding from the Department of Health and Human Services, Grant No. 1R41GM64067. The government has certain rights in the invention.

RELATED APPLICATION

This application claims the benefit of U.S. application Ser. No. 10/458,720, filed Jun. 9, 2003, the entire disclosure of which is incorporated by reference herein in its entirety.

1. FIELD OF THE INVENTION

The present invention relates to methods of conducting assays for enzymatic activity on microarrays useful for the large-scale study of protein function, screening assays, and high-throughput analysis of enzymatic reactions. The invention relates to methods of using protein chips to assay the presence, amount, activity and/or function of enzymes present in a protein sample on a protein chip. In particular, the methods of the invention relate to conducting enzymatic assays using a microarray wherein a protein and a substance are immobilized on the surface of a solid support and wherein the protein and the substance are in proximity to each other sufficient for the occurrence of an enzymatic reaction between the substance and the protein. The invention also relates to microarrays that have an enzyme and a substrate immobilized on their surface wherein the enzyme and the substrate are in proximity to each other sufficient for the occurrence of an enzymatic reaction between the enzyme and the substrate.

2. BACKGROUND OF THE INVENTION

A daunting task in the post-genome sequencing era is to understand the functions, modifications, and regulation of every protein encoded by a genome (Fields et al., 1999, Proc Natl Acad. Sci. 96:8825; Goffeau et al., 1996, Science 274: 563). Currently, much effort is devoted toward studying gene, and hence protein, function by analyzing mRNA expression profiles, gene disruption phenotypes, two-hybrid interactions, and protein subcellular localization (Ross-Macdonald et al., 1999, Nature 402:413; DeRisi et al., 1997, Science 278:680; Winzeler et al., 1999, Science 285:901; Uetz et al., 2000, Nature 403:623; Ito et al., 2000, Proc. Natl. Acad. Sci. U.S.A. 97:1143). Important advances in this effort have been possible, in part, by the ability to analyze thousands of gene sequences in a single experiment using gene chip technology. Although these studies are useful, transcriptional profiles do not necessarily correlate well with cellular protein levels or protein activities. Thus, the analysis of biochemical activities can provide information about protein function that complements genomic analyses to provide a more complete picture of the workings of a cell (Zhu et al., 2001, Curr. Opin. Chem. Biol. 5:40; Martzen, et al., 1999, Science 286:1153; Zhu et al., 2000, Nat. Genet. 26:283; MacBeath, 2000, Science 289: 1760; Caveman, 2000, J. Cell Sci. 113:3543).

Currently, biochemical analyses of protein function are performed by individual investigators studying a single protein at a time. This is a very time-consuming process since it can take years to purify and identify a protein based on its biochemical activity. The availability of an entire genome sequence makes it possible to perform biochemical assays on every protein encoded by the genome. Based on sequence comparison, genes encoding for proteins with a particular enzymatic activity can be identified. However, a detailed analysis of an individual proteins' biochemical properties, such as, substrate specificity, kinetic profile and sensitivities to inhibitors, is a time-consuming process. Thus, high-throughput ways of analyzing the biochemical activities of proteins are required.

It would be useful to analyze hundreds or thousands of protein samples using a single protein chip. Such approaches lend themselves well to high throughput experiments in which large amounts of data can be generated and analyzed. Microtiter plates containing 96 or 384 wells have been known in the field for many years. However, the size (at least 12.8 cm×8.6 cm) of these plates makes them unsuitable for the large-scale analysis of proteins.

Recently devised methods for expressing large numbers of proteins with potential utility for biochemical genomics in the budding yeast *Saccharomyces cerevisiae* have been developed. ORFs have been cloned into an expression vector that uses the GAL promoter and fuses the protein to a polyhistidine (e.g., His×6) label. This method has thus far been used to prepare and confirm expression of about 2000 yeast protein fusions (Heyman et al., 1999, "Genome-scale cloning and expression of individual open reading frames using topoisomerase I-mediated ligation," Genome Res. 9:383-392). Using a recombination strategy, about 85% of the yeast ORFs have been cloned in frame with a GST coding region in a vector that contains the CUP1 promoter (inducible by copper), thus producing GST fusion proteins (Martzen et al., 1999, "A biochemical genomics approach for identifying genes by the activity of their products," Science 286:1153-1155). Martzen et al. used a pooling strategy to screen the collection of fusion proteins for several biochemical activities (e.g., phosphodiesterase and Appr-1-P-processing activities) and identified the relevant genes encoding these activities.

Several groups have recently described microarray formats for the screening of protein activities (Zhu et al., 2000, Nat. Genet. 26:283; MacBeath et al., 2000, Science 289:1763; Arenkov et al, 2000, Anal. Biochem 278:123). In addition, a collection of overexpression clones of yeast proteins have been prepared and screened for biochemical activities (Martzen et al., 1999, Science 286: 1153).

Photolithographic techniques have been applied to making a variety of arrays, from oligonucleotide arrays on flat surfaces (Pease et al., 1994, "Light-generated oligonucleotide arrays for rapid DNA sequence analysis," PNAS 91:5022-5026) to arrays of channels (U.S. Pat. No. 5,843,767) to arrays of wells connected by channels (Cohen et al., 1999, "A microchip-based enzyme assay for protein kinase A," Anal Biochem. 273:89-97). Furthermore, microfabrication and microlithography techniques are well known in the semiconductor fabrication area. See, e.g., Moreau, Semiconductor Lithography: Principals, Practices and Materials, Plenum Press, 1988.

Screening a large number of proteins or even an entire proteome would entail the systematic probing of biochemical activities of proteins that are produced in a high throughput fashion, and analyzing the functions of hundreds or thousands of proteins samples in parallel (Zhu et al., 2000, Nat. Genet. 26:283; MacBeath et al., 2000, Science 289:1763; Arenkov et al, 2000, Anal. Biochem 278:123; International Patent Application publication WO 01/83827 and WO 02/092118). In vitro assays have previously been conducted using random expression libraries or pooling strategies, both of which have shortcomings (Martzen et al., 1999, Science 286:1153; Bussow et al., 2000, Genomics 65:1). Specifically, random expression libraries are tedious to screen, and contain clones that are often not full-length. Another recent approach has been to generate defined arrays and screen the array using a pooling strategy (Martzen et al. 1999, Science 286:1153). The pooling strategy obscures the actual number of proteins screened, however, and the strategy is cumbersome when large numbers of positives are identified.

Therefore, there remains a need in the art for the large-scale analysis of biochemical functions which would allow assessing the activities, in a high-throughput manner, of a large number of proteins.

Citation or identification of any reference in this application shall not be considered as admission that such reference is available as prior art to the present invention.

3. SUMMARY OF THE INVENTION

The present invention provides protein chips and methods useful for the study of protein activities in a high-throughput manner. The present invention also provides methods for identifying substrates of enzymes and modulators of enzymatic activities. The invention is directed to methods of using protein chips to assay the presence, amount, functionality, activity and sensitivity to modulators of enzymes. In particular, the invention is directed to methods of conducting assays for enzymatic activity on protein microarrays. In certain embodiments, a method of the invention for assaying an enzymatic reaction comprises the following steps: (a) incubating at least one protein and at least one substance under conditions conducive to the occurrence of an enzymatic reaction between the protein and the substance, wherein (i) the protein and the substance are immobilized on the surface of a solid support; (ii) the protein and the substance are in proximity sufficient for the occurrence of said enzymatic reaction; and (iii) the protein and the substance are not identical; and (b) determining whether said enzymatic reaction occurs.

Typically, in the methods of the present invention, a substance (e.g., a substrate of an enzymatic reaction) and a protein (e.g., an enzyme) are immobilized on the surface of a solid support before the protein and the substance are incubated under conditions conducive to the occurrence of an enzymatic reaction between the protein and the substance. Furthermore, the protein and the substance remain immobilized during at least a portion of the incubation step on the surface of the solid support at the location at which they were immobilized before the incubation step, for at least a time sufficient for the enzymatic reaction between the substance and the protein to take place. Accordingly, an incubating step (a) of a method of the invention can be performed with one aliquot of incubation buffer covering the entire surface of a solid support containing multiple different immobilized proteins and multiple different immobilized substances. Alternatively, an incubation step (a) of a method of the invention can be performed with one aliquot of incubation buffer covering the entire surface of a region of a solid support, wherein the region includes multiple different immobilized proteins and/or multiple different immobilized substances. In certain embodiments of the methods of the present invention, a substance (e.g., a substrate of an enzymatic reaction) and a protein (e.g., an enzyme) are immobilized on the surface of a solid support in a manner such that they remain immobilized throughout the incubation step, at the same location at which they were immobilized on the solid support before the incubation step, and optionally can remain immobilized during the determining step as well at the location.

The methods of the invention can be used to determine whether a protein catalyzes an enzymatic reaction of interest. In this embodiment, the substance is a known substrate of the enzymatic reaction to be tested, and substrate and protein are incubated in a reaction mixture that provides conditions conducive to the occurrence of the enzymatic reaction and that provides any cofactors required by the enzymatic reaction.

The methods of the invention can be used to determine whether a substance is a substrate of an enzymatic reaction of interest. In this embodiment, the protein is an enzyme known to catalyze the reaction of interest and substrate and protein are incubated in a reaction mixture that provides conditions conducive to the occurrence of the enzymatic reaction and that provides any cofactors required by the enzymatic reaction.

The protein, the substance, or the protein and the substance to be used with the methods of the invention can be purified. The substance can be a known substrate for the type of enzymatic activity assayed in the enzymatic reaction of a method of the invention, and the determining step of a method of the invention determines whether said protein is an enzyme having said type of enzymatic activity. The protein can be an enzyme known to have the type of enzymatic activity assayed in said enzymatic reaction, and said determining step determines whether said substrate is a substrate for said type of enzymatic activity. If the substance is a known substrate for the type of enzymatic activity assayed in said enzymatic reaction, the protein can comprise a region that is homologous to the catalytic domain of an enzyme that is known to have the type of enzymatic activity assayed in said enzymatic reaction. In certain embodiments, the enzyme is an oxidoreductase, a transferase, a hydrolase, a lyase, an isomerase, or a ligase. In a more specific embodiment, the enzyme is a kinase.

In certain embodiments, the substance is a known substrate for the type of enzymatic activity assayed in the enzymatic reaction of a method of the invention; and the protein is known to catalyze the type of enzymatic activity assayed in said enzymatic reaction. In these embodiments, substrate and enzyme can be incubated under conditions conducive to the occurrence the enzymatic reaction in the presence of one or more test molecules so as to determine whether said test molecules modulate said enzymatic reaction; and said determining step comprises detecting whether a change in the amount of said enzymatic reaction occurs relative to the amount of said enzymatic reaction in the absence of the test molecules. The determining step can comprise detecting a decrease in the amount of said enzymatic reaction relative to the amount of said enzymatic reaction in the absence of the test molecules, thereby identifying the test molecules as an inhibitor of said enzymatic reaction. In other embodiments, said determining step can comprise detecting an increase in the amount of said enzymatic reaction relative to the amount of said enzymatic reaction in the absence of the test molecules, thereby identifying the test molecules as an activator of said enzymatic reaction. In certain embodiments, the substance is known to be a substrate of the enzyme.

In certain embodiments, said at least one protein of a method of the invention is one of a plurality of different proteins organized on the surface of the solid support in a positionally addressable array. The plurality of different proteins can consist of between 2 different proteins and 100 different proteins. The plurality of different proteins can consist of between 100 different proteins and 1,000 different proteins. The plurality of different proteins can consist of between 1,000 different proteins and 10,000 different proteins. The substance can be coated onto the surface of the solid support. In certain, more specific embodiments, each protein of the plurality of proteins is in proximity with the substance sufficient for the occurrence of an enzymatic reaction between the protein and the substance, and said determining step comprises determining for at least a portion of said plurality of proteins whether said enzymatic reaction occurs.

In certain embodiments, said at least one substance of a method of the invention is one of a plurality of different substances organized on the surface of the solid support in a positionally addressable array. The protein can be coated onto the surface of the solid support. In certain, more specific embodiments, each substance of the plurality of different substances is in proximity with the protein sufficient for the occurrence of an enzymatic reaction between the protein and the substance, and said determining step comprises determining for at least a portion of said plurality of different substances whether said enzymatic reaction occurs. The plurality of different substances can consist of between 2 different substances and 100 different substances. The plurality of different substances can consist of between 100 different substances and 1,000 different substances. The plurality of different substances can consist of between 1,000 different substances and 10,000 different substances.

In certain embodiments, a first plurality of different substances is organized on the surface of the solid support in a positionally addressable array, and a second plurality of different proteins is organized on the surface of the solid support in a positionally addressable array. Said first plurality can consists of between 2 different substances and 100 different substances, and said second plurality can consist of between 2 different proteins and 100 different proteins. In other embodiments, the first plurality consists of between 100 different substances and 1,000 different substances, and said second plurality consists of between 100 different proteins and 1,000 different proteins. In even other embodiments, said first plurality consists of between 1,000 different substances and 10,000 different substances, and said second plurality consists of between 100 different proteins and 10,000 different proteins. In certain embodiments, copies of said first plurality are present 1 time, 2 times, 3, 4, 5, 6, 7, 8, 9, 10, 16, 24, at least 30, at least 50, or at least 100 times on the surface of the solid support. In certain embodiments, copies of said second plurality are present 1 time, 2 times, 3, 4, 5, 6, 7, 8, 9, 10, 16, 24, at least 30, at least 50, or at least 100 times on the surface of the solid support.

In certain embodiments, the substance, the protein, or the substance and the protein, are covalently bound to the surface of the solid support. In other embodiments, the substance, the protein, or the substance and the protein, are non-covalently immobilized to the surface of the solid support. In even other embodiments, the substance, the protein, or the substrate and the protein, are immobilized to the surface of the solid support via a linker.

In certain embodiments, a method of the invention also comprises quantifying the enzymatic reaction. In certain embodiments, the determining step of a method of the invention further comprises measuring a change in a detectable signal resulting from said enzymatic reaction.

In certain embodiments, the solid support has at least one well and wherein the well comprises one or more different proteins immobilized on the surface of the solid support within the well. In certain embodiments, the solid support has at least two wells and wherein each well comprises the same one or more different proteins immobilized on the surface of the solid support within the well.

In certain embodiments, the solid support has at least one well and wherein each well comprises one or more different substances immobilized on the surface of the solid support within the well. The solid support can have at least two wells and wherein each well comprises the same set of one or more different substances immobilized on the surface of the solid support within the well.

The invention provides, a positionally addressable array comprising at least one known enzyme and at least one candidate substrate of the enzyme, wherein (i) the enzyme and the substrate are immobilized on the surface of a solid support; (ii) the enzyme and the substrate are in proximity sufficient for the occurrence of the enzymatic reaction catalyzed by the enzyme between the enzyme and the substrate; and (iii) the enzyme and the substrate are not identical to each other.

The invention also provides a positionally addressable array comprising at least one known substrate of an enzymatic reaction and at least one candidate enzyme for the catalysis of the enzymatic reaction, wherein (i) the enzyme and the substrate are immobilized on the surface of a solid support; (ii) the enzyme and the substrate are in proximity sufficient for the occurrence of the enzymatic reaction between the enzyme and the substrate; and (iii) the enzyme and the substrate are not identical to each other.

The invention further provides a positionally addressable array comprising at least one known substrate of an enzymatic reaction and at least one enzyme that is known to catalyze the enzymatic reaction, wherein (i) the enzyme and the substrate are immobilized on the surface of a solid support; (ii) the enzyme and the substrate are in proximity sufficient for the occurrence of the enzymatic reaction between the enzyme and the substrate; and (iii) the enzyme and the substrate are not identical to each other.

In certain embodiments, a positionally addressable array of the invention further comprises a reaction mixture, said reaction mixture being (i) in contact with the enzyme and the substrate, and (ii) conducive to the occurrence of the enzymatic reaction.

In certain embodiments, the enzyme, the substrate, or the enzyme and the substrate of a positionally addressable array of the invention are purified. In certain embodiments, the surface of the solid support of a positionally addressable array of the invention is coated with the enzyme or with the substrate.

In certain embodiments, the coating of an array with substance or with protein covers the entire array. In other embodiments, the coating of an array with substance or with protein covers a part of the array. In certain embodiments, the area covered by the coating is larger than the area covered by a protein or substrate that is printed on the surface of the array.

In certain embodiments, a substrate on a positionally addressable array of the invention is one of a plurality of different substrates. In certain embodiments, each different substrate is in proximity with an enzyme sufficient for the occurrence of the enzymatic reaction between the substrate and the enzyme.

In certain embodiments, an enzyme on a positionally addressable array of the invention is one of a plurality of different enzymes. In certain embodiments, each different enzyme is in proximity with a substrate sufficient for the occurrence of the enzymatic reaction between the substrate and the enzyme.

In certain embodiments, an enzyme on a positionally addressable array of the invention is one of a plurality of different enzymes and a substrate on a positionally addressable array of the invention is one of a plurality of different substrates.

The invention also provides a positionally addressable array comprising at least one known enzyme immobilized on the surface of a solid support, wherein the surface is modified to allow for the immobilization of a candidate substrate of the enzymatic reaction catalyzed by said enzyme in proximity with the enzyme sufficient for the occurrence of the enzymatic reaction between the enzyme and the substrate.

The invention further provides a positionally addressable array comprising at least one substrate of an enzymatic reaction immobilized on the surface of a solid support, wherein the surface is modified to allow for the immobilization of a candidate enzyme capable of catalyzing said enzymatic reaction, wherein the enzyme is immobilized in proximity with the substrate sufficient for the occurrence of the enzymatic reaction between the enzyme and the substrate.

The invention also provides a kit comprising the positionally addressable array of the invention, and a container comprising a reaction mixture conducive to the occurrence of the enzymatic reaction.

In certain embodiments, the present invention is directed to protein chips, which are positionally addressable arrays comprising a plurality of proteins, with each protein being immobilized at a different position on a solid support and wherein at least one substrate of an enzymatic reaction is also immobilized to the solid support such that a protein and a substrate are in proximity sufficient for the occurrence of the enzymatic reaction between the protein and the substrate. In certain specific embodiments, the plurality of proteins represents a substantial proportion of all proteins expressed in a single species, wherein translation products of one open reading frame are considered a single protein.

In certain embodiments, a protein microarray of the invention further comprises a liquid phase (e.g., a glycerol-containing solution) that covers the immobilized protein(s) and the immobilized substance(s).

In certain embodiments, the present invention provides a positionally addressable array comprising a plurality of proteins, with each protein being immobilized at a different position on a solid support, wherein the plurality of proteins comprises at least 1%, 2%, 3%, 4%, 5%, 10%, 20%, 30%, 40%, 50%, 60%, 70%, 80%, 90%, 95%, or 99% of all proteins expressed in a single species and wherein at least one substrate of an enzymatic reaction is also immobilized to the solid support such that a protein and a substrate are in proximity sufficient for the occurrence of the enzymatic reaction between the protein and the substrate. In a specific embodiment, protein isoforms and splice variants are counted as a single protein.

In another embodiment, the present invention provides a positionally addressable array comprising a plurality of proteins, with each protein being immobilized at a different position on a solid support, wherein the plurality of proteins comprises at least 1, 2, 3, 4, 5, 10, 20, 30, 40, 50, 100, 200, 500, 1000, 1500, 2000, 2500, 3000, 4000, 5000, 6000, 7000, 8000, 9000, 10,000, 100,000, 500,000 or 1,000,000 protein(s) and wherein at least one substrates of an enzymatic reaction is also immobilized to the solid support such that a protein and a substrate are in proximity sufficient for the occurrence of the enzymatic reaction between the protein and the substrate.

In another embodiment, the invention provides a positionally addressable array comprising a plurality of proteins, with each protein being immobilized at a different position on a solid support, wherein the plurality of proteins in aggregate comprise proteins encoded by at least 1000 different known genes of a single species and wherein at least one substrate of an enzymatic reaction is also immobilized to the solid support such that a protein and a substrate are in proximity sufficient for the occurrence of the enzymatic reaction between the protein and the substrate.

In a further embodiment, the proteins are organized on the array according to a classification of proteins. The classification can be by abundance, function, functional class, enzymatic activity, homology, protein family, association with a particular metabolic or signal transduction pathway, association with a related metabolic or signal transduction pathway, or posttranslational modification. In a specific embodiment, the invention provides a positionally addressable array comprising a plurality of proteins with a specific enzymatic activity wherein at least one substrate of the enzymatic reaction that is catalyzed by the enzymatic activity of the proteins on the array is also immobilized on the solid support and wherein a protein and a substrate are in proximity sufficient for the occurrence of the enzymatic reaction between the protein and the substrate.

In certain embodiments, the invention provides a positionally addressable array of proteins on a solid support wherein at least one substrate of an enzymatic reaction is immobilized on the solid support, wherein the solid support comprises glass, ceramics, nitrocellulose, amorphous silicon carbide, castable oxides, polyimides, polymethylmethacrylates, polystyrenes, gold or silicone elastomers.

In one embodiment, the surface of the solid support is a flat surface, such as, but not limited to, glass slides. Dense protein arrays can be produced on, for example, glass slides, such that chemical reactions and assays can be conducted, thus allowing large-scale parallel analysis of the presence, amount, and/or functionality of proteins. In a specific embodiment, the flat surface array has proteins bound to its surface via a 3-glycidooxypropyltrimethoxysilane (GPTS) linker.

In certain embodiments, the invention relates to microarrays and methods of using the microarrays for enzymatic assays, wherein an enzyme is immobilized to the surface of a solid support and wherein a plurality of different substrates is also immobilized to the surface of the solid support such that enzyme and substrates are in physical contact. Each individual substrate of the plurality of substrates is immobilized at a different position of the surface of the solid support.

In certain embodiments, the amount of enzyme needed in an enzymatic reaction performed using the methods of the present invention to obtain a detectable signal is at least 10-fold, at least 100-fold, at least 1000-fold or at least 10,000-fold lower compared to performing the assay wherein only the enzyme or only the substrate is immobilized.

In certain embodiments, a positionally addressable array of the invention comprises at least one known enzyme and at least one candidate substrate of the enzyme, wherein (i) the enzyme and the substrate are immobilized on the surface of a solid support; (ii) the enzyme and the substrate are in proximity sufficient for the occurrence of the enzymatic reaction catalyzed by the enzyme between the enzyme and the substrate; and (iii) the enzyme and the substrate are not identical to each other.

In certain embodiments, a positionally addressable array of the invention comprises at least one known substrate of an enzymatic reaction and at least one candidate enzyme for the catalysis of the enzymatic reaction, wherein (i) the enzyme and the substrate are immobilized on the surface of a solid support; (ii) the enzyme and the substrate are in proximity sufficient for the occurrence of the enzymatic reaction between the enzyme and the substrate; and (iii) the enzyme and the substrate are not identical to each other.

In certain embodiments, a positionally addressable array of the invention comprises at least one known substrate of an enzymatic reaction and at least one enzyme that is known to catalyze the enzymatic reaction, wherein (i) the enzyme and the substrate are immobilized on the surface of a solid support; (ii) the enzyme and the substrate are in proximity sufficient for the occurrence of the enzymatic reaction between the enzyme and the substrate; and (iii) the enzyme and the substrate are not identical to each other.

In certain embodiments, a positionally addressable array of the invention further comprises a reaction mixture, said reaction mixture being (i) in contact with the enzyme and the substrate, and (ii) conducive to the occurrence of the enzymatic reaction. In certain embodiments, in a positionally addressable array of the invention the enzyme, the substrate, or the enzyme and the substrate, are purified. In certain embodiments, in a positionally addressable array of the invention the surface of the solid support is coated with the enzyme or with the substrate. In certain embodiments, in a positionally addressable array of the invention the substrate is one of a plurality of different substrates. In certain embodiments, in a positionally addressable array of the invention each different substrate is in proximity with an enzyme sufficient for the occurrence of the enzymatic reaction between the substrate and the enzyme. In certain embodiments, in a positionally addressable array of the invention said enzyme is one of a plurality of different enzymes. In certain embodiments, in a positionally addressable array of the invention each different enzyme is in proximity with a substrate sufficient for the occurrence of the enzymatic reaction between the substrate and the enzyme. In certain embodiments, in a positionally addressable array of the invention the enzyme is one of a plurality of different enzymes and said substrate is one of a plurality of different substrates.

In certain embodiments, a positionally addressable array of the invention comprises at least one known enzyme immobilized on the surface of a solid support, wherein the surface is modified to allow for the immobilization of a candidate substrate of the enzymatic reaction catalyzed by said enzyme in proximity with the enzyme sufficient for the occurrence of the enzymatic reaction between the enzyme and the substrate.

In certain embodiments, the invention provides a positionally addressable array comprising at least one substrate of an enzymatic reaction immobilized on the surface of a solid support, wherein the surface is modified to allow for the immobilization of a candidate enzyme capable of catalyzing said enzymatic reaction in proximity with the substrate sufficient for the occurrence of the enzymatic reaction between the enzyme and the substrate.

In certain embodiments, the invention provides a kit comprising a positionally addressable array of the invention and a container enclosing the addressable array. In certain embodiments, the kit includes an instruction manual for performing a method provided herein and/or a container comprising a reaction mixture conducive to the occurrence of the enzymatic reaction.

In another embodiment, provided herein is a microarray produced by immobilizing a protein and a substance on a solid support. For example, the microarray can be produced by immobilizing one or more enzymes, or candidate enzymes, and one or more substrates or candidate substrates, on the solid support, such as a glass slide. The microarray can be produced, for example, by coating or printing the enzyme(s) or candidate enzyme(s) on the solid support and coating or printing the substrate(s) or candidate substrate(s) on the solid support, as discussed in further detail herein. In certain embodiments, the microarray has not been exposed to conditions conducive to the occurrence of an enzymatic reaction between the protein and the substance. A candidate protein is a protein being analyzed for enzymatic activity. A candidate substrate is a substrate being analyzed for its ability to act as a substrate for the enzymatic activity.

4. DEFINITIONS AND ABBREVIATIONS

As used in this application, "protein" refers to a peptide or polypeptide. Proteins can be prepared from recombinant overexpression in an organism, preferably bacteria, yeast, insect cells or mammalian cells, or produced via fragmentation of larger proteins, or chemically synthesized.

As used in this application, "enzyme" refers to any protein with a catalytic activity.

As used in this application, "functional domain" is a domain of a protein which is necessary and sufficient to give a desired functional activity. Examples of functional domains include, inter alia, domains which exhibit an enzymatic activity such as oxidoreductase, transferase, hydrolase, lyase, isomerase, or ligase activity. In more specific embodiments, a functional domain exhibits kinase, protease, phosphatase, glycosidase, or acetylase activity. Other examples of functional domains include those domains which exhibit binding activity towards DNA, RNA, protein, hormone, ligand or antigen.

Each protein or substrate of an enzymatic reaction on a chip is preferably located at a known, predetermined position on the solid support such that the identity of each protein or probe can be determined from its position on the solid support. Further, the proteins and probes form a positionally addressable array on a solid support.

As used herein, the term "purified" refers to a molecule, a substance or a protein that is substantially free of different molecules of the same type, substances of the same type, or proteins, respectively, that are associated with it in its original state (from which it is purified). Preferably, a molecule is at least 50%, 60%, 70%, 80%, 90%, 95%, 98%, 99%, 99.5%, 99.8%, 99.9%, 99.98%, 99,998%, 99,9998%, 99,99998% or at least 99,999998% free of such different molecules, wherein, if the molecule is in solution, the solvent is not a different molecule. Preferably, a substance is at least 50%, 60%, 70%, 80%, 90%, 95%, 98%, 99%, 99.5%, 99.8%, 99.9%, 99.98%, 99,998%, 99,9998%, 99,99998% or at least 99,999998% free of such different substances. Preferably, a protein is at least 50%, 60%, 70%, 80%, 90%, 95%, 98%, 99%, 99.5%, 99.8%, 99.9%, 99.98%, 99,998%, 99,9998%, 99,99998% or at least 99,999998% free of such different proteins.

Abbreviations

| Abbreviation | |
|---|---|
| RIE | Reactive Ion Etching |
| GST | glutathione-S-transferase |
| GPTS | 3-glycidooxypropyltrimethoxysilane |
| ORF | Open reading frame |
| FRET | Fluorescence Resonance Energy Transfer |

4.1. BRIEF DESCRIPTION OF THE DRAWINGS

FIG. 1. Autoradiographs of kinase reactions on two different microarrays. The top microarray was coated with substrate and the bottom array was without substrate coating.

Figure 2:
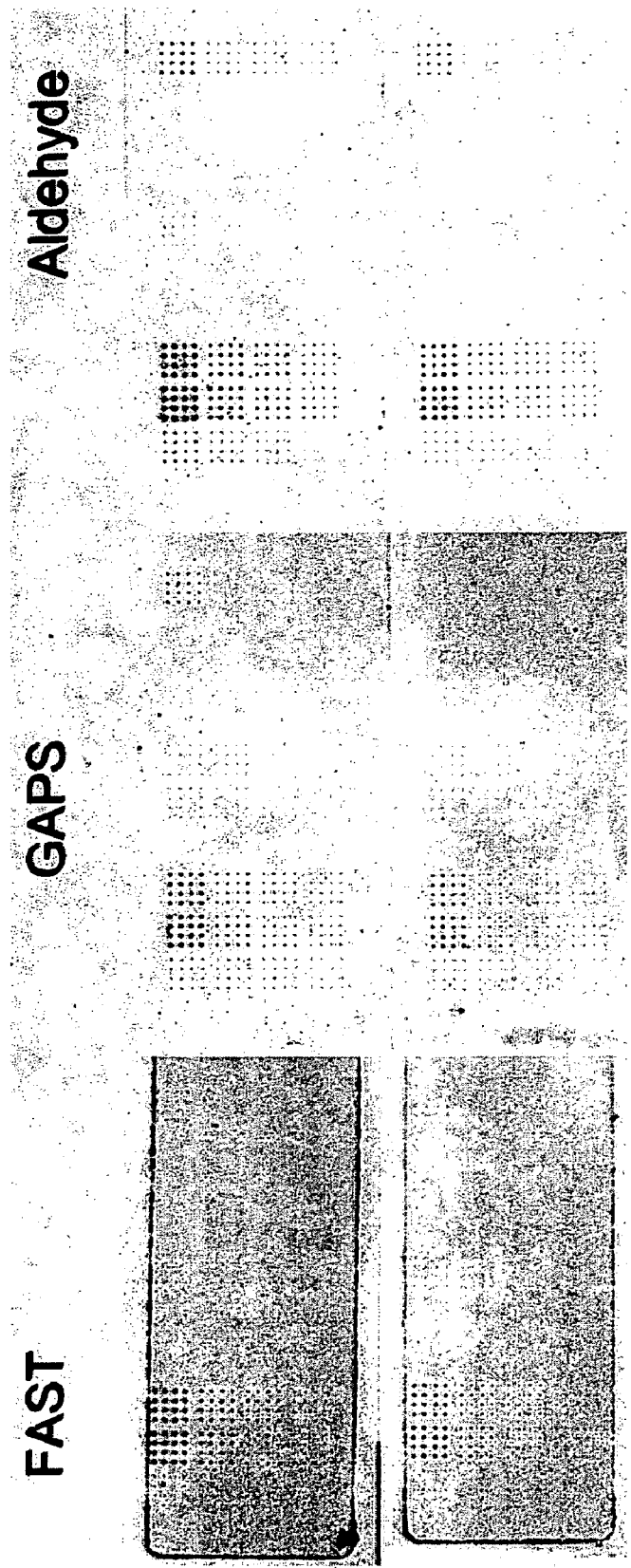

FIG. 2. Autoradiographs of kinase reactions on different microarrays demonstrating the superior signal-to-noise ratio if the slides are treated with an aldehyde. The aldehyde-treated slides were obtained from TeleChem International, Inc. The slide shown as FAST is a nitrocellulose coated slide (Schleicher & Schuell). The slide shown as GAPS is coated with an amino-silane surface (Corning®).

Figure 3:
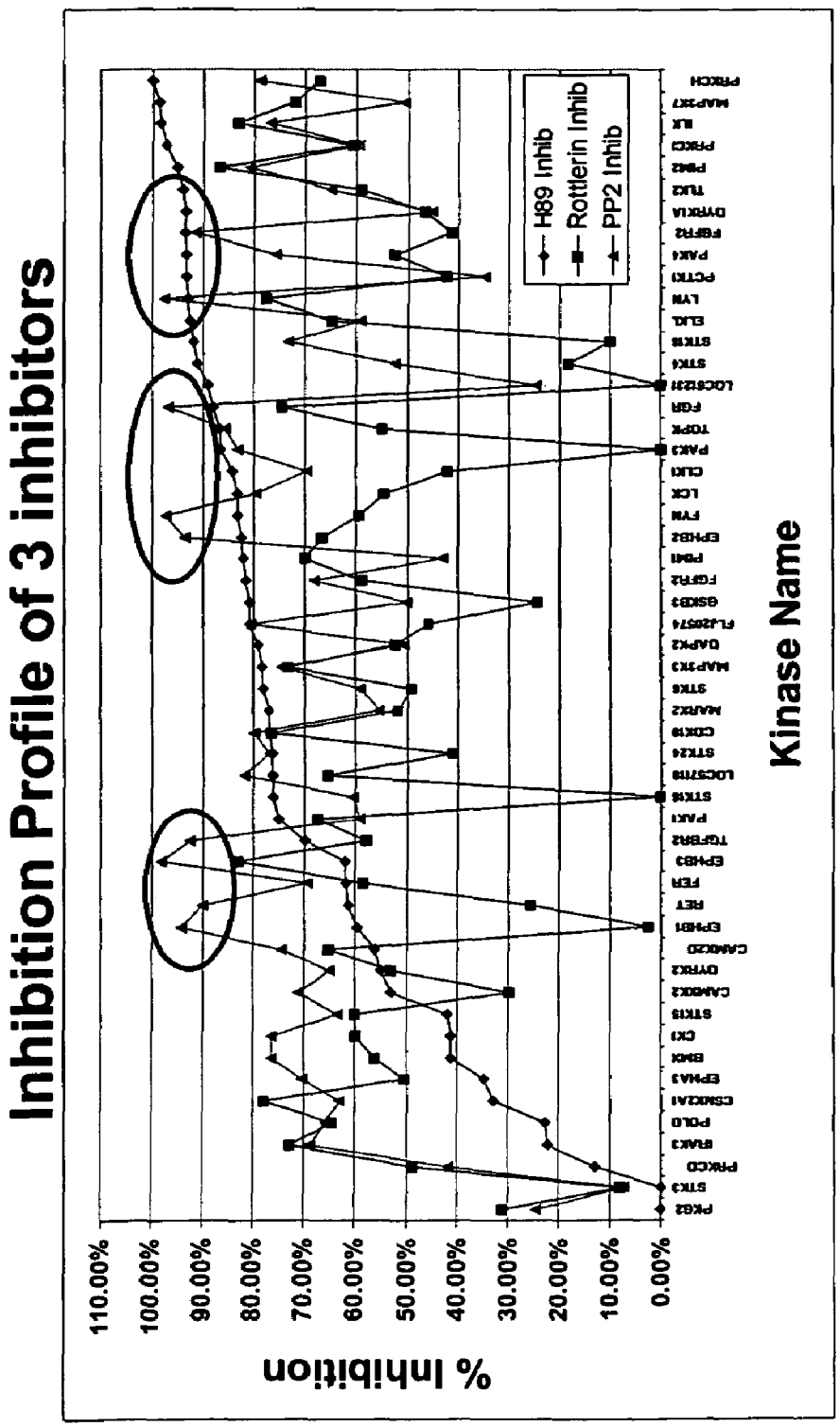

FIG. 3. Inhibitor Specificity Profiling. Kinase reactions with 50 different human kinases (x-axis) were performed in the presence of 100 μM H89 inhibitor (diamond squares), 100 μM rottlerin inhibitor (squares) or 100 μM PP2 inhibitor (triangles). The percentages of inhibition are plotted on the y-axis for each inhibitor.

Figure 4A:
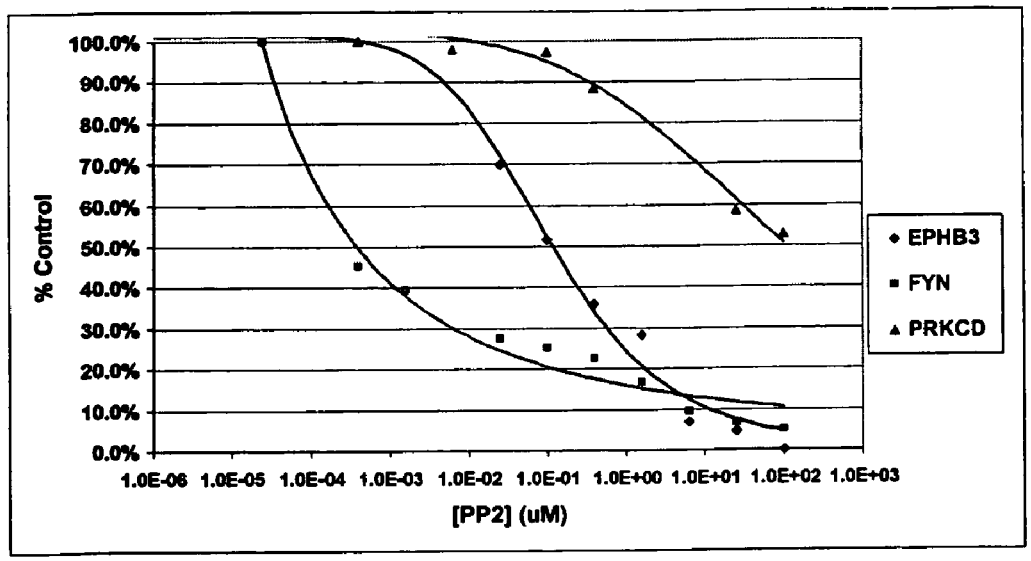

FIG. 4A. Dose-response curve for inhibition of the kinases FYN (squares), EPHB3 (diamond squares) and PRKCD (triangles) by PP2. PP2 concentration is shown on the x-axis and percent kinase activity compared to the control reaction without inhibitor is shown on the y-axis.

Figure 4B:
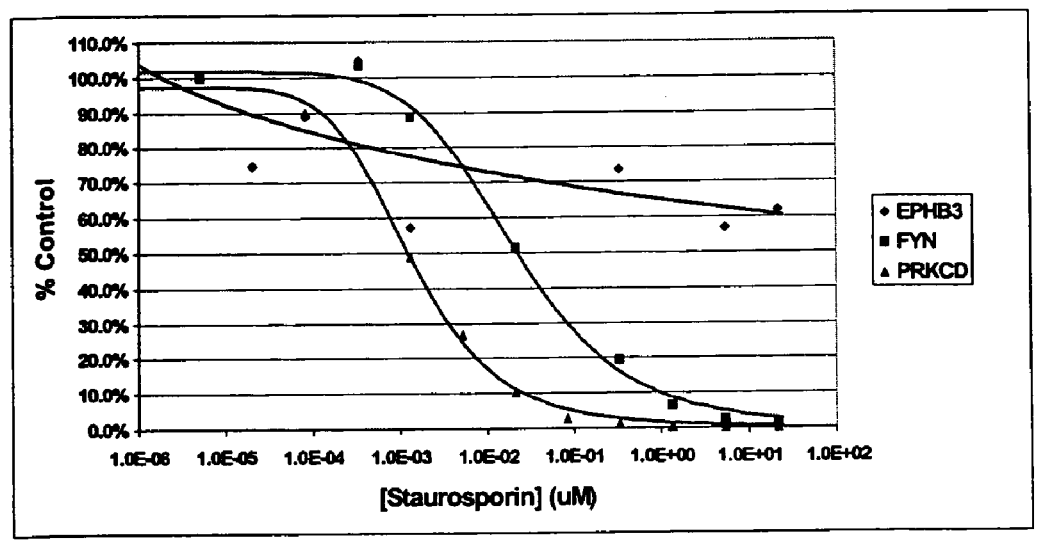

FIG. 4B. Dose-response curve for inhibition of the kinases FYN (squares), EPHB3 (diamond squares) and PRKCD (triangles) by Staurosporine. Staurosponrin concentration is shown on the x-axis and percent kinase activity compared to the control reaction without inhibitor is shown on the y-axis.

Figure 5:
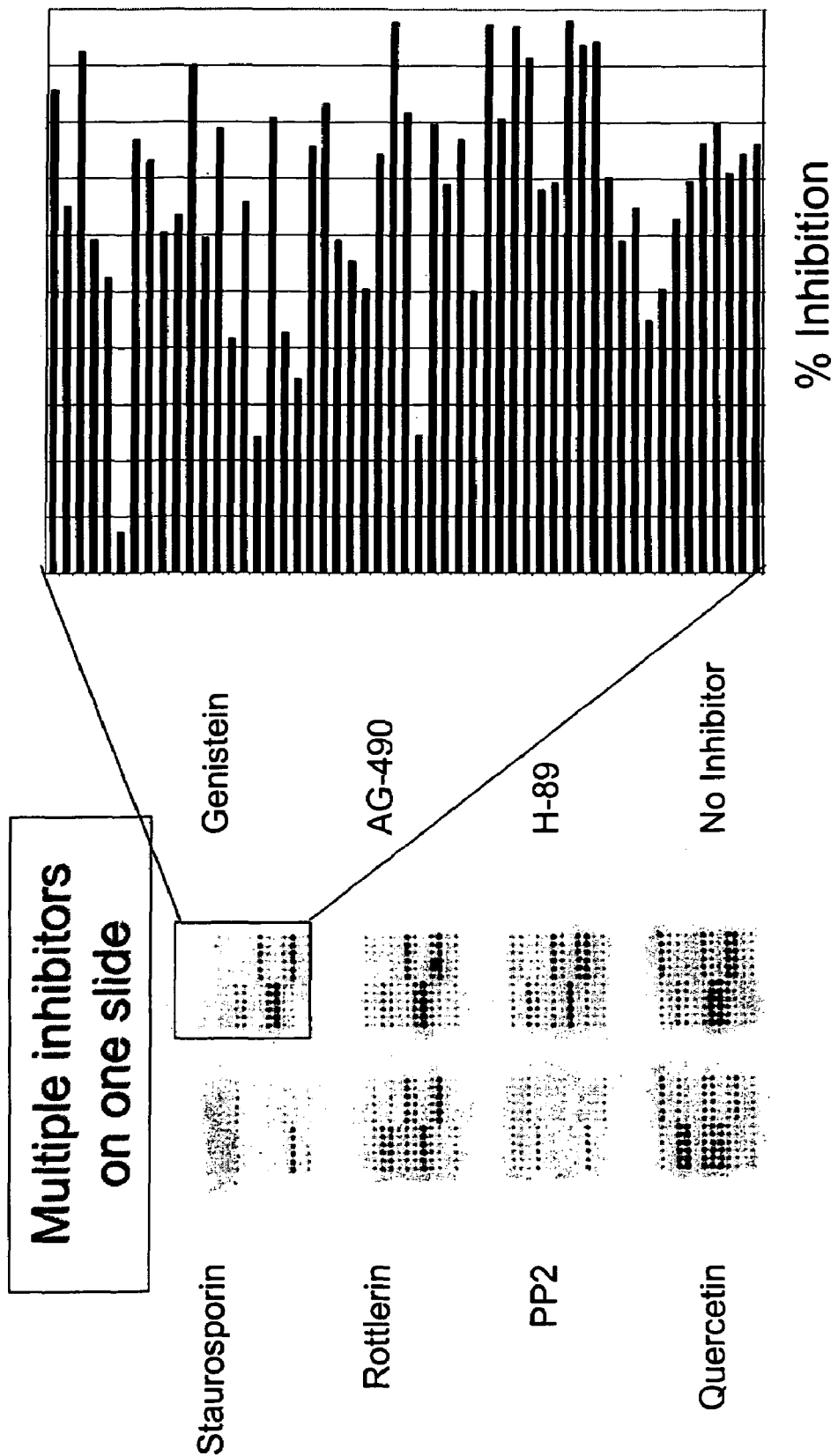

FIG. 5. Shows the susceptibility of different human kinases to different inhibitors. Eight different inhibitors were tested on a plurality of different human kinases on one slide.

Figure 6:
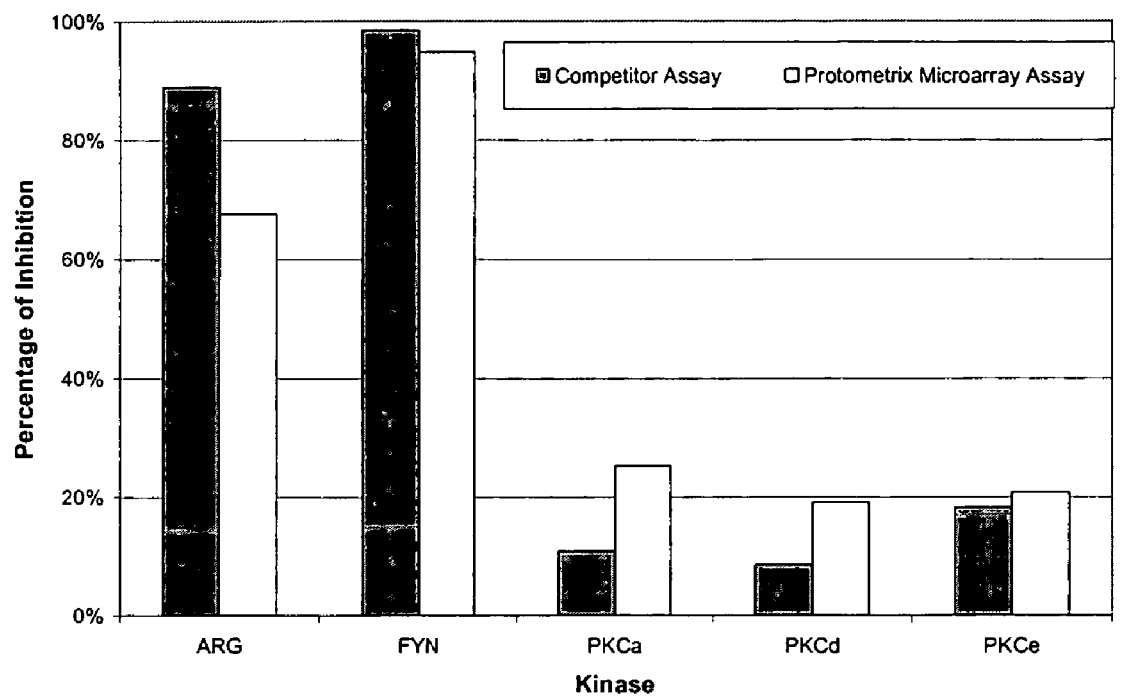

FIG. 6. Bar graphs comparing microarray and solution-based kinase inhibition results. Percentage of inhibition in the presence of the tyrosine kinase inhibitor PP2 at 1 micromolar is plotted for the indicated kinases. Shaded bars are competition assay results and open bars are results using the method provided herein as discussed in Example VI.

Figure 7A:
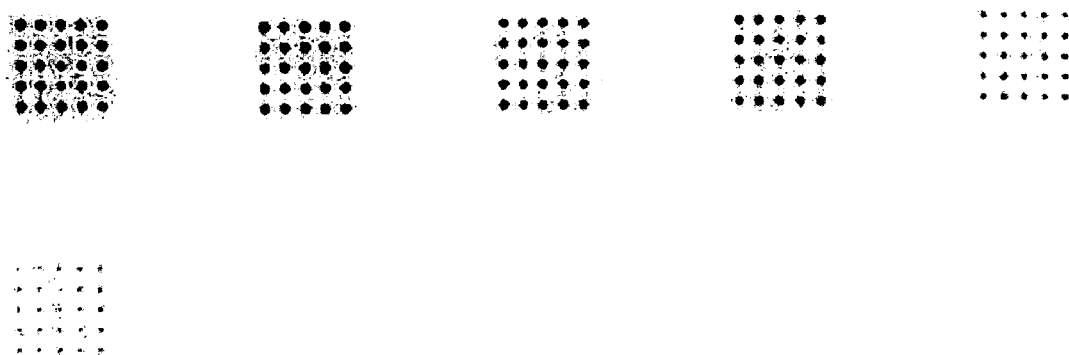
Figure 7B:
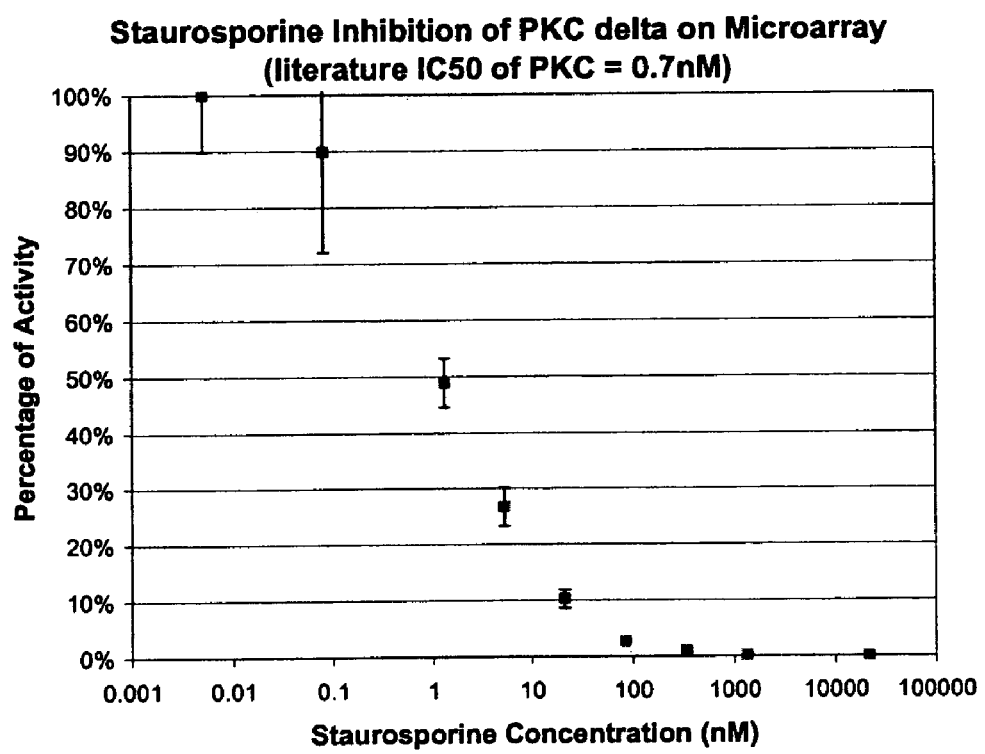

FIG. 7. Microarray images and graph illustrating an $IC_{50}$ experiment for PKC delta with the inhibitor staurosporine. FIG. 7A. Microarray images cropped from ten slides (PKC delta with increasing staurosporine concentrations). FIG. 7B. Plot of inhibition quantitated from images of FIG. 7A to provide a measurement of $IC_{50}$ using the microarray methods provided herein.

5. DETAILED DESCRIPTION OF THE INVENTION

The invention is directed to methods of conducting assays for enzymatic activity on protein microarrays. In the methods of the invention, a substance and a protein, both immobilized on the surface of the microarray, are in proximity with each other sufficient for the occurrence of an enzymatic reaction between the substance and the protein. The present invention also provides methods of using protein chips to assay the presence, amount, functionality, activity and sensitivity to modulators of enzymes. The invention further provides microarrays containing a substance and a protein, both immobilized on the surface of the microarray, wherein the substance and the protein are in proximity with each other sufficient for the occurrence of an enzymatic reaction between the substance and the protein, for use, e.g., to determine if the substance is a substrate and/or if the protein is an enzyme that acts on the substrate, for the enzymatic activity being assayed, or to identify inhibitors of the enzymatic reaction.

In certain embodiments, the methods of the invention can be used to identify enzymes that catalyze a specific reaction. In certain embodiments, the methods of the invention can be used to identify enzymes that use a specific substrate. In these embodiments, one or more proteins that are candidates for the enzyme that catalyzes the reaction of interest are immobilized on a protein chip for use with the invention.

In certain embodiments, the methods of the invention can be used to identify substrates of an enzymatic activity of interest. In certain embodiments, the methods of the invention can be used to identify substrates that are used by enzymes having a specific catalytic activity. In certain embodiments, the methods of the invention can be used to identify substrates that are used by a class of enzymes or by a specific enzyme of interest. In these embodiments, one or more substances that are candidates for substrates of the enzymatic activity of interest are immobilized on the surface of a solid support.

In certain embodiments of the invention, the protein immobilized on the solid support is an enzyme that catalyzes a reaction, wherein the substance immobilized on the solid support is a reactant (i.e., a substrate) of the reaction. In even more specific embodiments, the enzymatic reaction that occurs between the protein and the substance during the incubation step is a reaction that involves the substance as a reactant (e.g. substrate) and the protein as an enzymatic catalyst.

In additional embodiments, a plurality of substrates is immobilized on a solid support that includes at least one substrate for more than one different subclass of a class of enzyme. For example, a plurality of substrates can include substrates of different subclasses of kinases or phosphatases. Accordingly, methods provided herein allow the screening of test molecules in a single reaction, for their ability to modulate enzymatic reactions of many different subclasses of a class of enzymes. For example, the plurality of substrates can include substrates of many or all known subclasses of a class of enzymes in a species of organisms. In these examples, proteins immobilized on the solid support along with the plurality of substrates can include at least one representative enzyme from each subclass for which a corresponding substrate is immobilized. In an illustrative example, the substrate is a mixture of Myelin Basic Protein (MBP), histone and casein. In another illustrative example, the substrate is a mixture of Myelin Basic Protein (MBP), histone, casein and/or poly(Glu4Tyr).

In certain embodiments, the methods of the invention can be used to identify modulators of enzyme activity. In such screening assays, a molecule that increases or decreases the enzymatic activity being assayed can be identified. In certain embodiments, molecules that alter the substrate specificity of an enzyme can be identified. In other embodiments, the kinetic properties of an inhibitor, an activator or a molecule that alters the substrate specificity of an enzyme can be assessed.

In certain embodiments, a method of the invention for assaying an enzymatic reaction comprises the following steps: (a) incubating at least one protein and at least one substance under conditions conducive to the occurrence of an enzymatic reaction between the protein and the substance, wherein (i) the protein and the substance are immobilized on the surface of a solid support; (ii) the protein and the substance are in proximity sufficient for the occurrence of said enzymatic reaction; and (iii) the protein and the substance are not identical; and (b) determining whether said enzymatic reaction occurs.

In certain embodiments, a method of the invention comprises the steps of (i) immobilizing a substance on a solid support; (ii) printing a plurality of different proteins on the solid support such that a substance and a protein are in proximity sufficient for the occurrence of said enzymatic reaction between the substance and the proteins; and (iii) detecting the occurrence of the enzymatic reaction. In certain embodiments, a method of the invention comprises the steps of (i) immobilizing a protein on a solid support; (ii) printing a plurality of different substances on the solid support such that a substance and a protein are in proximity sufficient for the occurrence of said enzymatic reaction; and (iii) detecting the occurrence of the enzymatic reaction between the substance and the protein. In certain, more specific embodiments, the occurrence of the enzymatic reaction is visualized and/or quantified by a detectable signal.

In certain embodiments, the plurality of proteins is printed on the surface of the solid support in a positionally addressable fashion such that the identity of a protein that is located at a specific position of the array can be easily determined. In certain embodiments, the plurality of substances is printed on the surface of the solid support in a positionally addressable fashion such that the identity of a substance that is located at a particular position of the array can be easily determined. A positionally addressable array provides a configuration such that each substance and/or protein of interest is located at a known, predetermined position on the solid support such that the identity of each substrate and/or protein can be determined from its position on the array.

In certain aspects of the invention, a plurality of enzymes and a plurality of substrates are printed on the surface of a solid support. In these aspects, for example, a plurality of substrates and a plurality of enzymes can be immobilized in specific regions such that an enzyme is immobilized in a region that is identical to, or overlaps with, a region that includes a specific substrate for the immobilized enzyme. The regions of enzymes and substrates can be obtained, for example, by printing the enzymes and substrates using a microarray printer.

In certain embodiments, the surface of the solid support is coated with a substrate of an enzymatic reaction and the plurality of different proteins is printed on top of the substrate coating. In certain, more specific embodiments, each protein of the plurality of proteins is immobilized at a different position of the surface of the solid support. In other embodiments, the surface of the solid support is coated with a plurality of different substrates and the plurality of different proteins is printed on top of each substrate. In certain, more specific embodiments, the different substrates are coated on the surface as a mixture. In other embodiments, each substrate of the plurality of substrates is coated in a different area of the solid support. In other embodiments, a substrate is printed on the surface of the solid support and the plurality of different proteins is printed on top of the substrate. In certain embodiments, a plurality of different substrates is printed on the surface of the solid support and the plurality of different proteins is printed on top of the substrates. In a specific embodiment, all possible substrate-protein combinations of a set of proteins of interest and a set of substrates of interest are present on a single microarray. In certain, more specific, embodiments, the substrates and/or the proteins are purified.

Coating of a feature (i.e., a substance or a protein) typically involves a region of a solid support, i.e., the feature is contiguously immobilized on the surface of the solid support within the region such that one or more additional features (i.e., substance or protein) can be immobilized within the region, e.g., by printing. In more specific embodiments, a coated region is defined by walls that contain a liquid applied to the surface of the solid support, and by a region of the surface within the walls that is functionalized for immobilization of the protein or substance. In certain embodiments, the region covers the entire surface of the solid support. In other embodiments, multiple regions can be coated on the surface of a solid support by separating the surface of the solid support into distinct liquid regions using walls, such as walls of wells placed on top of the surface.

Printing on the other hand, typically involves applying a volume of liquid that is sufficiently small such that it does not cover the entire surface of a solid support or does not cover the entire surface of a region of a solid support that is defined by a liquid boundary, such as defined by a well. In this manner, a microarray containing spots of the printed feature is obtained. Therefore, where a protein is coated onto a surface of a solid support and the substance is printed onto the surface of the solid support, the coated protein will typically cover a larger area than the printed substance. Conversely, where a substance is coated onto a surface of a solid support and the protein is printed onto the surface of the solid support, the coated substance will typically cover a larger area than the printed protein. Illustrative methods for printing and coating onto microarrays are provided herein. Numerous methods for printing and coating onto solid supports are known in the art.

In certain embodiments, the different proteins of the plurality of different proteins are immobilized at different positions on the surface of the solid support. In certain, more specific embodiments, at least one protein of the plurality of different proteins is immobilized at at least 2, 3, 4, 5, 6, 7, 8, 9, 10, 12, 15, 20, 25, 50, or at at least 100 different locations on the surface of the solid support. In a preferred embodiment, each protein is immobilized at at least 4 different positions on the surface of the solid support.

In certain embodiments, the different substrates of the plurality of different substrates are immobilized at different positions on the surface of the solid support. In certain, more specific embodiments, at least one substrate of the plurality of different substrates is immobilized at at least 2, 3, 4, 5, 6, 7, 8, 9, 10, 12, 15, 20, 25, 50, or at at least 100 different locations on the surface of the solid support. In a preferred embodiment, each substrate is immobilized at at least 4 different positions on the surface of the solid support.

In certain embodiments, the surface of the solid support is coated with an enzyme and a plurality of different substances is printed on top of the enzyme coating. In certain, more specific embodiments, each substance of the plurality of substances is immobilized at a different position of the surface of the solid support. In other embodiments, the surface of the solid support is coated with a plurality of different enzymes and a plurality of different substances is printed on top of each different enzyme. In certain, more specific embodiments, the different enzymes are immobilized on the surface of the solid support as a mixture. In other, more specific embodiments, the different enzymes are immobilized in different regions of the surface of the solid support. In other embodiments, an enzyme is printed on the surface of the solid support and a plurality of different substances is printed on top of the enzyme. In certain embodiments, a plurality of different enzymes is printed on the surface of the solid support and the plurality of different substances is printed on top of the enzymes. In a specific embodiment, all possible protein-substance combinations are present on a single microarray. In certain, more specific, embodiments, the substances and/or the enzymes are purified.

In certain embodiments, the plurality of proteins consists of different proteins that are derived from the same source or the same species, e.g., human, yeast, mouse, rat, bacteria, and *C. elegans*. In certain embodiments, the plurality of proteins consists of different proteins that are known to have a specific enzymatic activity. In a specific embodiment, the plurality of enzymes consists of enzymes such as, but not limited to, Oxidoreductases, Transferases, Hydrolases, Lyases, Isomerases, and Ligases. In more specific embodiments, an enzyme can be a kinase, a protease, a phosphatase, a hydrolase, a RNAse, a DNAse, a tryptase, a phospholipase, or a glycosydase. In certain other embodiments, the plurality of protein on the microarray consists of different proteins, wherein the proteins can be derived from different sources or from different species and where the proteins may have different or unknown enzymatic activity. In certain embodiments, proteins with homologies to an enzyme of interest are used with the invention.

A substance and a protein can be immobilized on the surface of the solid support by any method known to the skilled artisan. In certain embodiments, a substance and/or a protein are directly immobilized on a glass surface. In certain embodiments, the surface of the solid support is treated with an aldehyde before a substance and/or protein is immobilized on the surface. Methods for immobilizing substrate and protein on the solid support are described in more detail in section 5.1.

Any kind of enzymatic reaction known to the skilled artisan can be used with the methods of the invention. Any group of enzymes that catalyzes a specific biochemical reaction can be used with the invention. Any substance can be used with the methods of the invention. A substance can be a candidate substrate or a known substrate of an enzymatic reaction of interest. Any substrate can be used with the methods of the invention. A substrate of an enzymatic reaction can be, but is not limited to, a proteinaceous substance (e.g., a protein or a peptide), an organic small molecule, an inorganic molecule, a nucleic acid (e.g., RNA or DNA), a lipid, or a carbohydrate.

In certain embodiments, the substance is a cofactor (see, e.g., section 5.3.1) or a candidate cofactor. Accordingly, in certain embodiments, an enzyme is immobilized on the surface of a solid support and a cofactor or a candidate cofactor is immobilized on the surface of a solid support such that the protein and the cofactor can physically interact with each other under suitable conditions (i.e., suitable buffer and temperature). Reaction buffer containing a substrate or a candidate substrate is then added to provide conditions suitable for the occurrence of an enzymatic reaction. In certain embodiments, multiple different proteins and multiple different cofactors are immobilized on the surface of a solid support such that different protein-cofactor combinations are immobilized in different locations of the solid support. In an illustrative, non-limiting, example, two different cofactors are each immobilized in a different region of the surface of the solid support. Five different enzymes are each immobilized in a different location within the each region such that ten different enzyme-cofactor combinations are located on the surface of the solid support and each combination is positionally addressable. Subsequently, reaction buffer with a substrate of the enzymes is added to determine which of the enzyme-cofactor combinations provides the highest enzymatic activity.

In certain embodiments, if enzymes that catalyze a specific reaction are to be identified, a plurality of different proteins is printed on the surface of the solid support together with a substrate that is known to be used in the specific reaction, wherein each protein is immobilized at a different position of the microarray. In other embodiments, if a substrate that is used by a specific enzyme is to be identified, a plurality of different substances (i.e., candidate substrates) is printed on the surface of the solid support together with a specific enzyme that is known to catalyze the specific reaction, wherein each substance is immobilized at a different position of the microarray. Any method known to the skilled artisan can be used to visualize and to quantify the enzymatic reaction. For a more detailed description of enzymatic reactions and their visualization see section 5.2.

In certain embodiments, a substance and a protein are immobilized on the surface of a solid support within a well. In certain embodiments, each well on the solid support contains at least one protein and at least one substance such that protein and substance are in proximity sufficient for the occurrence of an enzymatic reaction between the substance and the protein. In other embodiments, a plurality of different proteins or different substances is printed onto the surface of the solid support such that each well harbors a plurality of different proteins or substances. In certain, more specific embodiments, the plurality of proteins or substances is organized in a positionally addressable array on the surface within a well. The solid support, e.g., a slide, can have at least 1, 2, 3, 4, 5, 6, 7, 8, 9, 10, 15, 20, 25, 50, 100, 1,000 or at least 10,000 wells. The performance of the enzymatic reaction on a solid support with wells has the advantage that different reaction solutions can be added at the same time onto one solid support (e.g., on one slide).

In certain specific embodiments, the bottom surface of a well is coated with a substrate of an enzymatic reaction, wherein the substrate is immobilized on the surface, and a plurality of different proteins, e.g., enzymes, are immobilized on the bottom surface of the well. The substrate and the proteins are in proximity with each other sufficient for the occurrence of an enzymatic reaction. In more specific embodiments, each protein of the plurality of proteins is immobilized at a different position of the bottom surface of the well in a positionally addressable fashion.

In certain embodiments, the proteins of the plurality of proteins are derived from a single species. In other embodiments, the proteins of the plurality of proteins are derived from different species. In more specific embodiments, the proteins of the plurality of proteins are derived from a prokaryotic organism. In other embodiments, the proteins of the plurality of proteins are derived from an organism such as, but not limited to, yeast, *Caenorhabditis elegans, Drosophila melanogaster*, mouse, rat, horse, chimpanzee, or human.

In certain embodiments, a plurality of immobilized kinases includes one or more kinase from each branch of a kinome. In certain, more specific embodiments, a plurality of immobilized kinases includes one or more kinases from each branch of a mammalian kinome, such as a human kinome. A kinome includes all of the kinases within a species of organism.

In a specific embodiment, the enzyme assay of the invention can be used to analyze the activity of enzymes in a particular biological sample. This method is useful for, e.g., defining a pathological state of a cell based on the level of enzyme activity as opposed to abundance of mRNA or protein. In specific embodiments, enzymes whose activity is upregulated or downregulated in a preneoplastic, a neoplastic or a cancerous cell can be identified. Enzymes whose activity is modulated in a cell of a specific disease or disorder compared to a normal cell are candidates for drug targets to identify drugs for treating the disease or disorder.

In certain embodiments, a plurality of different substances is immobilized on the surface of a solid support and the extract of a cell is also immobilized on the surface of the solid support such that at least one substance of the plurality of different substances is in proximity with the extract sufficient for the occurrence of an enzymatic reaction between the substance and the protein. In a specific embodiment, at least one substance of the plurality of different substances is a known substrate of an enzymatic reaction. In certain embodiments, the different substances are organized in a positionally addressable array. This embodiment is useful for assessing enzymatic activities in a particular type of cell, wherein type of cell can refer to developmental state of the cell, stage of the cell cycle in the cell, or whether the cell is derived from a pathological tissue, e.g., is neoplastic or cancerous. In this embodiment, enzymatic activity is defined by the substrate used and the enzymatic reaction performed. In certain, more specific embodiments, the plurality of different substances is immobilized several times at different positions of the surface of the solid support. In certain embodiments, extracts from different types of cells are immobilized at the different positions such that each plurality or at least some of the pluralities of different substances are in contact with a different cellular extract. In certain embodiments, each plurality or at least some of the pluralities of different substances are in proximity with cellular extract from the same type of cell sufficient for the occurrence of an enzymatic reaction between the substances of the pluralities and the proteins of the cellular extract. In certain embodiments, different reaction mixtures, i.e., reaction mixtures providing different conditions and/or cofactors, are contacted with the different pluralities of different substances.

The invention also relates to protein microarrays. In certain embodiments the invention provides a positionally addressable array comprising at least one known enzyme and at least one candidate substrate of the enzyme, wherein (i) the enzyme and the substrate are immobilized on the surface of a solid support; (ii) the enzyme and the substrate are in proximity sufficient for the occurrence of the enzymatic reaction catalyzed by the enzyme between the enzyme and the substrate; and (iii) the enzyme and the substrate are not identical to each other. In other embodiments, the positionally addressable array of the invention comprises at least one known substrate of an enzymatic reaction and at least one candidate enzyme for the catalysis of the enzymatic reaction, wherein (i) the enzyme and the substrate are immobilized on the surface of a solid support; (ii) the enzyme and the substrate are in proximity sufficient for the occurrence of the enzymatic reaction between the enzyme and the substrate; and (iii) the enzyme and the substrate are not identical to each other. In even other embodiments, a positionally addressable array comprises at least one known substrate of an enzymatic reaction and at least one enzyme that is known to catalyze the enzymatic reaction, wherein (i) the enzyme and the substrate are immobilized on the surface of a solid support; (ii) the enzyme and the substrate are in proximity sufficient for the occurrence of the enzymatic reaction between the enzyme and the substrate; and (iii) the enzyme and the substrate are not identical to each other.

In certain embodiments, a plurality of proteins and a substance are immobilized on the microarrays of the invention. The plurality of proteins can be a selection of proteins, such as, but not limited to, proteins derived from a single species, proteins of a particular enzymatic activity, proteins with regions of homology to an enzyme of interest, and proteins derived from a specific cellular extract. The microarray of the invention can be coated with a substance, or the substance can be printed on different spots of the surface of the solid support and the proteins of the plurality of proteins are printed on top of the substance. In certain more specific embodiments, the substance is a known substrate of the enzymatic reaction to be assayed. In certain, more specific embodiments, each protein of the plurality of proteins is immobilized at a different position of the surface of the solid support. Alternatively, the plurality of proteins is printed first and the substance is printed subsequently on top of the proteins. In certain embodiments, the plurality of proteins is organized in a positionally addressable array.

In other embodiments, a plurality of substances and an enzyme are immobilized on the microarrays of the invention. The plurality of substances can be a selection of proteins, peptides, sugars, polysaccharides, small organic molecules, inorganic molecules, DNA or RNA. The microarray of the invention can be coated with the enzyme, or the enzyme can be printed on different spots of the surface of the solid support and the substances of the plurality of substances are printed on top of the enzyme. Alternatively, the plurality of substances is printed first and the enzyme is printed subsequently on top of the substances.

In certain embodiments, the microarrays of the invention have wells. In certain embodiments, at least one well is pre-coated or pre-printed with a substance and a plurality of different proteins is printed on the surface of the solid support in the well such that a substance and a protein are in proximity with each other sufficient for the occurrence of an enzymatic reaction between the protein and the substance. In certain embodiments, at least one well is pre-coated or pre-printed with an enzyme and a plurality of different substances is printed on the surface of the solid support in the well such that a substance and an enzyme are in proximity with each other sufficient for the occurrence of an enzymatic reaction between the protein and the substance. In certain, more specific embodiments, the substances are potential substrates of the enzyme. In other embodiments, the substances are known substrates of the enzyme.

In certain embodiments, each well of a microarray of the invention has the same combination of substances and proteins immobilized to the surface of the solid support within the well. In this embodiment, each well of the microarray can be filled with a different reaction buffer such that the enzymatic reaction(s) can be monitored under a plurality of different reaction conditions; in the presence and absence, respectively, of a plurality of different test molecules; or in the presence and absence, respectively, of different cofactors.

The invention also provides kits for carrying out the assay regimens of the invention and for manufacturing the microarrays of the invention. In a specific embodiment, kits of the invention comprise one or more arrays of the invention. Such kits may further comprise, in one or more containers, reagents useful for assaying biological activity of a protein or molecule, reagents useful for assaying interaction of a substrate and a protein or enzyme, reagents useful for assaying the biological activity of a protein or molecule having a biological activity of interest. The reagents useful for assaying biological activity of a protein or molecule, or assaying interactions between a probe and a protein or molecule, can be contained in each well or selected wells on the protein chip. Such reagents can be in solution or in solid form. The reagents may include either or both the proteins or molecules and the substrates required to perform the assay of interest.

In one embodiment, a kit comprises one or more protein microarrays of the invention. In certain embodiments, the proteins and substrates are already immobilized onto the surface of the solid support. In another embodiment, reagents are provided in the kit that can be used for immobilizing substrate and protein onto the surface of the solid support.

In certain embodiments, the substrate is different from the proteins of the plurality of proteins. In certain embodiments, the substrate is different from the enzyme.

In certain embodiments, the invention provides a method for assaying an enzymatic reaction, the method comprising: (a) incubating at least one protein, at least one first substance, and at least one second substance under conditions conducive to the occurrence of an enzymatic reaction between the protein and the first or the second substance, wherein (i) the protein, the first substance and the second substance are immobilized on the surface of a solid support; (ii) the protein, the first substance and the second substance are in proximity sufficient for the occurrence of said enzymatic reaction; (iii) the protein and the first substance are not identical and (iv) the protein and the second substance are not identical; and (b) determining whether said enzymatic reaction occurs.

5.1. Solid Support and Immobilization of Substrate and Protein

In the methods and microarrays of the invention, at least one substance and at least one protein are immobilized on the surface of a solid support such that substance and protein are in proximity sufficient for the occurrence of an enzymatic reaction. The substance is a candidate substrate or a known substrate of the enzymatic reaction. The protein is a candidate enzyme or an enzyme known to catalyze the enzymatic reaction of interest.

The substance and the protein can be immobilized to the surface of the solid support by any method known to the skilled artisan. In certain embodiments, the substance is immobilized before the protein is immobilized. In other embodiments, the protein is immobilized before the substance is immobilized. The suitability of a specific method of immobilizing a protein or a substrate may depend on the molecular nature of the protein or substance. If the substrate is a proteinaceous substance, e.g., a protein or a peptide, any method known to the skilled artisan can be used to immobilize a protein to the surface of a solid support. If the substance is not a proteinaceous substance, any method known to the skilled artisan can be used to immobilize a molecule of that type of molecules to surface of a solid support.

In certain embodiments of the invention, the substance and the protein are immobilized on the surface of the solid support such that substance and protein are in proximity with each other sufficient for the occurrence of the enzymatic reaction to be assayed. Typically, when the substance and the protein are in sufficient proximity immobilized on the surface of the solid support, physical contact between the substance and the protein occurs during incubation under conditions conducive to the occurrence of an enzymatic reaction between the protein and the substance. In certain embodiments of the invention, the substance and the protein are immobilized on the surface of the solid support such that substance and protein are in physical contact with each other.

In certain embodiments, the substance is purified. In certain embodiments, the protein is purified. In certain embodiments, the substance and the protein are purified.

In certain embodiments, the surface of a solid support is coated or printed with a mixture of at least 2, 3, 4, 5, 10, 15, 20, 25, 50 or 100 different substances. In certain embodiments, the surface of a solid support is coated or printed with a mixture of at most 2, 3, 4, 5, 10, 15, 20, 25, 50 or 100 different substances. In certain embodiments, a plurality of different mixtures of substances is immobilized on the surface of the solid support.

The solid support can be constructed from materials such as, but not limited to, silicon, glass, quartz, polyimide, acrylic, polymethylmethacrylate (LUCITE®), ceramic, gold, nitrocellulose, amorphous silicon carbide, polystyrene, and/or any other material suitable for microfabrication, microlithography, or casting. For example, the solid support can be a hydrophilic microtiter plate (e.g., MILLIPORE™) or a nitrocellulose-coated glass slide. In a specific embodiment, the solid support is a nitrocellulose-coated glass slide. Nitrocellulose-coated glass slides for making protein (and DNA) microarrays are commercially available (e.g., from Schleicher & Schuell (Keene, N.H.), which sells glass slides coated with a nitrocellulose based polymer (Cat. no. 10 484 182)). In a specific embodiment, each protein is spotted onto the nitrocellulose-coated glass slide using an OMNIGRID™ (GeneMachines, San Carlos, Calif.). The present invention contemplates other solid supports useful for constructing a protein chip, some of which are disclosed, for example, in International Patent Application publication WO 01/83827 which is incorporated herein by reference in its entirety.

In one embodiment, the solid support is a flat surface such as, but not limited to, a glass slide. Dense protein arrays can be produced on, for example, glass slides, such that assays for the presence, amount, and/or functionality of proteins can be conducted in a high-throughput manner.

In certain, more specific embodiments, the solid support is a glass slide that has been pre-treated with an aldehyde, such as paraformaldehyde or formaldehyde. In certain embodiments, the solid support is an aldehyde treated slide is obtained from TeleChem International, Inc. In other embodiments, the solid support is a nitrocellulose coated slide (Schleicher & Schuell). In other embodiments, the solid support is coated with an amino-silane surface (GAPS slide obtained from Corning®).

In certain embodiments, after immobilizing the substances and the proteins, the chip is blocked. Any blocking agent known to the skilled artisan can be used with the methods of the invention. In a specific embodiment, Bovine Serum Albumin, glycine or a detergent (e.g., Tween20) can be used as a blocking agent. In certain other embodiments, the chips are not blocked.

In a particular embodiment, the solid support comprises a silicone elastomeric material such as, but not limited to, polydimethylsiloxane ("PDMS"). An advantage of silicone elastomeric materials is their flexible nature.

In another particular embodiment, the solid support is a silicon wafer. The silicon wafer can be patterned and etched (see, e.g., G. Kovacs, 1998, Micromachined Transducers Sourcebook, Academic Press; M. Madou, 1997, Fundamentals of Microfabrication, CRC Press). The etched wafer can also be used to cast the microarrays to be used with the invention.

Accordingly, in certain embodiments, the plurality of proteins is applied to the surface of a solid support, wherein the density of the sites at which protein are applied is at least 1 site/cm$^2$, 2 sites/cm$^2$, 5 sites/cm$^2$, 10 sites/cm$^2$, 25 sites/cm$^2$, 50 sites/cm$^2$, 100 sites/cm$^2$, 1000 sites/cm$^2$, 10,000 sites/cm$^2$, 100,000 sites/cm$^2$, 1,000,000 sites/cm$^2$, 10,000,000 sites/cm$^2$, 25,000,000 sites/cm$^2$, 10,000,000,000 sites/cm$^2$, or 10,000,000,000,000 sites/cm$^2$. Each individual protein sample is preferably applied to a separate site on the chip. In certain specific embodiments, the identities of the protein(s) at each site on the chip is/are known. In certain other embodiments, a plurality of substances is applied to the surface of a solid support, wherein the density of the sites at which substances are applied is at least 1 site/cm$^2$, 2 sites/cm$^2$, 5 sites/cm$^2$, 10 sites/cm$^2$, 25 sites/cm$^2$, 50 sites/cm$^2$, 100 sites/cm$^2$, 1000 sites/cm$^2$, 10,000 sites/cm$^2$, 100,000 sites/cm$^2$, 1,000,000 sites/cm$^2$, 10,000,000 sites/cm$^2$, 25,000,000 sites/cm$^2$, 10,000,000,000 sites/cm$^2$, or 10,000,000,000,000 sites/cm$^2$. Each individual protein sample is preferably applied to a separate site on the chip. In certain specific embodiments, the identities of the proteins at each site on the chip are known, i.e., the chip is a positionally addressable array.

In certain aspects of the invention, a population of identical proteins is immobilized on a specific region on the surface of the solid support. Different populations of identical proteins can be immobilized on different specific regions of the surface of the solid support. The regions can be separated for example, by less than 10 millimeters, less than 1 millimeter, less than 500 microns, or less than 100 microns. The different regions containing populations of identical proteins can be formed, for example by printing the proteins to the surface of the solid support using a microarray printer.

In certain embodiments, a plurality of different proteins is applied to the surface, wherein the surface is either pre-coated with a substance or pre-printed with substance. If the surface is pre-printed with a substance, care should be taken that each of the different proteins is printed on top of the sites where a substance is present. In certain other embodiments, a plurality of different substances is applied to the surface, wherein the surface is either pre-coated with an enzyme or pre-printed with an enzyme. If the surface is pre-printed with an enzyme, care should be taken that each of the different substances is printed on top of the sites where enzyme is present. The substrate can be a candidate substrate for the enzymatic reaction to be assayed.

In certain embodiments, a substance and an enzyme are immobilized on the surface of a solid support, wherein the solid support has wells. In certain embodiments, a plurality of different enzymes or different substances is printed on the surface of the solid support such that each feature of the microarray is in a different well. In other embodiments, a plurality of different enzymes or different substances is printed onto the surface of the solid support such that each well harbors a plurality of different proteins or substrates. The performance of the enzymatic reaction on a solid support with wells has the advantage that different reaction solutions can be added at the same time onto one solid support (e.g., on one slide). Another advantage of wells over flat surfaces is an increased signal-to-noise ratio. Wells allow the use of larger volumes of reaction solution in a denser configuration, and therefore greater signal is possible. Furthermore, wells decrease the rate of evaporation of the reaction solution from the chip as compared to flat surface arrays, thus allowing longer reaction times. Another advantage of wells over flat surfaces is that the use of wells permit association studies using a specific volume of reaction volume for each well on the chip, whereas the use of flat surfaces usually involves indiscriminate probe application across the whole surface. The application of a defined volume of reaction buffer can be important if a reactant that is supplied in the reaction buffer is being depleted during the course of the reaction. In such a scenario, the application of a defined volume allows for more reproducible results. The use of microlithographic and micromachining fabrication techniques (see, e.g., International Patent Application publication WO 01/83827, which is incorporated herein by reference in its entirety) can be used to create well arrays with a wide variety of dimensions ranging from hundreds of microns down to 100 nm or even smaller, with well depths of similar dimensions. In one embodiment, a silicon wafer is micromachined and acts as a master mold to cast wells of 400 µm diameter that are spaced 200 µm apart, for a well density of about 277 wells per $cm^2$, with individual well volumes of about 30 nl for 100 µm deep wells (see, e.g., International Patent Application publication WO 01/83827, which is incorporated herein by reference in its entirety).

In certain embodiments, the wells of a microarray of the invention have depth. In other embodiments, the wells of a microarray of the invention do not have depth. In a nonlimiting example, the different wells are separated by barriers wherein the barrier comprises a different surface material than the surface material of the well. E.g., the wells are constituted by an area on the solid support that is a glass surface and the barriers are constituted by a surface material such as teflon. Such slides can be obtained, e.g., from Erie Scientific Company, NH. Without being bound by theory, the difference in surface tension provided by the different surface materials ensures that a liquid from one well will not leak into a neighboring well.

In one embodiment, the solid support comprises gold. In a preferred embodiment, the solid support comprises a gold-coated slide. In another embodiment, the solid support comprises nickel. In another preferred embodiment, the solid support comprises a nickel-coated slide. Solid supports comprising nickel are advantageous for purifying and attaching fusion proteins having a poly-histidine tag ("His tag"). In another embodiment, the solid support comprises nitrocellulose. In another preferred embodiment, the solid support comprises a nitrocellulose-coated slide.

The proteins and substances can be bound directly to the solid support, or can be attached to the solid support through a linker molecule or compound. The linker can be any molecule or compound that derivatizes the surface of the solid support to facilitate the attachment of proteins and/or substrates to the surface of the solid support. The linker may covalently or non-covalently bind the proteins or substrates to the surface of the solid support. In addition, the linker can be an inorganic or organic molecule. In certain embodiments, the linker may be a silane, e.g., sianosilane, thiosilane, aminosilane, etc. Compounds useful for derivatization of a protein chip are also described in International Patent Application publication WO 01/83827, which is incorporated herein by reference in its entirety.

Accordingly, in one embodiment, the proteins and/or substrates are bound non-covalently to the solid support (e.g., by adsorption). Proteins and/or substrates that are non-covalently bound to the solid support can be attached to the surface of the solid support by a variety of molecular interactions such as, for example, hydrogen bonding, van der Waals bonding, electrostatic, or metal-chelate coordinate bonding. In a particular embodiment, proteins and/or substrates are bound to a poly-lysine coated surface of the solid support. In addition, as described above, in certain embodiments, the proteins and/or substrates are bound to a silane (e.g., sianosilane, thiosilane, aminosilane, etc.) coated surface of the solid support.

In addition, crosslinking compounds commonly known in the art, e.g. homo- or heterofunctional crosslinking compounds (e.g., bis[sulfosuccinimidyl]suberate, N-[gamma-maleimidobutyryloxy]succinimide ester, or 1-ethyl-3-[3-dimethylaminopropyl]carbodiimide), may be used to attach proteins and/or substrates to the solid support via covalent or non-covalent interactions.

In another embodiment, proteins and/or substrates of the protein chip are bound covalently to the solid support. In other embodiments, proteins and/or substrates can be bound to the solid support by receptor-ligand interactions, which include interactions between antibodies and antigens, DNA-binding proteins and DNA, enzyme and substrate, avidin (or streptavidin) and biotin (or biotinylated molecules), and interactions between lipid-binding proteins and phospholipids (or membranes, vesicles, or liposomes comprising phospholipids).

Purified proteins and/or substrates can be placed on an array using a variety of methods known in the art. In one embodiment, the proteins and/or substrates are printed onto the surface of a solid support. In a further embodiment, the proteins and/or substrates are attached to the solid support using an affinity tag. In a specific embodiment, an affinity tag different from that used to purification of the protein or substrate is used for immobilizing the protein or substrate. If two different tags are used further purification is achieved when building the protein array.

In a specific embodiment, proteins and/or substrates are expressed as fusion proteins having at least one heterologous domain with an affinity for a compound that is attached to the surface of the solid support. Suitable compounds useful for binding fusion proteins onto the solid support (i.e., acting as binding partners) include, but are not limited to, trypsin/ anhydrotrypsin, glutathione, immunoglobulin domains, maltose, nickel, or biotin and its derivatives, which bind to bovine pancreatic trypsin inhibitor, glutathione-S-transferase, Protein A or antigen, maltose binding protein, poly-histidine (e.g., His×6 tag), and avidin/streptavidin, respectively. For example, Protein A, Protein G and Protein A/G are proteins capable of binding to the Fc portion of mammalian immunoglobulin molecules, especially IgG. These proteins can be covalently coupled to, for example, a Sepharose® support to provide an efficient method of purifying fusion proteins having a tag comprising an Fc domain. In a specific embodiment, the proteins are bound to the solid support via His tags, wherein the solid support comprises a flat surface. In a preferred embodiment, the proteins are bound to the solid support via His tags, wherein the solid support comprises a nickel-coated glass slide.

In certain embodiments, proteins and/or substrates are expressed as fusion proteins, wherein the protein and/or substrate is fused to a bifunctional tag. In an example of such an embodiment, the protein and/or substrate is fused to an intein and a chitin binding domain. In a more specific embodiment, the proteins and/or substrates are expressed using the IMPACT™-CN protein fusion and purification system from New England Biolabs Inc. In the presence of thiols such as DTT, b-mercaptoethanol or cysteine, the intein undergoes specific self-cleavage which releases the target protein from the chitin-bound intein tag.

The protein chips to be used with the present invention are not limited in their physical dimensions and can have any dimensions that are useful. Preferably, the protein chip has an array format compatible with automation technologies, thereby allowing for rapid data analysis. Thus, in one embodiment, the protein microarray format is compatible with laboratory equipment and/or analytical software. In a preferred embodiment, the protein chip is the size of a standard microscope slide. In another preferred embodiment, the protein chip is designed to fit into a sample chamber of a mass spectrometer.

In specific embodiments, protein and/or substrate are applied to a flat surface, such as, but not limited to, glass slides. Proteins and/or substrate are bound covalently or non-covalently to the flat surface of the solid support. The proteins and/or substrate can be bound directly to the flat surface of the solid support, or can be attached to the solid support through a linker molecule or compound. The linker can be any molecule or compound that derivatizes the surface of the solid support to facilitate the attachment of proteins and/or substrate to the surface of the solid support. The linker may covalently or non-covalently bind the proteins and/or substrate to the surface of the solid support. In addition, the linker can be an inorganic or organic molecule. Specific linkers are compounds with free amines. Preferred among linkers is 3-glycidooxypropyltrimethoxysilane (GPTS).

In a specific embodiment, by way of example and not limitation, proteins are immobilized on the solid support using the following procedure: Briefly, after washing with 100% ethanol (EtOH) three times at room temperature, the chips (e.g., chips made of polydimethylsiloxane or glass slides) are immersed in 1% GPTS solution (95% ethanol (EtOH), 16 mM acetic acid (HOAc)) with shaking for 1 hr at room temperature. After three washes with 95% EtOH, the chips are cured at 135° C. for 2 hrs under vacuum. Cured chips can be stored in dry Argon for months 12. To attach proteins and substrates to the chips, protein solutions are added to the wells and incubated on ice for 1 to 2 hours. After rinsing with cold HEPES buffer (10 mM HEPES, 100 mM NaCl, pH 7.0) three times, the wells are blocked with 1% BSA in PBS (Sigma, USA) on ice for >1 hr. Because of the use of GPTS, any reagent containing primary amine groups is avoided.

Printing of one or more proteins or one or more substances can be accomplished, for example, by microspotting, which encompasses deposition technologies that enable automated microarray production by printing small quantities of premade biochemical substances onto solid surfaces. Printing is accomplished by direct surface contact between the printing substrate and a delivery mechanism, such as a pin or a capillary. Robotic control systems and multiplexed printheads allow automated microarray fabrication.

Ink jet technologies utilize piezoelectric and other forms of propulsion to transfer biochemical substances from miniature nozzles to solid surfaces. Using piezoelectricity, the sample is expelled by passing an electric current through a piezoelectric crystal that expands to expel the sample. Piezoelectric propulsion technologies include continuous and drop-on-demand devices. Examples of the use of ink jet technology include U.S. Pat. No. 5,658,802 (issued Aug. 19, 1997).

In another embodiment, protein-containing cellular material, such as but not limited to vesicles, endosomes, subcellular organelles, and membrane fragments, can be placed on the protein chip. In another embodiment, a whole cell is placed on the protein chip. In a further embodiment, the protein, protein-containing cellular material, or whole cell is attached to the solid support of the protein chip. In a specific embodiments, the protein, protein-containing cellular material, or whole cell is attached to the surface of the solid support that is coated or preprinted with substrate.

Furthermore, proteins, substrate, protein- or substrate-containing cellular material, or cells can be embedded in artificial or natural membranes prior to or at the time of placement on the protein chip. Embedding enzymes in membranes is the preferred embodiment, if the enzyme assumes its enzymatically active conformation preferentially in a membrane. In another embodiment, proteins, protein-containing cellular material, or cells can be embedded in extracellular matrix component(s) (e.g., collagen or basal lamina) prior to or at the time of placement on the protein chip.

The proteins or substrates are bound covalently or non-covalently to the surface of the solid support in the wells. In more specific embodiments, the protein is bound covalently to the surface and the substrate is bound non-covalently to the surface. In other embodiments, the protein is bound non-covalently to the surface and the substrate is bound covalently to the surface. In other embodiments, both substrate and protein are bound covalently to the surface. In other embodiments, both substrate and protein are bound non-covalently to the surface. The proteins or substrates can be bound directly to the surface of the solid support, or can be attached to the solid support through a linker molecule or compound. The linker can be any molecule or compound that derivatizes the surface of the solid support to facilitate the attachment of proteins or substrates to the surface of the solid support. The linker may covalently bind the proteins or substrates to the surface of the solid support or the linker may bind via non-covalent interactions. In addition, the linker can be an inorganic or organic molecule. Preferred linkers are compounds with free amines. Most preferred among linkers is 3-glycidooxypropyltrimethoxysilane (GPTS).

Proteins or substrates which are non-covalently bound to the surface of the solid support may utilize a variety of molecular interactions to accomplish attachment to surface of the solid support such as, for example, hydrogen bonding, van der Waals bonding, electrostatic, or metal-chelate coordinate bonding. Further, DNA-DNA, DNA-RNA and receptor-ligand interactions are types of interactions that utilize non-covalent binding. Examples of receptor-ligand interactions include interactions between antibodies and antigens, DNA-binding proteins and DNA, enzyme and substrate, avidin (or streptavidin) and biotin (or biotinylated molecules), and interactions between lipid-binding proteins and phospholipid membranes or vesicles. For example, proteins and/or substrates can be expressed with fusion protein domains that have affinities for a binding partner that is attached to the surface of the solid support. Suitable binding partners for fusion protein binding include trypsin/anhydrotrypsin, glutathione, immunoglobulin domains, maltose, nickel, or biotin and its derivatives, which bind to bovine pancreatic trypsin inhibitor, glutathione-S-transferase, antigen, maltose binding protein, poly-histidine (e.g., His×6 tag), and avidin/streptavidin, respectively.

In certain embodiments, the proteins and/or the substrate is immobilized to the solid support via a peptide tag, wherein the affinity binding partner for the tag is attached (covalently or non-covalently) to the solid support. For a more detailed description of peptide tags see section 5.5.1.

In certain embodiments, a protein is immobilized directly on the surface of the solid support. In other embodiments, a protein is immobilized via a linker molecule to the solid support. In certain, more specific embodiments, the distance between a protein and the surface of a solid support is at most 0.1 nm, 1 nm, 5 nm, 10 nm, 15 nm, 25 nm, 50 nm, 100 nm, 1 µm or at most 5 µm. In certain embodiments, the distance between the protein and the surface of the solid support is at least 0.1 nm, 1 nm, 5 nm, 10 nm, 15 nm, 25 nm, 50 nm, 100 nm, 1 µm or at least 5 µm. In certain embodiments, a protein is immobilized to the underivatized surface of a solid support. In a more specific embodiment, a protein is immobilized to the underivitized glass surface of a solid support.

In certain embodiments, the substance is immobilized directly on a surface of a solid support. In other embodiments, a substance is immobilized via a linker molecule to a solid support. In certain, more specific embodiments, the distance between a substance and the surface of a solid support is at most 0.1 nm, 1 nm, 5 nm, 10 nm, 15 nm, 25 nm, 50 nm, 100 nm, 1 µm or at most 5 µm. In certain embodiments, the distance between a substance and the surface of a solid support is at least 0.1 nm, 1 nm, 5 nm, 10 nm, 15 nm, 25 nm, 50 nm, 100 nm, 1 µm or at least 5 µm. In certain embodiments, a substance is immobilized to the underivatized surface of a solid support. In a more specific embodiment, the substance is immobilized to the underivitized glass surface of a solid support.

In certain embodiments, a substance and a protein are immobilized directly on the surface of the solid support. In other embodiments, a substance and a protein are immobilized via a linker molecule to the solid support. In certain, more specific embodiments, the distance between a substance and the surface of the solid support and the distance between a protein and the surface of the solid support (i.e., the length of the linker molecule, or the distance by which the linker distances the substance or the protein from the solid support) is at most 0.1 nm, 1 nm, 5 nm, 10 nm, 15 nm, 25 nm, 50 nm, 100 nm, 1 µm or at most 5 µm. In certain embodiments, the distance between a substance and the surface of the solid support and the distance between a protein and the surface of the solid support is at least 0.1 nm, 1 nm, 5 nm, 10 nm, 15 nm, 25 nm, 50 nm, 100 nm, 1 µm or at least 5 µm. In certain embodiments, a substance and a protein are immobilized to the underivatized surface of the solid support. In a more specific embodiment, a substance and a protein are immobilized to the underivitized glass surface of a solid support.

The solid support can have a porous or a non-porous surface.

An aspect to be considered when choosing the surface chemistry for immobilizing substance and a protein are background signals created by the surface (see, e.g., FIG. 2 of section 6.1).

Proteins can be immobilized in many ways on a surface. In certain embodiments, a substrate or a protein can be immobilized reversibly. In other embodiments, a substrate or a protein can be immobilized irreversibly. The goal of immobilizing a substrate and a protein is to retain the protein and the substrate in a defined region on the microarray. The protein and/or the substrate can be encapsulated or entrapped in a porous surface or a vesicle. The protein and/or the substrate can be kinetically trapped but has free molecules in equilibrium with surface-bound ones.

In certain embodiments, the different proteins and/or the different substances on the surface of a solid support are present in approximately equimolar amounts. Without being bound by theory, using approximately equimolar amounts facilitates the quantification of the results obtained.

In certain embodiments of the invention, the amount of a protein or a substance is present on the surface of a solid support is at least $10^{-12}$ mol, $10^{-11}$ mol, $10^{-10}$ mol, $10^{-9}$ mol, $10^{-8}$ mol, $10^{-7}$ mol, $10^{-6}$ mol, $10^{-5}$ mol, $10^{-4}$ mol, $10^{-3}$ mol, $10^{-2}$ mol, or at least $10^{-1}$ mol. In certain embodiments of the invention, the amount of a protein or a substance is present on the surface of a solid support is at most $10^{-12}$ mol, $10^{-11}$ mol, $10^{-10}$ mol, $10^{-9}$ mol, $10^{-8}$ mol, $10^{-7}$ mol, $10^{-6}$ mol, $10^{-5}$ mol, $10^{-4}$ mol, $10^{-3}$ mol, $10^{-2}$ mol, or at least $10^{-1}$ mol.

Illustrative examples of immobilizing a protein and a substrate include, but are not limited to, 1. Immobilization by specific covalent bonds, such as disulfide with a cysteine, or non-specific covalent bonds, such as a Schiff base, formed between a protein or a substance and the surface of the solid support (e.g., a slide).

2. Immobilization by adsorption of a protein or a substance directly onto the surface of the solid support.

3. Immobilization by specific non-covalent interactions between a substance or a protein and the surface, such as His-tagged proteins or substances and Nickel surfaces.

4. Immobilization indirectly by interactions of a protein or a substance with immobilized molecules, including proteins, lipids, nucleic acids and carbohydrates.

5. The interactions of a protein or a substance with immobilized molecules can be specific, such as antibody/antigen or streptavidin/biotin.

6. The interactions of a protein or a substance with immobilized molecules can be non-specific.

7. Immobilization by cross linking to a matrix on the slide.

8. Immobilization by entrapment in a matrix on the slide.

9. The matrix can be made of polymers. The polymerization and/or the cross linking can occur before, during and after the printing of proteins.

10. The matrix can be made of interactions of non-covalent natures, such as hydrogen bonds and van der Waals interactions, between the same or different types of molecules.

11. A protein or a substance to be immobilized can be part of the matrix formation.

12. Immobilization by encapsulation of a protein or a substance in molecular-scale compartments, such as liposomes, vesicles or micelles, which are covalently or non-covalently attached to a surface.

13. Immobilization by protein aggregation, cross-linking, precipitation or denaturation on the surface of a solid support.

In certain embodiments, substrate and protein are immobilized by different procedures. In certain other embodiments, substrate and protein are immobilized by the same procedure.

Covalent bonding or other strong interactions between a protein and the surface of a solid support may modify the structure and thus function of a protein. Thus, the skilled artisan can, e.g., by means of structural prediction programs, available structures of proteins or experimental determination of a structure determine which region of a protein is best suited to be in contact with the surface or the linker. In an illustrative embodiment, a protein is known to have two structural domains, a first domain with catalytic activity and a second domain. In a specific embodiment, the second domain is linked to the surface of the solid support. In another embodiment, the first domain is linked to the surface of the solid support. Without being bound by theory, immobilization directly through the domain with the catalytic activity may inhibit activity. Immobilization of catalytic domains may not be desirable. Instead, immobilization through a fused domain or protein may offer better activity.

Other factors to be considered in generating the microarrays to be used with the methods of the invention are: Enzymatic activities increase with the amounts of enzymes and substrates. Higher activities will also result if the effective concentrations of enzyme and substrate are higher. Proteins may denature at liquid/solid or air/liquid interface, resulting in less activity. Restricting enzyme or substrate conformations on a surface may reduce productive interactions between the molecules. The diffusion rate of large molecules is low, and the rate of reaction can be diffusion-limited.

In certain embodiments, slides with high protein binding capacities are used to increase local enzyme and/or substrate concentrations. Without being limited by theory, bringing enzymes and substrates into closer proximity may increase the effective concentrations. Immobilization of a protein or a substance by non-specific adsorption may denature a protein. Interactions between slide surface and a protein or a substance may reduce their diffusion rates. The interactions increase with larger surface areas as on surfaces made of porous materials or matrices. Further, entrapment or immobilization using indirect methods may be less disruptive to the enzymes.

For the microarray assay to work effectively, the background signals from labeled molecules need to be minimized. In certain embodiments, the interactions between the surface and a labeled molecule that is used in the enzymatic reaction can be blocked with a non-labeled molecule before or during the enzymatic reaction to minimize background. The binding kinetics of molecules often depend on the concentrations of the probe, available slide surface areas for binding, temperature as well as the specific chemistry. Slides made of matrices or porous materials have much higher surface areas and thus potentially more interactions with the labeled molecules.

In certain embodiments, surfaces having slower binding kinetics compared to the assay time may offer better signal to background.

In certain embodiments, surfaces with lower protein binding capacities may reduce background. However, the binding capacity must be weighed with the sensitivity of the enzymatic assay as a reduction in enzyme will also reduce signal intensity.

Other considerations include that surface chemistry also affects the making of protein microarrays. The surface properties, such as hydrophobicity, flatness, and homogeneity, influence the amount of proteins delivered to the slide and the size and morphology of the spots. These factors will ultimately affect the assay sensitivity and reproducibility.

Typically, in the methods of the present invention, a substance (e.g., a substrate of an enzymatic reaction) and a protein (e.g., an enzyme) are immobilized on the surface of a solid support before the protein and the substance are incubated under conditions conducive to the occurrence of an enzymatic reaction between the protein and the substance. Furthermore, the protein and the substance remain immobilized during at least a portion of the incubation step on the surface of the solid support at the location at which they were immobilized before the incubation step, for at least a time sufficient for the enzymatic reaction between the substance and the protein to take place. In certain embodiments of the methods of the present invention, a substance (e.g., a substrate of an enzymatic reaction) and a protein (e.g., an enzyme) are immobilized on the surface of a solid support in a manner such that they remain immobilized throughout the incubation step, at the same location at which they were immobilized on the solid support before the incubation step, and optionally can remain immobilized during the determining step as well at the location. The immobilization of the substance and the protein before the incubation step provides a difference between the present invention and traditional solution based assays, in which both protein and substance were not immobilized before the incubation step.

Accordingly, an incubating step of a method of the invention can be performed with one aliquot of incubation buffer covering the entire surface of a solid support containing multiple different immobilized proteins and/or multiple different immobilized substances. Alternatively, an incubation step (a) of a method of the invention can be performed with one aliquot of incubation buffer covering the entire surface of a region of a solid support containing, wherein the region includes multiple different immobilized proteins and/or multiple different immobilized substances.

In an illustrative example, a mixture of five different substrates is immobilized on the surface of a solid support such that the surface of the solid support is coated with the mixture of the five different substrates. In addition, for example five hundred different proteins are immobilized on the surface of the solid support in a positionally addressable fashion, for example by printing the proteins on the solid support that has been coated with the mixture of substrates. Thus, 2500 different protein-substrate combinations are generated on the surface of the solid support, wherein the protein at any position on the surface can be identified because it was immobilized in a positionally addressable fashion. For the incubating step in this illustrative example, all 2500 different protein combinations are covered with one continuous aliquot of reaction buffer without any separation of reaction buffer over the surface of the solid support. The 2500 different substance-protein combinations remain immobilized before and throughout at least a portion of the incubation step. Without being bound by theory, because the proteins and the substrates are immobilized on the surface of the solid support, neither protein nor substrate diffuses away from its original position on the surface of the solid support during at least a portion of the incubation step sufficient for a reaction between the protein and the substrate to occur. In certain aspects, repeating regions of the 2500 different immobilized protein-substrate combinations are included on the surface of the same solid support. In these aspects, each different region containing the 2500 different substance-protein combinations can be covered with a different reaction buffer, for example where each different reaction buffer is identical except that it contains a different test molecule.

In another illustrative example, five different substrates are immobilized on the surface of a solid support by coating the substrates on the solid support, each different substrate is immobilized in a different region of the surface of the solid support. Thus, the surface of the solid support is coated with the different substrates. In addition, a plurality of five hundred different proteins is immobilized on the surface of the solid support in a positionally addressable fashion, such as by being printed onto the surface of the solid support. Thus, 2500 different protein-substrate combinations are generated on the surface of the solid support, wherein the protein at any position on the surface can be identified because it was immobilized in a positionally addressable fashion. For the incubating step in this illustrative example, all 2500 different protein combinations are covered with one continuous aliquot of reaction buffer without any separation of reaction buffer over the surface of the solid support.

The substrates and the proteins are immobilized before they are incubated under conditions conducive to the occurrence of an enzymatic reaction between a protein and a substrate that are in proximity sufficient for the occurrence of the enzymatic reaction. Furthermore, the substrates and the proteins remain immobilized for at least a portion of the incubation step such that the enzymatic reaction occurs. Furthermore, in certain embodiments, depending for example on the specific method used to immobilize the proteins and the substrates, the proteins and the substrate can remain immobilized throughout the incubation step. However, for the present invention it is not necessary that the protein remains immobilized throughout the incubating and determining steps, since a determination of whether the reaction occurs is typically made by detecting a reaction product, which typically remains immobilized throughout the incubation step.

In even another illustrative example, five different substances are immobilized on the surface of the solid support, each different substance forming a patch at a defined position of the surface of the solid support. In addition, five different proteins are immobilized on the surface of the solid support within each patch, also in a positionally addressable fashion. Thus, 25 different positionally addressable substance-protein combinations are generated on the surface of the solid support. For the incubating step, all 25 different combinations can be covered with one continuous aliquot of reaction buffer without any separation of reaction buffer over the areas of the different combinations.

In certain embodiments, the protein (e.g., an enzyme) and the substance (e.g., a substrate of the enzyme) are immobilized on the surface of a solid support such that the protein and the substance remain continuously immobilized on the surface of the solid support after one or more washing steps. In certain, more specific embodiments, the protein and the substance remain immobilized on the surface of the solid support after at least one, at least two, at least three, at least four, at least five, at least six, at least seven, at least eight, at least nine, or at least ten washing steps. The washing steps are carried out under conditions that do not break covalent bonds. In other embodiments, the protein is immobilized before an incubation step and remains immobilized on the surface of the solid support only for a period of time sufficient for the enzymatic reaction between the protein and the substance. In these embodiments, occurrence of the enzymatic reaction can be determined by detecting a product that is immobilized on the surface of the substrate at the location of the substance.

In certain embodiments, the protein (e.g., an enzyme) is immobilized on the surface of a solid support with a dissociation constant (i.e., dissociation from immobilized state into a liquid phase that covers the surface of the solid support) of less than 1000 $\mu M$, less than 100 $\mu M$, less than 10 $\mu M$, less than 1 $\mu M$, less than 0.1 $\mu M$, less than 0.01 $\mu M$, less than 0.001 $\mu M$, or less than 0.0001 $\mu M$, and the substance (e.g., the substrate of the enzyme) is immobilized on the surface of a solid support with a dissociation constant of less than 1000 $\mu M$, less than 100 $\mu M$, less than 10 $\mu M$, less than 1 $\mu M$, less than 0.1 $\mu M$, less than 0.01 $\mu M$, less than 0.001 $\mu M$, or less than 0.0001 $\mu M$. In certain embodiments, Phosphate Buffered Saline (PBS) is added to the surface of a solid support and the ratio between immobilized protein and protein that is dissolved in PBS can be determined. In certain embodiments, the ratio between immobilized protein and protein that is dissolved in PBS is at least 1:1; 10:1; 100:1; $10^3$:1; $10^4$:1; $10^5$:1; $10^6$:1; $10^7$:1; $10^8$:1; $10^9$:1; or at least $10^{10}$:1. In certain, more specific, embodiments, at least 1%, at least 5%, at least 10%, at least 25%, at least 50%, at least 75%, at least 90%, at least 95%, or at least 98% of the protein that was immobilized before the enzymatic reaction and the substance that was immobilized before the enzymatic reaction, respectively, remains immobilized after the enzymatic reaction.

In methods provided herein, the protein (e.g., a candidate enzyme) and the substance (e.g., a candidate substrate of the enzyme) are typically immobilized on the surface of a solid support before an enzymatic reaction occurs between the protein and the substrate. Occurrence of the enzymatic reaction can be determined by detecting an immobilized product at the same location on the surface of the solid support as was initially occupied by the substance.

In certain embodiments, the protein and the substance are immobilized on the surface of a solid support before the incubation step and remain associated to the solid support for a storage period of at least one day, two days, three days, four days, five days, six days, one week, one month, two months, three months, four months, six months, or one year. In certain embodiments, an interaction between the protein (e.g., a candidate enzyme) and the substance (e.g., a candidate substrate) is not required for immobilization of the protein and the substance. In certain embodiments, immobilization of the protein is independent of immobilization of the substance, and, conversely, immobilization of the substance is independent of immobilization of the protein.

In certain aspects of the methods provided herein, after a substance and a protein are immobilized on a solid support, but before incubating the protein and the substance under conditions conducive to the occurrence of an enzymatic reaction between the protein and the substance, the solid support is transported from a first location to a second location and/or between a first organization and a second organization. For example, the solid support with the immobilized protein and the immobilized substance can be shipped from a supplier to an end user. In certain aspects, methods provided herein include a purchase of the solid support containing the immobilized protein and the immobilized substance by a customer from a supplier and the transport of the substrate from the supplier to the customer. This purchase can be performed, for example, using an automated process, such as an internet-based process. The solid support with the immobilized proteins and the immobilized substances can be transported in a storage buffer, for example a storage buffer that includes glycerol.

5.2. Enzymatic Reactions and their Quantification

In certain embodiments, an enzymatic reaction of interest is performed wherein a substance and a protein are immobilized on the surface of a solid support such that the substance and the protein are in proximity sufficient for the occurrence of the enzymatic reaction. The reaction is performed by incubating the substance and the protein in a reaction mixture or reaction buffer that provides conditions conducive to the occurrence of the enzymatic reaction. The reaction conditions provided by the reaction buffer or mixture depend on the type of enzymatic reaction being performed and include, but are not limited to, salt concentration, detergent concentration, cofactors and pH. Other reaction conditions, such as temperature, also depend on the type of enzymatic reaction being performed.

Any enzymatic reaction known to the skilled artisan can be performed with the methods of the invention. If the reaction involves more than one substrate, at least one substrate is immobilized, the other substrates can also be immobilized or can be in solution. In certain embodiments, if the enzymatic reaction involves one or more co-factors, such as, but not limited to, NAD, NADH or ATP, such a co-factor can be in solution or can also be immobilized on the surface of the solid support. Any method known to the skilled artisan can be used to visualize and quantitate the activity of the enzyme.

In certain embodiments, the enzymatic reaction is performed such that the generation of the product of the reaction results in the emergence of a detectable signal. In certain embodiments, the enzymatic reaction is performed such that an increase in concentration of the product of the reaction results in an increase of a detectable signal. In other embodiments, the enzymatic reaction is performed such that an increase in concentration of the product of the reaction results in a decrease of a detectable signal. In certain embodiments, the enzymatic reaction is performed such that an decrease of substrate concentration results in the increase or decrease of a detectable signal.

In certain embodiments, standard enzymatic assays that produce chemiluminescence or fluorescence are performed using a microarray, wherein enzyme and substrate are immobilized on the surface of a solid support. Detection and quantification of an enzymatic reaction can be accomplished using, for example, photoluminescence, radioactivity, fluorescence using non-protein substrates, enzymatic color development, mass spectroscopic signature markers, and amplification (e.g., by PCR) of oligonucleotide tags. In a specific embodiment, peptides or other compounds released into solution by the enzymatic reaction of the array elements can be identified by mass spectrometry.

The types of assays to detect and quantify the products (or the decrease of substrate) of an enzymatic reaction fall into several general categories. Such categories of assays include, but not limited to: 1) using radioactively labeled reactants followed by autoradiography and/or phosphoimager analysis; 2) binding of hapten, which is then detected by a fluorescently labeled or enzymatically labeled antibody or high affinity hapten ligand such as biotin or streptavidin; 3) mass spectrometry; 4) atomic force microscopy; 5) fluorescent polarization methods; 6) rolling circle amplification-detection methods (Schweitzer et al., 2000, "Immunoassays With Rolling Circle DNA Amplification: A Versatile Platform For Ultrasensitive Antigen Detection", Proc. Natl. Acad. Sci. USA 97:10113-10119); 7) competitive PCR (Fini et al., 1999, "Development of a chemiluminescence competitive PCR for the detection and quantification of parvovirus B19 DNA using a microplate luminometer", Clin Chem. 45(9):1391-6; Kruse et al., 1999, "Detection and quantitative measurement of transforming growth factor-beta1 (TGF-beta1) gene expression using a semi-nested competitive PCR assay", Cytokine 11(2):179-85; Guenthner and Hart, 1998, "Quantitative, competitive PCR assay for HIV-1 using a microplate-based detection system", Biotechniques 24(5):810-6); 8) calorimetric procedures; and 9) FRET.

Useful information also can be obtained, for example, by performing the assays of the invention with cell extracts. In a specific embodiment, different substrates of an enzymatic reaction are immobilized on the surface of a solid support and the proteins of the cell extract are also immobilized on the surface. The proteins of the cell extract and the substrates of an enzymatic reaction are then incubated with a reaction mixture providing conditions conducive to the occurrence of the enzymatic reaction. The cellular repertoire of particular enzymatic activities can thereby be assessed.

In a more specific embodiment, a plurality of different substrates is immobilized on the surface of the solid support in a well. In specific embodiments, a plurality of wells is present on the microarray and each well contains the plurality of different substrates. The proteins of a cellular extract are also immobilized on the surface of the solid support in wells. Thus, different enzymatic reactions can be tested simultaneously on the microarray. In certain embodiments, the assay of the invention can be performed with whole cells or preparations of plasma membranes. Thus, use of several classes of substrates and reaction buffers can provide for large-scale or exhaustive analysis of cellular activities. In particular, one or several screens can form the basis of identifying a "footprint" of the cell type or physiological state of a cell, tissue, organ or system. For example, different cell types (either morphological or functional) can be differentiated by the pattern of cellular activities or expression determined by the protein chip. This approach also can be used to determine, for example, different stages of the cell cycle, disease states, altered physiologic states (e.g., hypoxia), physiological state before or after treatment (e.g., drug treatment), metabolic state, stage of differentiation or development, response to environmental stimuli (e.g., light, heat), cell-cell interactions, cell-specific gene and/or protein expression, and disease-specific gene and/or protein expression.

In a specific embodiment, compounds that modulate the enzymatic activity of a protein or proteins on a chip can be identified. For example, changes in the level of enzymatic activity are detected and quantified by incubation of a compound or mixture of compounds with an enzymatic reaction on the microarray, wherein a signal is produced (e.g., from substrate that becomes fluorescent upon enzymatic activity). Differences between the presence and absence of the compound are noted. Furthermore, the differences in effects of compounds on enzymatic activities of different proteins are readily detected by comparing their relative effect on samples within the protein chips and between chips.

In certain embodiments, the enzymatic activity detected using a method of the invention is in part due to autocatalysis, i.e., the enzyme acts on itself as well as on a substrate. A nonlimiting example of autocatalysis is auto-phosphorylation.

In certain embodiments, immobilizing a substance and a protein in proximity sufficient for the occurrence of an enzymatic reaction between the substance and the protein induces the catalytic activity of the protein. In certain embodiments, immobilizing a substance and a protein in proximity sufficient for the occurrence of an enzymatic reaction between the substance and the protein induces the autocatalytic activity of the protein.

In certain embodiments, an enzymatic activity is enhanced by immobilizing enzyme and substrate in proximity sufficient for the occurrence of the enzymatic reaction. In a specific embodiment, the activity is enhanced compared to the activity in solution.

In certain aspects of the invention, the protein is an enzyme that catalyzes a reaction in which a detectable group is associated with, or dissociated from, a substrate. For example, the detectable group can be a labeled moiety, such as a labeled phosphate group, sugar moiety, polysaccharide, nucleotide, oligonucleotide, amino acid, or peptide.

In certain embodiments, the protein immobilized in methods provided herein is typically an enzyme or a protein that is being analyzed to determine whether it is an enzyme. In certain aspects, a substrate and an enzyme are immobilized on a solid support in methods for assaying an enzymatic reaction provided herein. The enzyme can include any biomolecule known to possess enzymatic activity including, but not limited to, proteins and nucleic acids.

Any enzyme known to the skilled artisan can be used with the methods of the invention and with protein arrays of the invention. Classes of enzymes include, but are not limited to, Oxidoreductases, Transferases, Hydrolases, Lyases, Isomerases, and Ligases. Enzymes that can be used with the methods of the invention and immobilization on the microarrays of the invention include but are not limited to those shown in Table 1.

TABLE 1

List of Enzymes

OXIDOREDUCTASES

Alcohol dehydrogenase, Alcohol dehydrogenase (NADP+), Homoserine dehydrogenase, (R,R)-butanediol dehydrogenase, Acetoin dehydrogenase Glycerol dehydrogenase, Propanediol-phosphate dehydrogenase, Glycerol-3-phosphate dehydrogenase (NAD+), D-xylulose reductase, L-xylulose reductase, D-arabinitol 4-dehydrogenase, L-arabinitol 4-dehydrogenase, L-arabinitol 2-dehydrogenase (ribulose forming), L-iditol 2-dehydrogenase, D-iditol 2-dehydrogenase, Galactitol 2-dehydrogenase, Mannitol-1-phosphate 5-dehydrogenase, Myo-inositol 2-dehydrogenase, Glucuronate reductase, Glucuronolactone reductase, Aldehyde reductase, UDP-glucose 6-dehydrogenase, Histidinol dehydrogenase, Quinate 5-dehydrogenase, Shikimate 5-dehydrogenase, Glycolate reductase, L-lactate dehydrogenase, D-lactate dehydrogenase, Glycerate dehydrogenase, 3-hydroxybutyrate dehydrogenase, 3-hydroxyisobutyrate dehydrogenase, Mevaldate reductase, Mevaldate reductase (NADPH), Hydroxymethylglutaryl-CoA reductase (NADPH), 3-hydroxyacyl-CoA dehydrogenase, Acetoacetyl-CoA reductase, Malate dehydrogenase, Malate dehydrogenase (oxaloacetate decarboxylating), Malate dehydrogenase (decarboxylating), Malate dehydrogenase (oxaloacetate decarboxylating) (NADP+), Isocitrate dehydrogenase (NAD+), Isocitrate dehydrogenase (NADP+), 6-phosphogluconate 2-dehydrogenase, Phosphogluconate dehydrogenase (decarboxylating), L-gulonate 3-dehydrogenase, L-arabinose 1-dehydrogenase, Glucose 1-dehydrogenase, D-galactose 1-dehydrogenase, Glucose-6-phosphate 1-dehydrogenase, 3-alpha-hydroxysteroid dehydrogenase (B-specific), 3 (or 17)beta-hydroxysteroid dehydrogenase, 3-alpha-hydroxycholanate dehydrogenase, 3-alpha(or 20-beta)-hydroxysteroid dehydrogenase, Allyl-alcohol dehydrogenase, Lactaldehyde reductase (NADPH), Ribitol 2-dehydrogenase, Fructuronate reductase, Tagaturonate reductase, 3-hydroxypropionate dehydrogenase, 2-hydroxy-3-oxopropionate reductase, 4-hydroxybutyrate dehydrogenase, Estradiol 17 beta-dehydrogenase, Testosterone 17-beta-dehydrogenase, Testosterone 17-beta-dehydrogenase (NADP+), Pyridoxine 4-dehydrogenase, Omega-hydroxydecanoate dehydrogenase, Mannitol 2-dehydrogenase, Gluconate 5-dehydrogenase, Alcohol dehydrogenase (NAD(P)+), Glycerol dehydrogenase (NADP+), Octanol dehydrogenase, R)-aminopropanol dehydrogenase, (S,S)-butanediol dehydrogenase, Lactaldehyde reductase, D-lactaldehyde dehydrogenase, Glyoxylate reductase (NADP+), Isopropanol dehydrogenase (NADP+), Hydroxypyruvate reductase, Malate dehydrogenase (NADP+), D-malate dehydrogenase (decarboxylating), Dimethylmalate dehydrogenase, 3-isopropylmalate dehydrogenase, Ketol-acid reductoisomerase, 3-carboxy-2-hydroxyadipate dehydrogenase, Hydroxymethylglutaryl-CoA reductase, Aryl-alcohol dehydrogenase, Aryl-alcohol dehydrogenase (NADP+), Oxaloglycolate reductase (decarboxylating), Tartrate dehydrogenase, Glycerol-3-phosphate dehydrogenase (NAD(P)+), Phosphoglycerate dehydrogenase, Diiodophenylpyruvate reductase, 3-hydroxybenzyl-alcohol dehydrogenase, (R)-2-hydroxy-fatty-acid dehydrogenase, (S)-2-hydroxy-fatty-acid dehydrogenase, 3-oxoacyl-[acyl-carrier protein] reductase, Acylglycerone-phosphate reductase, 3-dehydrosphinganine reductase, L-threonine 3-dehydrogenase, 4-oxoproline reductase, Retinol dehydrogenase, Pantoate 4-dehydrogenase, Pyridoxal TABLE 1-continued List of Enzymes 4-dehydrogenase, Carnitine 3-dehydrogenase, Indole-3-lactate dehydrogenase, 3-(imidazol-5-yl)lactate dehydrogenase, Indanol dehydrogenase, L-xylose 1-dehydrogenase, Apiose 1-reductase, Ribose 1-dehydrogenase (NADP+), D-arabinose 1-dehydrogenase, D-arabinose 1-dehydrogenase (NAD(P)+), Glucose 1-dehydrogenase (NAD+), Glucose 1-dehydrogenase (NADP+), Galactose 1-dehydrogenase (NADP+), Aldose 1-dehydrogenase, D-threo-aldose 1-dehydrogenase, Sorbose 5-dehydrogenase (NADP+), Fructose 5-dehydrogenase (NADP+), 2-deoxy-D-gluconate 3-dehydrogenase, 2-dehydro-3-deoxy-D-gluconate 6-dehydrogenase, 2-dehydro-3-deoxy-D-gluconate 5-dehydrogenase, L-idonate 2-dehydrogenase,
L-threonate 3-dehydrogenase, 3-dehydro-L-gulonate 2-dehydrogenase, Mannuronate reductase, GDP-mannose 6-dehydrogenase, dTDP-4-dehydrorhamnose reductase, dTDP-6-deoxy-L-talose 4-dehydrogenase, GDP-
6-deoxy-D-talose 4-dehydrogenase, UDP-N-acetylglucosamine 6-dehydrogenase, Ribitol-5-phosphate 2-dehydrogenase, Mannitol 2-dehydrogenase (NADP+), Sorbitol-6-phosphate 2-dehydrogenase, 15-hydroxyprostaglandin dehydrogenase (NAD+), D-pinitol dehydrogenase, Sequoyitol dehydrogenase, Perillyl-alcohol dehydrogenase, 3-beta-hydroxy-delta(5)-steroid dehydrogenase, 11-beta-hydroxysteroid dehydrogenase, 16-alpha-hydroxysteroid dehydrogenase, Estradiol 17-alpha-dehydrogenase, 20-alpha-hydroxysteroid dehydrogenase, 21-hydroxysteroid dehydrogenase (NAD+), 21-hydroxysteroid dehydrogenase (NADP+), 3-alpha-hydroxy-5-beta-androstane-17-one 3-alpha-dehydrogenase, Sepiapterin reductase, Ureidoglycolate dehydrogenase, Homoisocitrate dehydrogenase, Glycerol 2-dehydrogenase (NADP+), 3-hydroxybutyryl-CoA dehydrogenase, UDP-N-acetylmuramate dehydrogenase,
7-alpha-hydroxysteroid dehydrogenase, Dihydrobunolol dehydrogenase, Cholestanetetraol 26-dehydrogenase, Erythrulose reductase, Cyclopentanol dehydrogenase, Hexadecanol dehydrogenase, 2-alkyn-1-ol dehydrogenase, Hydroxycyclohexanecarboxylate dehydrogenase, Hydroxymalonate dehydrogenase, 2-dehydropantolactone reductase (A-specific), 2-dehydropantoate 2-reductase, Sterol-4-alpha-carboxylate 3-dehydrogenase (decarboxylating), 2-oxoadipate reductase, L-rhamnose 1-dehydrogenase, Cyclohexane-1,2-diol dehydrogenase, D-xylose 1-dehydrogenase, 12-alpha-hydroxysteroid dehydrogenase, Glycerol-3-phosphate 1-dehydrogenase (NADP+), 3-hydroxy-2-methylbutyryl-CoA dehydrogenase, D-xylose 1-dehydrogenase (NADP+), Cholest-5-ene-3-beta, 7-alpha-diol 3-beta-dehydrogenase, Geraniol dehydrogenase, Carbonyl reductase (NADPH), L-glycol dehydrogenase, dTDP-galactose 6-dehydrogenase, GDP-4-dehydro-D-rhamnose reductase, Prostaglandin-F synthase, Prostaglandin-E2 9-reductase, Indole-3-acetaldehyde reductase (NADH), Indole-3-acetaldehyde reductase (NADPH), Long-chain-alcohol dehydrogenase, 5-amino-6-(5-phosphoribosylamino)uracil reductase, Coniferyl-alcohol dehydrogenase, Cinnamyl-alcohol dehydrogenase, 15-hydroxyprostaglandin-D dehydrogenase (NADP+), 15-hydroxyprostaglandin dehydrogenase (NADP+), (+)-borneol dehydrogenase, (S)-usnate reductase, Aldose-6-phosphate reductase (NADPH), 7-beta-hydroxysteroid dehydrogenase (NADP+), 1,3-propanediol dehydrogenase, Uronate dehydrogenase, Xanthine dehydrogenase, IMP dehydrogenase, Tropine dehydrogenase, (-)-menthol dehydrogenase, (+)-neomenthol dehydrogenase, 3(or 17)-alpha-hydroxysteroid dehydrogenase, 3-beta(or 20-alpha)-hydroxysteroid dehydrogenase, Long-chain-3-hydroxyacyl-CoA dehydrogenase, 3-oxoacyl-[acyl-carrier protein] reductase (NADH),3-alpha-hydroxysteroid dehydrogenase (A-specific), 2-dehydropantolactone reductase (B-specific), Gluconate 2-dehydrogenase, Farnesol dehydrogenase, Benzyl-2-methyl-hydroxybutyrate dehydrogenase, Morphine 6-
dehydrogenase, Dihydrokaempferol 4-reductase, 6-pyruvoyltetrahydropterin 2'-reductase, Vomifoliol 4'-dehydrogenase, (R)-4-hydroxyphenyllactate dehydrogenase, Isopiperitenol dehydrogenase, Mannose-6-phosphate 6-reductase, Chlordecone reductase, 4-hydroxycyclohexanecarboxylate dehydrogenase, (-)-borneol dehydrogenase, (+)-sabinol dehydrogenase, Diethyl 2-methyl-3-oxosuccinate reductase, 3-alpha-hydroxyglycyrrhetinate dehydrogenase, 15-hydroxyprostaglandin-I dehydrogenase (NADP+), 15-hydroxyicosatetraenoate dehydrogenase, N-acylmannosamine 1-dehydrogenase, Flavonone 4-reductase, 8-oxocoformycin
reductase, Tropinone reductase, Hydroxyphenylpyruvate reductase, 12-beta-hydroxysteroid dehydrogenase, 3-alpha (17-beta)-hydroxysteroid dehydrogenase (NAD+), N-acetylhexosamine 1-dehydrogenase, 6-endo-hydroxycineole dehydrogenase, Carveol dehydrogenase, Methanol dehydrogenase, Cyclohexanol dehydrogenase, Pterocarpin synthase, Codeinone
reductase (NADPH), Salutaridine reductase (NADPH), D-arabinitol 2-

TABLE 1-continued

List of Enzymes dehydrogenase, Galactitol-1-phosphate 5-dehydrogenase, Tetrahydroxynaphthalene reductase, Pteridine reductase, (S)-carnitine 3-dehydrogenase, Mannitol dehydrogenase, Fluoren-9-ol dehydrogenase, 4-(hydroxymethyl)benzenesulfonate dehydrogenase, 6-hydroxyhexanoate dehydrogenase, 3-hydroxypimeloyl-CoA dehydrogenase, Sulcatone reductase, Glycerol-1-phosphate dehydrogenase [NAD(P)], 4-hydroxythreonine-4-phosphate dehydrogenase, 1,5-anhydro-D-fructose reductase, L-idonate 5-dehydrogenase, 3-methylbutanal reductase, dTDP-4-dehydro-6-deoxyglucose reductase, 1-deoxy-D-xylulose-5-phosphate reductoisomerase, 2-(R)-hydroxypropyl-CoM dehydrogenase, 2-(S)-hydroxypropyl-CoM dehydrogenase, 3-keto-steroid reductase, GDP-L-fucose synthase, (R)-2-hydroxyacid dehydrogenase, Vellosimine dehydrogenase, 2,5-didehydrogluconate reductase, Mannitol dehydrogenase (cytochrome), L-lactate dehydrogenase (cytochrome), D-lactate dehydrogenase (cytochrome), D-lactate dehydrogenase (cytochrome c-553), Malate oxidase, Glucose oxidase, Hexose oxidase, Cholesterol oxidase, Aryl-alcohol oxidase, L-gulonolactone oxidase, Galactose oxidase, Pyranose oxidase, L-sorbose oxidase, Pyridoxine 4-oxidase, Alcohol oxidase, Catechol oxidase (dimerizing), (S)-2-hydroxy-acid oxidase, Ecdysone oxidase, Choline oxidase, Secondary-alcohol oxidase, 4-hydroxymandelate oxidase, Long-chain-alcohol oxidase, Glycerol-3-phosphate oxidase, Xanthine oxidase, Thiamine oxidase, L-galactonolactone oxidase, Cellobiose oxidase, Hydroxyphytanate oxidase, Nucleoside oxidase, N-acylhexosamine oxidase, Polyvinyl-alcohol oxidase, Methanol oxidase, D-arabinono-1,4-lactone oxidase, Vanillyl-alcohol oxidase, Nucleoside oxidase (H(2)O(2)-forming), D-mannitol oxidase, Xylitol oxidase, Vitamin-K-epoxide reductase (warfarin-sensitive), Vitamin-K-epoxide reductase (warfarin-insensitive), Choline dehydrogenase, 2-hydroxyglutarate dehydrogenase, Gluconate 2-dehydrogenase (acceptor), Dehydrogluconate dehydrogenase, Glycerol-3-phosphate dehydrogenase, D-2-hydroxy-acid dehydrogenase, Lactate--malate transhydrogenase, Alcohol dehydrogenase (acceptor), Pyridoxine 5-dehydrogenase, Glucose dehydrogenase (acceptor), Fructose 5-dehydrogenase, Sorbose dehydrogenase, Glucoside 3-dehydrogenase, Glycolate dehydrogenase, Malate dehydrogenase (acceptor), Glucose dehydrogenase (pyrroloquinoline-quinone), Cellobiose dehydrogenase (acceptor), Uracil dehydrogenase, Alkan-1-ol dehydrogenase (acceptor), D-sorbitol dehydrogenase, Glycerol dehydrogenase (acceptor), Polyvinyl-alcohol dehydrogenase (acceptor), Hydroxyacid-oxoacid transhydrogenase, Quinate dehydrogenase (pyrroloquinoline-quinone), 3-hydroxycyclohexanone dehydrogenase, (R)-pantolactone dehydrogenase (flavin), Glucose--fructose oxidoreductase, Formaldehyde dehydrogenase (glutathione), Formate dehydrogenase, Aldehyde dehydrogenase (NAD+), Aldehyde dehydrogenase (NADP+), Aldehyde dehydrogenase (NAD(P)+), Benzaldehyde dehydrogenase (NADP+), Betaine-aldehyde dehydrogenase, Glyceraldehyde-3-phosphate dehydrogenase (NADP+), Acetaldehyde dehydrogenase (acetylating), Aspartate-semialdehyde dehydrogenase, Glyceraldehyde 3-phosphate dehydrogenase (phosphorylating), Glyceraldehyde 3-phosphate dehydrogenase (NADP+) (phosphorylating), Malonate-semialdehyde dehydrogenase, Succinate-semialdehyde dehydrogenase (NAD(P)+), Glyoxylate dehydrogenase (acylating), Malonate-semialdehyde dehydrogenase (acylating), Aminobutyraldehyde dehydrogenase, Glutarate-semialdehyde dehydrogenase, Glycolaldehyde dehydrogenase, Lactaldehyde dehydrogenase, 2-oxoaldehyde dehydrogenase (NAD+), Succinate-semialdehyde dehydrogenase, 2-oxoisovalerate dehydrogenase (acylating), 2,5-dioxovalerate dehydrogenase, Methylmalonate-semialdehyde dehydrogenase (acylating), Benzaldehyde dehydrogenase (NAD+), Aryl-aldehyde dehydrogenase, Aryl-aldehyde dehydrogenase (NADP+), Aminoadipate-semialdehyde dehydrogenase, Aminomuconate-semialdehyde dehydrogenase, (R)-dehydropantoate dehydrogenase, Retinal dehydrogenase, N-acetyl-gamma-glutamyl-phosphate reductase, Phenylacetaldehyde dehydrogenase, 3-alpha, 7-alpha, 12-alpha-trihydroxycholestan-26-al 26-oxidoreductase, Glutamate-5-semialdehyde dehydrogenase, Hexadecanal dehydrogenase (acylating), Formate dehydrogenase (NADP+), Cinnamoyl-CoA reductase, 4-carboxy-2-hydroxymuconate-6-semialdehyde dehydrogenase, Formaldehyde dehydrogenase, 4-trimethylammoniobutyraldehyde dehydrogenase, Long-chain-aldehyde dehydrogenase, 2-oxoaldehyde dehydrogenase (NADP+), Long-chain- fatty-acyl-CoA reductase, Pyruvate dehydrogenase (NADP+), Oxoglutarate dehydrogenase (NADP+), 4-hydroxyphenylacetaldehyde dehydrogenase, Gamma-guanidinobutyraldehyde dehydrogenase, (R)-3-hydroxyacid ester dehydrogenase, (S)-3-hydroxyacid ester dehydrogenase, Butanal dehydrogenase, Phenylglyoxylate dehydrogenase (acylating), Glyceraldehyde 3-phosphate dehydrogenase (NAD(P)) (phosphorylating), 5-carboxymethyl-2-hydroxymuconic-semialdehyde dehydrogenase, 4-hydroxymuconic-semialdehyde dehydrogenase, 4-formylbenzenesulfonate dehydrogenase, 6-oxohexanoate dehydrogenase, 4-hydroxybenzaldehyde dehydrogenase, Salicylaldehyde dehydrogenase, Mycothiol-dependent formaldehyde dehydrogenase, Vanillin dehydrogenase, Coniferyl-aldehyde dehydrogenase, Formate dehydrogenase (cytochrome), Pyruvate dehydrogenase (cytochrome), Formate dehydrogenase (cytochrome c-553), Carbon monoxide oxygenase (cytochrome b-561), Aldehyde oxidase, Pyruvate oxidase, Oxalate oxidase, Glyoxylate oxidase, Pyruvate oxidase (CoA-acetylating), Indole-3-acetaldehyde oxidase, Pyridoxal oxidase, Aryl-aldehyde oxidase, Carbon-monoxide oxidase, Retinal oxidase, Vanillate demethylase, 4-hydroxyphenylpyruvate oxidase, Pyruvate dehydrogenase (lipoamide), Oxoglutarate dehydrogenase (lipoamide), 3-methyl-2-oxobutanoate dehydrogenase (lipoamide), Pyruvate synthase, 2-oxobutyrate synthase, 2-oxoglutarate synthase, Carbon-monoxide dehydrogenase, Aldehyde dehydrogenase (pyrroloquinoline-quinone), Formaldehyde dismutase, Formylmethanofuran dehydrogenase, Carboxylate reductase, Dihydrouracil dehydrogenase (NAD+), Dihydropyrimidine dehydrogenase (NADP+), Cortisone beta-reductase, Cortisone alpha-reductase, Cucurbitacin delta(23) reductase, Fumarate reductase (NADH), Meso-tartrate dehydrogenase, Acyl-CoA dehydrogenase (NADP+), Enoyl-[acyl-carrier protein] reductase (NADH), Enoyl-[acyl-carrier protein] reductase (NADPH, B-specific), Coumarate reductase, Prephenate dehydrogenase, Prephenate dehydrogenase (NADP+), Orotate reductase (NADH), Orotate reductase (NADPH), Beta-nitroacrylate reductase, 3-methyleneoxindole reductase, Kynurenate-7, 8-dihydrodiol dehydrogenase, Cis-1,2-dihydrobenzene-1,2-diol dehydrogenase, Trans-1,2-dihydrobenzene-1,2-diol dehydrogenase, 7-dehydrocholesterol reductase, Cholestenone 5-alpha-reductase, Cholestenone 5-beta-reductase, Biliverdin reductase, 1,6-dihydroxycyclohexa-2,4-diene-1-carboxylate dehydrogenase, Dihydrodipicolinate reductase, 2-hexadecenal reductase, 2,3-dihydro-2,3-dihydroxybenzoate dehydrogenase, Cis-1,2-dihydro-1,2-dihydroxynaphthalene dehydrogenase, Progesterone 5-alpha-reductase, 2-enoate reductase, Maleylacetate reductase, Protochlorophyllide reductase, 2,4-dienoyl-CoA reductase (NADPH), Phosphatidylcholine desaturase, Geissoschizine dehydrogenase, Cis-2-enoyl-CoA reductase (NADPH), Trans-2-enoyl-CoA reductase (NADPH), Enoyl-[acyl-carrier protein] reductase (NADPH, A-specific), 2-hydroxy-6-oxo-6-phenylhexa-2,4-dienoate reductase, Xanthommatin reductase, 12-oxophytodienoate reductase, Cyclohexadienyl dehydrogenase, Trans-2-enoyl-CoA reductase (NAD+), 2'-hydroxyisoflavone reductase, Biochanin-A reductase, Alpha-santonin 1,2-reductase, 15-oxoprostaglandin 13-reductase, Cis-3,4-dihydrophenanthrene-3,4-diol dehydrogenase, 2'-hydroxydaidzein reductase, 2-methyl-branched-chain-enoyl-CoA reductase, (3S,4R)-3,4-dihydroxycyclohexa-1,5-diene-1,4-dicarboxylate dehydrogenase, Precorrin-6X reductase, Cis-1,2-dihydroxycyclohexa-3,5-diene-1-carboxylate dehydrogenase, Cis-2,3-dihydrobiphenyl-2,3-diol dehydrogenase, Phloroglucinol reductase, 2,3-dihydroxy-2,3-dihydro-p-cumate dehydrogenase, 1,6-dihydroxy-5-methylcyclohexa-2,4-dienecarboxylate dehydrogenase, Dibenzothiophene dihydrodiol dehydrogenase, Terephthalate 1,2-cis-dihydrodiol dehydrogenase, Pimeloyl-CoA dehydrogenase, 2,4-dichlorobenzoyl-CoA reductase, Phthalate 4,5-cis-dihydrodiol dehydrogenase, 5,6-dihydroxy-3-methyl-2-oxo-1,2,5,6-tetrahydroquinoline dehydrogenase, Cis-dihydroethylcatechol dehydrogenase, Cis-1,2-dihydroxy-4-methylcyclohexa-3,5-diene-1-carboxylatedehydrogenase, 1,2-dihydroxy-6-methylcyclohexa-3,5-dienecarboxylate dehydrogenase, Zeatin reductase, Delta(14)-sterol reductase, Delta(24(24(1)))-sterol reductase, Delta(24)-sterol reductase, 1,2-dihydrovomilenine reductase, Galactonolactone dehydrogenase, Dihydroorotate oxidase, Lathosterol oxidase, Coproporphyrinogen oxidase, Protoporphyrinogen oxidase, Bilirubin oxidase, Acyl-CoA oxidase, Dihydrouracil oxidase, Tetrahydroberberine oxidase, Secologanin synthase, Succinate dehydrogenase (ubiquinone), 6-hydroxynicotinate reductase, 15,16-dihydrobiliverdin:ferredoxin

TABLE 1-continued

List of Enzymes oxidoreductase, Phycoerythrobilin:ferredoxin oxidoreductase, Phytochromobilin:ferredoxin oxidoreductase, Phycocyanobilin:ferredoxin oxidoreductase, Succinate dehydrogenase, Butyryl-CoA dehydrogenase, Acyl-CoA dehydrogenase, 3-oxosteroid 1-dehydrogenase, 3-oxo-5-alpha-steroid 4-dehydrogenase, 3-oxo-5-beta-steroid 4-dehydrogenase, Glutaryl-CoA dehydrogenase, 2-furoyl-CoA dehydrogenase, Isovaleryl-CoA dehydrogenase, Dihydroorotate dehydrogenase, 2-methylacyl-CoA dehydrogenase, Long-chain acyl-CoA dehydrogenase, Cyclohexanone dehydrogenase, Benzoyl-CoA reductase, Isoquinoline 1-oxidoreductase, Quinoline 2-oxidoreductase, Quinaldate 4-oxidoreductase, Quinoline-4-carboxylate 2-oxidoreductase, 4-hydroxybenzoyl-CoA reductase, Alanine dehydrogenase, Glutamate dehydrogenase, Glutamate dehydrogenase (NAD(P)+), Glutamate dehydrogenase (NADP+), L-amino-acid dehydrogenase, Serine dehydrogenase, Valine dehydrogenase (NADP+), Leucine dehydrogenase, Glycine dehydrogenase, L-erythro-3,5-diaminohexanoate dehydrogenase, 2,4-diaminopentanoate dehydrogenase, Glutamate synthase (NADPH), Glutamate synthase (NADH), Lysine dehydrogenase, Diaminopimelate dehydrogenase, N-methylalanine dehydrogenase, Lysine 6-dehydrogenase, Tryptophan dehydrogenase, Phenylalanine dehydrogenase, Glycine dehydrogenase (cytochrome), -aspartate oxidase, L-amino acid oxidase, D-amino acid oxidase, Amine oxidase (flavin-containing), Pyridoxamine-phosphate oxidase, Amine oxidase (copper-containing), D-glutamate oxidase, Ethanolamine oxidase, Putrescine oxidase, L-glutamate oxidase, Cyclohexylamine oxidase, Protein-lysine 6-oxidase, L-lysine oxidase, D-glutamate(D-aspartate) oxidase, L-aspartate oxidase, Tryptophan alpha, beta-oxidase, Glycine oxidase, Glycine dehydrogenase (decarboxylating), Glutamate synthase (ferredoxin), D-amino-acid dehydrogenase, Taurine dehydrogenase, Amine dehydrogenase, Aralkylamine dehydrogenase, Glycine dehydrogenase (cyanide-forming), Pyrroline-2-carboxylate reductase, Pyrroline-5-carboxylate reductase, Dihydrofolate reductase, Methylenetetrahydrofolate dehydrogenase (NADP+), Formyltetrahydrofolate dehydrogenase, Saccharopine dehydrogenase (NAD+, L-lysine forming), Saccharopine dehydrogenase (NADP+, L-lysine forming), Saccharopine dehydrogenase (NAD+, L-glutamate forming), Saccharopine dehydrogenase (NADP+, L-glutamate forming), D-octopine dehydrogenase, 1-pyrroline-5-carboxylate dehydrogenase, Nicotinate dehydrogenase, Methylenetetrahydrofolate dehydrogenase (NAD+), D-lysopine dehydrogenase, Alanopine dehydrogenase, Ephedrine dehydrogenase, D-nopaline dehydrogenase, Methylenetetrahydrofolate reductase (NADPH), Delta(1)-piperideine-2-carboxylate reductase, Strombine dehydrogenase, Tauropine dehydrogenase, N(5)-(carboxyethyl)ornithine synthase, Thiomorpholine-carboxylate dehydrogenase, Beta-alanopine dehydrogenase, 1,2-dehydroreticulinium reductase (NADPH), Opine dehydrogenase, FMN reductase, Flavin reductase, Berberine reductase, Vomilenine reductase, Sarcosine oxidase, N-methyl-L-amino-acid oxidase, N(6)-methyl-lysine oxidase, (S)-6-hydroxynicotine oxidase, (R)-6-hydroxynicotine oxidase, L-pipecolate oxidase, Dimethylglycine oxidase, Polyamine oxidase, Dihydrobenzophenanthridine oxidase, Pyrimidodiazepine synthase, Electron-transferring-flavoprotein dehydrogenase, Dimethylamine dehydrogenase, Trimethylamine dehydrogenase, Sarcosine dehydrogenase, Dimethylglycine dehydrogenase, L-pipecolate dehydrogenase, Nicotine dehydrogenase, Methylglutamate dehydrogenase, Spermidine dehydrogenase, Proline dehydrogenase, Methylenetetrahydromethanopterin dehydrogenase, Coenzyme F420-dependent N(5), N(10)-methenyltetrahydromethanopterin reductase, Cytokinin dehydrogenase, NAD(P)(+) transhydrogenase (B-specific), NAD(P)(+) transhydrogenase (AB-specific), Cytochrome-b5 reductase, NADPH--ferrihemoprotein reductase, NADPH--cytochrome c2 reductase, Leghemoglobin reductase, NADH dehydrogenase (ubiquinone), Monodehydroascorbate reductase (NADH), NADPH:quinone reductase, p-benzoquinone reductase (NADPH), 2-hydroxy-1,4-benzoquinone reductase, Trimethylamine-N-oxide reductase, NADPH dehydrogenase, NAD(P)H dehydrogenase (quinone), NADH dehydrogenase, NADH dehydrogenase (quinone), NADPH dehydrogenase (quinone), Dihydropteridine reductase, Nitrate reductase (NADH), Nitrate reductase (NAD(P)H), Nitrate reductase (NADPH), Nitrite reductase [NAD(P)H], Hyponitrite reductase, Azobenzene reductase, GMP reductase, Nitroquinoline-N-oxide reductase, Hydroxylamine reductase (NADH), 4-(dimethylamino)phenylazoxybenzene reductase, N-hydroxy-2-acetamidofluorene reductase, Nitrite reductase (NO-forming), Nitrite reductase (cytochrome; ammonia-forming), Trimethylamine-N-oxide reductase (cytochrome c), Nitroethane oxidase, Acetylindoxyl oxidase, Urate oxidase, Hydroxylamine oxidase, 3-aci-nitropropanoate oxidase, Ferredoxin--nitrite reductase, Ferredoxin--nitrate reductase, Hydroxylamine reductase, Nitrate reductase, 5,10-methylenetetrahydrofolate reductase (FADH), Nitrous-oxide reductase, Nitric-oxide reductase, Sulfite reductase (NADPH), Hypotaurine dehydrogenase, Dihydrolipoamide dehydrogenase, 2-oxopropyl-CoM reductase (carboxylating), Cystine reductase, Glutathione-disulfide reductase, Protein-disulfide reductase, Thioredoxin-disulfide reductase, CoA-glutathione reductase, Asparagusate reductase, Trypanothione-disulfide reductase, Bis-gamma-glutamylcystine reductase, CoA-disulfide reductase, Mycothione reductase, Sulfite dehydrogenase, Thiosulfate dehydrogenase, Sulfite oxidase, Thiol oxidase, Glutathione oxidase, Methanethiol oxidase, Prenylcysteine oxidase, Glutathione--homocystine transhydrogenase, Protein-disulfide reductase (glutathione), Glutathione--CoA-glutathione transhydrogenase, Glutathione--cystine transhydrogenase, Methionine-S-oxide reductase, Protein-methionine-S-oxide reductase, Enzyme-thiol transhydrogenase (glutathione-disulfide), Phosphoadenylyl-sulfate reductase (thioredoxin), Adenylyl-sulfate reductase (glutathione), Glutathione dehydrogenase (ascorbate), Sulfite reductase (ferredoxin), Sulfite reductase, Adenylylsulfate reductase, Hydrogensulfite reductase, Cytochrome-c oxidase, Nitrate reductase (cytochrome), Iron--cytochrome-c reductase, Trans-acenaphthene-1,2-diol dehydrogenase, L-ascorbate--cytochrome-b5 reductase, Ubiquinol--cytochrome c reductase, Catechol oxidase, Laccase, L-ascorbate oxidase, O-aminophenol oxidase, 3-hydroxyanthranilate oxidase, Rifamycin-B-oxidase, Plastoquinol--plastocyanin reductase, NADH peroxidase, NADPH peroxidase, Fatty acid peroxidase, Cytochrome-c peroxidase, Catalase, Peroxidase, Iodide peroxidase, Glutathione peroxidase, Chloride peroxidase, L-ascorbate peroxidase, Phospholipid-hydroperoxide glutathione peroxidase, Manganese peroxidase, Diarylpropane peroxidase, Hydrogen dehydrogenase, Hydrogen dehydrogenase (NADP), Cytochrome-c3 hydrogenase, Hydrogen:quinone oxidoreductase, Ferredoxin hydrogenase, Coenzyme F420 hydrogenase, N(5), N(10)-methenyltetrahydromethanopterin hydrogenase, Methanosarcina-phenazine hydrogenase, Hydrogenase (acceptor), Catechol 1,2-dioxygenase, Catechol 2,3-dioxygenase, Protocatechuate 3,4-dioxygenase, Gentisate 1,2-dioxygenase, Homogentisate 1,2-dioxygenase, 3-hydroxyanthranilate 3,4-dioxygenase, Protocatechuate 4,5-dioxygenase, 2,5-dihydroxypyridine 5,6-dioxygenase, 7,8-dihydroxykynurenate 8,8A-dioxygenase, Tryptophan 2,3-dioxygenase, Lipoxygenase, Ascorbate 2,3-dioxygenase, 2,3-dihydroxybenzoate 3,4-dioxygenase, 3,4-dihydroxyphenylacetate 2,3-dioxygenase, 3-carboxyethylcatechol 2,3-dioxygenase, Indole 2,3-dioxygenase, Sulfur dioxygenase, Cysteamine dioxygenase, Cysteine dioxygenase, Caffeate 3,4-dioxygenase, 2,3-dihydroxyindole 2,3-dioxygenase, Quercetin 2,3-dioxygenase, 3,4-dihydroxy-9,10-secoandrosta-1,3,5(10)-triene-9,17-dione4,5-dioxygenase, Peptide-tryptophan 2,3-dioxygenase, 4-hydroxyphenylpyruvate dioxygenase, 2,3-dihydroxybenzoate 2,3-dioxygenase, Stizolobate synthase, Stizolobinate synthase, Arachidonate 12-lipoxygenase, 2-nitropropane dioxygenase, Arachidonate 15-lipoxygenase, Arachidonate 5-lipoxygenase, Pyrogallol 1,2-oxygenase, Chloridazon-catechol dioxygenase, Hydroxyquinol 1,2-dioxygenase, 1-hydroxy-2-naphthoate 1,2-dioxygenase, Biphenyl-2,3-diol 1,2-dioxygenase, Arachidonate 8-lipoxygenase, 2,4'-dihydroxyacetophenone dioxygenase, Indoleamine-pyrrole 2,3-dioxygenase, Lignostilbene alpha beta-dioxygenase, Linoleate diol synthase, Linoleate 11-lipoxygenase, 4-hydroxymandelate synthase, 3-hydroxy-4-oxoquinoline 2,4-dioxygenase, 3-hydroxy-2-methyl-quinolin-4-one 2,4-dioxygenase, Chlorite O(2)-lyase, Arginine 2-monooxygenase, Lysine 2-monooxygenase, Tryptophan 2-monooxygenase, Lactate 2-monooxygenase, Renilla-luciferin 2-monooxygenase, Cypridina-luciferin 2-monooxygenase, Photinus-luciferin 4-monooxygenase (ATP-hydrolyzing), Watasemia-luciferin 2-monooxygenase, Phenylalanine 2-monooxygenase, Methylphenyltetrahydropyridine N-monooxygenase, Apo-beta-carotenoid-14', 13'-dioxygenase, Inositol oxygenase, Tryptophan 2'-dioxygenase, Gamma-butyrobetaine, 2-oxoglutarate dioxygenase, Procollagen-

TABLE 1-continued

List of Enzymes proline, 2-oxoglutarate-4-dioxygenase, Pyrimidine-deoxynucleoside 2'-dioxygenase, Procollagen-lysine 5-dioxygenase, Thymine dioxygenase, Procollagen-proline 3-dioxygenase, Trimethyllysine dioxygenase, Naringenin 3-dioxygenase, Pyrimidine-deoxynucleoside 1'-dioxygenase, Hyoscyamine (6S)-dioxygenase, Gibberellin-44 dioxygenase, Gibberellin 2-beta-dioxygenase, 6-beta-hydroxyhyoscyamine epoxidase, Gibberellin 3-beta-dioxygenase, Peptide-aspartate beta-dioxygenase, Taurine dioxygenase, Phytanoyl-CoA dioxygenase, Leucocyanidin oxygenase, Desacetoxyvindoline 4-hydroxylase, Anthranilate 1,2-dioxygenase (deaminating, decarboxylating), Benzene 1,2-dioxygenase, 3-hydroxy-2-methylpyridinecarboxylate dioxygenase, 5-pyridoxate dioxygenase, Phthalate 4,5-dioxygenase, 4-sulfobenzoate 3,4-dioxygenase, 4-chlorophenylacetate 3,4-dioxygenase, Benzoate 1,2-dioxygenase, Toluene dioxygenase, Naphthalene 1,2-dioxygenase, 2-chlorobenzoate 1,2-dioxygenase, 2-aminobenzenesulfonate 2,3-dioxygenase, Terephthalate 1,2-dioxygenase, 2-hydroxyquinoline 5,6-dioxygenase, Nitric oxide dioxygenase, Biphenyl 2,3-dioxygenase, Salicylate 1-monooxygenase, 4-hydroxybenzoate 3-monooxygenase, 4-hydroxyphenylacetate 3-monooxygenase, Melilotate 3-monooxygenase, Imidazoleacetate 4-monooxygenase, Orcinol 2-monooxygenase, Phenol 2-monooxygenase, Dimethylaniline monooxygenase (N-oxide forming), Kynurenine 3-monooxygenase, 2,6-dihydroxypyridine 3-monooxygenase, Trans-cinnamate 4-monooxygenase, Benzoate 4-monooxygenase, Calcidiol 1-monooxygenase, Trans-cinnamate 2-monooxygenase, Cholestanetriol 26-monooxygenase, Cyclopentanone monooxygenase, Cholesterol 7-alpha-monooxygenase, 4-hydroxyphenylacetate 1-monooxygenase, Taxifolin 8-monooxygenase, 2,4-dichlorophenol 6-monooxygenase, Flavonoid 3'-monooxygenase, Cyclohexanone monooxygenase, 3-hydroxybenzoate 4-monooxygenase, 3-hydroxybenzoate 6-monooxygenase, Methane monooxygenase, Phosphatidylcholine 12-monooxygenase, 4-aminobenzoate 1-monooxygenase, 3,9-dihydroxypterocarpan 6A-monooxygenase, 4-nitrophenol 2-monooxygenase, Leukotriene-B4 20-monooxygenase, 2-nitrophenol 2-monooxygenase, Albendazole monooxygenase, 4-hydroxybenzoate 3-monooxygenase (NAD(P)H), Leukotriene-E4 20-monooxygenase, Anthranilate 3-monooxygenase (deaminating), 5-O-(4-coumaroyl)-D-quinate 3'-monooxygenase, Methyltetrahydroprotoberberine 14-monooxygenase, Anhydrotetracycline monooxygenase, Nitric-oxide synthase, Anthraniloyl-CoA monooxygenase, Tyrosine N-monooxygenase, Hydroxyphenylacetonitrile 2-monooxygenase, Questin monooxygenase, 2-hydroxybiphenyl 3-monooxygenase, CMP-N-acetylneuraminate monooxygenase, (−)-menthol monooxygenase, (−)-limonene 3-monooxygenase, (−)-limonene 6-monooxygenase, (−)-limonene 7-monooxygenase, Pentachlorophenol monooxygenase, 6-oxocineole dehydrogenase, Isoflavone 3'-hydroxylase, Isoflavone 2'-hydroxylase, Ketosteroid monooxygenase, Protopine 6-monooxygenase, Dihydrosanguinarine 10-monooxygenase, Dihydrochelirubine 12-monooxygenase, Benzoyl-CoA 3-monooxygenase, L-lysine 6-monooxygenase (NADPH), 27-hydroxycholesterol 7-alpha-monooxygenase, 2-hydroxyquinoline 8-monooxygenase, 4-hydroxyquinoline 3-monooxygenase, 3-hydroxyphenylacetate 6-hydroxylase, 4-hydroxybenzoate 1-hydroxylase, 2-hydroxyquinoline 8-monooxygenase, 2-hydroxycyclohexanone 2-monooxygenase, Quinine 3-monooxygenase, 4-hydroxyphenylacetaldehyde oxime monooxygenase, Alkene monooxygenase, Sterol 14-demethylase, N-methylcoclaurine 3'-monooxygenase, Methylsterol monooxygenase, Tabersonine 16-hydroxylase, 7-deoxyloganin 7-hydroxylase, Vinorine hydroxylase, Taxane 10-beta-hydroxylase, Taxane 13-alpha-hydroxylase, Ent-kaurene oxidase, Ent-kaurenoic acid oxidase, Unspecific monooxygenase, Alkanal monooxygenase (FMN-linked), Alkanesulfonate monooxygenase, Camphor 5-monooxygenase, Camphor 1,2-monooxygenase, Alkane-1 monooxygenase, Steroid 11-beta-monooxygenase, Corticosterone 18-monooxygenase, Cholesterol monooxygenase (side-chain cleaving), Choline monooxygenase, Phenylalanine 4-monooxygenase, Tyrosine 3-monooxygenase, Anthranilate 3-monooxygenase, Tryptophan 5-monooxygenase, Glyceryl-ether monooxygenase, Mandelate 4-monooxygenase, Dopamine-beta-monooxygenase, Peptidylglycine monooxygenase, Monophenol monooxygenase, Stearoyl-CoA 9-desaturase, Acyl-[acyl-carrier protein] desaturase, Linoleoyl-CoA desaturase, Deacetoxycephalosporin-C synthase, (S)-stylopine synthase, (S)-cheilanthifoline synthase, Berbamunine synthase, Salutaridine synthase, (S)-canadine synthase, Prostaglandin-endoperoxide synthase, Kynurenine 7,8-hydroxylase, Heme oxygenase (decyclizing), Progesterone monooxygenase, Squalene monooxygenase, Steroid 17-alpha-monooxygenase, Steroid 21-monooxygenase, Estradiol 6-beta-monooxygenase, Androst-4-ene-3,17-dione monooxygenase, Progesterone 11-alpha-monooxygenase, 4-methoxybenzoate monooxygenase (O-demethylating), CMP-N-acetylneuraminate monooxygenase, Plasmenylethanolamine desaturase, Phylloquinone monooxygenase (2,3-epoxidizing), Latia-luciferin monooxygenase (demethylating), Ecdysone 20-monooxygenase, 3-hydroxybenzoate 2-monooxygenase, Steroid 9-alpha-monooxygenase, 2-hydroxypyridine 5-monooxygenase, Juglone 3-monooxygenase, Linalool 8-monooxygenase, Deoxyhypusine monooxygenase, Carotene 7,8-desaturase, Myristoyl-CoA 11-(E) desaturase, Myristoyl-CoA 11-(Z) desaturase, Delta(12)-fatty acid dehydrogenase, Monoprenyl isoflavone epoxidase, Thiophene-2-carbonyl-CoA monooxygenase, Beta-carotene 15,15'-dioxygenase, Taxadiene 5-alpha-hydroxylase, Superoxide dismutase, Superoxide reductase, Mercury (II) reductase, Diferric-transferrin reductase, Aquacobalamin reductase, Cob(II)alamin reductase, Aquacobalamin reductase (NADPH), Cyanocobalamin reductase (cyanide-eliminating), Ferric-chelate reductase, Ferroxidase, CDP-4-dehydro-6-deoxyglucose reductase, Pteridine oxidase, Ribonucleoside-diphosphate reductase, Ribonucleoside-triphosphate reductase, 4-cresol dehydrogenase (hydroxylating), Ethylbenzene hydroxylase, Rubredoxin--NAD(+) reductase, Ferredoxin--NADP(+) reductase, Ferredoxin--NAD(+) reductase, Rubredoxin--NADP(+) reductase, Nitrogenase, Nitrogenase (flavodoxin), Phosphonate dehydrogenase, Arsenate reductase (glutaredoxin), Methylarsonate reductase, Arsenate reductase (azurin), Arsenate reductase (donor), Isopenicillin-N synthase, Columbamine oxidase, D-proline reductase (dithiol), Reticuline oxidase, Sulochrin oxidase [(+)-bisdechlorogeodin-forming], Sulochrin oxidase [(−)-bisdechlorogeodin-forming], Beta-cyclopiazonate dehydrogenase, Chlorate reductase, Pyrogallol hydroxyltransferase, Sulfur reductase, Formate acetyltransferase activating enzyme, Tetrachloroethene reductive dehalogenase, cyt P450 linked enzyme systems

TRANSFERASES:

Nicotinamide N-methyltransferase, Guanidinoacetate N-methyltransferase, Thetin--homocysteine S-methyltransferase, Acetylserotonin O-methyltransferase, Betaine--homocysteine S-methyltransferase, Catechol O-methyltransferase, Nicotinate N-methyltransferase, Histamine N-methyltransferase, Thiol S-methyltransferase, Homocysteine S-methyltransferase, Magnesium-protoporphyrin O-methyltransferase, Methionine S-methyltransferase, 5-methyltetrahydrofolate--homocysteine S-methyltransferase, 5-methyltetrahydropteroyltriglutamate--homocysteine S-methyltransferase, Fatty-acid O-methyltransferase, Methylene-fatty-acyl-phospholipid synthase, Phosphatidylethanolamine N-methyltransferase, Polysaccharide O-methyltransferase, Trimethylsulfonium--tetrahydrofolate N-methyltransferase, Glycine N-methyltransferase, Methylamine--glutamate N-methyltransferase, Carnosine N-methyltransferase, Phenol O-methyltransferase, Iodophenol O-methyltransferase, Tyramine N-methyltransferase, Phenylethanolamine N-methyltransferase, tRNA (cytosine-5-)-methyltransferase, tRNA (guanine-N(1)-)-methyltransferase, tRNA (guanine-N(2)-)-methyltransferase, tRNA (guanine-N(7)-)-methyltransferase, tRNA (guanosine-2'-O-)-methyltransferase, tRNA (uracil-5-)-methyltransferase, tRNA (adenine-N(1)-)-methyltransferase, DNA (cytosine-5-)-methyltransferase, O-demethylpuromycin O-methyltransferase, Inositol 3-methyltransferase, Inositol 1-methyltransferase, Sterol 24-C-methyltransferase, Luteolin O-methyltransferase, Histone-lysine N-methyltransferase, Dimethylhistidine N-methyltransferase, Thymidylate synthase, Isoflavone 4'-O-methyltransferase, Indole-3-pyruvate C-methyltransferase, rRNA (adenine-N(6)-)-methyltransferase, Amine N-methyltransferase, Loganate O-methyltransferase, rRNA (guanine-N(1)-)-methyltransferase, rRNA (guanine-N(2)-)-methyltransferase, Putrescine N-methyltransferase, Deoxycytidylate C-methyltransferase, tRNA (adenine-N(6)-)-methyltransferase, mRNA (guanine-N(7)-)-methyltransferase, mRNA (nucleoside-2'-O-)-methyltransferase, [Cytochrome c]-lysine N-

TABLE 1-continued

List of Enzymes methyltransferase, Calmodulin-lysine N-methyltransferase, tRNA (5-methylaminomethyl-2-thiouridylate)-methyltransferase, mRNA (2'-O-methyladenosine-N(6)-)-methyltransferase, Methylated-DNA--[protein]-cysteine S-methyltransferase, 3-demethylubiquinone-9 3-O-methyltransferase, Licodione 2'-O-methyltransferase, rRNA (adenosine-2'-O-)-methyltransferase, Thiopurine S-methyltransferase, Caffeate O-methyltransferase, 5-hydroxyfuranocoumarin 5-O-methyltransferase, 8-hydroxyfuranocoumarin 8-O-methyltransferase, Phosphatidyl-N-methylethanolamine N-methyltransferase, Site-specific DNA-methyltransferase (adenine-specific), Site-specific DNA-methyltransferase (cytosine-specific), Methylenetetrahydrofolate--tRNA-(uracil-5-)-methyltransferase (FADH-oxidizing), Apigenin 4'-O-methyltransferase, Quercetin 3-O-methyltransferase, Protein-L-isoaspartate(D-aspartate) O-methyltransferase, Isoorientin 3'-O-methyltransferase, Cyclopropane-fatty-acyl-phospholipid synthase, Protein-glutamate O-methyltransferase, 3-methylquercetin 7-O-methyltransferase, 3,7-dimethylquercetin 4'-O-methyltransferase, Methylquercetagetin 6-O-methyltransferase, Protein-histidine N-methyltransferase, Tetrahydromethanopterin S-methyltransferase, Pyridine N-methyltransferase, 8-hydroxyquercetin 8-O-methyltransferase, Tetrahydrocolumbamine 2-O-methyltransferase, Methanol--5-hydroxybenzimidazolylcobamide Co-methyltransferase, Isobutyraldoxime O-methyltransferase, Bergaptol O-methyltransferase, Xanthotoxol O-methyltransferase, 11-O-demethyl-17-O-deacetylvindoline O-methyltransferase, Tocopherol O-methyltransferase, Thioether S-methyltransferase, 3-hydroxyanthranilate 4-C-methyltransferase, Diphthine synthase, 16-methoxy-2,3-dihydro-3-hydroxytabersonine N-methyltransferase, Protein-S isoprenylcysteine O-methyltransferase, Macrocin O-methyltransferase, Demethylmacrocin O-methyltransferase, Phosphoethanolamine N-methyltransferase, Caffeoyl-CoA O-methyltransferase, N-benzoyl-4-hydroxyanthranilate 4-O-methyltransferase, Tryptophan 2-C-methyltransferase, Uroporphyrin-III C-methyltransferase, 6-hydroxymellein O-methyltransferase, Demethylsterigmatocystin 6-O-methyltransferase, Sterigmatocystin 7-O-methyltransferase, Anthranilate N-methyltransferase, Glucuronoxylan 4-O-methyltransferase, Site-specific DNA-methyltransferase (cytosine-N(4)-specific), Hexaprenyldihydroxybenzoate methyltransferase, (R,S)-1-benzyl-1,2,3,4-tetrahydroisoquinoline N-methyltransferase, 3'-hydroxy-N-methyl-(S)-coclaurine 4'-O-methyltransferase, (S)-scoulerine 9-O-methyltransferase, Columbamine O-methyltransferase, 10-hydroxydihydrosanguinarine 10-O-methyltransferase, 12-hydroxydihydrochelirubine 12-O-methyltransferase, 6-O-methylnorlaudanosoline 5'-O-methyltransferase, (S)-tetrahydroprotoberberine N-methyltransferase, [Cytochrome-c]-methionine S-methyltransferase, [Cytochrome-c]-arginine N-methyltransferase, Histone-arginine N-methyltransferase, [Myelin basic protein]-arginine N-methyltransferase, [Ribulose-bisphosphate-carboxylase]-lysine N-methyltransferase, (R,S)-norcoclaurine 6-O-methyltransferase, Inositol 4-methyltransferase, Precorrin-2 C20-methyltransferase, Precorrin-3B C17-methyltransferase, Precorrin-6Y C5,15-methyltransferase (decarboxylating), Precorrin-4 C11-methyltransferase, [Methionine synthase]-cobalamin methyltransferase (cob(II)alamin reducing), Chlorophenol O-methyltransferase, Arsenite methyltransferase, Methylarsonite methyltransferase, 3'-demethylstaurosporine O-methyltransferase, (S)-coclaurine-N-methyltransferase, Jasmonate O-methyltransferase, Cycloartenol 24-C-methyltransferase, 24-methylenesterol C-methyltransferase, Trans-aconitate 2-methyltransferase, Trans-aconitate 3-methyltransferase, (Iso)eugenol O-methyltransferase, Corydaline synthase, Glycine hydroxymethyltransferase, Phosphoribosylglycinamide formyltransferase, Phosphoribosylaminoimidazolecarboxamide formyltransferase, Glycine formimidoyltransferase, Glutamate formimidoyltransferase, D-alanine hydroxymethyltransferase, Deoxycytidylate hydroxymethyltransferase, Methionyl-tRNA formyltransferase, Aminomethyltransferase, 3-methyl-2-oxobutanoate hydroxymethyltransferase, Methylmalonyl-CoA carboxyltransferase, Aspartate carbamoyltransferase, Ornithine carbamoyltransferase, Oxamate carbamoyltransferase, Putrescine carbamoyltransferase, 3-hydroxymethylcephem carbamoyltransferase, Lysine carbamoyltransferase, Glycine amidinotransferase, Scyllo-inosamine-4-phosphate amidinotransferase, Transketolase, Transaldolase, Formaldehyde transketolase, Acetoin--ribose-5-phosphate transaldolase, 2-hydroxy-3-oxoadipate synthase, Acetolactate synthase, 1-deoxy-D-xylulose 5-phosphate synthase, Amino-acid N-acetyltransferase, Imidazole N-acetyltransferase, Glucosamine N-acetyltransferase, Glucosamine 6-phosphate N-acetyltransferase, Arylamine N-acetyltransferase, Choline O-acetyltransferase, Carnitine O-acetyltransferase, Phosphate acetyltransferase, Acetyl-CoA C-acetyltransferase, Hydrogen-sulfide S-acetyltransferase, Thioethanolamine S-acetyltransferase, Dihydrolipoamide S-acetyltransferase, Glycine N-acyltransferase, Glutamine N-phenylacetyltransferase, Glycerol-3-phosphate O-acyltransferase, Acetyl-CoA C-acyltransferase, Aspartate N-acetyltransferase, Galactoside O-acetyltransferase, Phosphate butyryltransferase, Diacylglycerol O-acyltransferase, Carnitine O-palmitoyltransferase, 2-acylglycerol O-acyltransferase, 1-acylglycerophosphocholine O-acyltransferase, Sphingosine N-acyltransferase, Plasmalogen synthase, Sterol O-acyltransferase, Cortisol O-acetyltransferase, Chloramphenicol O-acetyltransferase, Glycine C-acetyltransferase, Serine O-acetyltransferase, Homoserine O-acetyltransferase, Lysine N-acetyltransferase, Histidine N-acetyltransferase, D-tryptophan N-acetyltransferase, Glutamate N-acetyltransferase, D-amino-acid N-acetyltransferase, 5-aminolevulinic acid synthase, [Acyl-carrier protein] S-acetyltransferase, [Acyl-carrier protein] S-malonyltransferase, Acyl-[acyl-carrier protein]--phospholipid O-acyltransferase, 3-oxoacyl-[acyl-carrier protein] synthase, Glycerone-phosphate O-acyltransferase, Phosphatidylcholine--sterol O-acyltransferase, N-acetylneuraminate 4-O-acetyltransferase, N-acetylneuraminate 7-O(or 9-O)-acetyltransferase, Homoserine O-succinyltransferase, 8-amino-7-oxononanoate synthase, Histone acetyltransferase, Deacetyl-[citrate-(pro-3S)-lyase] S-acetyltransferase, Serine C-palmitoyltransferase, 1-acylglycerol-3-phosphate O-acyltransferase, 2-acylglycerol-3-phosphate O-acyltransferase, Phenylalanine N-acetyltransferase, Formate C-acetyltransferase, Aromatic-hydroxylamine O-acetyltransferase, Diamine N-acetyltransferase, 2,3-diaminopropionate N-oxalyltransferase, Gentamicin 2'-N-acetyltransferase, Gentamicin 3'-N-acetyltransferase, Dihydrolipoamide S-succinyltransferase, 2-acylglycerophosphocholine O-acyltransferase, 1-alkylglycerophosphocholine O-acyltransferase, Agmatine N(4)-coumaroyltransferase, Glycine N-choloyltransferase, Leucine N-acetyltransferase, 1-alkylglycerophosphocholine O-acetyltransferase, Glutamine N-acyltransferase, Monoterpenol O-acetyltransferase, CDP-acylglycerol O-arachidonyltransferase, Glycine N-benzoyltransferase, Indoleacetylglucose--inositol O-acyltransferase, Diacylglycerol--sterol O-acyltransferase, Naringenin-chalcone synthase, Long-chain-alcohol O-fatty-acyltransferase, Retinol O-fatty-acyltransferase, Triacylglycerol--sterol O-acyltransferase, Heparan-alpha-glucosaminide N-acetyltransferase, Maltose O-acetyltransferase, Cysteine-S-conjugate N-acetyltransferase, Aminoglycoside N(3')-acetyltransferase, Kanamycin 6'-N-acetyltransferase, Phosphatidylcholine--dolichol O-acyltransferase, Alcohol O-acetyltransferase, Fatty-acid synthase, Fatty-acyl-CoA synthase, Aralkylamine N-acetyltransferase, Peptide alpha-N-acetyltransferase, Tetrahydrodipicolinate N-acetyltransferase, Beta-glucogallin O-galloyltransferase, Sinapoylglucose--choline O-sinapoyltransferase, Sinapoylglucose--malate O-sinapoyltransferase, 13-hydroxylupinine O-tigloyltransferase, Erythronolide synthase, Trihydroxystilbene synthase, Glycoprotein N-palmitoyltransferase, Glycylpeptide N-tetradecanoyltransferase, Chlorogenate--glucarate O-hydroxycinnamoyltransferase, Quinate O-hydroxycinnamoyltransferase, Myelin-proteolipid O-palmitoyltransferase, Formylmethanofuran--tetrahydromethanopterin N-formyltransferase, N(6)-hydroxylysine O-acetyltransferase, Sinapoylglucose--sinapoylglucose O-sinapoyltransferase, 1-alkenylglycerophosphocholine O-acyltransferase, Alkylglycerophosphate 2-O-acetyltransferase, Tartronate O-hydroxycinnamoyltransferase, 17-O-deacetylvindoline O-acetyltransferase, Tubulin N-acetyltransferase, Arginine N-succinyltransferase, Tyramine N-feruloyltransferase, Mycocerosate synthase, D-tryptophan N-malonyltransferase, Anthranilate N-malonyltransferase, 3,4-dichloroaniline N-malonyltransferase, Isoflavone-7-O-beta-glucoside 6"-O-malonyltransferase, Flavonol-3-O-beta-glucoside O-malonyltransferase, 2,3,4,5-tetrahydropyridine-2,6-dicarboxylate N-succinyltransferase, N-hydroxyarylamine O-acetyltransferase, Icosanoyl-CoA synthase, 1-alkenylglycerophosphoethanolamine O-acyltransferase, Trehalose O-mycolyltransferase, Dolichol O-acyltransferase, 1-alkyl-2-acetylglycerol O-acyltransferase, Isocitrate O-dihydroxycinnamoyltransferase, Ornithine N-benzoyltransferase, Ribosomal-protein-alanine N-acetyltransferase, Acyl-[acyl-carrier-protein]--UDP-N-acetylglucosamine O-acyltransferase, Galactarate O-hydroxycinnamoyltransferase, Glucarate O-hydroxycinnamoyltransferase, Glucarolactone O-hydroxycinnamoyltransferase, Shikimate O-hydroxycinnamoyltransferase, Galactolipid O-acyltransferase, Phosphatidylcholine--retinol O-acyltransferase, Polysialic-acid O-

TABLE 1-continued

List of Enzymes acetyltransferase, Carnitine O-octanoyltransferase, Putrescine N-hydroxycinnamoyltransferase, Ecdysone O-acyltransferase, Rosmarinate synthase, Galactosylacylglycerol O-acyltransferase, Glycoprotein O-fatty-acyltransferase, Beta-glucogallin--tetrakisgalloylglucose O-galloyltransferase, Anthranilate N-benzoyltransferase, Piperidine N-piperoyltransferase, Pinosylvin synthase, Glycerophospholipid arachidonoyl-transferase (CoA-independent), Glycerophospholipid acyltransferase (CoA-dependent), Platelet-activating factor acetyltransferase, Salutaridinol 7-O-acetyltransferase, Benzophenone synthase, Alcohol O-cinnamoyltransferase, Anthocyanin 5-aromatic acyltransferase, Propionyl-CoA C(2)-trimethyltridecanoyltransferase, Acetyl-CoA C-myristoyltransferase, Phloroisovalerophenone synthase, Glucosaxnine-1-phosphate N-acetyltransferase,
Phospholipid: diacylglycerol acyltransferase, Acridone synthase, Vinorine synthase, Lovastatin nonaketide synthase, Taxadien-5-alpha-ol O-acetyltransferase, 10-hydroxytaxane O-acetyltransferase, Isopenicillin N N-acyltransferase, 6-methylsalicylic acid synthase, 2-alpha-hydroxytaxane 2-O-benzoyltransferase, 10-deacetylbaccatin III 10-O-acetyltransferase, D-glutamyltransferase, Gamma-glutamyltransferase, Lysyltransferase, Gamma-glutamylcyclotransferase, Glutaminyl-peptide cyclotransferase, Leucyltransferase, Aspartyltransferase, Arginyltransferase, Agaritine gamma-glutamyltransferase, UDP-N-acetylmuramoylpentapeptide-lysine N(6)-alanyltransferase, Alanylphosphatidylglycerol synthase, Peptidyltransferase, Protein-glutamine gamma-glutamyltransferase, D-alanine gamma-glutamyltransferase, Glutathione gamma-glutamylcysteinyltransferase, Citrate (Si)-synthase, Decylcitrate synthase, Citrate (Re)-synthase, Decylhomocitrate synthase, 2-methylcitrate synthase, 2-ethylmalate synthase, 3-ethylmalate synthase, ATP citrate synthase, Malate synthase, Hydroxymethylglutaryl-CoA synthase, 2-hydroxyglutarate synthase, 3-propylmalate synthase, 2-isopropylmalate synthase, Homocitrate synthase, Phosphorylase, Dextrin dextranase, Amylosucrase, Dextransucrase, Sucrose phosphorylase, Maltose phosphorylase, Inulosucrase, Levansucrase, Glycogen (starch) synthase, Cellulose synthase (UDP-forming), Sucrose synthase, Sucrose-phosphate synthase, Alpha,alpha-trehalose-phosphate synthase (UDP-forming), Chitin synthase, UDP-glucuronosyltransferase, 1,4-alpha-glucan branching enzyme, Cyclomaltodextrin glucanotransferase, Cellobiose phosphorylase, Starch (bacterial glycogen) synthase, Lactose synthase, Sphingosine beta-galactosyltransferase, 1,4-alpha-glucan 6-alpha-glucosyltransferase, 4-alpha-glucanotransferase, DNA alpha-glucosyltransferase, DNA beta-glucosyltransferase, Glucosyl-DNA beta-glucosyltransferase, Cellulose synthase (GDP-forming), 1,3-beta-oligoglucan phosphorylase, Laminaribiose phosphorylase, Glucomannan 4-beta-mannosyltransferase, Alginate synthase, 1,3-beta-glucan synthase, Phenol beta-glucosyltransferase, Alpha,alpha-trehalose-phosphate synthase (GDP-forming), Fucosylgalactoside 3-alpha-galactosyltransferase, Beta-N-acetylglucosaminyl-glycopeptide beta-1,4-galactosyltransferase, Steroid N-acetylglucosaminyltransferase, Glycoprotein-fucosylgalactoside alpha-N-acetylgalactosaminyltransferase, Polypeptide N-acetylgalactosaminyltransferase, Polygalacturonate 4-alpha-galacturonosyltransferase, Lipopolysaccharide 3-alpha-galactosyltransferase, 2-hydroxyacylsphingosine 1-beta-galactosyltransferase, 1,2-diacylglycerol 3-beta-galactosyltransferase, N-acylsphingosine galactosyltransferase, Heteroglycan alpha-mannosyltransferase, Cellodextrin phosphorylase, Procollagen galactosyltransferase, Poly(glycerol-phosphate) alpha-glucosyltransferase, Poly(ribitol-phosphate) beta-glucosyltransferase, Undecaprenyl-phosphate mannosyltransferase, Lipopolysaccharide N-acetylglucosaminyltransferase, Phosphatidyl-myo-inositol alpha-mannosyltransferase, Lipopolysaccharide glucosyltransferase I, Abequosyltransferase, , Ganglioside galactosyltransferase, Linamarin synthase, Alpha,alpha-trehalose phosphorylase, 3-galactosyl-N-acetylglucosaminide 4-alpha-L-fucosyltransferase, Procollagen glucosyltransferase, Galactinol-raffinose galactosyltransferase, Glycoprotein 6-alpha-L-fucosyltransferase, Galactoside 2-alpha-L-fucosyltransferase, Poly(ribitol-phosphate) N-acetylglucosaminyltransferase, Arylamine glucosyltransferase, Lipopolysaccharide glucosyltransferase II, Glycosaminoglycan galactosyltransferase, UDP-galacturonosyltransferase, Phosphopolyprenol glucosyltransferase, Galactosylgalactosylglucosylceramide beta-D-acetyl- galactosaminyltransferase, Ceramide glucosyltransferase, Flavone 7-O-beta-glucosyltransferase, Galactinol--sucrose galactosyltransferase, Dolichyl-phosphate beta-D-mannosyltransferase, Cyanohydrin beta-glucosyltransferase,
Glucosaminylgalactosylglucosylceramide beta-galactosyltransferase, N-acetyllactosaminide 3-alpha-galactosyltransferase, Globoside alpha-N-acetylgalactosaminyltransferase, N-acetyllactosamine synthase, Flavonol 3-O-glucosyltransferase, (N-acetylneuraminyl)-galactosylglucosylceramide N-acetylgalactosaminyltransferase, Inulin fructotransferase (depolymerizing), Protein N-acetylglucosaminyltransferase, Bilirubin-glucuronoside glucuronosyltransferase, Sn-glycerol-3-phosphate 1-galactosyltransferase, 1,3-beta-glucan phosphorylase, Sucrose 1F-fructosyltransferase, 1,2-beta-fructan 1F-fructosyltransferase, Alpha-1,3-mannosyl-glycoprotein 2-beta-N- acetylglucosaminyltransferase, Beta-1,3-galactosyl-O-glycosyl-glycoprotein beta-1,6-N-acetylglucosaminyltransferase, Alizarin 2-beta-glucosyltransferase, O-dihydroxycoumarin 7-O-glucosyltransferase, Vitexin beta-glucosyltransferase, Isovitexin beta-glucosyltransferase, Dolichyl-phosphate-mannose--protein mannosyltransferase, tRNA-queuosine beta-mannosyltransferase, Coniferyl-alcohol glucosyltransferase, Alpha-1,4-glucan-protein synthase (UDP-forming), Alpha-1,4-glucan-protein synthase (ADP-forming), 2-coumarate O-beta-glucosyltransferase, Anthocyanidin 3-O-glucosyltransferase, Cyanidin-3-rhamnosylglucoside 5-O-glucosyltransferase, Dolichyl-phosphate beta-glucosyltransferase, Cytokinin 7-beta-glucosyltransferase, Dolichyl-diphosphooligosaccharide--protein glycosyltransferase, Sinapate 1-glucosyltransferase, Indole-3-acetate beta-glucosyltransferase, Glycoprotein-N-acetylgalactosamine 3-beta-galactosyltransferase, Inositol 1-alpha-galactosyltransferase, Sucrose-1,6-alpha-glucan 3(6)-alpha-glucosyltransferase, Hydroxycinnamate 4-beta-glucosyltransferase, Monoterpenol beta-glucosyltransferase, Scopoletin glucosyltransferase, Peptidoglycan glycosyltransferase, Dolichyl-phosphate-mannose-glycolipid alpha-mannosyltransferase, Glycolipid 2-alpha-mannosyltransferase, Glycolipid 3-alpha-mannosyltransferase, Xylosylprotein 4-beta-galactosyltransferase, Galactosylxylosylprotein 3-beta-galactosyltransferase, Galactosylgalactosylxylosylprotein 3-beta-glucuronosyltransferase, Gallate 1-beta-glucosyltransferase, Sn-glycerol-3-phosphate 2-alpha-galactosyltransferase, Mannotetraose 2-alpha-N-acetylglucosaminyltransferase, Maltose synthase, Alternansucrase, N-acetylglucosaminyldiphosphodolichol N-acetylglucosaminyltransferase, Chitobiosyldiphosphodolichol beta-mannosyltransferase, Alpha-1,6-mannosyl-glycoprotein 2-beta-N-acetylglucosaminyltransferase, Beta-1,4-mannosyl-glycoprotein 4-beta-N-acetylglucosaminyltransferase, Alpha-1,3-mannosyl-glycoprotein 4-beta-N-acetylglucosaminyltransferase, Beta-1,3-galactosyl-O-glycosyl-glycoprotein beta-1,3-N-acetylglucosaminyltransferase, Acetylgalactosaminyl-O-glycosyl-glycoprotein beta-1,3-N-acetylglucosaminyltransferase, Acetylgalactosaminyl-O-glycosyl-glycoprotein beta-1,6-N-acetylglucosaminyltransferase, N-acetyllactosaminide beta-1,3-N-acetylglucosaminyltransferase, N-acetyllactosaminide beta-1,6-N-acetylglucosaminyltransferase, 4-galactosyl-N-acetylglucosaminide 3-alpha-L-fucosyltransferase, Dolichyl-phosphate alpha-N-acetylglucosaminyltransferase, Globotriosylceramide beta-1,6-N-acetylgalactosaminyltransferase, Alpha-1,6-mannosyl-glycoprotein 6-beta-N-acetylglucosaminyltransferase, Indolylacetyl-myo-inositol galactosyltransferase, 1,2-diacylglycerol 3-glucosyltransferase, 13-hydroxydocosanoate 13-beta-glucosyltransferase, Flavonol-3-O-glucoside L-rhamnosyltransferase, Pyridoxine 5'-O-beta-D-glucosyltransferase, Oligosaccharide 4-alpha-D-glucosyltransferase, Aldose beta-D-fructosyltransferase, Beta-galactosyl-N-acetylglucosaminylgalactosyl-glucosylceramide Beta-1,3-acetylglucosaminyltransferase, Galactosyl-N-acetylglucosaminylgalactosyl-glucosylceramide beta-1,6-N-acetylglucosaminyltransferase, N-acetylneuraminylgalactosylglucosylceramide beta-1,4-N-acetylgalactosaminyltransferase, Raffinose--raffinose alpha-galactosyltransferase, Sucrose 6(F)-alpha-galactosyltransferase, Xyloglucan 4-glucosyltransferase, Xyloglucan 6-xylosyltransferase, Isoflavone 7-O-glucosyltransferase, Methyl-ONN-azoxymethanol glucosyltransferase, Salicyl-alcohol glucosyltransferase, Sterol glucosyltransferase, Glucuronylgalactosylproteoglycan 4-beta-N-acetylgalactosaminyltransferase, Glucuronosyl-N-acetylgalactosaminyl-proteoglycan 4-beta-N-acetylgalactosaminyltransferase, Gibberellin beta-glucosyltransferase, Cinnamate glucosyltransferase, Hydroxymandelonitrile glucosyltransferase, Lactosylceramide beta-1,3-galactosyltransferase, Lipopolysaccharide N-acetylmannosaminouronosyltransferase, Hydroxyanthraquinone glucosyltransferase, Lipid-A-disaccharide synthase, Alpha-1,3-glucan synthase, Galactolipid galactosyltransferase, Flavonone 7-O-beta-glucosyltransferase, Glycogenin glucosyltransferase, N-acetylglucosaminyldiphosphoundecaprenol N-acetyl-beta-D-

TABLE 1-continued

List of Enzymes mannosaminyltransferase, N-acetylglucosaminyldiphosphoundecaprenol glucosyltransferase, Luteolin 7-O-glucoronosyltransferase, Luteolin-7-O-glucuronide 7-O-glucuronosyltransferase, Luteolin-7-O-diglucuronide 4'-O-glucuronosyltransferase, Nuatigenin 3-beta-glucosyltransferase, Sarsapogenin 3-beta-glucosyltransferase, 4-hydroxybenzoate 4-O-beta-D-glucosyltransferase, Thiohydroximate beta-D-glucosyltransferase, Nicotinate glucosyltransferase, High-mannose-oligosaccharide beta-1,4-N-acetyl-glucosaminyltransferase, Phosphatidylinositol N-acetylglucosaminyltransferase, Beta-mannosylphosphodecaprenol-mannooligosaccharide 6-mannosyltransferase, Inulin fructotransferase (depolymerizing, difructofuranose-1,2':2',1-dianhydride-forming), Alpha-1,6-mannosyl-glycoprotein 4-beta-N-acetylglucosaminyltransferase, 2,4-dihydroxy-7-methoxy-2H-1,4-benzoxazin-3(4H)-one 2-D-glucosyltransferase, Trans-zeatin O-beta-D-glucosyltransferase, Zeatin O-beta-D-xylosyltransferase, Galactogen 6-beta-galactosyltransferase, Lactosylceramide 1,3-N-acetyl-beta-D-glucosaminyl-transferase, Xyloglucan:xyloglucosyl transferase, Diglucosyl diacylglycerol (DGlcDAG) synthase, Cis-p-coumarate glucosyltransferase, Limonoid glucosyltransferase, 1,3-beta-galactosyl-N-acetylhexosamine phosphorylase, Hyaluronan synthase, Glucosylglycerol-phosphate synthase, Glycoprotein 3-alpha-L-fucosyltransferase, Cis-zeatin O-beta-D-glucosyltransferase, Trehalose 6-phosphate phosphorylase, Mannosyl-3-phosphoglycerate synthase, Hydroquinone glucosyltransferase, Vomilenine glucosyltransferase, Indoxyl-UDPG glucosyltransferase, Peptide-O-fucosyltransferase, O-fucosylpeptide 3-beta-N-acetylglucosaminyltransferase, Glucuronyl-galactosyl-proteoglycan 4-alpha-N-acetylglucosaminyltransferase, Glucuronosyl-N-acetylglucosaminyl-proteoglycan 4-alpha-N-acetylglucosaminyltransferase, N-acetylglucosaminyl-proteoglycan 4-beta-glucuronosyltransferase, N-acetylgalactosaminyl-proteoglycan 3-beta-glucuronosyltransferase, Undecaprenyldiphospho-muramoylpentapeptide beta-N-acetylglucosaminyltransferase, Lactosylceramide 4-alpha-galactosyltransferase, Purine-nucleoside phosphorylase, Pyrimidine-nucleoside phosphorylase, Uridine phosphorylase, Thymidine phosphorylase, Nucleoside ribosyltransferase, Nucleoside deoxyribosyltransferase, Adenine phosphoribosyltransferase, Hypoxanthine phosphoribosyltransferase, Uracil phosphoribosyltransferase, Orotate phosphoribosyltransferase, Nicotinate phosphoribosyltransferase, Nicotinamide phosphoribosyltransferase, Amidophosphoribosyltransferase, Guanosine phosphorylase, Urate-ribonucleotide phosphorylase, ATP phosphoribosyltransferase, Anthranilate phosphoribosyltransferase, Nicotinate-nucleotide pyrophosphorylase (carboxylating), Dioxotetrahydropyrimidine phosphoribosyltransferase, Nicotinate-nucleotide-dimethylbenzimidazole phosphoribosyltransferase, Xanthine-guanine phosphoribosyltransferase, Deoxyuridine phosphorylase, 1,4-beta-D-xylan synthase, Flavone apiosyltransferase, Protein xylosyltransferase, dTDP-dihydrostreptose-streptidine-6-phosphate dihydrostreptosyltransferase, 5'-methylthioadenosine phosphorylase, Queuine tRNA-ribosyltransferase, NAD(+) ADP-ribosyltransferase, NAD(P) (+)--arginine ADP-ribosyltransferase, Dolichyl-phosphate D-xylosyltransferase, Dolichyl-xylosyl-phosphate--protein xylosyltransferase, Indolylacetylinositol arabinosyltransferase, Flavonol-3-O-glycoside xylosyltransferase, NAD(+)--diphthamide ADP-ribosyltransferase, NAD(+)--dinitrogen-reductase ADP-D-ribosyltransferase, Glycoprotein 2-beta-D-xylosyltransferase, Beta-galactosamide alpha-2,6-sialyltransferase, Monosialoganglioside sialyltransferase, Alpha-N-acetylgalactosaminide alpha-2,6-sialyltransferase, Beta-galactoside alpha-2,3-sialyltransferase, Galactosyldiacylglycerol alpha-2,3-sialyltransferase, N-acetyllactosaminide alpha-2,3-sialyltransferase, (Alpha-N-acetyl-neuraminyl-2,3-beta-galactosyl-1,3)-N-acetylgalactosaminide alpha-2,6-sialyltransferase, Alpha-N-acetyl-neuraminide alpha-2,8-sialyltransferase, Lactosylceramide alpha-2,3-sialyltransferase, Neolactotetraosylceramide alpha-2,3-sialyltransferase, Lactosylceramide alpha-2,6-N-sialyltransferase, Dimethylallyltransferase, Thiamine pyridinylase, Thiamine-phosphate pyrophosphorylase, Adenosylmethionine cyclotransferase, Galactose-6-sulfurylase, Methionine adenosyltransferase, UDP-N-acetylglucosamine 1-carboxyvinyltransferase, tRNA isopentenyltransferase, Riboflavin synthase, Geranyltranstransferase, Trans-octaprenyltranstransferase, Dihydropteroate synthase, Spermidine synthase, Cob(I)alamin adenosyltransferase, Glutathione transferase, 3-phosphoshikimate 1-carboxyvinyltransferase, Rubber cis-polyprenylcistransferase, Farnesyl-diphosphate farnesyltransferase, Spermine synthase, Sym-norspermidine synthase, Discadenine synthase, tRNA-uridine aminocarboxypropyltransferase, Alkylglycerone-phosphate synthase, Adenylate dimethylallyltransferase, Dimethylallylcistransferase, Farnesyltranstransferase, Trans-hexaprenyltranstransferase, Di-trans-poly-cis-decaprenylcistransferase, Geranylgeranyl-diphosphate geranylgeranyltransferase, Trans-pentaprenyltransferase, Tryptophan dimethylallyltransferase, Aspulvinone dimethylallyltransferase, Trihydroxypterocarpan dimethylallyltransferase, Leukotriene-C4 synthase, Isonocardicin synthase, 4-hydroxybenzoate nonaprenyltransferase, Phosphoglycerol geranylgeranyltransferase, Geranylgeranylglycerol-phosphate geranylgeranyltransferase, Nicotianamine synthase, Homospermidine synthase, Homospermidine synthase (spermidine-specific), Deoxyhypusine synthase, Aspartate aminotransferase, Alanine aminotransferase, Cysteine aminotransferase, Glycine aminotransferase, Tyrosine aminotransferase, Leucine aminotransferase, Kynurenine--oxoglutarate aminotransferase, 2,5-diaminovalerate aminotransferase, Histidinol-phosphate aminotransferase, Acetylornithine aminotransferase, Alanine--oxo-acid aminotransferase, Ornithine--oxo-acid aminotransferase, Asparagine--oxo-acid aminotransferase, Glutamine--pyruvate aminotransferase, Glutamine-fructose-6-phosphate transaminase (isomerizing), Succinyldiaminopimelate aminotransferase, Beta-alanine--pyruvate aminotransferase, 4-aminobutyrate aminotransferase, D-alanine aminotransferase, (S)-3-amino-2-methylpropionate aminotransferase, 4-hydroxyglutamate aminotransferase, Diiodotyrosine aminotransferase, Thyroid-hormone aminotransferase, Tryptophan aminotransferase, Tryptophan--phenylpyruvate aminotransferase, Diamine aminotransferase, Pyridoxamine--pyruvate aminotransferase, Pyridoxamine--oxaloacetate aminotransferase, Valine--3-methyl-2-oxovalerate aminotransferase, dTDP-4-amino-4,6-dideoxy-D-glucose aminotransferase, UDP-4-amino-2-acetamido-2,4,6-trideoxyglucose aminotransferase, Glycine--oxaloacetate aminotransferase, L-lysine aminotransferase, 2-aminoethylphosphonate--pyruvate transaminase, Histidine aminotransferase, 2-aminoadipate aminotransferase, (R)-3-amino-2-methylpropionate--pyruvate aminotransferase, D-methionine--pyruvate aminotransferase, Branched-chain amino acid aminotransferase, Aminolevulinate aminotransferase, Alanine--glyoxylate aminotransferase, Serine--glyoxylate aminotransferase, Diaminobutyrate--pyruvate aminotransferase, Alanine--oxomalonate aminotransferase, 5-aminovalerate aminotransferase, Dihydroxyphenylalanine aminotransferase, Glutamine--scyllo-inosose aminotransferase, Serine--pyruvate aminotransferase, Phosphoserine aminotransferase, Pyridoxamine-phosphate aminotransferase, Taurine aminotransferase, 1D-1-guanidino-3-amino-1,3-dideoxy-scyllo-inositol aminotransferase, Aromatic amino acid transferase, Phenylalanine(histidine) aminotransferase, dTDP-4-amino-4,6-dideoxygalactose aminotransferase, Aromatic-amino-acid--glyoxylate aminotransferase, (R)-3-amino-2-methylpropanoate aminotransferase, Adenosylmethionine--8-amino-7-oxononanoate aminotransferase, Kynurenine--glyoxylate aminotransferase, Glutamine--phenylpyruvate aminotransferase, N(6)-acetyl-beta-lysine aminotransferase, Valine--pyruvate aminotransferase, 2-aminohexanoate aminotransferase, Ornithine(lysine) aminotransferase, N(2)-acetylornithine 5-aminotransferase, Aspartate--phenylpyruvate aminotransferase, Lysine--pyruvate 6-aminotransferase, D-4-hydroxyphenylglycine aminotransferase, Methionine--glyoxylate transaminase, Cephalosporin-C transaminase, Cysteine-conjugate transaminase, Diaminobutyrate-2-oxoglutarate transaminase, Oximinotransferase, dATP(dGTP)--DNA purine transferase, Hexokinase, Glucokinase, Ketohexokinase, Fructokinase, Rhamnulokinase, Galactokinase, Mannokinase, Glucosamine kinase, Phosphoglucokinase, 6-phosphofructokinase, Gluconokinase, Dehydrogluconokinase, Sedoheptulokinase, Ribokinase, L-ribulokinase, Xylulokinase, Phosphoribokinase, Phosphoribulokinase, Adenosine kinase, Thymidine kinase, Ribosylnicotinamide kinase, NAD(+) kinase, Dephospho-CoA kinase, Adenylylsulfate kinase, Riboflavin kinase, Erythritol kinase, Triokinase, Glycerone kinase, Glycerol kinase, Glycerate kinase, Choline kinase, Pantothenate kinase, Pantetheine kinase, Pyridoxal kinase, Mevalonate kinase, Protein kinase, Phosphorylase kinase, Homoserine kinase, Pyruvate kinase, Glucose-1-phosphate phosphodismutase, Riboflavin phosphotransferase, Glucuronokinase, Galacturonokinase, 2-dehydro-3-deoxygluconokinase, L-arabinokinase, D-ribulokinase, Uridine kinase, Hydroxymethylpyrimidine kinase, Hydroxyethylthiazole kinase, L-fuculokinase, Fucokinase, L-xylulokinase, D-arabinokinase, Allose kinase, 1-phosphofructokinase, 2-dehydro-3-deoxygalactonokinase, N-acetylglucosamine kinase, N-acylmannosamine kinase, Acyl-phosphate-hexose phosphotransferase, Phosphoramidate-hexose phosphotransferase, Polyphosphate-glucose phosphotransferase, Inositol 3-kinase, Scyllo-inosamine kinase, Undecaprenol kinase, 1-phosphatidylinositol 4-kinase, 1-phosphatidylinositol-4-phosphate 5-kinase, Protein-N(pi)-

TABLE 1-continued

List of Enzymes phosphohistidine-sugar phosphotransferase, Protamine kinase, Shikimate kinase, Streptomycin 6-kinase, Inosine kinase, Deoxycytidine kinase, Deoxyadenosine kinase, Nucleoside phosphotransferase, Polynucleotide 5'-hydroxyl-kinase, Diphosphate--glycerol phosphotransferase, Diphosphate--serine phosphotransferase, Hydroxylysine kinase, Ethanolamine kinase, Pseudouridine kinase, Alkylglycerone kinase, Beta-glucoside kinase, NADH kinase, Streptomycin 3''-kinase, Dihydrostreptomycin-6-phosphate 3'-alpha-kinase, Thiamine kinase, Diphosphate--fructose-6-phosphate 1-phosphotransferase, Sphinganine kinase, 5-dehydro-2-deoxygluconokinase, Alkylglycerol kinase, Acylglycerol kinase, Kanamycin kinase, [Pyruvate dehydrogenase(lipoamide)] kinase, 5-methylthioribose kinase, Tagatose kinase, Hamamelose kinase, Viomycin kinase, Diphosphate-protein phosphotransferase, 6-phosphofructo-2-kinase, Glucose-1,6-bisphosphate synthase, Diacylglycerol kinase, Dolichol kinase, [Hydroxymethylglutaryl-CoA reductase (NADPH)] kinase, Dephospho-[reductase kinase] kinase, Protein-tyrosine kinase, Deoxyguanosine kinase, AMP--thymidine kinase, [3-methyl-2-oxobutanoate dehydrogenase (lipoamide)] kinase, [Isocitrate dehydrogenase (NADP+)] kinase, [Myosin light-chain] kinase, ADP--thymidine kinase, Hygromycin-B kinase, Caldesmon kinase, Phosphoenolpyruvate--glycerone phosphotransferase, Xylitol kinase, Calcium/calmodulin-dependent protein kinase, Tyrosine 3-monooxygenase kinase, Rhodopsin kinase, [Beta-adrenergic-receptor] kinase, Inositol-trisphosphate 3-kinase, [Acetyl-CoA carboxylase] kinase, [Myosin heavy-chain] kinase, Tetraacyldisaccharide 4'-kinase, [Low-density lipoprotein receptor] kinase, Tropomyosin kinase, Inositol-tetrakisphosphate 1-kinase, [Tau protein] kinase, Macrolide 2'-kinase, Phosphatidylinositol 3-kinase, Ceramide kinase, 1D-myo-inositol-tetrakisphosphate 5-kinase, [RNA-polymerase]-subunit kinase, Glycerol-3-phosphate-glucose phosphotransferase, Diphosphate-purine nucleoside kinase, Tagatose-6-phosphate kinase, Deoxynucleoside kinase, ADP-specific phosphofructokinase, ADP-specific glucokinase, 4-(cytidine 5'-diphospho)-2-C-methyl-D-erythritol kinase, 1-phosphatidylinositol-5-phosphate 4-kinase, 1-phosphatidylinositol-3-phosphate 5-kinase, Inositol-polyphosphate multikinase, Inositol-hexakisphosphate kinase, Phosphatidylinositol-4,5-bisphosphate 3-kinase, Phosphatidylinositol-4-phosphate 3-kinase, Acetate kinase, Carbamate kinase, Phosphoglycerate kinase, Aspartate kinase, Formate kinase, Butyrate kinase, Acetylglutamate kinase, Phosphoglycerate kinase (GTP), Glutamate 5-kinase, Acetate kinase (diphosphate), Glutamate 1-kinase, Branched-chain-fatty-acid kinase, Guanidoacetate kinase, Creatine kinase, Arginine kinase, Taurocyamine kinase, Lombricine kinase, Hypotaurocyamine kinase, Opheline kinase, Ammonia kinase, Phosphoenolpyruvate--protein phosphatase, Agmatine kinase, Protein-histidine pros-kinase, Protein-histidine tele-kinase, Polyphosphate kinase, Phosphomevalonate kinase, Adenylate kinase, Nucleoside-phosphate kinase, Nucleoside-diphosphate kinase, Phosphomethylpyrimidine kinase, Guanylate kinase, Thymidylate kinase, Nucleoside-triphosphate--adenylate kinase, (Deoxy) adenylate kinase, T2-induced deoxynucleotide kinase, (Deoxy)nucleoside-phosphate kinase, Cytidylate kinase, Thiamine-diphosphate kinase, Thiamine-phosphate kinase, 3-phosphoglyceroyl-phosphate-polyphosphate phosphotransferase, Farnesyl-diphosphate kinase, 5-methyldeoxycytidine-5'-phosphate kinase, Dolichyl-diphosphate--polyphosphate phosphotransferase, Ribose-phosphate pyrophosphokinase, Thiamine pyrophosphokinase, 2-amino-4-hydroxy-6-hydroxymethyldihydropteridine pyrophosphokinase, Nucleotide pyrophosphokinase, GTP pyrophosphokinase, Nicotinamide-nucleotide adenylyltransferase, FMN adenylyltransferase, Pantetheine-phosphate adenylyltransferase, Sulfate adenylyltransferase, Sulfate adenylyltransferase (ADP), DNA-directed RNA polymerase, DNA-directed DNA polymerase, Polyribonucleotide nucleotidyltransferase, UTP--glucose-1-phosphate uridylyltransferase, UTP--hexose-1-phosphate uridylyltransferase, UTP--xylose-1-phosphate uridylyltransferase, UDP--glucose--hexose-1-phosphate uridylyltransferase, Mannose-1-phosphate guanylyltransferase, Ethanolamine-phosphate cytidylyltransferase, Cholinephosphate cytidylyltransferase, Nicotinate-nucleotide adenylyltransferase, Polynucleotide adenylyltransferase, tRNA cytidylyltransferase, Mannose-1-phosphate guanylyltransferase (GDP), UDP-N-acetylglucosamine pyrophosphorylase, Glucose-1-phosphate thymidylyltransferase, tRNA adenylyltransferase, Glucose-1-phosphate adenylyltransferase, Nucleoside-triphosphate-hexose-1-phosphate nucleotidyltransferase, Hexose-1-phosphate guanylyltransferase, Fucose-1-phosphate guanylyltransferase, DNA nucleotidylexotransferase, Galactose-1-phosphate thymidylyltransferase, Glucose-1-phosphate cytidylyltransferase, Glucose-1-phosphate guanylyltransferase, Ribose-5-phosphate adenylyltransferase, Aldose-1-phosphate adenylyltransferase, Aldose-1-phosphate nucleotidyltransferase, 3-deoxy-manno-octulosonate cytidylyltransferase, Glycerol-3-phosphate cytidylyltransferase, D-ribitol-5-phosphate cytidylyltransferase, Phosphatidate cytidylyltransferase, Glutamate-ammonia-ligase adenylyltransferase, Acylneuraminate cytidylyltransferase, Glucuronate-1-phosphate uridylyltransferase, Guanosine-triphosphate guanylyltransferase, Gentamicin 2''-nucleotidyltransferase, Streptomycin 3''-adenylyltransferase, RNA-directed RNA polymerase, RNA-directed DNA polymerase, mRNA guanylyltransferase, Adenylylsulfate--ammonia adenylyltransferase, RNA uridylyltransferase, ATP adenylyltransferase, Phenylalanine adenylyltransferase, Anthranilate adenylyltransferase, tRNA nucleotidyltransferase, N-methylphosphoethanolamine cytidylyltransferase, (2,3-dihydroxybenzoyl)adenylate synthase, [Protein-PII] uridylyltransferase, 2-C-methyl-D-erythritol 4-phosphate cytidylyltransferase, Holo-citrate lyase synthase, Ethanolaminephosphotransferase, Diacylglycerol cholinephosphotransferase, Ceramide cholinephosphotransferase, Serine-phosphoethanolamine synthase, CDP-diacylglycerol--glycerol-3-phosphate 3-phosphatidyltransferase, Undecaprenyl-phosphate galactosephosphotransferase, Holo-[acyl-carrier protein] synthase, CDP-diacylglycerol--serine O-phosphatidyltransferase, Phosphomannan mannosephosphotransferase, Sphingosine cholinephosphotransferase, CDP-diacylglycerol--inositol 3-phosphatidyltransferase, CDP-glycerol glycerophosphotransferase, Phospho-N-acetylmuramoyl-pentapeptide-transferase, CDP-ribitol ribitolphosphotransferase, UDP-N-acetylglucosamine--dolichyl-phosphate N-acetylglucosaminephosphotransferase, UDP-N-acetylglucosamine--lysosomal-enzyme N-acetylglucosaminephosphotransferase, UDP-galactose--UDP-N-acetylglucosamine galactosephosphotransferase, UDP-glucose--glycoprotein glucosephosphotransferase, Phosphatidylglycerol--membrane-oligosaccharide glycerophosphotransferase, Membrane-oligosaccharide glycerophosphotransferase, 1-alkenyl-2-acylglycerol cholinephosphotransferase, Carboxyvinyl-carboxyphosphonate phosphorylmutase, Phosphatidylcholine synthase, Triphosphoribosyl-dephospho-CoA synthase, Pyruvate, phosphate dikinase, Pyruvate, water dikinase, Selenide, water dikinase, Alpha-glucan, water dikinase, Thiosulfate sulfurtransferase, 3-mercaptopyruvate sulfurtransferase, Thiosulfate--thiol sulfurtransferase, tRNA sulfurtransferase, Thiosulfate--dithiol sulfurtransferase, Biotin synthase, Aryl sulfotransferase, Alcohol sulfotransferase, Arylamine sulfotransferase, Estrone sulfotransferase, Chondroitin 4-sulfotransferase, Choline sulfotransferase, UDP-N-acetylgalactosamine-4-sulfate sulfotransferase, [Heparan sulfate]-glucosamine N-sulfotransferase, Tyrosine-ester sulfotransferase, Renilla-luciferin sulfotransferase, Galactosylceramide sulfotransferase, Psychosine sulfotransferase, Bile-salt sulfotransferase, Steroid sulfotransferase, Thiol sulfotransferase, Chondroitin 6-sulfotransferase, Cortisol sulfotransferase, Triglucosylalkylacylglycerol sulfotransferase, Protein-tyrosine sulfotransferase, Keratan sulfotransferase, Arylsulfate sulfotransferase, [Heparan sulfate]-glucosamine 3-sulfotransferase 1, Desulfoglucosinolate sulfotransferase, Flavonol 3-sulfotransferase, Quercetin-3-sulfate 3'-sulfotransferase, Quercetin-3-sulfate 4'-sulfotransferase, Quercetin-3,3'-bissulfate 7-sulfotransferase, [Heparan sulfate]-glucosamine 3-sulfotransferase 2, [Heparan sulfate]-glucosamine 3-sulfotransferase 3, Propionate CoA-transferase, Oxalate CoA-transferase, Malonate CoA-transferase, 3-oxoacid CoA-transferase, 3-oxoadipate CoA-transferase, Succinate-citramalate CoA-transferase, Acetate CoA-transferase, Butyrate-acetoacetate CoA-transferase, Citrate CoA-transferase, Citramalate CoA-transferase, Glutaconate CoA-transferase, Succinate-hydroxymethylglutarate CoA-transferase, 5-hydroxypentanoate CoA-transferase, Coenzyme-B sulfoethylthiotransferase, L-seryl-tRNA(Sec) selenium transferase

HYDROLASES

Carboxylesterase, Arylesterase, Triacylglycerol lipase, Phospholipase A2, Lysophospholipase, Acetylesterase, Acetylcholinesterase, Cholinesterase, Tropinesterase, Pectinesterase, Sterol esterase, Chlorophyllase, L-arabinonolactonase, Gluconolactonase, Uronolactonase, Tannase, Retinyl-palmitate esterase, Hydroxybutyrate-dimer hydrolase, Acylglycerol lipase, 3-oxoadipate enol-lactonase, 1,4-lactonase, Galactolipase, 4-pyridoxolactonase, Acylcarnitine hydrolase, Aminoacyl-tRNA hydrolase, D-arabinonolactonase, 6-phosphogluconolactonase, Phospholipase A1, 6-acetylglucose deacetylase, Lipoprotein lipase, Dihydrocoumarin lipase, Limonin-D-ring-lactonase, Steroid-lactonase, Triacetate-lactonase,

TABLE 1-continued

List of Enzymes

Actinomycin lactonase, Orsellinate-depside hydrolase, Cephalosporin-C deacetylase, Chlorogenate hydrolase, Alpha-amino-acid esterase, 4-methyloxaloacetate esterase, Carboxymethylenebutenolidase, Deoxylimonate A-ring-lactonase, 2-acetyl-1-alkylglycerophosphocholine esterase, Fusarinine-C ornithinesterase, Sinapine esterase, Wax-ester hydrolase, Phorbol-diester hydrolase, Phosphatidylinositol deacylase, Sialate O-acetylesterase, Acetoxybutynylbithiophene deacetylase, Acetylsalicylate deacetylase, Methylumbelliferyl-acetate deacetylase, 2-pyrone-4,6-dicarboxylate lactonase, N-acetylgalactosaminoglycan deacetylase, Juvenile-hormone esterase, Bis(2-ethylhexyl)phthalate esterase, Protein-glutamate methylesterase, 11-cis-retinyl-palmitate hydrolase, All-trans-retinyl-palmitate hydrolase, L-rhamnono-1,4-lactonase, 5-(3,4-diacetoxybut-1-ynyl)-2,2'-bithiophene deacetylase, Fatty-acyl-ethyl-ester synthase, Xylono-1,4-lactonase Cetraxate benzylesterase, Acetylalkylglycerol acetylhydrolase, Acetylxylan esterase, Feruloyl esterase, Cutinase, Poly(3-hydroxybutyrate) depolymerase, Poly(3-hydroxyoctanoate) depolymerase, Acyloxyacyl hydrolase, Polyneuridine-aldehyde esterase, Acetyl-CoA hydrolase, Palmitoyl-CoA hydrolase, Succinyl-CoA hydrolase, 3-hydroxyisobutyryl-CoA hydrolase, Hydroxymethylglutaryl-CoA hydrolase, Hydroxyacylglutathione hydrolase, Glutathione thioesterase Formyl-CoA hydrolase, Acetoacetyl-CoA hydrolase, S-formylglutathione hydrolase, S-succinylglutathione hydrolase, Oleoyl-[acyl-carrier protein] hydrolase, Ubiquitin thiolesterase, Citrate (pro-3S)-lyase thiolesterase, (S)-methylmalonyl-CoA hydrolase, ADP-dependent short-chain-acyl-CoA hydrolase, ADP-dependent medium-chain-acyl-CoA hydrolase, Acyl-CoA hydrolase, Dodecanoyl-[acyl-carrier protein] hydrolase, Palmitoyl-protein hydrolase, 4-hydroxybenzoyl-CoA thioesterase, 2-(2-hydroxyphenyl)benzenesulfinate hydrolase, Alkaline phosphatase, Acid phosphatase, Phosphoserine phosphatase, Phosphatidate phosphatase, 5'-nucleotidase, 3'-nucleotidase, 3'(2'), 5'-bisphosphate nucleotidase, 3-phytase, Glucose-6-phosphatase, Glucose-1-phosphatase, Fructose-bisphosphatase, Trehalose-phosphatase, Bisphosphoglycerate phosphatase, Methylphosphothioglycerate phosphatase, Histidinol-phosphatase, Serine/threonine specific protein phosphatase, Phosphorylase phosphatase, Phosphoglycolate phosphatase, Glycerol-2-phosphatase, Phosphoglycerate phosphatase, Glycerol-1-phosphatase, Mannitol-1-phosphatase, Sugar-phosphatase, Sucrose-phosphatase, Inositol-1 (or 4)-monophosphatase, 4-phytase, Phosphatidylglycerophosphatase, ADP-phosphoglycerate phosphatase, N-acylneuraminate-9-phosphatase, Nucleotidase, Polynucleotide 3'-phosphatase, Polynucleotide 5'-phosphatase, Deoxynucleotide 3'-phosphatase, Thymidylate 5'-phosphatase, Phosphoinositide 5-phosphatase, Sedoheptulose-bisphosphatase, 3-phosphoglycerate phosphatase, Streptomycin-6-phosphatase, Guanidinodeoxy-scyllo-inositol-4-phosphatase, 4-nitrophenylphosphatase, [Glycogen-synthase-D]-phosphatase, [Pyruvate dehydrogenase (lipoamide)]-phosphatase, [Acetyl-CoA carboxylase]-phosphatase, 3-deoxy-manno-octulosonate-8-phosphatase, Fructose-2,6-bisphosphate 2-phosphatase, [Hydroxymethylglutaryl-CoA reductase (NADPH)]-phosphatase, Protein-tyrosine-phosphatase, [Pyruvate kinase]-phosphatase, Sorbitol-6-phosphatase, Dolichyl-phosphatase, [3-methyl-2-oxobutanoate dehydrogenase (lipoamide)]-phosphatase, [Myosin light-chain]-phosphatase, Fructose-2,6-bisphosphate 6-phosphatase, Caldesmon-phosphatase, Inositol-polyphosphate 5-phosphatase, Inositol-1,4-bisphosphate 1-phosphatase, Sugar-terminal-phosphatase, Alkylacetylglycerophosphatase, Phosphoenolpyruvate phosphatase, Multiple inositol-polyphosphate phosphatase, 2-carboxy-D-arabinitol-1-phosphatase, Phosphatidylinositol-3-phosphatase, Phosphatidylinositol-3,4-bisphosphate 4-phosphatase, Phosphatidylinositol-3,4,5-trisphosphate 3-phosphatase, 2-deoxyglucose-6-phosphatase, Glucosylglycerol 3-phosphatase, Mannosyl-3-phosphoglycerate phosphatase, 2-phosphosulfolactate phosphatase, 5-phytase, Phosphodiesterase I, Glycerophosphocholine phosphodiesterase, Phospholipase C, Phospholipase D, Phosphoinositide phospholipase C, Sphingomyelin phosphodiesterase, Serine-ethanolaminephosphate phosphodiesterase, [Acyl-carrier protein] phosphodiesterase, Adenylyl-[glutamate--ammonia ligase] hydrolase, 2',3'-cyclic-nucleotide 2'-phosphodiesterase, 3',5'-cyclic-nucleotide phosphodiesterase, 3',5'-cyclic-GMP phosphodiesterase, 3'-cyclic nucleotide 3'-phosphodiesterase, Glycerophosphocholine cholinephosphodiesterase, Alkylglycerophosphoethanolamine phosphodiesterase, CMP-N-acylneuraminate phosphodiesterase, Sphingomyelin phosphodiesterase D, Glycerol-1,2-cyclic-phosphate 2-phosphodiesterase, Glycerophosphoinositol inositolphosphodiesterase, Glycerophosphoinositol glycerophosphodiesterase, N-acetylglucosamine-1-phosphodiester alpha-N-acetylglucosaminidase, Glycerophosphodiester phosphodiesterase, Variant-surface-glycoprotein phospholipase C, Dolichyl-phosphate-glucose phosphodiesterase, Dolichyl-phosphate-mannose phosphodiesterase, Glycosylphosphatidylinositol phospholipase D, Glucose-1-phospho-D-mannosylglycoprotein phosphodiesterase, Deoxyguanosinetriphosphate triphosphohydrolase, Arylsulfatase, Steryl-sulfatase, Glycosulfatase, N-acetylgalactosamine-6-sulfatase, Choline-sulfatase, Cellulose-polysulfatase, Cerebroside-sulfatase, Chondro-4-sulfatase, Chondro-6-sulfatase, Disulfoglucosamine-6-sulfatase, N-acetylgalactosamine-4-sulfatase, Iduronate-2-sulfatase, N-acetylglucosamine-6-sulfatase, N-sulfoglucosamine-3-sulfatase, Monomethyl-sulfatase, D-lactate-2-sulfatase, Glucuronate-2-sulfatase, Prenyl-pyrophosphatase, Guanosine-3',5'-bis (diphosphate) 3'-pyrophosphohydrolase, Monoterpenyl-pyrophosphatase, Aryldialkylphosphatase, Diisopropyl-fluorophosphatase, Exodeoxyribonuclease I, Exodeoxyribonuclease III, Exodeoxyribonuclease (Lambda-induced), Exodeoxyribonuclease (phage Sp3-induced), Exodeoxyribonuclease V, Exodeoxyribonuclease VII, Exoribonuclease II, Exoribonuclease H, Oligonucleotidase, Poly(A)-specific ribonuclease, Yeast ribonuclease, Venom exonuclease, Spleen exonuclease, Deoxyribonuclease I, Deoxyribonuclease IV (phage T4-induced), Type I site-specific deoxyribonuclease, Type II site-specific deoxyribonuclease, Type III site-specific deoxyribonuclease, CC-preferring endodeoxyribonuclease, Deoxyribonuclease V, Deoxyribonuclease II, Aspergillus deoxyribonuclease K1, Crossover junction endoribonuclease, Deoxyribonuclease X, Deoxyribonuclease (pyrimidine dimer), Physarum polycephalum ribonuclease, Ribonuclease alpha, Ribonuclease III, Ribonuclease H, Ribonuclease P, Ribonuclease IV, Ribonuclease P4, Ribonuclease M5, Ribonuclease (poly-(U)-specific), Ribonuclease IX, Ribonuclease Z, Ribonuclease T2, Bacillus subtilis ribonuclease, Ribonuclease T1, Ribonuclease U2, Pancreatic ribonuclease, Enterobacter ribonuclease, Ribonuclease F, Ribonuclease V, tRNA-intron endonuclease, rRNA endonuclease, Aspergillus nuclease S1, Serratia marcescens nuclease, Micrococcal nuclease, Alpha-amylase, Beta-amylase, Glucan 1,4-alpha-glucosidase, Cellulase, Endo-1,3(4)-beta-glucanase, Inulinase, Endo-1,4-beta-xylanase, Oligosaccharide alpha-1,6-glucosidase, Dextranase, Chitinase, Polygalacturonase, Lysozyme, Exo-alpha-sialidase, Alpha-glucosidase, Beta-glucosidase, Alpha-galactosidase, Beta-galactosidase, Alpha-mannosidase, Beta-mannosidase, Beta-fructofuranosidase, Alpha, alpha-trehalase, Beta-glucuronidase, Xylan endo-1,3-beta-xylosidase, Amylo-alpha-1,6-glucosidase, Hyaluronoglucosaminidase, Hyaluronoglucuronidase, Xylan 1,4-beta-xylosidase, Beta-D-fucosidase, Glucan endo-1,3-beta-D-glucosidase, Alpha-L-rhamnosidase, Pullulanase, GDP-glucosidase, Beta-L-rhamnosidase, Fucoidanase, Glucosylceramidase, Galactosylceramidase, Galactosylgalactosylglucosylceramidase, Sucrose alpha-glucosidase, Alpha-N-acetylgalactosaminidase, Alpha-N-acetylglucosaminidase, Alpha-L-fucosidase, Beta-N-acetylhexosaminidase, Beta-N-acetylgalactosaminidase, Cyclomaltodextrinase, Alpha-L-arabinofuranosidase, Glucuronosyl-disulfoglucosamine glucuronidase, Isopullulanase, Glucan 1,3-beta-glucosidase, Glucan endo-1,3-alpha-glucosidase, Glucan 1,4-alpha-maltotetrahydrolase, Mycodextranase, Glycosylceramidase, 1,2-alpha-L-fucosidase, 2,6-beta-fructan 6-levanbiohydrolase, Levanase, Quercitrinase, Galacturan 1,4-alpha-galacturonidase, Isoamylase, Glucan 1,6-alpha-glucosidase, Glucan endo-1,2-beta-glucosidase, Xylan 1,3-beta-xylosidase, Licheninase, Glucan 1,4-beta-glucosidase, Glucan endo-1,6-beta-glucosidase, L-iduronidase, Mannan 1,2-(1,3)-alpha-mannosidase, Mannan endo-1,4-beta-mannosidase, Fructan beta-fructosidase, Agarase, Exo-poly-alpha-galacturonosidase, Kappa-carrageenase, Glucan 1,3-alpha-glucosidase, 6-phospho-beta-galactosidase, 6-phospho-beta-glucosidase, Capsular-polysaccharide endo-1,3-alpha-glucosidase, Beta-L-arabinosidase, Arabinogalactan endo-1,4-beta-galactosidase, Cellulose 1,4-beta-cellobiosidase, Peptidoglycan beta-N-acetylmuramidase, Alpha, alpha-phosphotrehalase, Glucan 1,6-alpha-isomaltosidase, Dextran 1,6-alpha-isomaltotriosidase, Mannosyl-glycoprotein endo-beta-N-acetylglucosamidase, Glycopeptide alpha-N-acetylgalactosaminidase, Glucan 1,4-alpha-maltohexaosidase, Arabinan endo-1,5-alpha-L-arabinosidase, Mannan 1,4-beta-mannobiosidase, Mannan endo-1,6-beta-mannosidase, Blood-group-substance endo-1,4-beta-galactosidase, Keratan-sulfate endo-1,4-beta-galactosidase, Steryl-beta-glucosidase, Strictosidine beta-glucosidase, Mannosyl-oligosaccharide glucosidase, Protein-glucosylgalactosylhydroxylysine glucosidase, Lactase, Endogalactosaminidase, Mucinaminylserine mucinaminidase, 1,3-alpha-L-fucosidase, 2-deoxyglucosidase, Mannosyl-oligosaccharide 1,2-alpha-mannosidase, Mannosyl-oligosaccharide 1,3-1,6-alpha-mannosidase, Branched-dextran exo-1,2-alpha-glucosidase, Glucan 1,4-alpha-maltotriohydrolase, Amygdalin beta-glucosidase, Prunasin beta- TABLE 1-continued List of Enzymes glucosidase, Vicianin beta-glucosidase, Oligoxyloglucan beta-glycosidase, Polymannuronate hydrolase, Maltose-6'-phosphate glucosidase, Endoglycosylceramidase, 3-deoxy-2-octulosonidase, Raucaffricine beta-glucosidase, Coniferin beta-glucosidase, 1,6-alpha-L-fucosidase, Glycyrrhizinate beta-glucuronidase, Endo-alpha-sialidase, Glycoprotein endo-alpha-1,2-mannosidase, Xylan alpha-1,2-glucuronosidase, Chitosanase, Glucan 1,4-alpha-maltohydrolase, Difructose-anhydride synthase, Neopullulanase, Glucuronoarabinoxylan endo-1,4-beta-xylanase, Mannan exo-1,2-1,6-alpha-mannosidase, Anhydrosialidase, Alpha-glucosiduronase, Lacto-N-biosidase, 4-alpha-D-{(1->4)-alpha-D-glucano}trehalose trehalohydrolase, Limit dextrinase, Poly(ADP-ribose) glycohydrolase, 3-deoxyoctulosonase, Galactan 1,3-beta-galactosidase, Beta-galactofuranosidase, Thioglucosidase, Ribosylhomocysteinase, Beta-primeverosidase, Purine nucleosidase, Inosine nucleosidase, Uridine nucleosidase, AMP nucleosidase, NAD(+) nucleosidase, NAD(P) (+) nucleosidase, Adenosine nucleosidase, Ribosylpyrimidine nucleosidase, Adenosylhomocysteine nucleosidase, Pyrimidine-5'-nucleotide nucleosidase, Beta-aspartyl-N-acetylglucosaminidase, Inosinate nucleosidase, 1-methyladenosine nucleosidase, NMN nucleosidase, DNA-deoxyinosine glycosylase, Methylthioadenosine nucleosidase, Deoxyribodipyrimidine endonucleosidase, ADP-ribosylarginine hydrolase, DNA-3-methyladenine glycosylase I, DNA-3-methyladenine glycosylase II, rRNA N-glycosylase, DNA-formamidopyrimidine glycosylase, ADP-ribosyl-[dinitrogen reductase]
hydrolase, Adenosylhomocysteinase, Adenosylmethionine hydrolase, Isochorismatase, Alkenylglycerophosphocholine hydrolase, Epoxide hydrolase, Trans-epoxysuccinate hydrolase, Alkenylglycerophosphoethanolamine hydrolase, Leukotriene-A4 hydrolase, Hepoxilin-epoxide hydrolase, Limonene-1,2-epoxide hydrolase, Leucyl aminopeptidase, Membrane alanine aminopeptidase, Cystinyl aminopeptidase, Tripeptide aminopeptidase, Prolyl aminopeptidase, Aminopeptidase B, Glutamyl aminopeptidase, Xaa-Pro aminopeptidase, Bacterial leucyl aminopeptidase, Clostridial aminopeptidase, Cytosol alanyl aminopeptidase, Lysyl aminopeptidase, Xaa-Trp aminopeptidase, Tryptophanyl aminopeptidase, Methionyl aminopeptidase, D-stereospecific aminopeptidase, Aminopeptidase Ey, Aspartyl aminopeptidase, Aminopeptidase I, Xaa-His dipeptidase, Xaa-Arg dipeptidase, Xaa-methyl-His dipeptidase, Glu-Glu dipeptidase, Xaa-Pro dipeptidase, Met-Xaa dipeptidase, Non-stereospecific dipeptidase, Cytosol nonspecific dipeptidase, Membrane dipeptidase, Beta-Ala-His dipeptidase, Dipeptidase E, Dipeptidyl-peptidase I, Dipeptidyl-peptidase II, Dipeptidyl-peptidase III, Dipeptidyl-peptidase IV, Dipeptidyl-dipeptidase, Tripeptidyl-peptidase I, Tripeptidyl-peptidase II, Xaa-Pro dipeptidyl-peptidase, Peptidyl-dipeptidase A, Peptidyl-dipeptidase B, Peptidyl-dipeptidase Dcp, Lysosomal Pro-X carboxypeptidase, Serine-type D-Ala-D-Ala carboxypeptidase, Carboxypeptidase C, Carboxypeptidase D, Carboxypeptidase A, Carboxypeptidase B, Lysine(arginine) carboxypeptidase, Gly-X carboxypeptidase, Alanine carboxypeptidase, Muramoylpentapeptide carboxypeptidase, Carboxypeptidase H, Glutamate carboxypeptidase, Carboxypeptidase M, Muramoyltetrapeptide carboxypeptidase, Zinc D-Ala-D-Ala carboxypeptidase, Carboxypeptidase A2, Membrane Pro-X carboxypeptidase, Tubulinyl-Tyr carboxypeptidase, Carboxypeptidase T, Thermostable carboxypeptidase 1, Carboxypeptidase U, Glutamate carboxypeptidase II, Metallocarboxypeptidase D, Cysteine-type carboxypeptidase, Acylaminoacyl-peptidase, Peptidyl-glycinamidase, Pyroglutamyl-peptidase I, Beta-aspartyl-peptidase, Pyroglutamyl-peptidase II, N-formylmethionyl-peptidase, Gamma-glutamyl hydrolase, Gamma-D-glutamyl-meso-diaminopimelate peptidase I, Ubiquitinyl hydrolase 1, Chymotrypsin, Chymotrypsin C, Metridin, Trypsin, Thrombin, Coagulation factor Xa, Plasmin, Enteropeptidase, Acrosin, Alpha-lytic endopeptidase, Glutamyl endopeptidase, Cathepsin G, Coagulation factor VIIa, Coagulation factor IXa, Cucumisin, Prolyl oligopeptidase, Coagulation factor XIa, , Brachyurin, Plasma kallikrein, Tissue kallikrein, Pancreatic elastase, Leukocyte elastase, Coagulation factor XIIa, Chymase, Complement component C1r, Complement component C1s, Classical-complement pathway C3/C5 convertase, Complement factor I, Complement factor D, Alternative-complement pathway C3/C5 convertase, Cerevisin, Hypodermin C, Lysyl endopeptidase, Endopeptidase La, Gamma-renin, Venombin AB, Leucyl endopeptidase, Tryptase, Scutelarin, Kexin, Subtilisin, Oryzin, Proteinase K, Thermomycolin, Thermitase, Endopeptidase So, T-plasminogen activator, Protein C (activated), Pancreatic endopeptidase E, Pancreatic elastase II, IgA-specific serine endopeptidase, U-plasminogen activator, Venombin A, Furin, Myeloblastin, Semenogelase, Granzyme A, Granzyme B, Streptogrisin A, Streptogrisin B, Glutamyl endopeptidase II, Oligopeptidase B, Limulus clotting factor C, Limulus clotting factor B, Limulus clotting enzyme, Omptin, Repressor lexA, Signal peptidase I, Togavirin, Flavirin, Endopeptidase Clp, Proprotein convertase 1, Proprotein convertase 2, Snake venom factor V activator, Lactocepin, Assemblin, Hepacivirin, Spermosin, Pseudomonapepsin, Xanthomonapepsin, C-terminal processing peptidase, Cathepsin B, Papain, Ficain, Chymopapain, Asclepain, Clostripain, Streptopain, Actinidain, Cathepsin L, Cathepsin H, Calpain, Cathepsin T, Glycyl endopeptidase, Cancer procoagulant, Cathepsin S, Picornain 3C, Picornain 2A, Caricain, Ananain, Stem bromelain, Fruit bromelain, Legumain, Histolysain, Caspase-1, Gingipain R, Cathepsin K, Adenain, Bleomycin hydrolase, Cathepsin F, Cathepsin O, Cathepsin V, Nuclear-inclusion-a endopeptidase, Helper-component proteinase, L-peptidase, Pepsin A, Pepsin B, Gastricsin, Chymosin, Cathepsin D, Neopenthesin, Renin, HIV-1 retropepsin, Pro-opiomelanocortin converting enzyme, Aspergillopepsin I, Aspergillopepsin II, Penicillopepsin, Rhizopuspepsin, Endothiapepsin, Mucoropepsin, Candidapepsin, Saccharopepsin, Rhodotorulapepsin, Physaropepsin, Acrocylindropepsin, Polyporopepsin, Pycnoporopepsin, Scytalidopepsin A, Scytalidopepsin B, Cathepsin E, Barrierpepsin, Signal peptidase II, Plasmepsin I, Plasmepsin II, Phytepsin, Yapsin 1, Thermopsin, Prepilin peptidase, Nodavirus endopeptidase, Atrolysin A, Microbial collagenase, Leucolysin, Interstitial collagenase, Neprilysin, Envelysin, IgA-specific metalloendopeptidase, Procollagen N-endopeptidase, Thimet oligopeptidase, Neurolysin, Stromelysin 1, Meprin A, Procollagen C-endopeptidase, Peptidyl-Lys metalloendopeptidase, Astacin, Stromelysin 2, Matrilysin, Gelatinase A, Aeromonolysin, Pseudolysin, Thermolysin, Bacillolysin, Aureolysin, Coccolysin, Mycolysin, Beta-lytic metalloendopeptidase, Peptidyl-Asp metalloendopeptidase, Neutrophil collagenase, Gelatinase B, Leishmanolysin, Saccharolysin, Gametolysin, Deuterolysin, Serralysin, Atrolysin B, Atrolysin C, Atroxase, Atrolysin E, Atrolysin F, Adamalysin, Horrilysin, Ruberlysin, Bothropasin, Bothrolysin, Ophiolysin, Trimerelysin I, Trimerelysin II, Mucrolysin, Pitrilysin, Insulysin, O-sialoglycoprotein endopeptidase, Russellysin, Mitochondrial intermediate peptidase, Dactylysin, Nardilysin, Magnolysin, Meprin B, Mitochondrial processing peptidase, Macrophage elastase, Choriolysin L, Choriolysin H, Tentoxilysin, Bontoxilysin, Oligopeptidase A, Endothelin-converting enzyme 1, Fibrolase, Jararhagin, Fragilysin, Lysostaphin, Flavastacin, Snapalysin, Proteasome endopeptidase complex, Asparaginase, Glutaminase, Omega-amidase, Amidase, Urease, Beta-ureidopropionase, Ureidosuccinase, Formylaspartate deformylase, Arylformamidase, Formyltetrahydrofolate deformylase, Penicillin amidase, Biotinidase, Aryl-acylamidase, Aminoacylase, Aspartoacylase, Acetylornithine deacetylase, Acyl-lysine deacylase, Succinyl-diaminopimelate desuccinylase, Nicotinamidase, Citrullinase, N-acetyl-beta-alanine deacetylase, Pantothenase, Ceramidase, Choloylglycine hydrolase, N-acetylglucosamine-6-phosphate deacetylase, N(4)-(beta-N-acetylglucosaminyl)-L-asparaginase, N-formylmethionylaminoacyl-tRNA deformylase, N-acetylmuramoyl-L-alanine amidase, 2-(acetamidomethylene) succinate hydrolase, 5-aminopentanamidase, Formylmethionine deformylase, Hippurate hydrolase, N-acetylglucosamine deacetylase, D-glutaminase, N-methyl-2-oxoglutaramate hydrolase, Glutaminase-(asparagin-)ase, Alkylamidase, Acylagmatine amidase, Chitin deacetylase, Nicotinamide-nucleotide amidase, Peptidyl-glutaminase, Protein-glutamine glutaminase, 6-aminohexanoate-dimer hydrolase, N-acetyldiaminopimelate deacetylase, Acetylspermidine deacetylase, Formamidase, Pentanamidase, 4-acetamidobutyryl-CoA deacetylase, Peptide-N(4)-(N-acetyl-beta-glucosaminyl)asparagine amidase, N-carbamoylputrescine amidase, Allophanate hydrolase, Long-chain-fatty-acyl-glutamate deacylase, N,N-dimethylformamidase, Tryptophanamidase, N-benzyloxycarbonylglycine hydrolase, N-carbamoylsarcosine amidase, N-(long-chain-acyl)ethanolamine deacylase, Mimosinase, Acetylputrescine deacetylase, 4-acetamidobutyrate deacetylase, N(alpha)-benzyloxycarbonyl-leucine hydrolase, Theanine hydrolase, 2-(hydroxymethyl)-3-(acetamidomethylene) succinate hydrolase, 4-methyleneglutaminase, N-formylglutamate deformylase, Glycosphingolipid deacylase, Aculeacin-A deacylase, N-feruloylglycine deacylase, D-benzoylarginine-4-nitroanilide amidase, Carnitinamidase, Chenodeoxycholoyltaurine hydrolase, Urethanase, Arylalkyl acylamidase, N-carbamoyl-D-amino acid hydrolase, Glutathionylspermidine amidase, Phthalyl amidase, N-acyl-D-amino-acid deacylase, N-acyl-D-glutamate deacylase, N-acyl-D-aspartate deacylase, Biuret amidohydrolase, (S)-N-acetyl-1-phenylethylamine hydrolase, Mandelamide amidase, N-carbamoyl-L-amino-acid hydrolase, Peptide deformylase, N-acetylglucosaminylphosphatidylinositol deacetylase, Barbiturase, Dihydropyrimidinase, Dihydroorotase, Carboxymethylhydantoinase, Allantoinase, Beta-lactamase,

TABLE 1-continued

List of Enzymes

Imidazolonepropionase, 5-oxoprolinase (ATP-hydrolyzing), Creatininase, L-lysine-lactamase, 6-aminohexanoate-cyclic dimer hydrolase, 2,5-dioxopiperazine hydrolase, N-methylhydantoinase (ATP-hydrolyzing), Cyanuric acid amidohydrolase, Maleimide hydrolase, Arginase, Guanidinoacetase, Creatinase, Allantoicase, Formimidoylaspartate deiminase, Arginine deiminase, Guanidinobutyrase, Formimidoylglutamase, Allantoate deiminase, D-arginase, Agmatinase, Agmatine deiminase, Formimidoylglutamate deiminase, Amidinoaspartase, Protein-arginine deiminase, Methylguanidinase, Guanidinopropionase, Dimethylargininase, Ureidoglycolate hydrolase, Diguanidinobutanase, Methylenediurea deiminase, Cytosine deaminase, Adenine deaminase, Guanine deaminase, Adenosine deaminase, Cytidine deaminase, AMP deaminase, ADP deaminase,
Aminoimidazolase, Methenyltetrahydrofolate cyclohydrolase, IMP cyclohydrolase, Pterin deaminase, dCMP deaminase, dCTP deaminase, Deoxycytidine deaminase, Guanosine deaminase, GTP cyclohydrolase I, Adenosine-phosphate deaminase, ATP deaminase, Phosphoribosyl-AMP cyclohydrolase, Pyrithiamine deaminase, Creatinine deaminase, 1-pyrroline-4-hydroxy-2-carboxylate deaminase, Blasticidin-S deaminase, Sepiapterin deaminase, GTP cyclohydrolase II, Diaminohydroxyphosphoribosylaminopyrimidine deaminase, Methenyltetrahydromethanopterin cyclohydrolase, S-adenosylhomocysteine deaminase, Nitrilase, Ricinine nitrilase, Cyanoalanine nitrilase, Arylacetonitrilase, Bromoxynil nitrilase, Aliphatic nitrilase, Thiocyanate hydrolase, Riboflavinase, Thiaminase, Hydroxydechloroatrazine ethylaminohydrolase, N-isopropylammelide isopropylaminohydrolase, 2-aminomuconate deaminase, Glucosamine-6-phosphate deaminase, 1-aminocyclopropane-1-carboxylate deaminase, Inorganic pyrophosphatase, Trimetaphosphatase, Adenosinetriphosphatase, Apyrase, Nucleoside-diphosphatase, Acylphosphatase, ATP pyrophosphatase, Nucleotide pyrophosphatase, Endopolyphosphatase, Exopolyphosphatase, dCTP pyrophosphatase, ADP-ribose pyrophosphatase, Adenosine-tetraphosphatase, Nucleoside-triphosphatase, CDP-glycerol pyrophosphatase, Bis(5'-nucleosyl)-tetraphosphatase (asymmetrical), FAD pyrophosphatase, Nucleoside-triphosphate pyrophosphatase, 5'-acylphosphoadenosine hydrolase, ADP-sugar diphosphatase, NAD+ pyrophosphatase, dUTP pyrophosphatase, Nucleoside phosphoacylhydrolase,
Triphosphatase, CDP-diacylglycerol pyrophosphatase, Undecaprenyl-diphosphatase, Thiamine-triphosphatase, Bis(5'-adenosyl)-triphosphatase, M(7)G(5')pppN pyrophosphatase, Phosphoribosyl-ATP pyrophosphatase, Thymidine-triphosphatase, Guanosine-5'-triphosphate, 3'-diphosphate pyrophosphatase, Bis(5'-nucleosyl)-tetraphosphatase (symmetrical), Guanosine-diphosphatase, Dolichyldiphosphatase, Oligosaccharide-diphosphodolichol pyrophosphatase, UDP-sugar diphosphatase, Heterotrimeric G-protein GTPase, Small monomeric GTPase, Protein-synthesizing GTPase, Signal-recognition-particle GTPase, Dynamin GTPase, Tubulin GTPase, Diphosphoinositol-polyphosphate diphosphatase, Adenylylsulfatase, Phosphoadenylylsulfatase, Magnesium-ATPase, Magnesium-importing ATPase,
Cadmium-exporting ATPase, Copper-exporting ATPase, Zinc-exporting ATPase, Proton-exporting ATPase, Sodium-exporting ATPase, Calcium-transporting ATPase, Sodium/potassium-exchanging ATPase, Hydrogen/potassium-exchanging ATPase, Chloride-transporting ATPase, Potassium-transporting ATPase, H(+)-transporting two-sector ATPase, Sodium-transporting two-sector ATPase, Arsenite-transporting ATPase, Monosaccharide-transporting ATPase, Oligosaccharide-transporting ATPase, Maltose-transporting ATPase, Glycerol-3-phosphate-transporting ATPase, Polar-amino-acid-transporting ATPase, Nonpolar-amino-acid-transporting ATPase, Oligopeptide-transporting ATPase, Nickel-transporting ATPase, Sulfate-transporting ATPase, Nitrate-transporting ATPase, Phosphate-transporting ATPase, Phosphonate-transporting ATPase, Molybdate-transporting ATPase, Fe(3+)-transporting ATPase, Polyamine-transporting ATPase, Quaternary-amine-transporting ATPase, Vitamin B12-transporting ATPase, Iron-chelate-transporting ATPase, Manganese-transporting ATPase, Taurine-transporting ATPase, Guanine-transporting ATPase, Capsular-polysaccharide-transporting ATPase, Lipopolysaccharide-transporting ATPase, Teichoic-acid-transporting ATPase, Heme-transporting ATPase, Beta-glucan-transporting ATPase, Peptide-transporting ATPase, Xenobiotic-transporting ATPase, Steroid-transporting ATPase, Cadmium-transporting ATPase, Fatty-acyl-CoA-transporting ATPase, Alpha-factor-transporting ATPase, Channel-conductance-controlling ATPase, Protein-secreting ATPase, Mitochondrial protein-transporting ATPase, Chloroplast protein-transporting ATPase, Ag(+)-exporting ATPase, Myosin ATPase, Dynein ATPase, Microtubule-severing ATPase, Plus-end-directed kinesin ATPase, Minus-end-directed kinesin ATPase, Vesicle-fusing ATPase, Peroxisome-assembly ATPase, Proteasome ATPase, Chaperonin ATPase, Non-chaperonin molecular chaperone ATPase, Nucleoplasmin ATPase, Oxaloacetase, Fumarylacetoacetase, Kynureninase, Phloretin hydrolase, Acylpyruvate hydrolase, Acetylpyruvate hydrolase, Beta-diketone hydrolase, 2,6-dioxo-6-phenylhexa-3-enoate hydrolase, 2-hydroxymuconate-semialdehyde hydrolase, Cyclohexane-1,3-dione hydrolase, Alkylhalidase, 2-haloacid dehalogenase, Haloacetate dehalogenase, Thyroxine deiodinase, Haloalkane dehalogenase, 4-chlorobenzoate dehalogenase, 4-chlorobenzoyl-CoA dehalogenase, Atrazine chlorohydrolase, Phosphoamidase, N-sulfoglucosamine sulfohydrolase, Cyclamate sulfohydrolase, Phosphonoacetaldehyde hydrolase, Phosphonoacetate hydrolase, Trithionate hydrolase, UDP-sulfoquinovose synthase,

LYASES:

Pyruvate decarboxylase, Oxalate decarboxylase, Oxaloacetate decarboxylase, Acetoacetate decarboxylase, Acetolactate decarboxylase, Aconitate decarboxylase, Benzoylformate decarboxylase, Oxalyl-CoA decarboxylase, Malonyl-CoA decarboxylase, Aspartate 1-decarboxylase, Aspartate 4-decarboxylase, Valine decarboxylase, Glutamate decarboxylase, Hydroxyglutamate decarboxylase, Ornithine decarboxylase, Lysine decarboxylase, Arginine decarboxylase, Diaminopimelate decarboxylase, Phosphoribosylaminoimidazole carboxylase, Histidine decarboxylase, Orotidine-5'-phosphate decarboxylase, Aminobenzoate decarboxylase, Tyrosine decarboxylase, Aromatic-L-amino-acid decarboxylase, Sulfinoalanine decarboxylase, Pantothenoylcysteine decarboxylase, Phosphoenolpyruvate carboxylase, Phosphoenolpyruvate carboxykinase (GTP), Diphosphomevalonate decarboxylase, Dehydro-L-gulonate decarboxylase, UDP-glucuronate decarboxylase, Phosphopantothenoylcysteine decarboxylase, Uroporphyrinogen decarboxylase, Phosphoenolpyruvate carboxykinase (pyrophosphate), Ribulose-bisphosphate carboxylase, Hydroxypyruvate decarboxylase, Methylmalonyl-CoA decarboxylase, Carnitine decarboxylase, Phenylpyruvate decarboxylase, 4-carboxymuconolactone decarboxylase, Aminocarboxymuconate-semialdehyde decarboxylase, O-pyrocatechuate decarboxylase, Tartronate-semialdehyde synthase, Indole-3-glycerol-phosphate synthase, Phosphoenolpyruvate carboxykinase (ATP), Adenosylmethionine decarboxylase, 3-hydroxy-2-methylpyridine-4,5-dicarboxylate 4-decarboxylase, 6-methylsalicylate decarboxylase, Phenylalanine decarboxylase, Dihydroxyfumarate decarboxylase, 4,5-dihydroxyphthalate decarboxylase, 3-oxolaurate decarboxylase, Methionine decarboxylase, Orsellinate decarboxylase, Gallate decarboxylase, Stipitatonate decarboxylase, 4-hydroxybenzoate decarboxylase, Gentisate decarboxylase, Protocatechuate decarboxylase, 2,2-dialkylglycine decarboxylase (pyruvate), Phosphatidylserine decarboxylase, Uracil-5-carboxylate decarboxylase, UDP-galacturonate decarboxylase, 5-oxopent-3-ene-1,2,5-tricarboxylate decarboxylase, 3,4-dihydroxyphthalate decarboxylase, Glutaconyl-CoA decarboxylase, 2-oxoglutarate decarboxylase, Branched-chain-2-oxoacid decarboxylase, Tartrate decarboxylase, Indolepyruvate decarboxylase, 5-guanidino-2-oxopentanoate decarboxylase, Arylmalonate decarboxylase, 4-oxalocrotonate decarboxylase, Acetylenedicarboxylate decarboxylase, Sulfopyruvate decarboxylase, 4-hydroxyphenylpyruvate decarboxylase, Ketotetrose-phosphate aldolase, Deoxyribose-phosphate aldolase, Threonine aldolase, Phosphoketolase, Mandelonitrile lyase, Hydroxymandelonitrile lyase, 2-dehydropantoate aldolase, Fructose-bisphosphate aldolase, 2-dehydro-3-deoxyphosphogluconate aldolase, 2-dehydro-3-deoxyphosphoheptonate aldolase, 2-dehydro-3-deoxyphosphooctonate aldolase, L-fuculose-phosphate aldolase, 2-dehydro-3-deoxy-L-pentonate aldolase, Rhamnulose-1-phosphate aldolase, 2-dehydro-3-deoxyglucarate aldolase, 2-dehydro-3-deoxyphosphogalactonate aldolase, Fructose-6-phosphate phosphoketolase, 3-deoxy-D-manno-octulosonate aldolase, Dimethylaniline-N-oxide aldolase, Dihydroneopterin aldolase, Phenylserine aldolase, Sphinganine-1-phosphate aldolase, 2-dehydro-3-deoxy-D-pentonate aldolase, 5-dehydro-2-deoxyphosphogluconate aldolase, 17-alpha-hydroxyprogesterone aldolase, Trimethylamine-oxide aldolase, Fucosterol-epoxide lyase, 4-(2-carboxyphenyl)-2-oxobut-3-enoate aldolase, Propioin synthase, Lactate aldolase, Acetone-cyanohydrin lyase, Benzoin aldolase, Hydroxynitrilase, Tagatose-bisphosphate aldolase, Vanillin synthase, Isocitrate lyase, N-acetylneuraminate lyase, Hydroxymethylglutaryl-CoA lyase, Citrate lyase, Oxalomalate lyase, 3-hydroxyaspartate aldolase, 4-hydroxy-2-oxoglutarate aldolase, 4-hydroxy-4-methyl-2-oxoglutarate aldolase, N-acetylneuraminate synthase, N-acetylneuraminate-9-phosphate synthase, Citramalate lyase, Malyl-CoA lyase, Citramalyl-CoA lyase, 3-hydroxy-3-isohexenylglutaryl-CoA lyase, Anthranilate synthase, Methylisocitrate lyase, 2,3-

TABLE 1-continued

List of Enzymes dimethylmalate lyase, Citryl-CoA lyase, (1-hydroxycyclohexan-1-yl)acetyl-CoA lyase, Naphthoate synthase, Tryptophanase, Tyrosine phenol-lyase, Deoxyribodipyrimidine photolyase, Octadecanal decarbonylase, Benzylsuccinate synthase, Carbonate dehydratase, Fumarate hydratase, Aconitate hydratase, Citrate dehydratase, Arabinonate dehydratase, Galactonate dehydratase, Altronate dehydratase, Mannonate dehydratase, Dihydroxy-acid dehydratase, 3-dehydroquinate dehydratase, Phosphopyruvate hydratase, Phosphogluconate dehydratase, Enoyl-CoA hydratase, Methylglutaconyl-CoA hydratase, Imidazoleglycerol-phosphate dehydratase, Tryptophan synthase, Cystathionine beta-synthase, Porphobilinogen synthase, L-arabinonate dehydratase, Malonate-semialdehyde dehydratase, Propanediol dehydratase, Indoleacetaldoxime dehydratase, Glycerol dehydratase, Maleate hydratase, L(+)-tartrate dehydratase, 3-isopropylmalate dehydratase, (S)-2-methylmalate dehydratase, (R)-2-methylmalate dehydratase, Homoaconitate hydratase, Gluconate dehydratase, Glucarate dehydratase, 5-dehydro-4-deoxyglucarate dehydratase, Galactarate dehydratase, 2-dehydro-3-deoxy-L-arabinonate dehydratase, Myo-inosose-2 dehydratase, CDP-glucose 4,6-dehydratase, dTDP-glucose 4,6-dehydratase, GDP-mannose 4,6-dehydratase, D-glutamate cyclase, Urocanate hydratase, Pyrazolylalanine synthase, Prephenate dehydratase, Dihydrodipicolinate synthase, Oleate hydratase, Lactoyl-CoA dehydratase, 3-hydroxybutyryl-CoA dehydratase, Itaconyl-CoA hydratase, Isohexenylglutaconyl-CoA hydratase, Crotonoyl-[acyl-carrier protein] hydratase, 3-hydroxyoctanoyl-[acyl-carrier protein] dehydratase, 3-hydroxydecanoyl-[acyl-carrier protein] dehydratase, 3-hydroxypalmitoyl-[acyl-carrier protein] dehydratase, 5-alpha-hydroxysteroid dehydratase, 3-cyanoalanine hydratase, Cyanide hydratase, D-fuconate hydratase, L-fuconate hydratase, Cyanamide hydratase, Pseudouridylate synthase, Acetylenecarboxylate hydratase, Protoaphin-aglucone dehydratase (cyclizing), Long-chain-enoyl-CoA hydratase, Uroporphyrinogen-III synthase, UDP-glucose 4,6-dehydratase, Trans-L-3-hydroxyproline dehydratase, (S)-norcoclaurine synthase, 2-methylcitrate dehydratase, 2-oxopent-4-enoate hydratase, D(−)-tartrate dehydratase, Xylonate dehydratase, 4-oxalmesaconate hydratase, Nitrile hydratase, Dimethylmaleate hydratase, 16-dehydroprogesterone hydratase, Octopamine dehydratase, Synephrine dehydratase, L-carnitine dehydratase, L-rhamnonate dehydratase, Carboxycyclohexadienyl dehydratase, Hydroperoxide dehydratase, ATP-dependent H(4)NAD(P)OH dehydratase, Scytalone dehydratase, Kievitone hydratase, 4a-hydroxytetrahydrobiopterin dehydratase, Phaseollidin hydratase, 16-alpha-hydroxyprogesterone dehydratase, 2-methylisocitrate dehydratase, Cyclohexa-1,5-dienecarbonyl-CoA hydratase, Trans-feruloyl-CoA hydratase, Cyclohexyl-isocyanide hydratase, Cyanate hydratase, Hyaluronate lyase, Pectate lyase, Poly(beta-D-mannuronate) lyase, Chondroitin ABC lyase, Chondroitin AC lyase, Oligogalacturonide lyase, Heparin lyase, Heparitin-sulfate lyase, Pectate disaccharide-lyase, Pectin lyase, Poly(alpha-L-guluronate) lyase, Xanthan lyase, Exo-(1,4)-alpha-D-glucan lyase, Glucuronan lyase, Threonine synthase, Ethanolamine-phosphate phospho-lyase, Methylglyoxal synthase, 3-dehydroquinate synthase, Chorismate synthase, Trichodiene synthase, Pentalenene synthase, Casbene synthase, Aristolochene synthase, (−)-endo-fenchol synthase, Sabinene-hydrate synthase, 6-pyruvoyltetrahydropterin synthase, (+)-delta-cadinene synthase, Pinene synthase, Myrcene synthase, (−)-(4S)-limonene synthase, Taxadiene synthase, Abietadiene synthase, Ent-kaurene synthase, Cysteine synthase, O-succinylhomoserine (thiol)-lyase, O-acetylhomoserine (thiol)-lyase, Carboxymethyloxysuccinate lyase, Beta-(9-cytokinin)-alanine synthase, Beta-pyrazolylalanine synthase (acetylserine), L-mimosine synthase, Uracilylalanine synthase, DNA-(apurinic or apyrimidinic site) lyase, 2-hydroxypropyl-CoM lyase, Aspartate ammonia-lyase, Methylaspartate ammonia-lyase, Histidine ammonia-lyase, Formimidoyltetrahydrofolate cyclodeaminase, Phenylalanine ammonia-lyase, Beta-alanyl-CoA ammonia-lyase, Ethanolamine ammonia-lyase, Hydroxymethylbilane synthase, Glucosaminate ammonia-lyase, Serine-sulfate ammonia-lyase, Dihydroxyphenylalanine ammonia-lyase, Ornithine cyclodeaminase, Carbamoyl-serine ammonia-lyase, 3-aminobutyryl-CoA ammonia-lyase, Diaminopropionate ammonia-lyase, Threo-3-hydroxyaspartate ammonia-lyase, L-serine ammonia-lyase, D-serine ammonia-lyase, Threonine ammonia-lyase, Erythro-3-hydroxyaspartate ammonia-lyase, Aminodeoxygluconate ammonia-lyase, Argininosuccinate lyase, Adenylosuccinate lyase, Ureidoglycolate lyase, Purine imidazole-ring lyase, Peptidylamidoglycolate lyase, 3-ketovalidoxylamine C-N-lyase, Strictosidine synthase, Deacetylisoipecoside synthase, Deacetylipecoside synthase, Cystathionine gamma-lyase, Homocysteine desulfhydrase, Dimethylpropiothetin dethiomethylase, Alliin lyase, Lactoylglutathione lyase, S-alkylcysteine lyase, Cystathionine beta-lyase, L-3-cyanoalanine synthase, Cysteine lyase, Methionine gamma-lyase, Sulfoacetaldehyde lyase, Cysteine-S-conjugate beta-lyase, 1-aminocyclopropane-1-carboxylate synthase, D-cysteine desulfhydrase, Selenocysteine lyase, Holocytochrome-c synthase, DDT-dehydrochlorinase, 3-chloro-D-alanine dehydrochlorinase, Dichloromethane dehalogenase, L-2-amino-4-chloropent-4-enoate dehydrochlorinase, S-carboxymethylcysteine synthase, Adenylate cyclase, Guanylate cyclase, Cytidylate cyclase, 2-C-methyl-D-erythritol 2,4-cyclodiphosphate synthase, Phosphatidylinositol diacylglycerol-lyase, Ferrochelatase, Alkylmercury lyase

ISOMERASES

Alanine racemase, Methionine racemase, Glutamate racemase, Proline racemase, Lysine racemase, Threonine racemase, Diaminopimelate epimerase, 4-hydroxyproline epimerase, Arginine racemase, Amino-acid racemase, Phenylalanine racemase (ATP-hydrolyzing), Ornithine racemase, Aspartate racemase, Nocardicin-A epimerase, 2-aminohexano-6-lactam racemase, Protein-serine epimerase, Isopenicillin-N epimerase, Lactate racemase, Mandelate racemase, 3-hydroxybutyryl-CoA epimerase, Acetoin racemase, Tartrate epimerase, Isocitrate epimerase, Ribulose-phosphate 3-epimerase, UDP-glucose 4-epimerase, Aldose 1-epimerase, L-ribulose-phosphate 4-epimerase, UDP-arabinose 4-epimerase, UDP-glucuronate 4-epimerase, UDP-N-acetylglucosamine 4-epimerase, N-acylglucosamine 2-epimerase, N-acylglucosamine-6-phosphate 2-epimerase, CDP-abequose epimerase, Cellobiose epimerase, UDP-glucuronate 5'-epimerase, dTDP-4-dehydrorhamnose 3,5-epimerase, UDP-N-acetylglucosamine 2-epimerase, Glucose-6 phosphate 1-epimerase, UDP-glucosamine epimerase, Heparosan-N-sulfate-glucuronate 5-epimerase, GDP-mannose 3,5-epimerase, Chondroitin-glucuronate 5-epimerase, ADP-glyceromanno-heptose 6-epimerase, Maltose epimerase, Methylmalonyl-CoA epimerase, 16-hydroxysteroid epimerase, Allantoin racemase, Alpha-methylacyl-CoA racemase, Maleate isomerase, Maleylacetoacetate isomerase, Retinal isomerase, Maleylpyruvate isomerase, Linoleate isomerase, Furylfuramide isomerase, Retinol isomerase, Peptidylprolyl isomerase, Farnesol 2-isomerase, 2-chloro-4-carboxymethylenebut-2-en-1,4-olide isomerase, 4-hydroxyphenylacetaldehyde-oxime isomerase, Triosephosphate isomerase, Arabinose isomerase, L-arabinose isomerase, Xylose isomerase, Ribose 5-phosphate epimerase, Mannose isomerase, Mannose-6-phosphate isomerase, Glucose-6-phosphate isomerase, Glucuronate isomerase, Arabinose-5-phosphate isomerase, L-rhamnose isomerase, D-lyxose ketol-isomerase, 1-(5-phosphoribosyl)-5-[(5-phosphoribosylamino)methylideneamino] imidazole-4-carboxamide isomerase, 4-deoxy-L-threo-5-hexosulose-uronate ketol-isomerase, Ribose isomerase, Corticosteroid side-chain-isomerase, Hydroxypyruvate isomerase, 5-methylthioribose-1-phosphate isomerase, Phosphoribosylanthranilate isomerase, L-fucose isomerase, Galactose-6-phosphate isomerase, Phenylpyruvate tautomerase, Oxaloacetate tautomerase, Steroid delta-isomerase, Isopentenyl-diphosphate delta-isomerase, Vinylacetyl-CoA delta-isomerase, Muconolactone isomerase, Cholestenol delta-isomerase, Methylitaconate delta-isomerase, Aconitate delta-isomerase, Dodecenoyl-CoA delta-isomerase, Prostaglandin-A1 delta-isomerase, 5-carboxymethyl-2-hydroxymuconate delta-isomerase, Isopiperitenone delta-isomerase, Dopachrome isomerase, Protein disulfide isomerase, Prostaglandin-D synthase, Prostaglandin-E synthase, Prostaglandin-I synthase, Thromboxane-A synthase, Allene-oxide cyclase, Styrene-oxide isomerase, Lysolecithin acylmutase, Precorrin-8X methylmutase, Phosphoglycerate mutase, Phosphoglucomutase, Phosphoacetylglucosamine mutase, Bisphosphoglycerate mutase, Phosphoglucomutase (glucose-cofactor), Beta-phosphoglucomutase, Phosphopentomutase, Phosphomannomutase, Phosphoenolpyruvate mutase, Phosphoglucosamine mutase, Lysine 2,3-aminomutase, Beta-lysine 5,6-aminomutase, D-lysine 5,6-aminomutase, D-ornithine 4,5-aminomutase, Tyrosine 2,3-aminomutase, Leucine 2,3-aminomutase, Glutamate-1-semialdehyde 2,1-aminomutase, Methylaspartate mutase, Methylmalonyl-CoA mutase, 2-acetolactate mutase, 2-methyleneglutarate mutase, Chorismate mutase, Isochorismate mutase, Lanosterol synthase, Cycloartenol synthase, UDP-galactopyranose mutase, Isomaltulose synthase, tRNA-pseudouridine synthase I, Isobutyryl-CoA mutase, 4-carboxymethyl-4-methylbutenolide mutase, (1,4)-alpha-D-glucan 1-alpha-D-glucosylmutase, Maltose alpha-D-glucosyltransferase, Squalene--hopene cyclase, Muconate cycloisomerase, 3-carboxy-cis, cis-muconate cycloisomerase, Tetrahydroxypteridine cycloisomerase, Inositol-3-phosphate synthase, Carboxy-cis, cis-muconate cyclase, Chalcone isomerase, Chloromuconate cycloisomerase, Geranyl-diphosphate cyclase, Cycloeucalenol cycloisomerase, Alpha-pinene-oxide decyclase, Dichloromuconate cycloisomerase, Copalyl diphosphate synthase, Ent-copalyl diphosphate

TABLE 1-continued

List of Enzymes synthase, Thiocyanate isomerase, DNA topoisomerase, DNA topoisomerase (ATP-hydrolyzing)

LIGASES

Tyrosine--tRNA ligase, Tryptophan--tRNA ligase, Threonine--tRNA ligase, Leucine--tRNA ligase, Isoleucine--tRNA ligase, Lysine--tRNA ligase, Alanine--tRNA ligase, Valine--tRNA ligase, Methionine--tRNA ligase, Serine--tRNA ligase, Aspartate--tRNA ligase, D-alanine--poly(phosphoribitol)ligase, Glycine--tRNA ligase, Proline--tRNA ligase, Cysteine--tRNA ligase, Glutamate--tRNA ligase, Glutamine--tRNA ligase, Arginine--tRNA ligase, Phenylalanine--tRNA ligase, Histidine--tRNA ligase, Asparagine--tRNA ligase, Aspartate--tRNA(Asn) ligase, Glutamate--tRNA(Gln) ligase, Lysine--tRNA(Pyl) ligase, Acetate--CoA ligase, Butyrate--CoA ligase, Long-chain-fatty-acid--CoA ligase, Succinate--CoA ligase (GDP-forming), Succinate--CoA ligase (ADP-forming), Glutarate--CoA ligase, Cholate--CoA ligase, Oxalate--CoA ligase, Malate--CoA ligase, Acid--CoA ligase (GDP-forming), Biotin--CoA ligase, 4-coumarate--CoA ligase, Acetate--CoA ligase (ADP-forming), 6-carboxyhexanoate--CoA ligase, Arachidonate--CoA ligase, Acetoacetate--CoA ligase, Propionate--CoA ligase, Citrate--CoA ligase, Long-chain-fatty-acid--luciferin-component ligase, Long-chain-fatty-acid--acyl-carrier protein ligase, [Citrate (pro-3S)-lyase] ligase, Dicarboxylate--CoA ligase, Phytanate--CoA ligase, Benzoate--CoA ligase, O-succinylbenzoate--CoA ligase, 4-hydroxybenzoate--CoA ligase, 3-alpha, 7-alpha-dihydroxy-5-beta-cholestanate--CoA ligase, 3-alpha, 7-alpha, 12-alpha-trihydroxy-5-beta-cholestanate--CoA ligase, Phenylacetate--CoA ligase, 2-furoate--CoA ligase, Anthranilate--CoA ligase, 4-chlorobenzoate-CoA ligase, Trans-feruloyl-CoA synthase, Aspartate--ammonia ligase, Glutamate--ammonia ligase, Aspartate--ammonia ligase (ADP-forming), NAD(+) synthase, Glutamate--ethylamine ligase, 4-methyleneglutamate--ammonia ligase, Glutathionylspermidine synthase, Trypanothione synthase, Pantoate--beta-alanine ligase, Glutamate--cysteine ligase, Glutathione synthase, D-alanine--D-alanine ligase, Phosphopantothenate--cysteine ligase, Phosphoribosylaminoimidazole-succinocarboxamide synthase, UDP-N-acetylmuramoyl-L-alanyl-D-glutamate--L-lysine ligase, UDP-N-acetylmuramate--L-alanine ligase, UDP-N-acetylmuramoylalanine--D-glutamate ligase, UDP-N-acetylmuramoyl-tripeptide--D-alanyl-D-alanine ligase, Carnosine synthase, Dihydrofolate synthase, UDP-N-acetylmuramoylalanyl-D-glutamate--2,6-diaminopimelate ligase, 2,3-dihydroxybenzoate--serine ligase, D-alanine--alanyl-poly(glycerolphosphate) ligase, Folylpolyglutamate synthase, Gamma-glutamylhistamine synthase, Ubiquitin--protein ligase, Indoleacetate--lysine ligase, Ubiquitin--calmodulin ligase, Diphthine--ammonia ligase, Homoglutathione synthase, Tyrosine--arginine ligase, Tubulin--tyrosine ligase, N-(5-amino-5-carboxypentanoyl)-L-cysteinyl-D-valine synthase, Aerobactin synthase, Phosphoribosylformylglycinamidine cyclo-ligase, 5-formyltetrahydrofolate cyclo-ligase, Dethiobiotin synthase, GMP synthase, CTP synthase, Formate--tetrahydrofolate ligase, Adenylosuccinate synthase, Argininosuccinate synthase, Urea carboxylase, Ribose-5-phosphate--ammonia ligase, Imidazoleacetate--phosphoribosyldiphosphate ligase, Biotin--[methylmalonyl-CoA-carboxyltransferase] ligase, Biotin--[propionyl-CoA-carboxylase (ATP-hydrolyzing)] ligase, Biotin--[methylcrotonoyl-CoA-carboxylase] ligase, Glutamate--methylamine ligase, Phosphoribosylamine--glycine ligase, Biotin carboxylase, Biotin--[acetyl-CoA-carboxylase] ligase, Carbamoyl-phosphate synthase (ammonia), Formate--dihydrofolate ligase, NAD(+) synthase (glutamine-hydrolyzing), GMP synthase (glutamine-hydrolyzing), Phosphoribosylformylglycinamidine synthase, Asparagine synthase (glutamine-hydrolyzing), Carbamoyl-phosphate synthase (glutamine-hydrolyzing), Asparaginyl-tRNA synthase (glutamine-hydrolyzing), Glutaminyl-tRNA synthase (glutamine-hydrolyzing), Pyruvate carboxylase, Acetyl-CoA carboxylase, Propionyl-CoA carboxylase, Methylcrotonyl-CoA carboxylase, Geranoyl-CoA carboxylase, Acetone carboxylase, DNA ligase (ATP), DNA ligase (NAD+), RNA ligase (ATP), RNA-3'-phosphate cyclase Identifying substrates of enzymes can also be conducted with the methods of the present invention. For example, a wide variety of different potential substrates are attached to the protein chip and are assayed for their ability to act as a substrate for particular enzyme(s) that is also immobilized to the surface of the solid substrate.

In certain embodiments, candidate-substrates are identified in a parallel experiment on the basis of a substrates' ability to bind to the enzyme of interest. A substrate can be a cell, protein-containing cellular material, protein, oligonucleotide, polynucleotide, DNA, RNA, small molecule substrate, drug candidate, receptor, antigen, steroid, phospholipid, antibody, immunoglobulin domain, glutathione, maltose, nickel, dihydrotrypsin, or biotin. After incubation of proteins on a chip with test molecules, the candidate substrates can be identified by mass spectrometry (Lakey et al., 1998, "Measuring protein-protein interactions", Curr Opin Struct Biol. 8:119-23).

The identity of targets of a specific enzymatic activity can be assayed by treating a protein chip with complex protein mixtures, such as cell extracts, and determining protein activity, wherein the complex protein mixture is also immobilized on the surface of the solid support. For example, a protein chip containing an array of different kinases can be contacted with a cell extract from cells treated with a compound (e.g., a drug), and assayed for kinase activity. In another example, a protein chip containing an array of different kinases can be contacted with a cell extract from cells at a particular stage of cell differentiation (e.g., pluripotent) or from cells in a particular metabolic state (e.g., mitotic), and assayed for kinase activity. Proteins of the cell extract can be immobilized to the solid support by methods as described above. The results obtained from such assays, comparing for example, cells in the presence or absence of a drug, or cells at several differentiation stages, or cells in different metabolic states, can provide information regarding the physiologic changes in the cells between the different conditions.

Alternatively, the identity of targets of specific cellular activities can be assayed by treating a protein chip, containing many different proteins (e.g., a peptide library) immobilized to the surface of the solid support of the protein chip, with a complex protein mixture (e.g., such as a cell extract), and assaying for modifications to the proteins on the chip, wherein the protein mixture is also immobilized to the surface of the solid support. For example, a protein chip containing an array of different proteins can be contacted with a cell extract from cells treated with a compound (e.g., a drug), and assayed for oxidoreductase, transferase, hydrolase, lyase, isomerase, or ligase activity. In more specific embodiments, kinase, protease, glycosidase, actetylase, phosphatase, or other transferase activity can for example be assayed. In another example, a protein chip containing an array of different proteins can be contacted with a cell extract from cells at a particular stage of cell differentiation (e.g., pluripotent) or from cells in a particular metabolic state (e.g., mitotic). The results obtained from such assays, comparing for example, cells in the presence or absence of a drug, or cells at several stages of differentiation, or cells in different metabolic states, can provide information regarding the physiologic effect on the cells under these conditions.

The activity of proteins exhibiting differences in function, such as enzymatic activity, can be analyzed with the protein methods of the present invention. For example, differences in protein isoforms derived from different alleles are assayed for their activities relative to one another.

The methods of the invention can be used for drug discovery, analysis of the mode of action of a drug, drug specificity, and prediction of drug toxicity. As many enzymes and substrates can be tested at the same time, the methods of the invention are suitable to determine profiles for different drugs. In certain embodiments, such a profile relates to sensitivities of different enzymes to the drug of interest. In other embodiments, such a profile relates to effects of the drug of interest on the substrate specificity of different enzymes. For example, the identity of proteins whose activity is susceptible to a particular compound can be determined by performing the assay of the invention in the presence and absence of a compound. For a more detailed description of screening assays using the methods of the invention, see section 5.6.

Moreover, the methods of the present invention can be used to determine the presence of potential inhibitors, catalysts, modulators, or enhancers of the enzymatic activity. In one example, a cellular extract of a cell is added to an enzymatic assay of the invention.

The protein chips of the invention can be used to determine the effects of a drug on the modification of multiple targets by complex protein mixtures, such as for example, whole cells, cell extracts, or tissue homogenates. The net effect of a drug can be analyzed by screening one or more protein chips with drug-treated cells, tissues, or extracts, which then can provide a "signature" for the drug-treated state, and when compared with the "signature" of the untreated state, can be of predictive value with respect to, for example, potency, toxicity, and side effects. Furthermore, time-dependent effects of a drug can be assayed by, for example, adding the drug to the cell, cell extract, tissue homogenate, or whole organism, and applying the drug-treated cells or extracts to a protein chip at various timepoints of the treatment.

In the subsections below, exemplary enzyme assays for use with the invention are described. These examples are meant to illustrate the present invention and are not intended to limit in any way the scope of the present invention.

5.2.1. Kinase Assay

In certain embodiments of the invention, the enzymatic reaction to be performed with the methods of the invention is a kinase reaction. In certain embodiments, a kinase is a tyrosine kinase or a serine/threonine kinase. Exemplary kinases to be used with the methods of the invention include, but not limited to, ABL, ACK, AFK, AKT (e.g., AKT-1, AKT-2, and AKT-3), ALK, AMP-PK, ATM, Aurora1, Aurora2, bARK1, bArk2, BLK, BMX, BTK, CAK, CaM kinase, CDC2, CDK, CK, COT, CTD, DNA-PK, EGF-R, ErbB-1, ErbB-2, ErbB-3, ErbB-4, ERK (e.g., ERK1, ERK2, ERK3, ERK4, ERK5, ERK6, ERK7), ERT-PK, FAK, FGR (e.g., FGF1R, FGF2R), FLT (e.g., FLT-1, FLT-2, FLT-3, FLT-4), FRK, FYN, GSK (e.g., GSK1, GSK2, GSK3-alpha, GSK3-beta, GSK4, GSK5), G-protein coupled receptor kinases (GRKs), HCK, HER2, HKII, JAK (e.g., JAK1, JAK2, JAK3, JAK4), JNK (e.g., JNK1, JNK2, JNK3), KDR, KIT, IGF-1 receptor, IKK-1, IKK-2, INSR (insulin receptor), IRAK1, IRAK2, IRK, ITK, LCK, LOK, LYN, MAPK, MAP-KAPK-1, MAPKAPK-2, MEK, MET, MFPK, MHCK, MLCK, MLK3, NEU, NIK, PDGF receptor alpha, PDGF receptor beta, PHK, PI-3 kinase, PKA, PKB, PKC, PKG, PRK1, PYK2, p38 kinases, p135tyk2, p34cdc2, p42cdc2, p42mapk, p44 mpk, RAF, RET, RIP, RIP-2, RK, RON, RS kinase, SRC, SYK, S6K, TAK1, TEC, TIE1, TIE2, TRKA, TXK, TYK2, UL13, VEGFR1, VEGFR2, YES, YRK, ZAP-70, and all subtypes of these kinases (see e.g., Hardie and Hanks (1995) The Protein Kinase Facts Book, I and II, Academic Press, San Diego, Calif.). A recent list of human kinases can be found in Manning et al., 2002, Science 298: 1912-1934. In certain embodiments of the invention, proteins to be used with the methods of the invention and on the arrays of the invention are proteins that have sequence homologies to a known kinase.

In certain embodiments, the plurality of proteins and a kinase substrate are immobilized on the surface of the solid support. In certain, more specific embodiments, the plurality of proteins consists of different known kinases. In certain embodiments, a kinase and a plurality of different substrates are immobilized on the surface of the solid support. In a specific embodiment, at least one substrate is a known kinase substrate. The substrates can be candidate substrates.

The kinase reaction can be visualized and quantified by any method known to the skilled artisan. In specific embodiments, to visualize the kinase reaction, ATP whose gamma-phosphate is detectably labeled is added to the microarray in a reaction buffer. The reaction buffer provides, in addition to ATP, reaction conditions conducive to the kinase reaction. Reaction conditions include, but are not limited to, pH, salt concentration, concentration of $Mg^{++}$, and detergent concentration. After incubation in the reaction buffer, the microarray is washed to remove any labeled ATP and the product is quantified via the detectably labeled phosphate that has been transferred during the kinase reaction from ATP to the substrate. The signal intensity is proportional to the amount of labeled phosphate on the substrate and thus to the activity of the kinase reaction.

The gamma phosphate of ATP can be detectably labeled by any method known to the skilled artisan. In certain embodiments, the gamma phosphate of ATP is labeled with radioactive phosphorus, such as, but not limited to, $^{32}P$ or $^{33}P$. $^{35}S$-gamma-ATP can also be used with the methods of the invention. If the phosphate is labeled radioactively, the signal intensity can be evaluated using autoradiography.

Without being bound by theory, some kinases act on a substrate only in a particular molecular context. Such a molecular context may, e.g., consist of certain scaffold proteins. In certain embodiments of the invention, such scaffold proteins are provided with the reaction buffer. In other embodiments, the scaffold proteins are also immobilized on the surface of the solid support.

In certain embodiments, a kinase reaction can be visualized and quantified using antibodies that bind specifically to phosphorylated proteins or peptides. Such antibodies include, but are not limited to antibodies that bind to phospho-serine or antibodies that bind to phospho-tyrosine. The antibody that binds to the phosphorylated protein or peptide can be directly labeled and detected by any method known to the skilled artisan. In other embodiments, a secondary antibody is used to detect the antibody that is bound to the phosphorylated protein or peptide. The more active the kinase reaction is the more antibody will be bound and the stronger the signal will be.

In certain embodiments, phosphorylation can be detected using a molecule that binds to phosphate and that is linked to a detectable label such as, but not limited to, a dye. In a specific embodiment, a phosphorylated protein or peptide is detected using Pro-Q Diamond stain from Molecular Probes.

5.2.2. Phosphatase

Any phosphatase known to the skilled artisan can be used with the methods of the present invention or for the manufacture of the arrays of the present invention. Examples of protein tyrosine phosphatases (PTPases) include, but are not limited to, PTP1B, PTPMEG, PTP1c, Yop51, VH1, cdc25, CD45, HLAR, PTP18, HPTP.alpha. and DPTP10D. See Zhang and Dixon, 1994, Adv. Enzym. 68: 1-36. Examples of protein serine-threonine phosphatases include PP1, PP2A, PP2B and PP2C. See Meth. Enzym., Hunter & Sefton, Academic press, New York, 201:389-398 (1991). In certain embodiments, the proteins to be used with the methods of the present invention or for the manufacture of the arrays of the present invention have homologies with known phosphatases.

In certain embodiments, the plurality of proteins and a phosphatase substrate are immobilized on the surface of the solid support. In certain, more specific embodiments, the plurality of proteins consists of different known phosphatases. In certain embodiments, a phosphatase and a plurality of different substrates are immobilized on the surface of the solid support. In a specific embodiment, at least one substrate is a phosphatase substrate.

In certain embodiments, the phosphatase reaction is performed by adding a phosphatase reaction buffer to phosphatase and substrate on the surface of the solid support. The phosphatase reaction buffer provides conditions conducive to the phosphatase reaction.

Any method known to the skilled artisan can be employed to detect and quantify phosphatase activity. In certain embodiments, the phosphatase substrate is a phosphorylated peptide or protein, wherein the phosphate is detectably labeled. Phosphatase activity can be detected and quantified by virtue of a decrease in detectable label on the substrate and thus on the surface of the solid support. In other embodiments, the release of the detectably labeled phosphate into the reaction buffer is determined.

The phosphate can be detectably labeled by any method known to the skilled artisan. In certain embodiments, the phosphate is radioactively labeled, such as, but not limited to, $^{32}P$ or $^{33}P$. $^{35}S$-gamma-ATP can also be used. If the phosphate is labeled radioactively, the signal intensity can be evaluated using autoradiography.

In certain embodiments, a phosphatase reaction can be visualized and quantified using antibodies that bind specifically to phosphorylated proteins or peptides. Such antibodies include, but are not limited to antibodies that bind to phosphoserine or antibodies that bind to phospho-tyrosine. The antibody that binds to the phosphorylated protein or peptide can be directly labeled and detected by any method known to the skilled artisan. In other embodiments, a secondary antibody is used to detect the antibody that is bound to the phosphorylated protein or peptide. The more active the phosphatase reaction is the less antibody will be bound and the weaker the signal will be.

5.2.3. Glycosidase

Any glycosidase known to the skilled artisan can be used with the present invention. Glycosidases include, but are not limited to, both endo- and exo-glucosidases which can cleave both alpha- and beta-glycosidic bonds, for example amylase, maltase, cellulase, endoxylanase, beta-glucanase, mannanase, or lysozyme, and in addition galactosidase or beta-glucuronidases. In certain embodiments, proteins to be used with the invention have homologies to a known glycosidase.

In certain embodiments, the plurality of proteins and a glycosidase substrate are immobilized on the surface of the solid support. In certain, more specific embodiments, the plurality of proteins consists of different known glycosidases. In certain embodiments, a glycosidase and a plurality of different substrates are immobilized on the surface of the solid support. In a specific embodiment, at least one substrate is a glycosidase substrate.

In certain embodiments, the glycosidase reaction is performed by adding a glycosidase reaction buffer to glycosidase and substrate on the surface of the solid support. The glycosidase reaction buffer provides conditions conducive to the glycosidase reaction.

Any method known to the skilled artisan can be employed to detect and quantify glycosidase activity. In certain embodiments, the glycosidase substrate is, e.g., a polysaccharide. Glycosidase activity can be detected and quantified by virtue of a decrease in detectable label on the substrate and thus on the surface of the solid support. In other embodiments, the release of the detectably labeled monomers of the polysaccharide into the reaction buffer is measured.

The glycosidase substrate can be detectably labeled by any method known to the skilled artisan. In certain embodiments, the polysaccharide is radioactively labeled. In certain embodiments, the polysaccharide is attached to the surface of the solid support on one end and is detectably labeled on the other end. The decrease of detectable label on the surface of the solid support is a measure for the activity of the glycosidase activity.

5.2.4. Protease

Any protease known to the skilled artisan can be used with the present invention. Proteases include, but are not limited to, Bromelain, Cathepsins, Chymotrypsin, Collagenase, Elastase, Kallikrein, Papain, Pepsin, Plasmin, Renin, Streptokinase, Subtilisin, Thermolysin, Thrombin, Trypsin, and Urokinase.

In certain embodiments, the plurality of proteins and a protease substrates are immobilized on the surface of the solid support. In certain, more specific embodiments, the plurality of proteins consists of different known proteases. In certain embodiments, a protease and a plurality of different protease substrates are immobilized on the surface of the solid support.

In certain embodiments, the protease reaction is performed by adding a protease reaction buffer to protease and substrate on the surface of the solid support. The protease reaction buffer provides conditions conducive to the glycosidase reaction.

Any method known to the skilled artisan can be employed to detect and quantify protease activity. In certain embodiments, the protease substrate is, e.g., a polypeptide or a protein. Protease activity can be detected and quantified by virtue of a decrease in detectable label on the substrate and thus on the surface of the solid support. In other embodiments, the release of the detectably labeled amino acids or peptides of the polypeptide into the reaction buffer is measured. In certain other embodiments, FRET or fluorescence polarization is used to detect and quantify a protease reaction.

The protease substrate can be detectably labeled by any method known to the skilled artisan. In certain embodiments, the protein or polypeptide is radioactively labeled. In certain embodiments, the protein or polypeptide is attached to the surface of the solid support on one end and is detectably labeled on the other end. The decrease of detectable label on the surface of the solid support is a measure for the activity of the protease activity.

In a specific embodiment, protease activity is assayed in the following way. First, protein probes are prepared consisting of various combinations of amino acids, with a C-terminal or N-terminal mass spectroscopic label attached, with the only proviso being that the molecular weight of the label should be sufficiently large so that all labeled cleavage products of the protein can be detected. The protein substrate is immobilized to the protein chip and the proteases are immobilized to the protein chip in proximity with each other sufficient to allow occurrence of the protease reaction. After incubation at 37° C. for an appropriate period of time, and washing with acetonitrile and trifluoroacetic acid, protease activity is measured by detecting the proteolytic products using mass spectrometry. This assay provides information regarding both the proteolytic activity and specificity of the proteases attached to the protein chip.

Another rapid assay for protease activity analysis is to attach proteins of known sequence to the chip. The substrate proteins are fluorescently labeled at the end not attached to the chip. Upon incubation with the protease(s) of interest, the fluorescent label is lost upon proteolysis, such that decreases in fluorescence indicate the presence and extent of protease activity. This same type of assay can be carried out wherein the protein substrates are attached to beads placed in the wells of the chips.

5.2.5 Nuclease

Nuclease activity can be assessed in the same manner as described for protease activity (see section 5.2.4) except that nucleic acid substrates are used instead of protein substrates. As such, fluorescently tagged nucleic acid fragments that are released by nuclease activity can be detected by fluorescence, or the nucleic acid fragments can be detected directly by mass spectrometry.

5.3 Substrates and Cofactors

If substances are to be identified that serve as substrates for a particular enzymatic reaction, any substance can be used with the methods of the invention. In certain embodiments, combinatorial libraries of molecules can be used as substances (see section 5.6.1 for libraries).

Substrates to be used as substrates of a particular enzymatic reaction with the methods of the present invention can be any substrate known to the skilled artisan of that particular enzymatic reaction.

In certain embodiments, generic substrates for a particular enzymatic reaction can be used. In other embodiments, the substrates are specific for class of enzymes. In even other embodiments, the substrates are specific for individual enzymes.

In an illustrative embodiments, a substrate of an enzyme that catalyzes the phosphorylation of tyrosine residues in a protein or peptide is a protein or peptide with tyrosines. In another illustrative embodiment, a substrate of an enzyme that catalyzes the phosphorylation of serine and threonine residues in a protein or peptide is a protein or peptide with serine and/or threonine. A substrate for a dual specificity kinase has tyrosine and/or serine and/or threonine. Certain kinases require a conserved target motif in their substrate for phosphorylation. In certain embodiments, such a conserved target motif is present in the substrate. In a specific embodiment, a kinase substrate is, but is not limited to, casein. In another specific embodiment, a mixture of Myelin Basic Protein (MBP), histone and casein is used as substrate. In another specific embodiment, a mixture of Myelin Basic Protein (MBP), histone, casein and/or poly(Glu4Tyr) is used as substrate.

Certain enzymes that use proteins or peptides as substrate require the presence of a particular amino acid or amino acid motif in their substrates for the enzymatic reaction to occur. Such sites in a amino acid sequence that are used by a particular enzymatic activity can be predicted using such databases as PROSITE.

Illustrative substrates for exemplary enzymes are listed in Table 2.

TABLE 2

| Class of Enzyme | Type of Reaction Catalyzed | Examples | Substrate and Specific Reaction Catalyzed |
| --- | --- | --- | --- |
| Oxidoreductases | Oxidation-reduction reactions | Alcohol dehydrogenase. | An alcohol + NAD(+) <=> an aldehyde or ketone + NADH |
| Transferases | Transfer of functional groups | Nicotinamide N-methyltransferase. | S-adenosyl-L-methionine + nicotinamide <=> S-adenosyl-L-homocysteine + 1-methylnicotinamide |
| | | Protein-tyrosine kinase. | ATP + a protein tyrosine <=> ADP + protein tyrosine phosphate |
| | | Amino-acid N-acetyltransferase. | Acetyl-CoA + L-glutamate <=> CoA + N-acetyl-L-glutamate |
| | | Phosphorylase. | {(1,4)-alpha-D-glucosyl}(N) + phosphate <=> {(1,4)-alpha-D-glucosyl}(N-1) + alpha-D-glucose 1-phosphate |
| | | Aspartate aminotransferase. | L-aspartate + 2-oxoglutarate <=> oxaloacetate + L-glutamate |
| | | Hexokinase. | ATP + D-hexose <=> ADP + D-hexose 6-phosphate |
| | | Thiosulfate sulfurtransferase. | Thiosulfate + cyanide <=> sulfite + thiocyanate |

TABLE 2-continued

| Class of Enzyme | Type of Reaction Catalyzed | Examples | Substrate and Specific Reaction Catalyzed |
|---|---|---|---|
| Hydrolases | Hydrolysis reactions | Leucyl aminopeptidase. | Release of an N-terminal amino acid, Xaa-l-Xbb-, in which Xaa is preferably Leu, but may be other amino acids including Pro although not Arg or Lys, and Xbb may be Pro. |
| Lyases | Group Elimination to form double bonds | Pyruvate decarboxylase. | A 2-oxo acid <=> an aldehyde + $CO(2)$ |
| Isomerases | Isomerization | Phosphoglycerate mutase. | 2-phospho-D-glycerate + 2,3-diphosphoglycerate <=> 3-phospho-D-glycerate + 2,3-diphosphoglycerate |
| Ligases | Bond formation coupled with ATP hydrolysis | Tyrosine--tRNA ligase. | ATP + L-tyrosine + tRNA(Tyr) <=> AMP + diphosphate + L-tyrosyl-tRNA(Tyr) |

5.3.1 Cofactors

In certain embodiments of the invention, the enzymatic reaction being assayed requires a cofactor. Cofactors can be added to the reaction in the reaction mixture. Cofactors that can be used with the methods of the invention include, but are not limited to, 5,10-methenyltetrahydrofolate, Ammonia, Ascorbate, ATP, Bicarbonate, Bile salts, Biotin, Bis(molybdopterin guanine dinucleotide)molybdenum cofactor, Cadmium, Calcium, Cobalamin, Cobalt, Coenzyme F430, Coenzyme-A, Copper, Dipyrromethane, Dithiothreitol, Divalent cation, FAD, Flavin, Flavoprotein, FMN, Glutathione, Heme, Heme-thiolate, Iron, Iron(2+), Iron-molybdenum, Iron-sulfur, Lipoyl group, Magnesium, Manganese, Metal ions, Molybdenum, Molybdopterin, Monovalent cation, NAD, NAD(P)H, Nickel, Potassium, PQQ, Protoheme IX, Pyridoxal-phosphate, Pyruvate, Selenium, Siroheme, Sodium, Tetrahydropteridine, Thiamine pyrophosphate, Topaquinone, Tryptophan tryptophylquinone (TTQ), Tungsten, Vanadium, Zinc.

5.4. Properties of the Protein Chips to be Used with the Methods of the Invention In various specific embodiments, the microarray of the invention is a positionally addressable array comprising a plurality of different proteins and a substance immobilized on the surface of a solid support. In other embodiments, the microarray of the invention is a positionally addressable array comprising a plurality of different substances and an enzyme immobilized on the surface of a solid support. In certain embodiments, the proteins comprise a functional domain on a solid support. Each different protein or substance is at a different position on the solid support. In certain embodiments, the plurality of different proteins or molecules consists of at least 50%, 75%, 90%, or 95% of all expressed proteins with the same type of biological activity in the genome of an organism. For example, such organism can be eukaryotic or prokaryotic, and is preferably a mammal, a human or non-human animal, primate, mouse, rat, cat, dog, horse, cow, chicken, fungus such as yeast, Drosophila, C. elegans, etc. Such type of biological activity of interest can be, but is not limited to, enzymatic activity (e.g., kinase activity, protease activity, phosphatase activity, glycosidase, acetylase activity, and other chemical group transferring enzymatic activity), nucleic acid binding, hormone binding, etc.

In certain embodiments, the plurality of different proteins or substances is immobilized on the surface of the solid support at a density of about 1 to 10, 5 to 20, 10 to 50, 30 to 100, about 30, between 30 and 50, between 50 and 100, at least 100, between 100 and 1000, between 1000 and 10,000, between 10,000 and 100,000, between 100,000 and 1,000, 000, between 1,000,000 and 10,000,000, between 10,000, 000 and 25,000,000, at least 25,000,000, at least 10,000,000, 000, or at least 10,000,000,000,000 different proteins or substances, per $cm^2$.

In certain embodiments, the plurality of different proteins and a plurality of different substances are immobilized on the surface of the solid support at a density of about 1 to 10, 5 to 20, 10 to 50, 30 to 100, about 30, between 30 and 50, between 50 and 100, at least 100, between 100 and 1000, between 1000 and 10,000, between 10,000 and 100,000, between 100, 000 and 1,000,000, between 1,000,000 and 10,000,000, between 10,000,000 and 25,000,000, at least 25,000,000, at least 10,000,000,000, or at least 10,000,000,000,000 different proteins or substances, respectively, per $cm^2$.

The protein chips to be used with the present invention are not limited in their physical dimensions and may have any dimensions that are convenient. For the sake of compatibility with current laboratory apparatus, protein chips the size of a standard microscope slide or smaller are preferred. In certain embodiments, protein chips are sized such that two chips fit on a microscope slide. Also preferred are protein chips sized to fit into the sample chamber of a mass spectrometer. Also preferred are microtiter plates.

In certain embodiments, a substance and enzyme are immobilized on the surface of a solid support within wells. In certain embodiments, a plurality of different enzymes or different substances is printed or coated on the surface of the solid support such that each protein or substance of the microarray is in a different well. In other embodiments, a plurality of different enzymes or different substances is printed onto the surface of the solid support such that each well harbors a plurality of different proteins or substrates. The performance of the enzymatic reaction on a solid support with wells has the advantage that different reaction solutions can be added at the same time onto one solid support (e.g., on one slide). Another advantage of wells over flat surfaces is increased signal-to-noise ratios. Wells allow the use of larger volumes of reaction solution in a denser configuration, and therefore greater signal is possible. Furthermore, wells decrease the rate of evaporation of the reaction solution from the chip as compared to flat surface arrays, thus allowing longer reaction times. Another advantage of wells over flat surfaces is that the use of wells permit association studies using a specific volume of reaction volume for each well on the chip, whereas the use of flat surfaces usually involves indiscriminate probe application across the whole substrate. The application of a defined volume of reaction buffer can be important if a reactant that is supplied in the reaction buffer is being depleted during the course of the reaction. In such a scenario, the application of a defined volume allows for more reproducible results.

In certain embodiments, if the microarrays to be used with the methods of the invention and the microarrays of the invention have wells, the wells in the protein chips may have any shape such as rectangular, square, or oval, with circular being preferred. The wells in the protein chips may have square or round bottoms, V-shaped bottoms, or U-shaped bottoms. Square bottoms are slightly preferred because the preferred reactive ion etch (RIE) process, which is anisotropic, provides square-bottomed wells. The shape of the well bottoms need not be uniform on a particular chip, but may vary as required by the particular assay being carried out on the chip.

The wells in the protein chips to be used with the methods of the present invention may have any width-to-depth ratio, with ratios of width-to-depth between about 10:1 and about 1:10 being preferred. The wells in the protein chips may have any volume, with wells having volumes of at least 1 pl, at least 10 pl, at least 100 pl, at least 1 nl, at least 10 nl, at least 100 nl, at least 1 µl, at least 10 µl, or at least 100 µl. The wells in the protein chips may have any volume, with wells having volumes of at most 1 pl, at most 10 pl, at most 100 pl, at most 1 nl, at most 10 nl, at most 100 nl, at most 1 µl, at most 10 µl, or at most 100 µl.

In certain embodiments, the wells are formed by placing a gasket with openings on the surface of the solid support such that the openings in the gasket form the wells. In certain, more specific embodiments, an array has at least 1, 2, 4, 6, 8, 10, 12, 14, 16, 18, 20, 24, 50 or at least 100 wells. In certain, more specific embodiments, an array has at most 1, 2, 4, 6, 8, 10, 12, 14, 16, 18, 20, 24, 50 or at least 100 wells.

The protein chips of the invention can have a wide variety of density of wells/cm$^2$. The density of wells is between about 1 well/cm$^2$ and about 10,000,000,000,000 wells/cm$^2$. Densities of wells on protein chips cast from master molds of laser milled Lucite are generally between 1 well/cm$^2$ and 2,500 wells/cm$^2$. Appropriate milling tools produce wells as small as 100 µm in diameter and 100 µm apart. Protein chips cast from master mold etched by wet-chemical microlithographic techniques have densities of wells generally between 50 wells/cm$^2$ and 10,000,000,000 wells/cm$^2$. Wet-chemical etching can produce wells that are 10 µm deep and 10 µm apart, which in turn produces wells that are less than 10 µm in diameter. Protein chips cast from master mold etched by RIE microlithographic techniques have densities of wells generally between 100 wells/cm$^2$ and 25,000,000 wells/cm$^2$. RIE in combination with optical lithography can produce wells that are 500 nm in diameter and 500 nm apart. Use of electron beam lithography in combination with RIE can produce wells 50 nm in diameter and 50 nm apart. Wells of this size and with equivalent spacing produces protein chips with densities of wells 10,000,000,000,000 wells/cm$^2$. Preferably, RIE is used to produce wells of 20 µm in diameter and 20 µm apart. Wells of this size that are equivalently spaced will result in densities of 25,000,000 wells/cm$^2$.

In a specific embodiment, the microarray is prepared on a slide with 8 to 10 wells per slide, wherein the plurality of proteins is present in each well on the slide. In another embodiment, microarray is prepared on a slide with 8 to 10 wells per slide, wherein the plurality of substrates is present in each well on the slide.

In one embodiment, the array comprises a plurality of wells on the surface of a solid support wherein the density of wells is at least 1 well/cm$^2$, at least 10 wells/cm$^2$, 100 wells/cm$^2$. In another embodiment, said density of wells is between 100 and 1000 wells/cm$^2$. In another embodiment, said density of wells is between 1000 and 10,000 wells/cm$^2$. In another embodiment, said density of wells is between 10,000 and 100,000 wells/cm$^2$. In yet another embodiment, said density of wells is between 100,000 and 1,000,000 wells/cm$^2$. In yet another embodiment, said density of wells is between 1,000,000 and 10,000,000 wells/cm$^2$. In yet another embodiment, said density of wells is between 10,000,000 and 25,000,000 wells/cm$^2$. In yet another embodiment, said density of wells is at least 25,000,000 wells/cm$^2$. In yet another embodiment, said density of wells is at least 10,000,000,000 wells/cm$^2$. In yet another embodiment, said density of wells is at least 10,000,000,000,000 wells/cm$^2$.

The placement of a proteins or a substance can be accomplished by using any dispensing means, such as bubble jet or ink jet printer heads. A micropipette dispenser can also be used. The placement of proteins or probes can either be conducted manually or the process can be automated through the use of a computer connected to a machine.

The present invention contemplates a variety of solid supports cast from a microfabricated mold, some of which are disclosed, for example, in international patent application publication WO 01/83827, published Nov. 8, 2001, which is incorporated herein by reference in its entirety.

In certain embodiments, the plurality of proteins comprises all proteins that are encoded by at least 1%, 2%, 3%, 4%, 5%, 10%, 20%, 30%, 40%, 50%, 60%, 70%, 80%, 90%, 95%, or 99% of the known genes in a single species. In certain embodiments, the plurality of substances comprises all proteins that are encoded by at least 1%, 2%, 3%, 4%, 5%, 10%, 20%, 30%, 40%, 50%, 60%, 70%, 80%, 90%, 95%, or 99% of the known genes in a single species.

In certain embodiments, the plurality of proteins comprises at least 1%, 2%, 3%, 4%, 5%, 10%, 20%, 30%, 40%, 50%, 60%, 70%, 80%, 90%, 95%, or 99% of all proteins expressed in a single species, wherein protein isoforms and splice variants are counted as a single protein. In certain embodiments, the plurality of substances comprises at least 1%, 2%, 3%, 4%, 5%, 10%, 20%, 30%, 40%, 50%, 60%, 70%, 80%, 90%, 95%, or 99% of all proteins expressed in a single species, wherein protein isoforms and splice variants are counted as a single protein.

In another embodiment, the plurality of proteins comprises at least 1, 2, 3, 4, 5, 10, 20, 30, 40, 50, 100, 200, 500, 1000, 1500, 2000, 2500, 3000, 4000, 5000, 6000, 7000, 8000, 9000, 10,000, 100,000, 500,000 or 1,000,000 protein(s) expressed in a single species. In another embodiment, the plurality of substances comprises at least 1, 2, 3, 4, 5, 10, 20, 30, 40, 50, 100, 200, 500, 1000, 1500, 2000, 2500, 3000, 4000, 5000, 6000, 7000, 8000, 9000, 10,000, 100,000, 500,000 or 1,000,000 protein(s) expressed in a single species.

In yet another embodiment, the plurality of proteins comprises proteins that are encoded by 1, 2, 3, 4, 5, 10, 20, 30, 40, 50, 100, 200, 500, 1000, 5000, 10000, 20000, 30000, 40000, or 50000 different known genes in a single species. In yet another embodiment, the plurality of substances comprises proteins that are encoded by 1, 2, 3, 4, 5, 10, 20, 30, 40, 50, 100, 200, 500, 1000, 5000, 10000, 20000, 30000, 40000, or 50000 different known genes in a single species.

5.5. Methods for Making and Purifying Proteins

Any method known to the skilled artisan can be used to make and to purify the proteins to be used with the methods of the invention and for the preparation of the microarrays of the invention. In certain embodiments, the substrate is also a proteinaceous molecule, such as a protein, a polypeptide or a peptide and can be prepared and purified as described in this section.

Proteins to be used with the methods of the invention and for the preparation of the microarrays of the invention can be fusion proteins, in which a defined domain is attached to one of a variety of natural proteins, or can be intact non-fusion proteins. In certain embodiments, if the substrate is a protein or a peptide, a substrate to be used with the methods of the invention and for the preparation of the microarrays of the invention can be fusion protein, in which a defined domain is attached to the substrate, or can be intact non-fusion substrate.

The present invention also relates to methods for making and isolating viral, prokaryotic or eukaryotic proteins in a readily scalable format, amenable to high-throughput analysis. Preferred methods include synthesizing and purifying proteins in an array format compatible with automation technologies. Accordingly, in one embodiment, the invention provides a method for making and isolating eukaryotic proteins comprising the steps of growing a eukaryotic cell transformed with a vector having a heterologous sequence operatively linked to a regulatory sequence, contacting the regulatory sequence with an inducer that enhances expression of a protein encoded by the heterologous sequence, lysing the cell, contacting the protein with a binding agent such that a complex between the protein and binding agent is formed, isolating the complex from cellular debris, and isolating the protein from the complex, wherein each step is conducted, e.g., in a 96-well format.

In certain embodiments, the plurality of proteins comprises at least one protein with a first tag and a second tag. In yet another embodiment, the plurality of substrates comprises at least one substrate with a first tag and a second tag.

In one embodiment, each step in the synthesis and purification procedures is conducted in an array amenable to rapid automation. Such arrays can comprise a plurality of wells on the surface of a solid support wherein the density of wells is at least 10, 20, 30, 40, 50, 100, 1000, 10,000, 100,000, or 1,000,000 wells/cm$^2$, for example. Alternatively, such arrays comprise a plurality of sites on the surface of a solid support, wherein the density of sites is at least 10, 20, 30, 40, 50, 100, 1000, 10,000, 100,000, or 1,000,000 sites/cm$^2$, for example.

In a particular embodiment, proteins and/or substrates are made and purified in a 96-array format (i.e., each site on the solid support where processing occurs is one of 96 sites), e.g., in a 96-well microtiter plate. In a preferred embodiment, the surface of the microtiter plate that is used for the production of the proteins and/or substrates does not bind proteins (e.g., a non-protein-binding microtiter plate).

In certain embodiments, proteins and/or substrates are synthesized by in vitro translation according to methods commonly known in the art.

Any expression construct having an inducible promoter to drive protein synthesis and/or the synthesis of a substrate (if the substrate(s) is a protein or peptide) can be used in accordance with the methods of the invention. Preferably, the expression construct is tailored to the cell type to be used for transformation. Compatibility between expression constructs and host cells are known in the art, and use of variants thereof are also encompassed by the invention.

Any host cell that can be grown in culture can be used to synthesize the proteins and/or substrates of interest. Preferably, host cells are used that can overproduce a protein and/or a substrate of interest, resulting in proper synthesis, folding, and posttranslational modification of the protein. Preferably, such protein processing forms epitopes, active sites, binding sites, etc. useful for the activity of an enzyme or the suitability as a substrate. Posttranslational modification is relevant if the enzyme's activity is affected by posttranslational modification of the enzyme. Posttranslational modification is also relevant if the substrates ability to serve as a substrate for the enzymatic reaction of interest is affected by the posttranslational modification of the substrate. In a specific embodiment, phosphorylation of a protein is required for the enzymatic activity of the protein. In such a case the protein should be expressed in a system that promotes the phosphorylation of the protein at the appropriate site. In a specific embodiment, phosphorylation or glycosylation of a substrate is required for the substrate to modified by the enzymatic reaction of interest. In such a case the substrate should be synthesized in a system that promotes the phosphorylation or glycosylation of the substrate at the appropriate site.

Accordingly, a eukaryotic cell (e.g., yeast, human cells) is preferably used to synthesize eukaryotic proteins or substrates of eukaryotic enzymes. Further, a eukaryotic cell amenable to stable transformation, and having selectable markers for identification and isolation of cells containing transformants of interest, is preferred. Alternatively, a eukaryotic host cell deficient in a gene product is transformed with an expression construct complementing the deficiency. Cells useful for expression of engineered viral, prokaryotic or eukaryotic proteins are known in the art, and variants of such cells can be appreciated by one of ordinary skill in the art.

For example, the InsectSelect system from Invitrogen (Carlsbad, Calif., catalog no. K800-01), a non-lytic, single-vector insect expression system that simplifies expression of high-quality proteins and eliminates the need to generate and amplify virus stocks, can be used. A preferred vector in this system is pIB/V5-His TOPO TA vector (catalog no. K890-20). Polymerase chain reaction ("PCR") products can be cloned directly into this vector, using the protocols described by the manufacturer, and the proteins can be expressed with N-terminal histidine tags useful for purifying the expressed protein.

Another eukaryotic expression system in insect cells, the BAC-TO-BAC™ system (LIFETECH™, Rockville, Md.), can also be used. Rather than using homologous recombination, the BAC-TO-BAC™ system generates recombinant baculovirus by relying on site-specific transposition in *E. coli*. Gene expression is driven by the highly active polyhedrin promoter, and therefore can represent up to 25% of the cellular protein in infected insect cells.

In a particular embodiment, yeast cultures are used to synthesize eukaryotic fusion proteins. Fresh cultures are preferably used for efficient induction of protein synthesis, especially when conducted in small volumes of media. Also, care is preferably taken to prevent overgrowth of the yeast cultures. In addition, yeast cultures of about 3 ml or less are preferable to yield sufficient protein for purification. To improve aeration of the cultures, the total volume can be divided into several smaller volumes (e.g., four 0.75 ml cultures can be prepared to produce a total volume of 3 ml).

Cells are then contacted with an inducer, and harvested. The nature of the inducer depends on the expression system used. The nature of the inducer particularly depends on the promoter used. In certain embodiments, the expression system used for the preparation of the proteins and/or substrates is an inducible expression system. Any inducible expression system known to the skilled artisan can be used with the methods of the invention and for the preparation of the microarrays of the invention. Examples of inducers include, but are not limited to, galactose, enhancer-binding proteins, and other transcription factors. In one embodiment, galactose is contacted with a regulatory sequence comprising a galactose-inducible GAL1 promoter.

Induced cells are washed with cold (i.e., 4° C. to about 15° C.) water to stop further growth of the cells, and then washed with cold (i.e., 4° C. to about 15° C.) lysis buffer to remove the culture medium and to precondition the induced cells for protein purification, respectively. Before protein purification, the induced cells can be stored frozen to protect the proteins from degradation. In a specific embodiment, the induced cells are stored in a semi-dried state at −80° C. to prevent or inhibit protein degradation.

Cells can be transferred from one array to another using any suitable mechanical device. For example, arrays containing growth media can be inoculated with the cells of interest using an automatic handling system (e.g., automatic pipette). In a particular embodiment, 96-well arrays containing a growth medium comprising agar can be inoculated with yeast cells using a 96-pronger. Similarly, transfer of liquids (e.g., reagents) from one array to another can be accomplished using an automated liquid-handling device (e.g., Q-FILL™, Genetix, UK).

Although proteins can be harvested from cells at any point in the cell cycle, cells are preferably isolated during logarithmic phase when protein synthesis is enhanced. For example, yeast cells can be harvested between $OD_{600}$=0.3 and $OD_{600}$=1.5, preferably between $OD_{600}$=0.5 and $OD_{600}$=1.5. In a particular embodiment, proteins are harvested from the cells at a point after mid-log phase. Harvested cells can be stored frozen for future manipulation.

The harvested cells can be lysed by a variety of methods known in the art, including mechanical force, enzymatic digestion, and chemical treatment. The method of lysis should be suited to the type of host cell. For example, a lysis buffer containing fresh protease inhibitors is added to yeast cells, along with an agent that disrupts the cell wall (e.g., sand, glass beads, zirconia beads), after which the mixture is shaken violently using a shaker (e.g., vortexer, paint shaker).

In a specific embodiment, zirconia beads are contacted with the yeast cells, and the cells lysed by mechanical disruption by vortexing. In a further embodiment, lysing of the yeast cells in a high-density array format is accomplished using a paint shaker. The paint shaker has a platform that can firmly hold at least eighteen 96-well boxes in three layers, thereby allowing for high-throughput processing of the cultures. Further the paint shaker violently agitates the cultures, even before they are completely thawed, resulting in efficient disruption of the cells while minimizing protein degradation. In fact, as determined by microscopic observation, greater than 90% of the yeast cells can be lysed in under two minutes of shaking.

The resulting cellular debris can be separated from the protein and/or substrate of interest by centrifugation. Additionally, to increase purity of the protein sample in a high-throughput fashion, the protein-enriched supernatant can be filtered, preferably using a filter on a non-protein-binding solid support. To separate the soluble fraction, which contains the proteins of interest, from the insoluble fraction, use of a filter plate is highly preferred to reduce or avoid protein degradation. Further, these steps preferably are repeated on the fraction containing the cellular debris to increase the yield of protein.

Proteins and/or substrates can then be purified from the protein-enriched supernatant using a variety of affinity purification methods known in the art. Affinity tags useful for affinity purification of fusion proteins by contacting the fusion protein preparation with the binding partner to the affinity tag, include, but are not limited to, calmodulin, trypsin/anhydrotrypsin, glutathione, immunoglobulin domains, maltose, nickel, or biotin and its derivatives, which bind to calmodulin-binding protein, bovine pancreatic trypsin inhibitor, glutathione-S-transferase ("GST tag"), antigen or Protein A, maltose binding protein, poly-histidine ("His tag"), and avidin/streptavidin, respectively. Other affinity tags can be, for example, myc or FLAG. Fusion proteins can be affinity purified using an appropriate binding compound (i.e., binding partner such as a glutathione bead), and isolated by, for example, capturing the complex containing bound proteins on a non-protein-binding filter. Placing one affinity tag on one end of the protein (e.g., the carboxy-terminal end), and a second affinity tag on the other end of the protein (e.g., the amino-terminal end) can aid in purifying full-length proteins.

In certain embodiments, a protein and/or a substance is expressed as a fusion protein with a chitin binding domain. In other embodiments, a protein and/or a substance is expressed as a fusion protein with a chitin binding domain and an intein. In a more specific embodiment, the proteins and/or substrates are expressed using the IMPACT™-CN protein fusion and purification system from New England Biolabs Inc.

In a particular embodiment, the fusion proteins have GST tags and are affinity purified by contacting the proteins with glutathione beads. In further embodiment, the glutathione beads, with fusion proteins attached, can be washed in a 96-well box without using a filter plate to ease handling of the samples and prevent cross contamination of the samples.

In addition, fusion proteins can be eluted from the binding compound (e.g., glutathione bead) with elution buffer to provide a desired protein concentration.

For purified proteins and/or substrates that will eventually be printed or coated onto the surface of the solid support, such as, but not limited to, a microscope slide, the glutathione beads are separated from the purified proteins and/or substrates. Preferably, all of the glutathione beads are removed to avoid blocking of the microarrays pins used to spot the purified proteins onto a solid support. In a preferred embodiment, the glutathione beads are separated from the purified proteins using a filter plate, preferably comprising a non-protein-binding solid support. Filtration of the eluate containing the purified proteins should result in greater than 90% recovery of the proteins.

The elution buffer preferably comprises a liquid of high viscosity such as, for example, 15% to 50% glycerol, preferably about 25% glycerol. The glycerol solution stabilizes the proteins and/or substrates in solution, and prevents dehydration of the protein solution during the printing step using a microarrayer.

Purified proteins and/or substrates are preferably stored in a medium that stabilizes the proteins and prevents dessication of the sample. For example, purified proteins can be stored in a liquid of high viscosity such as, for example, 15% to 50% glycerol, preferably in about 25% glycerol. It is preferred to aliquot samples containing the purified proteins, so as to avoid loss of protein activity caused by freeze/thaw cycles.

The skilled artisan can appreciate that the purification protocol can be adjusted to control the level of protein purity desired. In some instances, isolation of molecules that associate with the protein of interest is desired. For example, dimers, trimers, or higher order homotypic or heterotypic complexes comprising an overproduced protein of interest can be isolated using the purification methods provided herein, or modifications thereof. Furthermore, associated molecules can be individually isolated and identified using methods known in the art (e.g., mass spectroscopy).

In certain embodiments, an enzyme to be used with the invention is composed of two or more proteins in a complex. In such a case, any method known to the skilled artisan can be used to provide the complex for use with the methods of the invention. In a specific embodiment, the proteins of the complex are co-expressed and the proteins are purified as a complex. In other embodiments, the proteins of the complex are expressed as a fusion protein that comprises all proteins of the complex. The fusion protein may or may not comprise linker peptides between the individual proteins of the complex. In other embodiments, the proteins of the complex are expressed, purified and subsequently incubated under conditions that allow formation of the complex. In certain embodiments, the proteins of the complex are assembled on the surface of the solid support before they become immobilized. In even other embodiments, the individual proteins of an enzymatic complex of interest are printed on top of each other on the surface of the solid support. Without being bound by theory, once the proteins of the complex are immobilized on the surface the close physical proximity of the proteins of the complex to each other allows for the enzymatic reaction to take place even though the complex is not assembled.

The protein and/or substrate can be purified prior to placement on the protein chip or can be purified during placement on the chip via the use of reagents that bind to particular proteins, which have been previously placed on the protein chip. Partially purified protein-containing cellular material or cells can be obtained by standard techniques (e.g., affinity or column chromatography) or by isolating centrifugation samples (e.g., P1 or P2 fractions).

5.5.1. Tagged Proteins

In certain embodiments, the proteins and/or substances to be used with the methods of the invention or for the preparation of the microarrays of the invention comprise a first tag and a second tag. The advantages of using double-tagged proteins include the ability to obtain highly purified proteins, as well as providing a streamlined manner of purifying proteins from cellular debris and attaching the proteins to a solid support. In a particular embodiment, the first tag is a glutathione-S-transferase tag ("GST tag") and the second tag is a poly-histidine tag ("His tag"). In a specific embodiment, the poly-histidine tag consists of six histidines (His×6). In other embodiments, the poly-histidine tag consists of 4, 5, 7, 8, 9, 10, 11, or 12 histidines. In a further embodiment, the GST tag and the His tag are attached to the amino-terminal end of the protein or the substrate. Alternatively, the GST tag and the His tag are attached to the carboxy-terminal end of the protein or substrate.

In a preferred embodiment, a protein and/or a substrate is expressed using the IMPACT™-CN protein fusion purification system from New England Biolabs Inc.

In yet another embodiment, the GST tag is attached to the amino-terminal end of the protein or substrate. In a further embodiment, the His tag is attached to the carboxy-terminal end of the protein or substrate. In yet another embodiment, the His tag is attached to the amino-terminal end of the protein or substrate. In a further embodiment, the GST tag is attached to the carboxy-terminal end of the protein or substrate.

In yet another embodiment, the protein or substrate comprises a GST tag and a His tag, and neither the GST tag nor the His tag is located at the amino-terminal or carboxy-terminal end of the protein. In a specific embodiment, the GST tag and His tag are located within the coding region of the protein or substrate of interest; preferably in a region of the protein not affecting the enzymatic activity of interest and preferably in a region of the substrate not affecting the suitability of the substrate to be modified by the enzymatic reaction of interest.

In one embodiment, the first tag is used to purify a fusion protein. In another embodiment, the second tag is used to attach a fusion protein to a solid support. In a specific further embodiment, the first tag is a GST tag and the second tag is a His tag.

A binding agent that can be used to purify a protein or a substrate can be, but is not limited to, a glutathione bead, a nickel-coated solid support, and an antibody. In one embodiment, the complex comprises a fusion protein having a GST tag bound to a glutathione bead. In another embodiment, the complex comprises a fusion protein having a His tag bound to a nickel-coated solid support. In yet another embodiment, the complex comprises the protein of interest bound to an antibody and, optionally, a secondary antibody.

5.6. Screening Assays

The methods of the invention and the protein microarrays of the invention can be used to identify molecules that modify the activity or substrate-specificity of an enzyme or a class of enzymes. In particular, the methods of the invention and the protein microarrays of the invention can be used to identify a molecule with a particular profile of activity, i.e., the molecule modifies certain enzymes and does not affect the activity of other enzymes. Such an assay is particularly useful to identify compounds that are modulators of a desired specificity, wherein the compound with the highest specificity modifies the activity of only one specific enzyme and a compound with a lower specificity modifies the activity of a subclass of enzymes. Modulators of an enzymatic activity can be activators of the enzymatic activity, inhibitors of the enzymatic activity or modulators of the enzyme's substrate specificity. An inhibitor of an enzymatic reaction can inhibit the enzyme reversably, irreversably, competitively, or non-competitively.

In certain embodiments, a screening assay of the invention is performed by conducting the enzyme assay on a microarray as described in section 5.2, wherein the reaction is performed in the presence and the absence of a molecule that is to be tested for its effect on the enzymatic reaction. The effect of the test molecule on the enzymatic reaction can be determined by comparing the activity in the presence of the test molecule with the activity in the absence of the test compound. In certain embodiments, if the assay is performed in wells, several molecules can be tested simultaneously on the same microarray. In certain embodiments, if the assay is performed in wells, different concentrations of a molecule can be tested simultaneously on the same microarray.

In certain embodiments, a molecule is tested for its effect on the activity of an enzymatic reaction, wherein a plurality of different enzymes and a substrate are immobilized to the surface of the solid support. In a specific embodiment, the substrate may be a known substrate of at least one of the enzymes. This is the preferred embodiment, if the molecule is tested for an effect on enzyme activity. If substrate specificity of an enzyme of interest is to be tested, the preferred embodiment is to perform the assay on a microarray wherein a plurality of different substrates and the enzyme of interest are immobilized on the surface of a solid support.

In other embodiments, the methods of the invention and the microarrays of the invention can be used to identify a substrate that is utilized by an enzyme of interest, a subclass of interest or a class of enzymes.

In certain embodiments, the methods of the invention are used to determine a profile of enzymatic activities of a cell in a particular state of development or proliferation or of a cell of a particular cell type. In a specific embodiment, the methods of the invention are used to determine a profile of enzymatic activities of a cell that is pre-neoplastic, neoplastic or cancerous in comparison to a non-neoplastic or non-cancerous, respectively, cell. In a specific embodiment, a cell extract of a cell type of interest is immobilized on the surface of a solid support and a plurality of different substrates is also immobilized on the surface. In a more specific embodiment, the cell extract is size fractionated and the different fractions are used with the methods of the invention to enrich for the enzymes of interest in the cell extract. In an even more specific embodiment, at least one enzyme is isolated from a cell of interest and tested for its activity using the methods of the invention.

In certain embodiments, kinetic properties of a known inhibitor of a certain enzymes are assessed using the methods of the invention. In certain, more specific embodiments, at least 1, 2, 3, 4, 5, 6, 7, 8, 9, 10, 12, 14, 16, 18, 20, 30, 40, 50 or at least 100 copies of the plurality of different proteins are immobilized on the surface of a solid support at different positions of the microarray. The different proteins of at least 1 copy of the plurality of different proteins on the microarray are in proximity with a substance sufficient for the occurrence of an enzymatic reaction between the protein of the plurality of different proteins and the substance. The different copies of the plurality of different proteins can then incubated with different reaction mixtures. The different reaction mixtures can each contain a different test molecule that is to be tested for its effect on the enzymatic reaction being assayed. In other embodiments, the different reaction mixtures can each contain a different concentration of a test molecule or known inhibitor or activator of the enzymatic reaction. In certain embodiments, the different copies of the plurality of different proteins are in different wells on the solid support.

In certain, more specific embodiments, a at least 1, 2, 3, 4, 5, 6, 7, 8, 9, 10, 12, 14, 16, 18, 20, 30, 40, 50 or at least 100 copies of a plurality of different substances are immobilized on the surface of a solid support at different positions of the microarray. The different substances of at least 1 copy of the plurality of different substances on the microarray are in proximity with a protein sufficient for the occurrence of an enzymatic reaction between the substances of the plurality of different substance and the protein. The different copies of the plurality of different substances can then incubated with different reaction mixtures. The different reaction mixtures can each contain a different test molecule that is to be tested for its effect on the enzymatic reaction being assayed. In other embodiments, the different reaction mixtures can each contain a different concentration of a test molecule or known inhibitor or activator of the enzymatic reaction. In certain embodiments, the different copies of the plurality of different substances are in different wells on the solid support.

In certain embodiments, the $IC_{50}$ of an inhibitor of an enzymatic reaction can be determined. As described above, different concentrations of the inhibitor can be tested for their effects on an enzymatic reaction. Based on the different effects of different concentrations of the inhibitor on the enzymatic reaction, the $IC_{50}$ can be determined. In a specific embodiment, a dose-response curve is established based on the different effects of different concentrations of the inhibitor on the enzymatic reaction, wherein the $IC_{50}$ is the concentration of the inhibitor where the enzymatic activity is 50% of the activity in the absence of inhibitor.

In certain illustrative examples, provided herein is a method for identifying a test molecule (see section 5.6.1 for test molecules) that modulates an enzymatic reaction, including:

(a) incubating at least one enzyme, at least one substrate, and at least one test molecule under conditions conducive to the occurrence of an enzymatic reaction between the enzyme and the substrate (i.e. a reaction involving the substrate that is catalyzed by the enzyme), wherein (i) the enzyme and the substrate are immobilized on the surface of a solid support; (ii) the enzyme and the substrate are in proximity sufficient for the occurrence of said enzymatic reaction; and (iii) the enzyme and the substrate are not identical; and (b) determining whether the enzymatic reaction is modulated by the test molecule. Typically, the protein and the substance are immobilized before the incubation step.

In one illustrative example, a plurality of substrates are coated onto the surface of the solid support and a plurality of enzymes are printed onto the surface of the solid support before the incubation step, and the method identifies test molecules that modulate phosphorylation of the substrate by the kinase during the incubation step.

5.6.1 Libraries of Molecules

Any molecule known to the skilled artisan can be used with the methods of the invention to test the molecule's effect on the enzymatic reaction being assayed. In other embodiments, any molecule can be used as a candidate substrate with the methods of the invention. For example, a test molecule can be a polypeptide, carbohydrate, lipid, amino acid, nucleic acid, fatty acid, steroid, or a small organic compound. In addition, a test molecule can be lipophilic, hydrophilic, plasma membrane permeable, or plasma membrane impermeable. The molecule can be of natural origin or synthetic origin The test molecule can be a small molecule, such as a synthetic compound.

In certain embodiments, a library of different molecules is used with the methods of the invention, or an individual molecule is used with the methods of the invention, from a library of different molecules or of the same chemical class as the molecules discussed in this section, as non-limiting examples. One or more members of a library, including, for example, each member of a library, can be used as a test molecule to test its effect on the enzymatic reaction or as a substance to test its suitability as a substrate for the reaction being assayed.

In certain embodiments, the members of the library are tested individually. In other embodiments, the members of a library are tested initially in pools. The size of a pool can be at least 2, 10, 50, 100, 500, 1000, 5,000, or at least 10,000 different molecules. Once a positive pool is identified, fractions of the pool can be tested or the individual members of the pool of molecules are tested.

Libraries can contain a variety of types of molecules. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the molecules in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In certain embodiments, combinatorial libraries of small organic molecules including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides;, vinylogous polypeptides; nonpeptidal peptidomimetics; oligocarbamates; peptidyl phosphonates; peptide nucleic acid libraries; antibody libraries; or carbohydrate libraries can be used with the methods of the invention. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that molecules of the library are of the general type of molecules that are being used in the enzymatic reaction of interest.

The combinatorial molecule library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial molecule libraries to be used in accordance with the methods of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial molecule library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of special-ized protocols for monitoring the individual steps of a multi-step solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial molecule libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

In certain embodiments of the invention, the compound is a small molecule (less than 10 kDa), e.g., a non-peptide small molecule.

6. EXAMPLES

6.1. Example I

Kinase Activity Assay on Microarray

Materials & Reagents

| Materials/Equipment/Reagents | Vendor | Part Number |
|---|---|---|
| Disposables/Reagents | | |
| Gamma-AT$^{33}$P (10 μCi/μl, 250 μCi) | Perkin Elmer | NEG602H250UC |
| Histone, Calf Thymus | Calbiochem | 38205 |
| Casein | Sigma | C-4032 |
| Myelin Basic Protein | Sigma | M-1891 |
| Poly-glutamic acid-tyrosine | Sigma | P-2075 |
| PBS Tablets | American Bioanalytical | AB11108 |
| Tween-20 | American Bioanalytical | AB02038 |
| 60 × 24 mm Hybridization Cover slips | Schleicher & Schuell | 10 484 907 |
| Equipment | | |
| Cyclone Phospho-imager | Perkin Elmer | B431220 |
| 8 × 10 Autoradiography Cassettes | Fisher | FB-XC-810 |
| Phosphor Storage Screens (MS) | Perkin Elmer | 7001723 |
| Lab Rotator | Lab-Line Instruments | 1314 |
| Eppendorf Centrifuge (5810) | Fisher Scientific | 05-400-60 |

Reagent/Stock Preparation
Kinase Substrate Stocks
Dissolve protein substrates in 20 mM Tris to a final concentration of 10 mg/mL.
1 L of 1×PBS
Dissolve 5 PBS tablets in 1 L dH2O.
Mix thoroughly.
1 L PBST
Dissolve 5 PBS tablets in 1 L dH2O.
Add 1 mL Tween-20.

Mix thoroughly.
Kinase Assay Dilution Buffer
20 mM MOPS, pH 7.2
25 mM b-glycerol phosphate
5 mM EGTA
1 mM sodium orthovanadate

| Assay Solution (1 ml nominal -- total = ~1.1 ml) | |
|---|---|
| In 1 ml of Kinase Assay Dilution Buffer, add | (~final concentration) |
| 1 µl of 1 M DTT | (1 mM) |
| 1 µl of 30% BSA | (3 mg/ml) |
| 1 µl of 1 M MnCl$_2$ | (1 mM) |
| 1 µl of 1 M CaCl$_2$ | (1 mM) |
| 25 µl of 1 M MgCl$_2$ | (25 mM) |

Methods

Step 1: Coating of Slides with Kinase Substrates

To coat slides with kinase substrate, the substrates are diluted to 10 ng/µL in 1×PBS and 180-200 µL of substrate solution are pipetted onto one slide, e.g., a glass slide, aldehyde treated slides (TeleChem International, Inc.), nitrocellulose-coated slides (Schleicher & Schuell), slides with an amino-silane surface (Corning). A second slide is then placed on top of the first slide so that the sides to be printed with kinases face each other. Care should be taken that the liquid covers the entire slide and that there are no air bubbles. The slides are placed in a 50 mL conical tube, making sure they are laying flat and incubated at 4° C. for one hour to several days.

Alternatively, substrates may be printed on the slides using a microarrayer, wherein the samples are kept at 4° C. The substrates should be diluted in the proper printing buffer. The spot size should be 150-200 µm, and the spacing should be between 0.5 and 1 mm. After printing, incubate at 4° C. for one hour to several days.

Step 2: Washing and Blocking of Coated Slides

The substrate-coated or substrate-printed slides obtained in step 1 are removed from the conical tubes and placed in a slide staining dish. Subsequently, approximately 100 mL of PBST are added to the dish. The slides are then washed for one hour at 4° C. with shaking. The PBST is then discarded and the slides are gently rinsed with dH$_2$O using a squirt bottle. After rinsing, the slides are placed into a slide boxes and centrifuged at 4000 rpm for one minute. The slides are then stored at 4° C. until printing with kinase.

Step 3: Printing of Kinases on Substrate-Coated Slides

Kinases are diluted in the proper printing buffer. The concentration should be between 1 and 10 ng/µL. The kinases are printed on the substrate-coated slides obtained in step 1 and 2 using a microarrayer. The spot size should be 150-200 µm, and the spacing should be between 0.5 and 1 mm. If the substrate is printed on the slides, the spacing of the kinase array should match that of the substrate array (i.e., the kinases should be printed on top of the substrate). The slides can be stored at 4° C. until the kinase activity assay is performed.

Step 4: Assay of Kinase Activity on Microarray 1 mL of kinase assay buffer for every 12 glass slides to be probed is prepared. 6 µL of gamma-AT$^{33}$P (10 µCi/µL) are added to the assay buffer. The slides are placed in 50 mL conical tubes, laying flat, proteins facing up. 70 µL to 150 µL of the kinase assay buffer with gamma-AT$^{33}$P are added onto each slide. Using tweezers, the slide is covered with a hybridization slip, making sure that the solution completely covers the microarray. The conical tube is then closed and placed in a 30° C. incubator. Care should be taken that the slide is laying flat. The reaction is then incubated for 90 minutes. Subsequently, the tubes are removed from the incubator. Approximately 40 mL of dH$_2$O are added to each tube and, using the tweezers, the hybridization slip is removed, the tube is closed and inverted several times for 1-2 minutes to rinse the slide inside the conical tube. The wash solution is then discarded. Approximately 40 mL of dH$_2$O are added again to each tube, the tubes are closed and inverted several times for 1-2 minutes, the wash solution is discarded. The slides are then removed from the tubes and place in a slide box and centrifuged at 4000 rpm for 1-2 minutes.

A phosphor screen (suitable for $^{33}$P) is re-activated for each membrane by exposing it to light for at least 30 minutes. A piece of filter paper is placed in an autoradiography cassette and the dried slides are placed on the filter paper, facing up. The slides are covered with a piece of clear plastic film (such as SaranWrap). The phosphor screen is placed on top of the SaranWrap, facing the slides. The cassette is then closed and locked and exposed for a few hours to a couple of days, depending on the activity. In a dark room (or a room with dim light), the cassette is opened and the phosphor screen is removed. The phosphor screen is then mounted on the Cyclone rotor and scanned at 600 dpi.

An exemplary autoradiograph of a kinase reaction of the present invention is shown in FIG. 1. The data shown in FIG. 1 were obtained essentially using the method described above. As shown in FIG. 1, the presence of substrate is required for the kinase reaction. Thus, the signal obtained in this experiment is due to specific phosphorylation of the substrate and not due to autophosphorylation or binding of the labeled ATP to some of the enzymes.

The data shown in FIG. 2 demonstrate that treatment of the slide with aldehyde improves the signal-to-noise ratio. The experiments were conducted essentially using the method described above but with different types of slides. The aldehyde-treated slides were obtained from TeleChem International, Inc. The slide shown as FAST is a nitrocellulose coated slide and was obtained from Schleicher & Schuell. The slide shown as GAPS is coated with an amino-silane surface and was obtained from Corning®. Successful kinase assays according to the method provided herein have also been obtained using ZetaGrip slides (available from TeleChem International, Inc., ArrayIt™ Division, Sunnyvale, Calif.; on the Internet at www.arrayit.com).

Safety Considerations

1. The operator must follow proper procedures and use cautions when handling radioactive materials.

2. Before using the microarrayer, the operator should be trained to avoid injuries to the person and/or damages to the machine.

Approximately fifty human protein kinases have been successfully employed (i.e. validated; see FIG. 3) in the methods provided in this Example. Validated kinases include a variety of kinases of direct relevance to disease, including Ab1, EGFR, FGFR, members of the src kinase family and a variety of PKC isoforms. The methods provided herein are broadly applicable to all kinase families, as validated kinases represent all branches of the kinase phylogenetic tree of the human kinome.

6.2. Example II

Inhibitor Specificity Profiling

Fifty different kinases were immobilized on a slide together with a substrate as described in section 6.1. A mixture of Myelin Basic Protein (MBP), histone and casein was used as substrate. The kinase reactions were performed in the presence of H89 inhibitor, Rottlerin inhibitor or PP2 inhibitor (FIG. 3). The inhibitors were obtained from Calbiochem. The PP2 inhibitor is an inhibitor of tyrosine kinases. The concentration of inhibitor was 100 μm for each inhibitor. The control reaction was performed in the absence of inhibitor. The specificity of the assay was demonstrated by the fact that PP2 inhibitor strongly inhibited tyrosine kinases (see circled data points in FIG. 3).

6.3. Example III

Dose-Response Analyses

Microarrays were prepared with 10 wells/slide, wherein the kinases EPHB3, FYN, and PRKCD and their substrate were immobilized in each well. The slide was coated with substrate essentially as described in section 6.1. Subsequently, a gasket with 10 openings was applied to the surface of the slide thereby creating 10 wells, i.e., the gasket provides the barriers between the wells. The accession numbers for the different kinases in the NCBI database are: for FYN: NM_002037; for PRKCD: NM_006254; and for EPHB3: NM_004443. A mixture of Myelin Basic Protein (MBP), histone and casein was used as substrate. The kinase reaction was performed in each well with a different concentration of PP2 inhibitor.

The dose-response curve obtained is shown in FIG. 4a. The data show that PP2 strongly inhibits the tyrosine kinases FYN and EPHB3 but not the serine/threonine kinase PRKCD. In a second experiment, the kinase reaction was performed in each well with a different concentration of staurosporine. The dose-response curve shown in FIG. 4b demonstrates that staurosporine strongly inhibits PRKCD and FYN but not EPHB3.

6.4 Example IV

Comprehensive Inhibitor Assays

The present example provides a method for performing inhibitor assays using methods provided herein, and provides results obtained using those methods. The surface of a slide is coated with substrate within the wells of a multiwell array. The surface is coated with substrate, and washed and blocked as described in section 6.1. Subsequently, a gasket with openings is applied to the surface of the slide thereby creating wells, i.e., the gasket provides the barriers between the wells.

The kinases are printed on the surface by the following procedure. The dimensions of the wells of the multi-well array used are obtained and the areas on the slides that will match the wells are defined. These numbers are used to calibrate the microarrayer so that the printed spots will locate within the wells. The wells are formed later by placing the gasket with openings on top of the surface of the solid support.

The number of proteins that can be printed per well depends on the dimension of the well and the spacing required. The chambers made by Scleicher&Schuell and Grace Bio-labs have 7000 μm×7000 μm wells and allow up to 12×12 spots/well printed if the spacing is 500 μm. At least 4 replicate per kinase is recommended for quantitative experiments.

The plate of kinases to be printed is made so that the printing pins pick up the identical kinase preparation (identical volume, concentration, buffer components, etc.) at the same time. This will ensure comparable results among the arrays. In addition, kinase activities should be assessed and normalized to give uniform signals within the array. The kinases are printed onto the slide as described in section 6.1.

The kinase assay is performed by removing the plastic covering from sticky side of the chamber, placing the chamber carefully on the printed slides, aligning the wells to the printed areas. The chamber is placed on the slide to make a tight seal between wells. Subsequently, the kinase assay buffer with gamma-AT$^{33}$P is prepared as described in section 6.1. Inhibitors (or other molecules of interest or concentrations of the same molecule) are prepared in aliquots. The cover slip is removed from the chamber, thereby exposing the wells. Appropriate amounts of inhibitor and kinase assay buffer is added to wells (volumes that will cover the well but not exceed the well capacity). The cover slip is placed on the slide and the entire slide/chamber assembly is placed in a 50 ml tube. The slides are incubated at 30° C. for 90 minutes, making sure the slides sit flat. The slides are washed as described in section 6.1. The chamber is removed from the tube using a pair of tweezers and the wash procedure is repeated once. The kinase reaction is evaluated as described in section 6.1.

The data shown in FIG. 5 were obtained by the procedure described in this section. The type of inhibitor used in the reactions is shown on the side of the slide shown in FIG. 5. A reaction was performed on the same slide without an inhibitor as control (lower right part of the slide).

6.5 Example V

Sequential Printing of Substrate and Enzyme

Introduction

The following experiments were conducted to test whether sequential printing of substrate and enzyme affects the enzymatic reaction between the substrate and the enzyme on the surface of a solid support. The experiments were further conducted to test the effect of (i) the chemistry used for immobilizing substrate and enzyme on the surface of the solid support; and (ii) the effect of a washing step before printing of substrate and enzyme on the surface of a solid support on the signal-to-noise ratio of the enzymatic reaction between substrate and enzyme.

Materials and Methods

Kinase substrates were printed on the surface of a solid support as disclosed in section 6.1. Subsequently, kinases were printed on the same spots as the kinase substrates. The kinase reaction was performed as described above in section 6.1. The kinases printed on the array were Isoforms of PKC (including PKCh, PKCd, PKCi, and mixture), LCK, LYN, FYN, PKA. Some of the kinases used were obtained from commercial sources (PKC mixture, PKA, FYN, LYN, and LCK). Other kinases (PKC isoforms, FYN, LYN, and LCK) were produced by standard techniques. The substrate that was printed was a Casein, Histone, MBP, and poly(GluTyr) mixture. Eight concentrations (2× dilutions; 250, 125, 62.5, 31.25, 15,6, 7.8, 3.9, 1.9 ug/ml for each substrate in the mixture) were used. Slides were washed in 40 ml of PBS in a 50 ml conical tube for 1-2 minutes, twice.

Results

A detectable signal specific for the enzymatic reaction was obtained for each sample, except the FAST sample without washing. In other words, when FAST slides were used, a detectable signal was obtained only if the slide had been washed before the substrate and the kinase were printed on the slide. However, when SuperAldehyde slides (TeleChem International, Inc.) or GAPS slides, respectively, were used, a washing step before printing of kinase and substrate improved the signal of the kinase reaction only slightly. Further, FAST slides gave the highest background and SuperAldehyde the lowest. Higher kinase concentrations gave higher signals on all three types of slides. In summary, the experiment illustrates that both the protein and the substance can be printed on the solid support in methods provided herein.

6.6 Example VI

Comparison of Microarray Assays where Enzymes and Substrates are Immobilized on a Solid Support Versus Conventional Solution Assays To compare results obtained from microarray assay methods of the present invention to conventional solution assays, five kinases (ARG, FYN, PKCa, PKCd, and PKCe) were assayed using methods provided herein and compared to solution assays performed by a commercial service (Upstate, Waltham, Mass.) using PP2 (a tyrosine kinase specific inhibitor) at 1 µM. The kinase microarray assay with immobilized kinases and immobilized substrates was performed according to the method provided in Example I (section 6.1). The substrates, which included a mixture of 10 mg/ml of histone, casein, myelin basic protein (MBP), and poly-glutamic acid-tyrosine (polyEY), were coated on the surface of a glass slide.

The concentration of substrates that was used for coating slides was 10 µg/ml for each of the 4 substrates. SuperAldehyde slides from TeleChem International were used for the assay.

The percentage of inhibition data from these experiments is shown in FIG. 6. The data show an excellent agreement between the microarray assay of the present invention and the traditional solution-based assay. The microarray assays of the present invention provide significant advantages, as discussed herein. For example, the microarray assays of the present invention are performed with significantly less inhibitor and kinase than the solution assay. Furthermore, the microarray assay method of the present invention employ a solid-phase co-localization of kinase substrate pairs, enabling parallel processing of large numbers of kinases in a single reaction.

6.7 Example VII

Global Specificity Profiling Experiment

This example demonstrates that single point inhibition assays using methods provided herein, enable global evaluation of compound specificity. To assess the application of microarray assays for compound profiling, seven known inhibitors (see Table of inhibitors used in global specificity profiling experiment) and one control (2% DMSO) were tested on microarrays printed with a group of kinases (as well as positive and negative controls). The method of Example I (section 6.1) was used. Twelve spots of each kinase or control were printed on each array, and three arrays were used for each inhibitor. A mixture of generic kinase substrates (histone, casein, MBP, and polyEY) was used in the assay. The average of all signals from the same inhibitor or control experiment was calculated.

The percentage-of-inhibition data for 39 kinases active on these substrates (activity>negative+2 standard deviations) obtained from this experiment were in agreement with published specificity data For example, the broad spectrum of kinases inhibited by staurosporine was clearly evident, while FYN (kinase 33) was inhibited only by PP2 (aside from staurosporine). The general specificities observed were consistent with the known general specificities for these inhibitors, which are listed in Table 3. For instance, PP2 primarily inhibited tyrosine kinases, while Ro-31-8220 more specifically targeted the serine-threonine kinases. The complete list of kinases analyzed in this experiment are provided in Table 4. To expedite data analysis regarding the kinase families that are inhibited by a particular substrate or group of substrates, a graphical representation can be constructed of inhibition data for substrates in such a manner that phylogenetically related kinases can be spatially arranged on the graphical representation.

TABLE 3

Inhibitors used in global specificity profiling experiment

| Name | General Specificity |
|---|---|
| H-89 | serine/threonine |
| SB 202190 | serine/threonine |
| Ro-31-8220 | serine/threonine |
| Staurosporine | broad |
| Genistein | tyrosine |
| PP2 | tyrosine |
| AG 490 | tyrosine |

TABLE 4

Kinases used in the global specificity profiling experiment

| Kinase Number | Kinase Name |
|---|---|
| 1 | MAPK3K7 |
| 2 | AZK |
| 3 | ILK |
| 4 | BMPR1B |
| 5 | SYK |
| 6 | SYK |
| 7 | RET |
| 8 | LCK |
| 9 | LYN |
| 10 | BLK |
| 11 | FGR |
| 12 | FYN |
| 13 | FRK |
| 14 | EPHA3 |
| 15 | EPHA4 |
| 16 | STK3 |
| 17 | CAMK2D |
| 18 | NA |
| 19 | PIM2 |
| 20 | PIM1 |
| 21 | STK22 |
| 22 | TLK2 |
| 23 | MAPKAPK2 |
| 24 | CLK2 |
| 25 | DYRK1A |
| 26 | PCTAIRE |
| 27 | CDKL1 |
| 28 | MAPK8 |
| 29 | PRKCZ |
| 30 | PRKCI |
| 31 | PRKCH |
| 32 | PRKCE |
| 33 | PRKCD |
| 34 | PRKCL2 |
| 35 | MAST205 |
| 36 | ADRBK1 |
| 37 | VRK3 |
| 38 | STK16 |
| 39 | TBK1 |

6.8 Example VIII

Validation of IC$_{50}$ Measurement Using Kinase Activity Microarrays of the Present Invention The present Example illustrates that by measuring single-point inhibitions at varying inhibitor concentrations, kinase microarrays can be used to measure IC$_{50}$ values in a highly parallel fashion. The experiment was performed according to Example I (section 6.1), wherein various concentrations of staurosporine, as indicated in FIG. 7, were included in the kinase assay buffer (i.e. the buffer included in the incubating step). Substrates for Protein kinase C$_{delta}$ were coated on a series of ten slides, and subsequently Protein Kinase C$_{delta}$ was printed on the slides. Each slide contained 50 replicates of Protein Kinase C$_{delta}$. Substrates used to coat slides:

The same 4 substrates at 10 ug/ml each (casein, MBP, histone, pEY) as in Example VII were used. A Microarray printer from GeneMachines™, made by Genomic Solutions was used for printing the arrays. Accordingly, both substrate and Protein Kinase C$_{delta}$ were immobilized on the slide. As illustrated in FIG. 4, an IC$_{50}$ of 1 nm was calculated using the methods provided herein, in good agreement with the literature value of 0.7 nm. Accordingly, methods of the present invention can be used to calculate IC$_{50}$ values for inhibitors.

6.9 Example IX

Further Analysis of a Plurality of Inhibitors and a Plurality of Kinases

The present Example provides experiments that illustrate that the methods provided herein are effective for many types of kinases and can be used to analyze various test molecules. The assays were performed essentially as disclosed in Example 6.1. A large number of kinases and enzymes were analyzed (See Table 5, Parts I and II). The following tables summarize qualitatively the inhibition by the inhibitors. Inhibitors showed different potency and specificity, as expected for this type of assay.

TABLE 5

Inhibition Results

| Subarray_Row | Subarray_Column | Plate_Block | Plate_Row1 | Plate_Column1 | Name | Domain | GST_Expression | Solution_Activity | Microarray_Activity | H-89 100 uM | Rottlerin (Mallotoxin) 100 uM |
|---|---|---|---|---|---|---|---|---|---|---|---|
| 1 | 1 | 1 | A | 12 | RAF1 | 0 | 1 | 2 | 0 | | |
| 1 | 1 | 2 | C | 12 | LOC51231 | 1 | 1 | 3 | 2 | 2 | 0 |
| 1 | 1 | 3 | E | 12 | Homo sapiens, p | 0 | 1 | 3 | 2 | 1 | 1 |
| 1 | 1 | 4 | G | 12 | EGFR | 1 | 1 | 2 | 0 | | |
| 1 | 1 | 5 | A | 6 | LCK | 0 | 1 | 3 | 2 | 2 | 2 |
| 1 | 1 | 6 | C | 6 | STK6 | 1 | 1 | 3 | 1 | 0 | 2 |
| 1 | 1 | 7 | E | 6 | MAP2K4 | 1 | 1 | 3 | 1 | 1 | 1 |
| 1 | 1 | 8 | G | 6 | DYRK1A | 1 | 1 | 2.5 | 2 | 2 | 0 |
| 2 | 1 | 1 | A | 11 | MAP3K2 | 1 | 1 | 3 | 1 | | |
| 2 | 1 | 2 | C | 11 | JIK | 1 | 1 | 3 | 0 | | |
| 2 | 1 | 3 | E | 11 | Homo sapiens, s | 0 | 1 | 3 | 1 | 1 | 2 |
| 2 | 1 | 4 | G | 11 | STK13 | 1 | 1 | 3 | 1 | 1 | 1 |
| 2 | 1 | 5 | A | 5 | LYN | 0 | 1 | 3 | 2 | 2 | 2 |
| 2 | 1 | 6 | C | 5 | MAP4K3 | 1 | 0 | 3 | 0 | 1 | 1 |
| 2 | 1 | 7 | E | 5 | EPHB2 | 1 | 1 | 3 | 2 | 2 | 2 |
| 2 | 1 | 8 | G | 5 | PTK2B | 1 | 1 | 3 | 1 | 1 | 2 |
| 3 | 1 | 1 | A | 10 | CAMK1 | 1 | 1 | 3 | 0 | | |
| 3 | 1 | 2 | C | 10 | STK38 | 1 | 0 | 2 | 0 | | |
| 3 | 1 | 3 | E | 10 | Homo sapiens, S | 0 | 1 | 3 | 0 | | |
| 3 | 1 | 4 | G | 10 | MAST205 | 1 | 1 | 2.5 | 0 | | |
| 3 | 1 | 5 | A | 4 | FYN | 0 | 1 | 3 | 2 | 2 | 2 |
| 3 | 1 | 6 | C | 4 | MARK2 | 1 | 1 | 3 | 2 | 2 | 2 |
| 3 | 1 | 7 | E | 4 | ITK | 0 | 1 | 3 | 1 | 1 | 1 |
| 3 | 1 | 8 | G | 4 | PINK1 | 1 | 1 | 3 | 0 | | |
| 4 | 1 | 1 | A | 9 | MET | 1 | 1 | 3 | 0 | | |
| 4 | 1 | 2 | C | 9 | IRAK3 | 1 | 1 | 2 | 2 | 0 | 2 |
| 4 | 1 | 3 | E | 9 | Homo sapiens, S | 0 | 1 | 2 | 2 | 2 | 2 |
| 4 | 1 | 4 | G | 9 | MAP3K7 | 0 | 1 | 3 | 2 | 2 | 2 |
| 4 | 1 | 5 | A | 3 | PCTK1 | 0 | 0 | 3 | 2 | 2 | 0 |
| 4 | 1 | 6 | C | 3 | STK16 | 1 | 1 | 3 | 2 | 2 | 0 |
| 4 | 1 | 7 | E | 3 | CLK1 | 1 | 1 | 3 | 1 | | |
| 4 | 1 | 8 | G | 3 | SRC | 1 | 1 | 3 | 0 | | |
| 5 | 1 | 1 | A | 8 | LYN | 1 | 1 | 3 | 0 | | |
| 5 | 1 | 2 | C | 8 | TLK2 | 1 | 1 | 3 | 2 | 2 | 2 |
| 5 | 1 | 3 | E | 8 | PAK1 | 1 | 1 | 3 | 0 | | |
| 5 | 1 | 4 | G | 8 | FGFR2 | 1 | 1 | 3 | 2 | 2 | 2 |
| 5 | 1 | 5 | A | 2 | PRKCI | 0 | 1 | 3 | 2 | 2 | 2 |
| 5 | 1 | 6 | C | 2 | PIM1 | 1 | 1 | 3 | 2 | 2 | 2 |
| 5 | 1 | 7 | E | 2 | SRPK1 | 1 | 1 | 3 | 0 | | |
| 5 | 1 | 8 | G | 2 | FLJ20574 | 0 | 1 | 3 | 0 | | |
| 6 | 1 | 1 | A | 7 | FYN | 1 | 1 | 3 | 0 | | |
| 6 | 1 | 2 | C | 7 | TGFBR2 | 1 | 1 | 2 | 2 | 2 | 2 |
| 6 | 1 | 3 | E | 7 | MAP3K4 | 1 | 1 | 3 | 1 | 1 | 1 |
| 6 | 1 | 4 | G | 7 | TOPK | 1 | 1 | 3 | 2 | 2 | 2 |
| 6 | 1 | 5 | A | 1 | MAP3K3 | 0 | 1 | 3 | 2 | 2 | 2 |
| 6 | 1 | 6 | C | 1 | ADRBK1 | 1 | 1 | 3 | 0 | | |
| 6 | 1 | 7 | E | 1 | MAPKAPK3 | 1 | 1 | 3 | 0 | | |
| 6 | 1 | 8 | G | 1 | TBK1 | 0 | 1 | 3 | 2 | 2 | 1 |

TABLE 5-continued

Inhibition Results

| Subarray_Row | Quercetin 100 uM | SB 202190 100 uM | KN-62 100 uM | Ro-31-8220 100 uM | Ro-31-8220 90 uM | Staurosporine 21.5 uM | Genistein 100 uM | Genistein <3.7 mM | PP2 100 uM | AG 490 100 uM | AG 1296 100 uM | AG 1478 100 uM |
|---|---|---|---|---|---|---|---|---|---|---|---|---|
| 1 | | | | | | | | | | | | |
| 1 | 0 | | | 2 | 0 | 0 | 2 | 0 | 0 | 0 | 0 | 0 |
| 1 | 0 | | | 1 | | | 2 | | 2 | 0 | | 1 |
| 1 | | | | | | | | | | | | |
| 1 | 0 | | | 2 | 0 | 0 | 2 | 0 | 2 | 2 | | 2 |
| 1 | 0 | | | 2 | 0 | 0 | 2 | 0 | 2 | 2 | | 0 |
| 1 | 0 | | | 1 | 0 | 0 | 2 | 0 | 2 | 0 | | 0 |
| 1 | 0 | | | 2 | 0 | 0 | 2 | 1 | 1 | 2 | | 0 |
| 2 | | | | | | | | | | | | |
| 2 | | | | | | | | | | | | |
| 2 | 1 | | | 2 | | | 2 | | 2 | 2 | | 2 |
| 2 | 2 | | | 2 | | | 2 | | 2 | 2 | | 1 |
| 2 | 2 | | | 2 | 0 | 0 | 2 | 2 | 2 | 2 | | 2 |
| 2 | 1 | | | 2 | | | 2 | | 2 | 1 | | 2 |
| 2 | 2 | | | 2 | 0 | 0 | 2 | 0 | 2 | 2 | | 2 |
| 2 | 1 | | | 2 | 0 | 0 | 2 | | 2 | 2 | | 2 |
| 3 | | | | | | | | | | | | |
| 3 | | | | | | | | | | | | |
| 3 | | | | | | | | | | | | |
| 3 | | | | | | | | | | | | |
| 3 | 0 | | | 2 | 0 | 2 | 2 | 1 | 2 | 2 | | 2 |
| 3 | 0 | | | 2 | | | 2 | | 2 | 2 | | 2 |
| 3 | 0 | | | 2 | | | 2 | | 2 | 1 | | 1 |
| 3 | | | | | | | | | | | | |
| 4 | | | | | | | | | | | | |
| 4 | 0 | | | 2 | | | 2 | | 2 | 0 | | 2 |
| 4 | 0 | | | 0 | | | 2 | | 2 | 0 | | 0 |
| 4 | 0 | | | 2 | 2 | 2 | 1 | 0 | 2 | 0 | | 0 |
| 4 | 0 | | | 0 | | | 1 | | 1 | 0 | | 0 |
| 4 | 0 | | | 1 | 2 | 2 | 0 | 0 | 2 | 0 | | 0 |
| 4 | | | | | | | | | | | | |
| 4 | | | | | | | | | | | | |
| 5 | | | | | | | | | | | | |
| 5 | 0 | | | 1 | 2 | 2 | 2 | 0 | 2 | 2 | | 2 |
| 5 | | | | | | | | | | | | |
| 5 | 0 | | | 2 | 2 | 2 | 2 | 0 | 2 | 2 | | 2 |
| 5 | 0 | | | 0 | 2 | 2 | 2 | 0 | 1 | 2 | | 0 |
| 5 | 0 | | | 0 | 2 | 2 | 2 | 0 | 2 | 2 | | 1 |
| 5 | | | | | | | | | | | | |
| 5 | | | | | | | | | | | | |
| 6 | | | | | | | | | | | | |
| 6 | 0 | | | 2 | 2 | 2 | 2 | 1 | 2 | 2 | | 2 |
| 6 | 0 | | | 2 | | | 1 | | 2 | 2 | | 1 |
| 6 | 0 | | | 0 | 2 | 2 | 2 | 0 | 2 | 2 | | 1 |
| 6 | 0 | | | 0 | 2 | 2 | 2 | 2 | 2 | 2 | | 2 |
| 6 | | | | | | | | | | | | |
| 6 | | | | | | | | | | | | |
| 6 | 0 | | | 2 | | | 2 | | 1 | 2 | | 2 |

| Subarray_Row | Subarray_Column | Plate_Block | Plate_Row2 | Plate_Column2 | Name | Domain | GST_Expression | Solution_Activity | Microarray_Activity | H-89 100 uM | Rottlerin (Mallotoxin) 100 uM |
|---|---|---|---|---|---|---|---|---|---|---|---|
| 1 | 2 | 1 | B | 12 | BMX | 1 | 1 | 3 | 2 | 1 | 1 |
| 1 | 2 | 2 | D | 12 | FGFR1 | 1 | 1 | 3 | 2 | 1 | 1 |
| 1 | 2 | 3 | F | 12 | CDKL3 | 0 | 1 | 2 | 1 | 1 | 1 |
| 1 | 2 | 4 | H | 12 | Empty | 0 | 0 | | 0 | | |
| 1 | 2 | 5 | B | 6 | ABL1 | 1 | 1 | 3 | 2 | 0 | 0 |
| 1 | 2 | 6 | D | 6 | STK4 | 1 | 1 | 3 | 2 | 2 | 0 |
| 1 | 2 | 7 | F | 6 | *Homo sapiens*, S | 0 | 1 | 2 | 2 | 2 | 0 |
| 1 | 2 | 8 | H | 6 | PRKG1 | 1 | 1 | 2 | 0 | | |
| 2 | 2 | 1 | B | 11 | MERTK | 1 | 1 | 3 | 2 | 2 | 2 |
| 2 | 2 | 2 | D | 11 | DYRK2 | 1 | 1 | 3 | 2 | 2 | 2 |
| 2 | 2 | 3 | F | 11 | STK24 | 0 | 1 | 3 | 2 | 2 | 1 |
| 2 | 2 | 4 | H | 11 | Empty | 0 | 0 | | 0 | | |
| 2 | 2 | 5 | B | 5 | EPHB3 | 1 | 1 | 3 | 2 | 1 | 2 |
| 2 | 2 | 6 | D | 5 | TTK | 1 | 1 | 3 | 0 | | |
| 2 | 2 | 7 | F | 5 | *Homo sapiens*, o | 0 | 1 | 2 | 2 | 1 | 0 |
| 2 | 2 | 8 | H | 5 | FER | 1 | 1 | 3 | 2 | 2 | 2 |
| 3 | 2 | 1 | B | 10 | FGR | 0 | 1 | 3 | 2 | 2 | 2 |
| 3 | 2 | 2 | D | 10 | CDK10 | 0 | 1 | 2 | 0 | | |
| 3 | 2 | 3 | F | 10 | *Homo sapiens* p | 0 | 1 | 3 | 2 | 2 | 2 |
| 3 | 2 | 4 | H | 10 | GST | 0 | 1 | | 0 | | |

TABLE 5-continued

Inhibition Results

| | | | | | | | | | | | |
|---|---|---|---|---|---|---|---|---|---|---|---|
| 3 | 2 | 5 | B | 4 | FGFR2 | 1 | 1 | 3 | 2 | 2 | 0 |
| 3 | 2 | 6 | D | 4 | PAK3 | 1 | 1 | 3 | 2 | 2 | 0 |
| 3 | 2 | 7 | F | 4 | *Homo sapiens* c | 0 | 0 | 3 | 1 | 2 | 0 |
| 3 | 2 | 8 | H | 4 | RIPK1 | 1 | 0 | 3 | 0 | | |
| 4 | 2 | 1 | B | 9 | TEK | 1 | 1 | 3 | 0 | | |
| 4 | 2 | 2 | D | 9 | CSNK2A1 | 0 | 1 | 3 | 2 | 0 | 2 |
| 4 | 2 | 3 | F | 9 | *Homo sapiens* in | 0 | 1 | 3 | 2 | 2 | 0 |
| 4 | 2 | 4 | H | 9 | GST | 0 | 1 | | 0 | | |
| 4 | 2 | 5 | B | 3 | PRKCH | 0 | 1 | 3 | 2 | 2 | 2 |
| 4 | 2 | 6 | D | 3 | PAK4 | 1 | 1 | 2 | 0 | | |
| 4 | 2 | 7 | F | 3 | *Homo sapiens*, s | 0 | 1 | 2 | 2 | 2 | 0 |
| 4 | 2 | 8 | H | 3 | DAPK2 | 1 | 1 | 3 | 2 | 2 | 1 |
| 5 | 2 | 1 | B | 8 | EPHB1 | 1 | 1 | 3 | 2 | 1 | 1 |
| 5 | 2 | 2 | D | 8 | EPHA3 | 1 | 1 | 2 | 0 | | |
| 5 | 2 | 3 | F | 8 | *Homo sapiens*, s | 0 | 1 | 3 | 2 | 1 | 0 |
| 5 | 2 | 4 | H | 8 | Cell | 0 | 0 | | 0 | | |
| 5 | 2 | 5 | B | 2 | PRKCD | 0 | 1 | 3 | 2 | 1 | 0 |
| 5 | 2 | 6 | D | 2 | LOC57118 | 1 | 1 | 3 | 1 | 1 | 0 |
| 5 | 2 | 7 | F | 2 | *Homo sapiens*, p | 0 | 1 | 2 | 2 | 0 | 2 |
| 5 | 2 | 8 | H | 2 | FLJ20574 | 1 | 1 | 3 | 1 | | |
| 6 | 2 | 1 | B | 7 | RET | 1 | 1 | 3 | 2 | 0 | 0 |
| 6 | 2 | 2 | D | 7 | ACVR1B | 1 | 1 | 3 | 0 | | |
| 6 | 2 | 3 | F | 7 | *Homo sapiens*, B | 0 | 1 | 3 | 2 | 0 | 2 |
| 6 | 2 | 4 | H | 7 | Cell | 0 | 0 | | 0 | | |
| 6 | 2 | 5 | B | 1 | CAMK2D | 1 | 1 | 3 | 2 | 0 | 2 |
| 6 | 2 | 6 | D | 1 | MKNK2 | 1 | 1 | 3 | 0 | | |
| 6 | 2 | 7 | F | 1 | *Homo sapiens*, p | 0 | 1 | 3 | 2 | 0 | 1 |
| 6 | 2 | 8 | H | 1 | PHKG1 | 1 | 0 | 3 | 0 | | |

| Subarray_Row | Quercetin 100 uM | SB 202190 100 uM | KN-62 100 uM | Ro-31-8220 100 uM | Ro-31-8220 | Staurosporine | Genistein 100 uM | Genistein | PP2 100 uM | AG 490 100 uM | AG 1296 100 uM | AG 1478 100 uM |
|---|---|---|---|---|---|---|---|---|---|---|---|---|
| 1 | 0 | | | 2 | | | 0 | | 2 | 0 | | 1 |
| 1 | 0 | | | 2 | | | 0 | | 2 | 0 | | 1 |
| 1 | 0 | | | 2 | | | 0 | | 2 | 2 | | 1 |
| 1 | | | | | | | | | | | | |
| 1 | 0 | | | 2 | 0 | 0 | 0 | 0 | 2 | 0 | | 1 |
| 1 | 0 | | | 2 | 0 | 0 | 0 | 0 | 2 | 0 | | 1 |
| 1 | 0 | | | 2 | 0 | 0 | 0 | 0 | 2 | 0 | | 1 |
| 1 | | | | | | | | | | | | |
| 2 | 1 | | | 2 | | | 2 | | 2 | 2 | | 2 |
| 2 | 2 | | | 2 | 0 | 0 | 2 | 1 | 2 | 2 | | 2 |
| 2 | 1 | | | 2 | | | 2 | | 2 | 2 | | 1 |
| 2 | | | | | | | | | | | | |
| 2 | 2 | | | 2 | 0 | 0 | 2 | 0 | 2 | 2 | | 2 |
| 2 | | | | | | | | | | | | |
| 2 | 2 | | | 2 | 0 | 0 | 2 | 0 | 2 | 2 | | 2 |
| 2 | 1 | | | 2 | | | 2 | | 2 | 2 | | 1 |
| 3 | 2 | | | 2 | 2 | 2 | 2 | 2 | 2 | 2 | | 2 |
| 3 | | | | | | | | | | | | |
| 3 | 2 | | | 2 | 2 | 2 | 2 | 2 | 2 | 2 | | 2 |
| 3 | 0 | | | 2 | 0 | 2 | 2 | 1 | 2 | 2 | | 2 |
| 3 | 2 | | | 2 | 2 | 2 | 2 | 0 | 2 | 1 | | 2 |
| 3 | 1 | | | 2 | | | 2 | | 2 | 2 | | 2 |
| 3 | | | | | | | | | | | | |
| 4 | 0 | | | 2 | 0 | 2 | 2 | 0 | 2 | 2 | | 2 |
| 4 | 0 | | | 0 | 2 | 2 | 1 | 0 | 2 | 1 | | 2 |
| 4 | | | | | | | | | | | | |
| 4 | 0 | | | 2 | 2 | 2 | 2 | 0 | 2 | 2 | | 0 |
| 4 | 0 | | | 2 | 2 | 2 | 1 | 0 | 2 | 0 | | 2 |
| 4 | 0 | | | 2 | 2 | 2 | 2 | 0 | 2 | 2 | | 0 |
| 5 | 0 | | | 0 | 2 | 2 | 1 | 0 | 2 | 0 | | 2 |
| 5 | | | | | | | | | | | | |
| 5 | 0 | | | 0 | 2 | 2 | 0 | 0 | 0 | 0 | | 0 |
| 5 | | | | | | | | | | | | |
| 5 | 0 | | | 0 | 2 | 2 | 0 | 0 | 0 | 0 | | 0 |
| 5 | 0 | | | 0 | | | 0 | | 0 | 1 | | 0 |
| 5 | 0 | | | 0 | 2 | 2 | 2 | 0 | 2 | 2 | | 2 |
| 5 | | | | | | | | | | | | |
| 6 | 0 | | | 0 | 2 | 2 | 2 | 0 | 2 | 2 | | 2 |
| 6 | | | | | | | | | | | | |
| 6 | 0 | | | 0 | 2 | 2 | 2 | 0 | 2 | 2 | | 2 |
| 6 | | | | | | | | | | | | |

TABLE 5-continued

| | | | | Inhibition Results | | | | | |
|---|---|---|---|---|---|---|---|---|---|
| 6 6 | 0 | | 0 | 2 | 2 | 2 | 0 | 2 | 2 | 2 |
| 6 6 | 0 | | 0 | 0 | 2 | 1 | 0 | 1 | 2 | 1 |

Level 0 means no inhibition or unclear.
Level 1 means little or marginal inhibition.
Level 2 means substantial inhibition.

References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A method for assaying an enzymatic reaction, the method comprising:
   (a) incubating at least one protein and at least one substance under conditions conducive to the occurrence of an enzymatic reaction between the protein and the substance, wherein (i) the protein and the substance are immobilized on the surface of a solid support, wherein the at least one protein and the at least one substance are immobilized on a solid support before the incubating step; (ii) the protein and the substance are in proximity sufficient for the occurrence of said enzymatic reaction; and (iii) the protein and the substance are not identical; and
   (b) determining whether said enzymatic reaction occurs, wherein the at least one substance is coated onto the solid support and the at least one protein is printed on the solid support.

2. The method of claim 1, wherein the protein, the substance, or the protein and the substance, are purified prior to being immobilized.

3. The method of claim 1, wherein the substance is a mixture of different substances.

4. The method of claim 1, wherein the protein is immobilized prior to immobilizing the substance.

5. The method of claim 1, wherein the substance is immobilized prior to immobilizing the protein.

6. The method of claim 1, wherein the substance and the protein are immobilized simultaneously.

7. The method of claim 1, wherein the substance is a known substrate for the type of enzymatic activity assayed in said enzymatic reaction, and said determining step determines whether said protein is an enzyme having said type of enzymatic activity.

8. The method of claim 7, wherein the protein comprises a region that is homologous to the catalytic domain of an enzyme that is known to have the type of enzymatic activity assayed in said enzymatic reaction.

9. The method of claim 1, wherein the protein is an enzyme known to have the type of enzymatic activity assayed in said enzymatic reaction, and said determining step determines whether said substance is a substrate for said type of enzymatic activity.

10. The method of claim 9, wherein the enzyme is an oxidoreductase, a transferase, a hydrolase, a lyase, an isomerase, or a ligase.

11. The method of claim 10, wherein the transferase is a kinase.

12. The method of claim 1, wherein (i) the substance is a known substrate for the type of enzymatic activity assayed in said enzymatic reaction, or a mixture of known substrates for the type of enzymatic activity assayed; and (ii) the protein is known to catalyze the type of enzymatic activity assayed in said enzymatic reaction.

13. The method of claim 12, wherein said incubating step is done in the presence of one or more test molecules so as to determine whether said test molecules modulate said enzymatic reaction; and said determining step comprises detecting whether a change in the amount of said enzymatic reaction occurs relative to the amount of said enzymatic reaction in the absence of the test molecules.

14. The method of claim 13, wherein said determining step comprises detecting a decrease in the rate of said enzymatic reaction relative to the rate of said enzymatic reaction in the absence of the test molecules, thereby identifying the test molecules as an inhibitor of said enzymatic reaction.

15. The method of claim 13, wherein said determining step comprises detecting an increase in the rate of said enzymatic reaction relative to the rate of said enzymatic reaction in the absence of the test molecules, thereby identifying the test molecules as an activator of said enzymatic reaction.

16. The method of claim 13, wherein the substrate is a mixture of known substrates for different subclasses of enzymes having the type of enzymatic activity assayed.

17. The method of claim 1, wherein the substance, the protein, or the substance and the protein, are covalently bound to the surface of the solid support.

18. The method of claim 1, wherein the substance, the protein, or the substance and the protein, are non-covalently immobilized to the surface of the solid support.

19. The method of claim 1, wherein the substance, the protein, or the substance and the protein, are immobilized to the surface of the solid support via a linker.

20. The method of claim 1, wherein the method further comprises quantifying the enzymatic reaction.

21. The method of claim 1, wherein the solid support has at least two wells and wherein each well comprises the same one or more different proteins immobilized on the surface of the solid support within the well.

22. The method of claim 21, wherein the solid support has at least two wells and wherein each well comprises the same set of one or more different substances immobilized on the surface of the solid support within the well.

23. The method of claim 1, wherein said determining step comprises measuring a change in a detectable signal resulting from said enzymatic reaction.

24. The method of claim 1, wherein a plurality of different proteins are printed on the solid support in a positionally addressable array.

25. The method of claim 24, wherein said plurality consists of between 2 different proteins and 10,000 different proteins.

26. The method of claim 24, wherein said plurality consists of between 2 different substances and 10,000 different substances.

27. The method of claim 24, wherein a plurality of different proteins are printed on the solid support in a positionally addressable array and a plurality of different substances are coated on the solid support.

28. The method of claim 24, wherein the proteins are printed on the solid support in a positionally addressable array at a density of at least $100/cm^2$.

29. The method of claim 1, wherein a plurality of different substances are coated on the solid support.

* * * * *